US007132437B2

(12) United States Patent
Reitz et al.

(10) Patent No.: US 7,132,437 B2
(45) Date of Patent: *Nov. 7, 2006

(54) RENAL-SELECTIVE BIPHENYLALKYL 1H-SUBSTITUTED-1,2,4-TRIAZOLE ANGIOTENSIN II ANTAGONISTS FOR TREATMENT OF HYPERTENSION

(75) Inventors: David B. Reitz, Chesterfield, MO (US); Robert E. Manning, St. Louis, MO (US)

(73) Assignee: G.D. Searle, Chicago, IL (US)

( * ) Notice: Subject to any disclaimer, the term of this patent is extended or adjusted under 35 U.S.C. 154(b) by 0 days.

This patent is subject to a terminal disclaimer.

(21) Appl. No.: 10/852,711

(22) Filed: May 24, 2004

(65) Prior Publication Data

US 2004/0220245 A1 Nov. 4, 2004

Related U.S. Application Data

(63) Continuation of application No. 10/326,942, filed on Dec. 19, 2002, now abandoned, which is a continuation of application No. 09/634,668, filed on Aug. 8, 2000, now abandoned, which is a continuation of application No. 09/382,330, filed on Aug. 24, 1999, now abandoned, which is a continuation of application No. 09/160,560, filed on Sep. 24, 1998, now abandoned, which is a continuation of application No. 08/788,865, filed on Jan. 23, 1997, now abandoned, which is a continuation of application No. 08/236,803, filed on May 2, 1994, now Pat. No. 5,436,088, which is a continuation-in-part of application No. 07/949,804, filed on Dec. 7, 1992, now abandoned, which is a continuation-in-part of application No. 07/574,314, filed on Aug. 28, 1990, now Pat. No. 5,217,985.

(51) Int. Cl.
*A61K 31/41* (2006.01)
*C07D 249/08* (2006.01)

(52) U.S. Cl. .................. 514/383; 514/381; 548/262.2; 548/265.8; 548/266.2; 548/250

(58) Field of Classification Search ............ 548/262.2, 548/265.8, 266.2, 250; 514/383, 381
See application file for complete search history.

(56) References Cited

U.S. PATENT DOCUMENTS 5,098,920 A * 3/1992 Reitz .......................... 514/381
5,217,985 A * 6/1993 Reitz et al. ................. 514/381

* cited by examiner

*Primary Examiner*—Joseph K. McKane
*Assistant Examiner*—Robert Shiao
(74) *Attorney, Agent, or Firm*—Steven R. Eck; Charles W. Ashbrook

(57) ABSTRACT

Renal-selective compounds are described which, in one embodiment, are prodrugs preferentially converted in the kidney to compounds capable of blocking angiotensin II (AII) receptors. These prodrugs are conjugates formed from two components, namely, a first component provided by an AII antagonist compound and a second component which is capable of being cleaved from the first component when both components are chemically linked within the conjugate. The two components are chemically linked by a bond which is cleaved selectively in the kidney, for example, by an enzyme. The liberated AII antagonist compound is then available to block AII receptors within the kidney. Conjugates of particular interest are glutamyl derivatives of biphenylmethyl 1H-substituted-1,2,4-triazole compounds, of which N-acetylglutamic acid, 5-[[4'-[(3,5-dibutyl-1H-1,2,4-triazol-1-yl)methyl][1,1'-biphenyl]-2-yl]]carbonylhydrazide, (shown below) is an example:

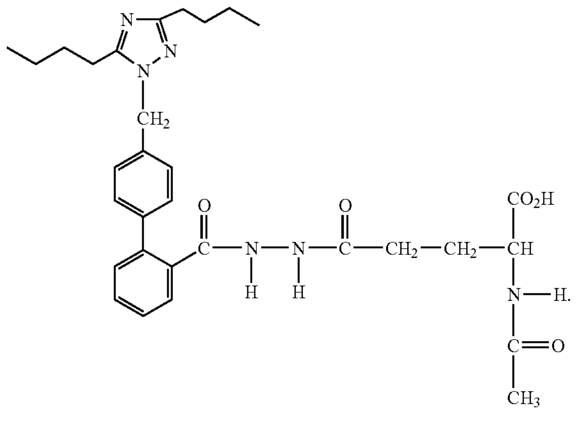

18 Claims, 3 Drawing Sheets

RENAL-SELECTIVE BIPHENYLALKYL 1H-SUBSTITUTED-1,2,4-TRIAZOLE ANGIOTENSIN II ANTAGONISTS FOR TREATMENT OF HYPERTENSION

RELATED APPLICATION

This is a continuation of application Ser. No. 10/326,942, filed on Dec. 19, 2002 now abandoned, which is a continuation of application Ser. No. 09/634,668, filed on Aug. 8, 2000, now abandoned, which is a continuation of application Ser. No. 09/382,330, filed on Aug. 24, 1999, now abandoned, which is a continuation of application Ser. No. 09/160,560 filed on Sep. 24, 1998, now abandoned, which is a continuation of application Ser. No. 08/788,865, filed on Jan. 23, 1997, now abandoned, which is a continuation of application Ser. No. 08/236,803, filed on May 2, 1994, which issued as U.S. Pat. No. 5,436,088, which is a continuation-in-part of application Ser. No. 07/949,804, filed on Dec. 7, 1992, now abandoned, which is a continuation-in-part of application Ser. No. 07/574,314, filed Aug. 28, 1990, which issued as U.S. Pat. No. 5,217,985.

FIELD OF THE INVENTION

This invention is in the field of cardiovascular therapeutics and relates to a class of compounds useful in control of hypertension. Of particular interest is a class of prodrugs of angiotensin II antagonists which, when selectively hydrolyzed in the kidney, provide hypertension control.

BACKGROUND OF THE INVENTION

The renin-angiotensin system is one of the hormonal mechanisms involved in regulation of pressure/volume homeostasis and in expression of hypertension. Activation of the renin-angiotensin cascade begins with renin secretion from the juxtaglomerular apparatus of the kidney and culminates in the formation of angiotensin II, an octapeptide which is the primary active species of this system. Angiotensin II is a potent vasoconstrictor agent and also produces other physiological effects such as promoting aldosterone secretion, promoting sodium and fluid retention, inhibiting renin secretion, increasing sympathetic nervous system activity, increasing vasopressin secretion, causing positive cardiac inotropic effect and modulating other hormonal systems.

Previous studies have shown that antagonizing angiotensin II at its receptors is a viable approach to inhibit the renin-angiotensin system, given the pivotal role of this octapeptide which mediates the actions of the renin-angiotensin system through interaction with various tissue receptors. There are several known angiotensin II antagonists, most of which are peptidic in nature. Such peptidic compounds are of limited use due to their lack of oral bioavailability or their short duration of action. Also, commercially-available peptidic angiotensin II antagonists (e.g., Saralasin) have a significant residual agonist activity which further limit their therapeutic application.

Non-peptidic compounds with angiotensin II antagonist properties are known. For example, the sodium salt of 2-n-butyl-4-chloro-1-(2-chlorobenzyl)imidazole-5-acetic acid has specific competitive angiotensin II antagonist activity as shown in a series of binding experiments, functional assays and in vivo tests [P. C. Wong et al, *J. Pharmacol. Exp. Ther.,* 247 (1), 1–7 (1988)]. Also, the sodium salt of 2-butyl-4-choloro-1-(2-nitrobenzyl)imidazole-5-acetic acid has specific competitive angiotensin II antagonist activity as shown in a series of binding experiments, functional assays and in vivo tests [A. T. Chiu et al, *European J. Pharmacol.,* 157, 3121 (1988)]. A family of 1-benzylimidazole-5-acetate derivatives has been shown to have competitive angiotensin II antagonist properties [A. T. Chiu et al, *J. Pharmacol. Exp. Ther.,* 250 (3), 867–874 (1989)]. U.S. Pat. No. 4,816,463 to Blankey et al describes a family of 4,5,6,7-tetrahydro-1H-imidazo (4,5-c)-tetrahydro-pyridine derivatives useful as antihypertensives, some of which are reported to antagonize the binding of labelled angiotensin II to rat adrenal receptor preparation and thus cause a significant decrease in mean arterial blood pressure in conscious hypertensive rats. EP No. 253,310, published 20 Jan. 1988, describes a series of aralkyl imidazole compounds, including in particular a family of biphenylmethyl substituted imidazoles, as antagonists to the angiotensin II receptor. EP No. 323,841, published 12 Jul. 1989, describes four classes of angiotensin II antagonists, namely, biphenylmethylpyrroles, biphenylmethylpyrazoles, biphenylmethyl-1,2,3-triazoles and biphenylmethyl 4-substituted-4H-1,2,4-triazoles, including the compound 3,5-dibutyl-4-[(2'-carboxybiphenyl-4-yl)methyl]-4H-1,2,4-triazole. U.S. Pat. No. 4,880,804 to Carini et al describes a family of biphenylmethylbenzimidazole compounds as angiotensin II receptor blockers for use in treatment of hypertension and congestive heart failure.

One disadvantage of these angiotensin II antagonist compounds is that the desired hypertension-reducing effect may be offset by hypotension-induced compensatory stimulation of the renin-angiotensin system or stimulation of the sympathetic nervous system, either of which may result in promotion of sodium and water retention. Also, some angiotensin II antagonists may have toxicological effects systemically which preclude their use at doses necessary to be effective in reducing blood pressure.

To avoid such systemic side effects, drugs may be targetted to the kidney by creating a conjugate compound that would be a renal-specific prodrug containing the targetted drug modified with a chemical carrier moiety. Cleavage of the drug from the carrier moiety by enzymes predominantly localized in the kidney releases the drug in the kidney. Gamma glutamyl transpeptidase and acylase are examples of such cleaving enzymes found in the kidney which have been used to cleave a targetted drug from its prodrug carrier within the kidney.

Renal targetted prodrugs are known for delivery of a drug selectively to the kidney. For example, the compound L-γ-glutamyl amide of dopamine when administered to dogs was reported to generate dopamine in vivo by specific enzymatic cleavage by γ-glutamyl transpeptidase [J. J. Kyncl et al, *Adv. Biosc.,* 20, 369–380 (1979)]. In another study, γ-glutamyl and N-acyl-γ-glutamyl derivatives of the anti-bacterial compound sulfamethoxazole were shown to deliver relatively high concentrations of sulfamethoxazole to the kidney which involved enzymatic cleavage of the prodrug by acylamino acid deacylase and γ-glutamyl transpeptidase [M. Orlowski et al, *J. Pharmacol. Exp. Ther.,* 212, 167–172 (1980)]. The N-γ-glutamyl derivatives of 2-, 3-, or 4-aminophenol and p-fluoro-L-phenylalanine have been found to be readily solvolyzed in vitro by γ-glutamyl transpeptidase [S. D. J. Magnan et al, *J. Med. Chem.,* 25, 1018–1021 (1982)]. The hydralazine-like vasodilator 2-hydrazino-5-γ-butylpyridine (which stimulates guanylate cyclase activity) when substituted with the N-acetyl-γ-glutamyl residue resulted in a prodrug which provided selective renal vasodilation [K. G. Hofbauer et al, *J. Pharmacol. Exp. Ther.,* 212, 838–844 (1985)]. The dopamine prodrug γ-L-glutamyl-L- dopa ("gludopa") has been shown to be relatively specific for the kidney and to increase renal blood flow, glomerular filtration and urinary sodium excretion in normal subjects [D. P. Worth et al, *Clin. Sci.,* 69, 207–214 (1985)]. In another study, gludopa was reported to be an effective renal dopamine prodrug whose activity can be blocked by the dopa-decarboxylase inhibitor carbidopa [R. F. Jeffrey et al, *Br. J. Clin. Pharmac.,* 25, 195–201 (1988)]. A class of 4-ureido derivatives of isoquinolin-3-ol has been investigated for renal specific effects, such as increases in renal vasodilation and renal blood flow [R. M. Kanojia et al, *J. Med. Chem.,* 32, 990–997 (1989)].

BRIEF DESCRIPTION OF THE DRAWING FIGURES

DESCRIPTION OF THE INVENTION

Figure 1:
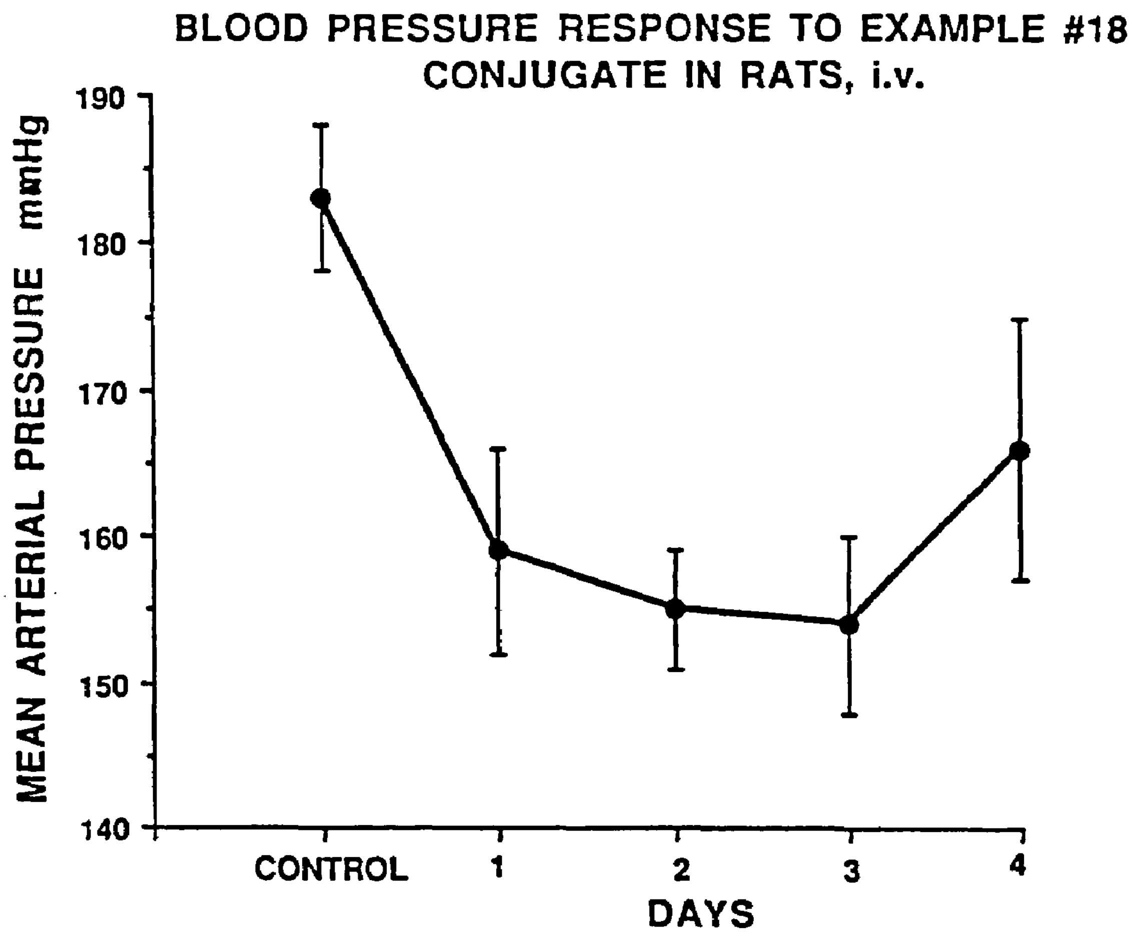
FIG. 1 is a graph showing reduction in mean arterial pressure by intravenous administration of a conjugate of the invention to rats over a period of four days.

Treatment of circulatory disorders, which include cardiovascular disorders, such as chronic hypertension, sodium-retaining disorders, congestive heart failure, cirrhosis and nephrosis, may be accomplished by administering to a susceptible or afflicted subject a therapeutically-effective amount of a renal-selective prodrug capable of causing blood-pressure reducing effects by selective action in the kidney. An advantage of such renal-selective prodrug therapy resides in reduction or avoidance of adverse side effects associated with systemically-acting drugs.

Advantages of a renal-selective antihypertensive compound are several. First, the renal-selective compound is targetted at those pathophysiological mechanisms which occur primarily in the kidney. Second, the regulation of other organ systems is unaffected; thus, normal physiological regulation of other organ systems is maintained. Third, fewer side-effects may be anticipated, since the compound remains inactive until cleaved in the kidneys. Similarly, fewer negative drug-drug interactions may be anticipated. Finally, since a renal-selective accumulation of active compound may occur, which is not dependent on plasma levels of the parent compound, lower doses of the renal-selective compound compared to active parent compound may be used.

A renal-selective prodrug is provided by a conjugate comprising a residue of an angiotensin II antagonist compound, which conjugate is renal selective. The conjugate will typically comprise a first component and a second component connected together by a cleavable or hydrolyzable bond. The term "renal-selective", as used to characterize a conjugate of the invention, embraces any of the following four pharmacological events: (1) the conjugate is selectively taken up by the kidney and is selectively cleaved in the kidney; (2) the conjugate is not taken up selectively by the kidney, but is selectively cleaved in the kidney; (3) the conjugate is selectively taken up by the kidney and then cleaved in the kidney; or (4) where the conjugate itself is active as an angiotensin II antagonist, the conjugate is selectively taken up by the kidney without cleavage of the hydrolyzable bond.

The first component of a conjugate of the invention is a residue derived from an antagonist compound capable of inhibiting angiotensin II (AII) receptors, especially those AII receptors located in the kidney. The second residue is capable of being cleaved from the first residue preferentially. Cleaving of the first and second residues may be accomplished by a variety of mechanisms. For example, the bond may be cleaved by an enzyme in the kidney.

The residue providing the first component may be characterized as the "AII antagonist active" residue. Such "active" residue may be provided by a compound having AII antagonist activity or by a metabolite of such compound having AII antagonist activity. The residue providing the second component may be characterized in being capable of forming a cleavable bond connecting the "active" first residue and the second residue. Such bond is cleavable by an enzyme located in the kidney. In a preferred embodiment, this cleavable bond is typically a hydrolyzable amide bond, that is, a bond between a carbonyl-terminated moiety and an reactive nitrogen-terminated moiety, such as an amino-terminated moiety, which may be cleaved by enzyme found in the kidney, but which is not cleaved substantially by enzymes located in other organs or tissues of the body. Preferred bond-cleaving enzymes would be found predominantly in the kidney.

The conjugate containing the residue of an AII antagonist compound and containing the cleavable fragment or residue may possess AII antagonist activity comparable to, or more than, or less than, the AII antagonist compound which forms the conjugate. In one embodiment of the invention, the conjugate will have AII receptor blocking activity comparable to the AII antagonist component forming the conjugate. In another embodiment of the invention, the conjugate will have AII receptor blocking activity less than the AII receptor blocking activity forming the conjugate. One advantage of such differential activity between the conjugate and the AII antagonist component is that certain side effects associated with non-renal, systemic AII receptor blocking may be avoided or reduced. For example, at least one conjugate of the invention has been found to have very large differential in AII receptor blocking activities between the conjugate and the AII antagonist component forming the conjugate. Such differential activity is advantageous in that therapeutically-effective antihypertensive doses of the conjugate may be administered to give renal-selective AII receptor blocking action resulting from kidney-specific enzyme hydrolysis or metabolism of the conjugate to free the active AII receptor blocker within the kidney. Inasmuch as this renal-selective conjugate has relatively low AII receptor blocking activity, compared to the AII receptor compound forming the conjugate, this conjugate will have fewer adverse side effects associated with unwanted systemic interaction with non-renal AII receptors such as found in the vascular bed.

DETAILED DESCRIPTION OF THE INVENTION

The first residue of the conjugate may be selected from any class of compounds, or metabolites thereof, having angiotensin II antagonist activity. An example of one such class of angiotensin II antagonist compounds is provided by a class of biphenylalkyl 1H-substituted-1,2,4-triazole compounds defined by Formula I:

(I)

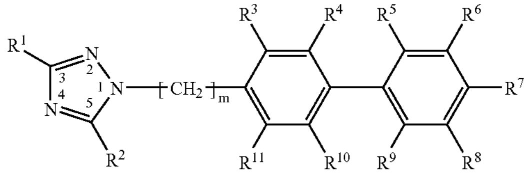

wherein m is a number selected from one to four, inclusive;

wherein each of $R^1$ through $R^{11}$ is independently selected from hydrido, alkyl, hydroxyalkyl, halo, haloalkyl, cycloalkyl, cycloalkylalkyl, formyl, alkoxy, aralkyl, aryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptothiocarbonyl, mercaptoalkyl, alkoxycarbonyloxy, alkylthio, cycloalkylthio, alkylthiocarbonyl, alkylcarbonylthio, alkylthiocarbonyloxy, alkylthiocarbonylthio, alkylthiothiocarbonyl, alkylthiothiocarbonylthio, arylthio, arylthiocarbonyl, arylcarbonylthio, arylthiocarbonyloxy, arylthiocarbonylthio, arylthiothiocarbonyl, arylthiothiocarbonylthio, aralkylthio, aralkylthiocarbonyl, aralkylcarbonylthio, aralkylthiocarbonyloxy, aralkylthiocarbonylthio, alkylthiocarbonyl, aralkylthiocarbonylthio, mercapto, alkylsulfinyl, alkylsulfonyl, aralkylsulfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cyclohetero-containing groups has one or more ring atoms selected from oxygen, sulfur and nitrogen atoms, and wherein each of $R^1$ through $R^{11}$ may be further independently selected from amino and amido radicals of the formula

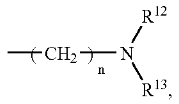

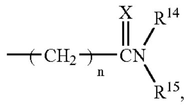

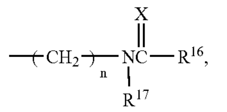

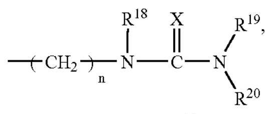

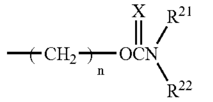

and

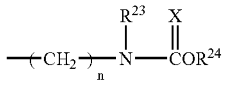

wherein X is oxygen atom or sulfur atom;

wherein each n is a number independently selected from zero to six, inclusive;

wherein each of $R^{12}$ through $R^{24}$ is independently selected from hydrido, alkyl, cycloalkyl, cyano, amino, monoalkylamino, dialkylamino, hydroxyalkyl, cycloalkylalkyl, alkoxyalkyl, aralkyl and aryl, and wherein $R^{12}$ and $R^{13}$ taken together, $R^{14}$ and $R^{15}$ taken together, $R^{16}$ and $R^{17}$ taken together, $R^{19}$ and $R^{20}$ taken together and $R^{21}$ and $R^{22}$ taken together may each form a heterocyclic group having five to seven ring members including the nitrogen atom of said amino or amido radical and which heterocyclic group may further contain one or more hetero atoms as ring members selected from oxygen, nitrogen and sulfur atoms and which heterocyclic group may be saturated or partially unsaturated; wherein $R^{12}$ and $R^{13}$ taken together, $R^{14}$ and $R^{15}$ taken together, $R^{19}$ and $R^{20}$ taken together and $R^{21}$ and $R^{22}$ taken together may each form an aromatic heterocyclic group having five ring members including the nitrogen atom of said amino or amido radical and which aromatic heterocyclic group may further contain one or more hetero atoms as ring atoms selected from oxygen, nitrogen and sulfur atoms;

and wherein each of $R^3$ through $R^{11}$ may be further independently selected from hydroxy and from acidic moieties of the formula $$—Y_nA$$

wherein n is a number selected from zero through three, inclusive, and wherein A is an acidic group selected to contain at least one acidic hydrogen atom, and the amide, ester and salt derivatives of said acidic moieties; wherein Y is a spacer group independently selected from one or more of alkyl, cycloalkyl, cycloalkylalkyl, alkenyl, alkynyl, aryl, aralkyl and heteroaryl having one or more ring atoms selected from oxygen, sulfur and nitrogen atoms;

and wherein any of the foregoing $R^1$ through $R^{24}$, Y and A groups having a substitutable position may be substituted with one or more groups selected from hydroxy, alkyl, alkenyl, alkynyl, aralkyl, hydroxyalkyl, trifluoromethyl, difluoroalkyl, oxo, alkoxy, aryloxy, aralkoxy, aralkylthio, alkoxyalkyl, cycloalkyl, cycloalkylalkyl, aryl, aroyl, cycloalkenyl, cyano, cyanoamino, nitro, alkylcarbonyloxy, alkoxycarbonyloxy, alkylcarbonyl, alkoxycarbonyl, carboxyl, mercapto, mercaptocarbonyl, alkylthio, arylthio, alkylthiocarbonyl, alkylsulfinyl, alkylsulfonyl, aralkylsulfinyl, aralkylsulfonyl, arylsulfinyl, arylsulfonyl, heteroaryl having one or more ring atoms selected from oxygen, sulfur and nitrogen atoms, and amino and amido radicals of the formula

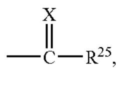

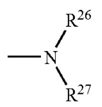

and

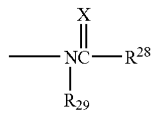

wherein X is selected from oxygen atom and sulfur atom;

wherein each of $R^{25}$, $R^{26}$, $R^{27}$, $R^{28}$ and $R^{29}$ is selected from hydrido, alkyl, cycloalkyl, cycloalkylalkyl, aralkyl, aryl, $DR^{30}$ and

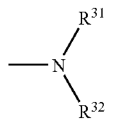

wherein D is selected from oxygen atom and sulfur atom and $R^{30}$ is selected from hydrido, alkyl, cycloalkyl, cycloalkylalkyl, aralkyl and aryl; wherein each of $R^{25}$, $R^{26}$, $R^{27}$, $R^{28}$, $R^{29}$, $R^{31}$ and $R^{32}$ is independently selected from hydrido, alkyl, cycloalkyl, cyano, hydroxyalkyl, haloalkyl, cycloalkylalkyl, alkoxyalkyl, alkylcarbonyl, alkoxycarbonyl, carboxyl, alkylsulfinyl, alkylsulfonyl, arylsulfinyl, arylsulfonyl, haloalkylsulfinyl, haloalkylsulfonyl, aralkyl and aryl, and wherein each of $R^{25}$, $R^{26}$, $R^{27}$, $R^{28}$, $R^{29}$, $R^{31}$ and $R^{32}$ is further independently selected from amino and amido radicals of the formula

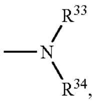, 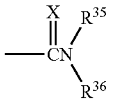 and 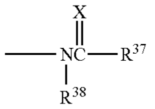

wherein X is oxygen atom or sulfur atom;

wherein each of $R^{33}$, $R^{34}$, $R^{35}$, $R^{36}$, $R^{37}$ and $R^{38}$ is independently selected from hydrido, alkyl, cycloalkyl, cyano, amino, monoalkylamino, dialkylamino, hydroxyalkyl, cycloalkylalkyl, alkoxyalkyl, haloalkylsulfinyl, haloalkylsulfonyl, aralkyl and aryl, and wherein $R^{26}$ and $R^{27}$ taken together and $R^{28}$ and $R^{29}$ taken together may each form a heterocyclic group having five to seven ring members including the nitrogen atom of said amino or amido radical, which heterocyclic group may further contain one or more hetero atoms as ring members selected from oxygen, nitrogen and sulfur atoms and which heterocyclic group may be saturated or partially unsaturated; wherein $R^{26}$ and $R^{27}$ taken together and $R^{31}$ and $R^{32}$ taken together may each form an aromatic heterocyclic group having five ring members including the nitrogen atom of said amino or amido radical and which aromatic heterocyclic group may further contain one or more hetero atoms as ring atoms selected from oxygen, nitrogen and sulfur atoms;

with the proviso that at least one of said $R^1$ through $R^{24}$, Y and A substituents contains a terminal primary or secondary amino moiety or a moiety convertible to a primary or secondary amino moiety.

or a tautomer thereof or a pharmaceutically-acceptable salt thereof.

Conjugates of the invention are therapeutically effective in treatment of cardiovascular disorders by acting directly on, or by providing cleavable components selected from Formula I compounds which act directly on, or as antagonists to, or as blockers of, the angiotensin II (AII) receptor. Thus, conjugates of Formula I would be therapeutically effective in treatment of cardiovascular disorders or would be precursors to, or prodrugs of, therapeutically-effective compounds.

Preferred compounds of Formula I, from which a cleavable component may be selected, are all characterized in having a substituent, other than hydrido, at each of the three- and five-positions of the triazole ring. Such substituents are selected from the aforementioned $R^1$ and $R^2$ groups. Also especially useful are compounds having one of the $R^1$ and $R^2$ substituents selected from alkylcarbonyl, monoalkoxyalkyl, dialkoxyalkyl and difluoroalkyl groups. When the selected substituent for $R^1$ and $R^2$ is difluoroalkyl, then it is particularly useful for both of the fluoro atoms of the difluoroalkyl group to be substituted on the difluoroalkyl group carbon atom attached at the $R^1$ or $R^2$ positions of the triazole ring. Such difluoroalkyl group may be characterized as an "alpha-carbon difluoro-substituted difluoroalkyl group", or as an "alpha, alpha-difluoro-substituted alkyl group". When the selected substituent for $R^1$ or $R^2$ is monoalkoxyalkyl or dialkoxyalkyl, then it is particularly useful for the single alkoxy group or the two alkoxy groups, respectively, to be substituted on the carbon atom of the selected substituent which is attached at the $R^1$ or $R^2$ positions of the triazole ring. Such alkoxyalkyl groups may be characterized as "alpha-carbon monoalkoxy- or dialkoxy-substituted alkoxyalkyl groups", respectively, or "alpha-monoalkoxy-substituted or alpha, alpha-dialkoxy-substituted alkyl groups", respectively. When the selected substituent is alkylcarbonyl, then it is particularly useful for the carbonyl group to be attached at the $R^1$ or $R^2$ positions of the triazole ring. Such alkylcarbonyl group may be characterized as an "alpha-oxo-substituted alkyl group", and may be exemplified by the substituents 1-oxoethyl, 1-oxopropyl and 1-oxobutyl. Where compounds of Formula I contain any of these above-mentioned particularly-useful alpha-carbon substituted $R^1$ or $R^2$ groups at the triazole ring three- or five-position, it is preferred that such particularly-useful group be attached at the three-position, that is, as an $R^1$ substituent.

The phrase "acidic group selected to contain at least one acidic hydrogen atom", as used to define the —$Y_nA$ moiety, is intended to embrace chemical groups which, when attached to any of the $R^3$ through $R^{11}$ positions of Formula I, confers acidic character to the compound of Formula I. "Acidic character" means proton-donor capability, that is, the capacity of the compound of Formula I to be a proton donor in the presence of a proton-receiving substance such as water. Typically, the acidic group should be selected to have proton-donor capability such that the product compound of Formula I has a $pK_a$ in a range from about one to about twelve. More typically, the Formula I compound would have a $pK_a$ in a range from about two to about seven. An example of an acidic group containing at least one acidic hydrogen atom is carboxyl group (—COOH). Where n is zero and A is —COOH, in the —$Y_nA$ moiety, such carboxyl group would be attached directly to one of the $R^3$ through $R^{11}$ positions. The Formula I compound may have one —$Y_nA$ moiety attached at one of the $R^3$ through $R^{11}$ positions, or may have a plurality of such —$Y_nA$ moieties attached at more than one of the $R^3$ through $R^{11}$ positions, up to a maximum of nine such —$Y_nA$ moieties. There are many examples of acidic groups other than carboxyl group, selectable to contain at least one acidic hydrogen atom. Such other acidic groups may be collectively referred to as "bioisosteres of carboxylic acid" or referred to as "acidic bioisosteres". Specific examples of such acidic bioisosteres are described hereinafter. Compounds of Formula I having the —$Y_nA$ moiety attached at one of positions $R^5$, $R^6$, $R^8$ and $R^9$ would be expected to have preferred properties, while attachment at $R^5$ or $R^9$ would be more preferred.

A preferred class of compounds within the sub-class defined by Formula I consists of those compounds wherein m is one; wherein each of $R^1$ through $R^{11}$ is independently selected from alkyl, hydroxyalkyl, halo, haloalkyl, cycloalkyl, cycloalkylalkyl, alkoxy, aralkyl, aryl, aroyl, aryloxy, aryloxyalkyl, aralkoxy, alkoxyalkyl, alkylcarbonyl, alkoxycarbonyl, alkenyl, cycloalkenyl, alkynyl, cycloalkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptothiocarbonyl, mercaptoalkyl, alkoxycarbonyloxy, alkylthio, cycloalkylthio, alkylthiocarbonyl, alkylcarbonylthio, alkylthiocarbonyloxy, alkylthiocarbonylthio, alkylthiothiocarbonyl, alkylthiothiocarbonylthio, arylthio, arylthiocarbonyl, arylcarbonylthio, arylthiocarbonyloxy, arylthiocarbonylthio, arylthiothiocarbonyl, arylthiothiocarbonylthio, aralkylthio, aralkylthiocarbonyl, aralkylcarbonylthio, aralkylthiocarbonyloxy, aralkylthiocarbonylthio, aralkylthiocarbonyl, aralkylthiocarbonylthio, mercapto, alkylsulfinyl, alkylsulfonyl, aralkylsulfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cycloheteroalkyl-containing groups has one or more hetero ring atoms selected from oxygen, sulfur and nitrogen atoms, and wherein each of $R^1$ through $R^{11}$ may be further independently selected from amino and amido radicals of the formula

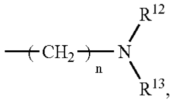
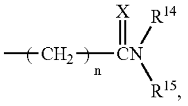
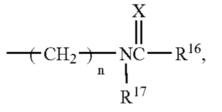
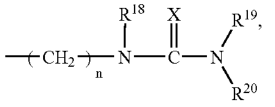
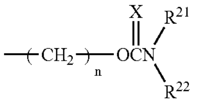
and
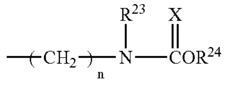

wherein X is selected from oxygen atom or sulfur atom;

wherein each n is a number independently selected from zero to six, inclusive;

wherein each of $R^{12}$ through $R^{24}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;

and wherein each of $R^3$ through $R^{11}$ may be further independently selected from hydroxy and from acidic moieties of the formula $$-Y_nA$$

wherein n is a number selected from zero through three, inclusive; wherein A is an acidic group selected from acids containing one or more atoms selected from oxygen, sulfur, phosphorus and nitrogen atoms, and wherein said acidic group is selected to contain at least one acidic hydrogen atom, and the amide, ester and salt derivatives of said acidic moieties; wherein Y is a spacer group independently selected from one or more of alkyl, cycloalkyl, cycloalkylalkyl, alkenyl, alkynyl, aryl, aralkyl and heteroaryl having one or more ring atoms selected from oxygen, sulfur and nitrogen atoms;

and wherein any of the foregoing $R^1$ through $R^{24}$, Y and A groups having a substitutable position may be substituted with one or more groups selected from alkyl, alkenyl, aralkyl, hydroxyalkyl, trifluoromethyl, difluoroalkyl, alkoxy, aryloxy, aralkoxy, alkoxyalkyl, alkylcarbonyl, alkoxycarbonyl, carboxyl, mercaptocarbonyl, alkylthio, alkylthiocarbonyl, and amino and amido radicals of the formula

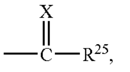
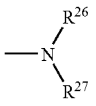
and
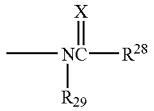

wherein X is selected from oxygen atom and sulfur atom; wherein each of $R^{25}$, $R^{26}$, $R^{27}$, $R^{28}$ and $R^{29}$ is selected from hydrido, alkyl, cycloalkyl, cycloalkylalkyl, aralkyl, aryl, and $DR^{30}$ and

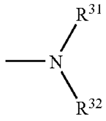

wherein D is selected from oxygen atom and sulfur atom, and $R^{30}$ is selected from hydrido, alkyl, cycloalkyl, cycloalkylalkyl, aralkyl and aryl; wherein each of $R^{25}$, $R^{26}$, $R^{27}$, $R^{28}$, $R^{29}$, $R^{31}$ and $R^{32}$ is independently selected from hydrido, alkyl, cycloalkyl, cyano, hydroxyalkyl, haloalkyl, cycloalkylalkyl, alkoxyalkyl, alkanoyl, alkoxycarbonyl, carboxyl, haloalkylsulfinyl, haloalkylsulfonyl, aralkyl and aryl, and wherein each of $R^{25}$, $R^{26}$, $R^{27}$, $R^{28}$, $R^{29}$, $R^{31}$ and $R^{32}$ is further independently selected from amino and amido radicals of the formula

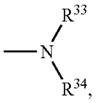
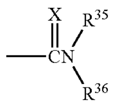
and
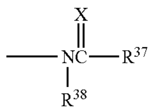

wherein X is selected from oxygen atom or sulfur atom;

wherein each of $R^{33}$ through $R^{38}$ is independently selected from hydrido, alkyl, cycloalkyl, cyano, amino, monoalkylamino, dialkylamino, hydroxyalkyl, cycloalkylalkyl, alkoxyalkyl, haloalkylsulfinyl, haloalkylsulfonyl, aralkyl and aryl;

with the proviso that at least one of said $R^1$ through $R^{24}$, Y and A substituents contains a terminal primary or secondary amino moiety or a moiety convertible to a primary or secondary amino moiety;

or a tautomer thereof or a pharmaceutically-acceptable salt thereof.

A more preferred class of compounds within the sub-class defined by Formula I consists of those compounds wherein m is one; wherein each of $R^1$ through $R^{11}$ is independently selected from alkyl, hydroxyalkyl, halo, haloalkyl, cycloalkyl, cycloalkylalkyl, alkoxy, aralkyl, aryl, aroyl, aryloxy, aryloxyalkyl, aralkoxy, alkoxyalkyl, alkylcarbonyl, alkoxycarbonyl, alkenyl, cycloalkenyl, alkynyl, cycloalkynyl, cyano, nitro, carboxyl, carboxyalkyl, alkylcarbonyloxy, mercaptocarbonyl, alkoxycarbonyloxy, alkylcarbonyloxyalkyl, alkoxycarbonylalkyl, aralkoxycarbonylalkyl, aralkylcarbonyloxyalkyl, alkylthio, cycloalkylthio, arylthio, aralkylthio, aralkylthiocarbonylthio, mercapto, alkylsulfinyl, alkylsulfonyl, aralkylsulfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalklylcarbonylalkyl wherein each of said heteroaryl- and cycloheteroalkyl-containing groups has one or more hetero ring atoms selected from oxygen, sulfur and nitrogen atoms, and wherein each of $R^1$ through $R^{11}$ may be further independently selected from amino and amido radicals of the formula

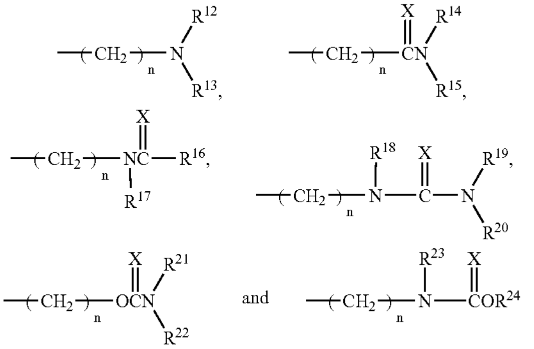

and wherein X is selected from oxygen atom or sulfur atom;

wherein each n is a number independently selected from zero to six, inclusive;

wherein each of $R^{12}$ through $R^{24}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;

and wherein each of $R^3$ through $R^{11}$ may be an further independently selected from hydroxy and from acidic moieties of the formula $-Y_nA$ wherein n is a number selected from zero through three, inclusive;

wherein A is selected from carboxylic acid and bioisosteres of carboxylic acid selected from

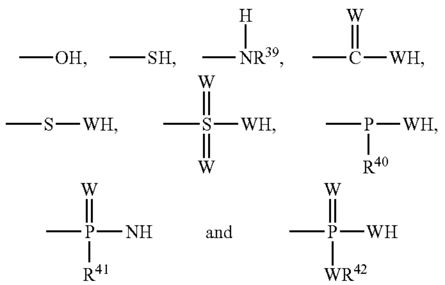

and wherein each W is independently selected from oxygen atom, sulfur atom and $NR^{43}$; wherein each of $R^{39}$, $R^{40}$, $R^{41}$, $R^{42}$ and $R^{43}$ is independently selected from hydrido, alkyl, haloalkyl, haloalkylsulfonyl, haloalkylcarbonyl, cycloalkyl, cycloalkylalkyl, aryl and aralkyl; wherein each of $R^{39}$, $R^{40}$, $R^{41}$ and $R^{42}$ may be further independently selected from amino radical of the formula

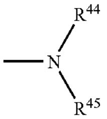

wherein each of $R^{44}$ and $R^{45}$ is independently selected from hydrido, alkyl, cycloalkyl, hydroxyalkyl, haloalkyl, cycloalkylalkyl, alkoxyalkyl, aralkyl and aryl, and wherein $R^{44}$ and $R^{45}$ taken together may form a heterocyclic group having five to seven ring members including the nitrogen atom of said amino radical, which heterocyclic group may further contain one or more hetero atoms as ring members selected from oxygen, nitrogen and sulfur atoms and which heterocyclic group may be saturated or partially unsaturated; wherein $R^{44}$ and $R^{45}$ taken together may form an aromatic heterocyclic group having five ring members including the nitrogen atom of said amino radical and which aromatic heterocyclic group may further contain one or more hetero atoms as ring atoms selected from oxygen, nitrogen and sulfur atoms; wherein each of $R^{44}$ and $R^{45}$ may be further independently selected from hydroxy, alkoxy, alkylthio, aryloxy, arylthio, aralkylthio and aralkoxy; and the amide, ester and salt derivatives of said acidic groups;

wherein said bioisostere of carboxylic acid may be further selected from heterocyclic acidic groups consisting of heterocyclic rings of four to about nine ring members, which heterocyclic ring contains at least one hetero atom selected from oxygen, sulfur and nitrogen atoms, which heterocyclic ring may be saturated, fully unsaturated or partially unsaturated, and which heterocyclic ring may be attached at a single position selected from $R^3$ through $R^{11}$ or may be attached at any two adjacent positions selected from $R^3$ through $R^{11}$ so as to form a fused-ring system with one of the phenyl rings of the biphenyl moiety of Formula I; and the amide, ester and salt derivatives of said heterocyclic acidic groups;

wherein Y is a spacer group independently selected from one or more of alkyl, cycloalkyl, cycloalkylalkyl, alkenyl, aryl and aralkyl;

and wherein any of the foregoing $R^1$ through $R^{24}$, Y and A groups having a substitutable position may be substituted by one or more groups selected from alkyl, difluoroalkyl, alkenyl, aralkyl, hydroxyalkyl, trifluoromethyl, alkoxy, aryloxy, aralkoxy, alkoxyalkyl, alkylcarbonyl, alkoxycarbonyl, carboxyl, mercaptocarbonyl, alkylthio, alkylthiocarbonyl, and amino and amido radicals of the formula

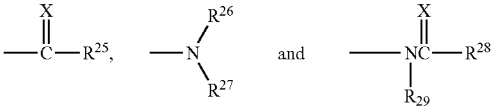

and wherein X is selected from oxygen atom and sulfur atom;

wherein each of $R^{25}$, $R^{26}$, $R^{27}$, $R^{28}$ and $R^{29}$ is selected from hydrido, alkyl, cycloalkyl, cycloalkylalkyl, aralkyl, aryl and $DR^{30}$ and

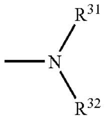

wherein D is selected from oxygen atom and sulfur atom, wherein $R^{30}$ is selected from hydrido, alkyl, cycloalkyl, cycloalkylalkyl, aralkyl and aryl;

wherein each of $R^{25}$, $R^{26}$, $R^{27}$, $R^{28}$, $R^{29}$, $R^{31}$ and $R^{32}$ is independently selected from hydrido, alkyl, cycloalkyl, cyano, hydroxyalkyl, haloalkyl, cycloalkylalkyl, alkoxyalkyl, alkanoyl, alkoxycarbonyl, carboxyl, haloalkylsulfinyl, haloalkylsulfonyl, aralkyl and aryl;

with the proviso that at least one of said $R^1$ through $R^{24}$, Y and A substituents contains a terminal primary or secondary amino moiety or a moiety convertible to a primary or secondary amino moiety;

or a tautomer thereof or a pharmaceutically-acceptable salt thereof.

An even more preferred class of compounds within the sub-class defined by Formula I consists of those compounds wherein m is one; wherein each of $R^1$ and $R^2$ is independently selected from alkyl, hydroxyalkyl, halo, haloalkyl, cycloalkyl, cycloalkylalkyl, alkoxy, aralkyl, aryl, aroyl, aryloxy, aryloxyalkyl, aralkoxy, alkoxyalkyl, alkylcarbonyl, alkoxycarbonyl, alkenyl, cycloalkenyl, alkynyl, cycloalkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptoalkyl, alkoxycarbonyloxy, alkylthio, cycloalkylthio, arylthio, aralkylthio, mercapto, alkylsulfinyl, alkylsulfonyl, aralkylsulfinyl, aralkylsulfonyl, arylsulfinyl, arylsulfonyl, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cycloheteroalkyl-containing groups has one or more hetero ring atoms selected from oxygen, sulfur and nitrogen atoms, and wherein each of $R^1$ through $R^{11}$ may be further independently selected from amino and amido radicals of the formula

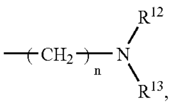

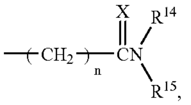

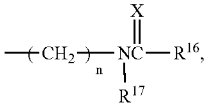

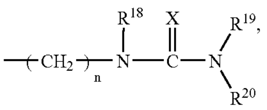

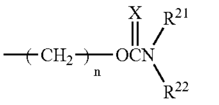

and

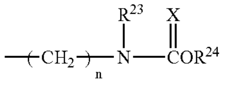

wherein X is selected from oxygen atom and sulfur atom;

wherein each n is a number independently selected from zero to six, inclusive;

wherein each of $R^{12}$ through $R^{24}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;

wherein each of $R^3$ through $R^{11}$ is independently selected from hydrido, hydroxy, alkyl, hydroxyalkyl, halo, haloalkyl, cycloalkyl, cycloalkylalkyl, alkoxy, aralkyl, aryl, aroyl, aryloxy, aralkoxy, alkoxyalkyl, alkylcarbonyl, alkoxycarbonyl, alkenyl, cycloalkenyl, alkynyl, cycloalkynyl, cyano, nitro, carboxyl, alkylthio, aralkylthio, mercapto, alkylsulfinyl, alkylsulfonyl, aralkylsulfinyl, aralkylsulfonyl, arylsulfinyl, arylsulfonyl and heteroaryl having one or more ring atoms selected from oxygen, sulfur and nitrogen atoms;

and wherein each of $R^3$ through $R^{11}$ may be an acidic moiety further independently selected from acidic moieties of the formula $$-Y_nA$$

wherein n is a number selected from zero through three, inclusive; wherein A is selected from carboxylic acid and bioisosteres of carboxylic acid selected from

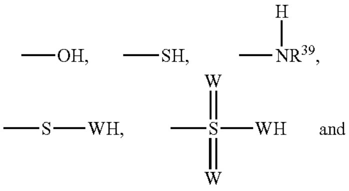

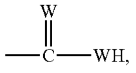

and

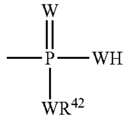

wherein each W is independently selected from oxygen atom, sulfur atom and $NR^{43}$; wherein each of $R^{39}$, $R^{42}$ and $R^{43}$ is independently selected from hydrido, alkyl, haloalkyl, haloalkylsulfonyl, haloalkylcarbonyl, cycloalkyl, cycloalkylalkyl, aryl and aralkyl; wherein each of $R^{39}$ and $R^{42}$ may be further independently selected from amino radical of the formula

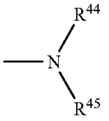

wherein each of $R^{44}$ and $R^{45}$ is independently selected from hydrido, alkyl, cycloalkyl, hydroxyalkyl, haloalkyl, cycloalkylalkyl, alkoxyalkyl, aralkyl and aryl, and wherein $R^{44}$ and $R^{45}$ taken together may form a heterocyclic group having five to seven ring members including the nitrogen atom of said amino radical, which heterocyclic group may further contain one or more hetero atoms as ring members selected from oxygen, nitrogen and sulfur atoms, and which heterocyclic group may be saturated or partially unsaturated; wherein $R^{44}$ and $R^{45}$ taken together may form an aromatic heterocyclic group having five ring members including the nitrogen atom of said amino radical and which aromatic heterocyclic group may further contain one or more hetero atoms as ring atoms selected from oxygen, nitrogen and sulfur atoms; and the amide, ester and salt derivatives of said acidic groups; wherein said bioisostere of carboxylic acid may be further selected from heterocyclic acidic groups consisting of heterocyclic rings of four to about nine ring members, which ring contains at least one hetero atom, selected from oxygen, sulfur and nitrogen atoms, which heterocyclic ring may be saturated, fully unsaturated or partially unsaturated, and which heterocyclic ring may be attached at a single position selected from $R^3$ through $R^{11}$ or may be attached at any two adjacent positions selected from $R^3$ through $R^{11}$ so as to form a fused-ring system with one of the phenyl rings of Formula I; and the amide, ester and salt derivatives of said heterocyclic acidic groups;

wherein Y is a spacer group independently selected from one or more of alkyl, cycloalkyl, cycloalkylalkyl, alkenyl, aryl and aralkyl;

wherein each of $R^1$ through $R^{11}$, Y and A independently may be substituted at any substitutable position with one or more groups selected from alkyl, cycloalkyl, cycloalkylalkyl, hydroxy, oxo, trifluoromethyl, difluoroalkyl, alkoxycarbonyl, cyano, nitro, alkylsulfonyl, haloalkylsulfonyl, aryl, aralkyl, alkoxy, aryloxy and aralkoxy;

with the proviso that at least one of said $R^1$ through $R^{24}$, Y and A substituents contains a terminal primary or secondary amino moiety or a moiety convertible to a primary or secondary amino moiety;

or a tautomer thereof or a pharmaceutically-acceptable salt thereof.

A highly preferred class of compounds within the subclass defined by Formula I consists of those compounds wherein m is one; wherein each of $R^1$ and $R^2$ is independently selected from alkyl, hydroxyalkyl, halo, haloalkyl, cycloalkyl, cycloalkylalkyl, alkoxy, aralkyl, aryl, benzoyl, phenoxy, phenoxyalkyl, phenalkyloxy, phenylthio, phenalkylthio, aralkoxy, alkoxyalkyl, alkylcarbonyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptoalkyl, alkoxycarbonyloxy, alkylthio, cycloalkylthio, phthalimido, phthalimidoalkyl, heteroaryl, heteroarylalkyl, cycloheteroalkyl, cycloheteroalkylalkyl and cycloheteroalkylcarbonylalkyl wherein each of said heteroaryl- and cycloheteroalkyl-containing groups has one or more hetero ring atoms selected from oxygen, sulfur and nitrogen atoms, and wherein each of $R^1$ through $R^{11}$ may be further independently selected from amino and amido radicals of the formula

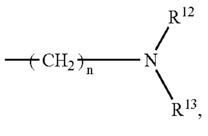

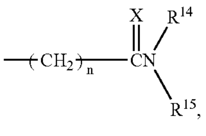

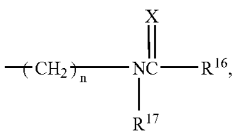

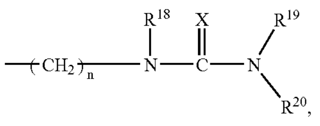

-continued

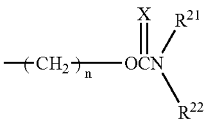

and

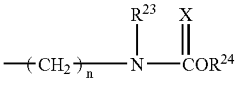

wherein X is selected from oxygen atom and sulfur atom;

wherein each n is a number independently selected from zero to six, inclusive;

wherein each of $R^{12}$ through $R^{24}$ is independently selected from hydrido, alkyl, cycloalkyl, cyano, amino, hydroxyalkyl, alkoxyalkyl, phenalkyl and phenyl;

wherein each of $R^3$ through $R^{11}$ is independently selected from hydrido, hydroxy, alkyl, hydroxyalkyl, halo, haloalkyl, cycloalkyl, cycloalkylalkyl, alkoxy, phenalkyl, phenyl, benzoyl, phenoxy, phenalkyloxy, alkoxyalkyl, alkylcarbonyl, alkoxycarbonyl, alkenyl, cyano, nitro, carboxyl, alkylthio, mercapto and heteroaryl having one or more ring atoms selected from oxygen, sulfur and nitrogen atoms;

and wherein each of $R^3$ through $R^{11}$ may be an acidic moiety further independently selected from acidic moieties of the formula $$—Y_nA$$

wherein n is a number selected from zero through two, inclusive; wherein A is selected from carboxylic acid and bioisosteres of carboxylic acid selected from

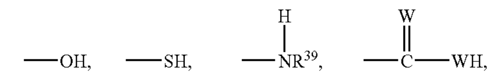

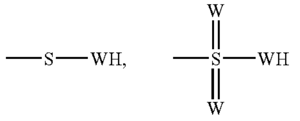

and

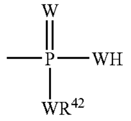

wherein each W is independently selected from oxygen atom, sulfur atom and $NR^{43}$; wherein each of $R^{39}$, $R^{42}$ and $R^{43}$ is independently selected from hydrido, alkyl, haloalkyl, haloalkylsulfonyl, haloalkylcarbonyl, cycloalkyl, phenyl and benzyl; wherein each of $R^{39}$ and $R^{42}$ may be further independently selected from amino radical of the formula

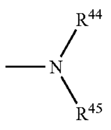

wherein each of $R^{44}$ and $R^{45}$ is independently selected from hydrido, alkyl, cycloalkyl, hydroxyalkyl, haloalkyl, alkoxyalkyl, benzyl and phenyl; and the amide, ester and salt derivatives of said acidic groups;

wherein said bioisostere of carboxylic acid may be further selected from heterocyclic acidic groups consisting of heterocyclic rings of four to about nine ring members, which ring contains at least one hetero atom, selected from oxygen, sulfur and nitrogen atoms, which heterocyclic ring may be saturated, fully unsaturated or partially unsaturated, and which heterocyclic ring may be attached at a single position selected from $R^3$ through $R^{11}$ or may be attached at any two adjacent positions selected from $R^3$ through $R^{11}$ so as to form a fused-ring system with one of the phenyl rings of the biphenyl moiety of Formula I; and the amide, ester and salt derivatives of said heterocyclic acidic groups;

wherein Y is a spacer group independently selected from one or more of alkyl, cycloalkyl, cycloalkylalkyl, alkenyl, phenyl, phenalkyl and aralkyl;

wherein each of $R^1$ through $R^{11}$, Y and A and independently may be substituted at any substitutable position with one or more groups selected from alkyl, cycloalkyl, cycloalkylalkyl, hydroxy, oxo, trifluoromethyl, difluoroalkyl, alkoxycarbonyl, cyano, nitro, alkylsulfonyl, haloalkylsulfonyl, aryl, aralkyl, alkoxy, aryloxy and aralkoxy;

with the proviso that at least one of said $R^1$ through $R^{24}$, Y and A substituents contains a terminal primary or secondary amino moiety or a moiety convertible to a primary or secondary amino moiety;

or a tautomer thereof or a pharmaceutically-acceptable salt thereof.

An even more highly preferred class of compounds within Formula I consists of those compounds wherein m is one; wherein each of $R^1$ and $R^2$ is independently selected from alkyl, aminoalkyl, hydroxyalkyl, halo, haloalkyl, cycloalkyl, cycloalkylalkyl, alkoxy, aralkyl, aryl, benzoyl, phenoxy, phenoxyalkyl, phenalkyloxy, phenylthio, phenalkylthio, aralkoxy, alkoxyalkyl, acetyl, alkoxycarbonyl, alkenyl, cycloalkenyl, alkynyl, cyano, nitro, carboxyl, carboxyalkyl, alkylcarbonyloxy, mercaptoalkyl, mercaptocarbonyl, alkoxycarbonyloxy, alkylcarbonyloxyalkyl, alkoxycarbonylalkyl, aralkoxycarbonylalkyl, aralkylcarbonyloxyalkyl, phthalimido, phthalimidoalkyl, imidazoalkyl, tetrazole, tetrazolealkyl, alkylthio, cycloalkylthio, and amino and amido radicals of the formula

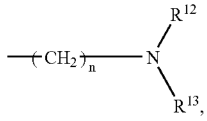

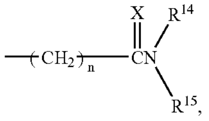

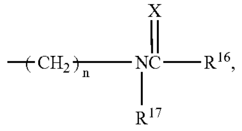

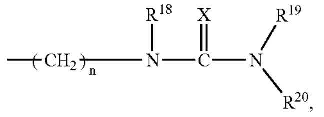

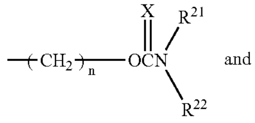 and 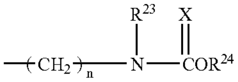

wherein X is selected from oxygen atom and sulfur atom;

wherein each n is a number independently selected from zero to six, inclusive;

wherein each of $R^{12}$ through $R^{24}$ is independently selected from hydrido, alkyl, cycloalkyl, cyano, amino, hydroxyalkyl, alkoxyalkyl, phenalkyl and phenyl;

wherein each of $R^3$ through $R^{11}$ is independently selected from hydrido, hydroxy, alkyl, hydroxyalkyl, halo, haloalkyl, cycloalkyl, cycloalkylalkyl, alkoxy, phenalkyl, phenyl, benzoyl, phenoxy, phenalkyloxy, alkoxyalkyl, acetyl, alkoxycarbonyl, alkenyl, cyano, nitro, carboxyl, alkylthio and mercapto;

and wherein each of $R^3$ through $R^{11}$ may be an acidic moiety further independently selected from acidic moieties consisting of $CO_2H$, $CO_2CH_3$, SH, $CH_2SH$, $C_2H_4SH$, $PO_3H_2$, $NHSO_2CF_3$, $NHSO_2C_6F_5$, $SO_3H$, $CONHNH_2$, $CONHNHSO_2CF_3$, $CONHOCH_3$, $CONHOC_2H_5$, $CONHCF_3$, OH, $CH_2OH$, $C_2H_4OH$, $OPO_3H_2$, $OSO_3H$,

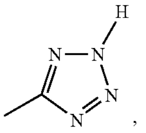, 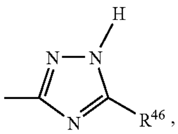, 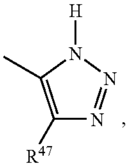,

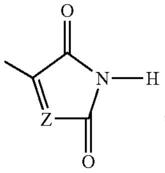, 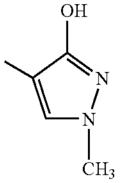, 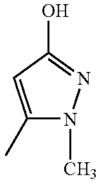,

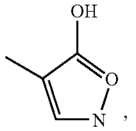, 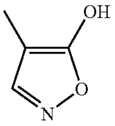, 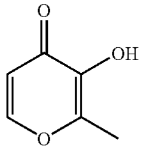,

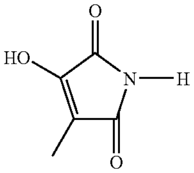, 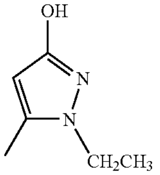,

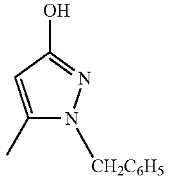 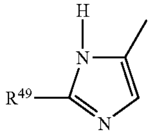,

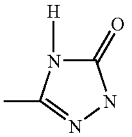 and 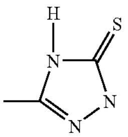

wherein each of $R^{46}$, $R^{47}$ and $R^{48}$ is independently selected from H, Cl, CN, $NO_2$, $CF_3$, $C_2F_5$, $C_3F_7$, $CHF_2$, $CH_2F$, $CO_2CH_3$, $CO_2C_2H_5$, $SO_2CH_3$, $SO_2CF_3$ and $SO_2C_6F_5$; wherein Z is selected from O, S, $NR^{49}$ and $CH_2$; wherein $R^{49}$ is selected from hydrido, $CH_3$ and $CH_2C_6H_5$; and wherein said acidic moiety may be a heterocyclic acidic group attached at any two adjacent positions of $R^3$ through $R^{11}$ so as to form a fused ring system so as to include one of the phenyl rings of the biphenyl moiety of Formula I, said biphenyl fused ring system selected from

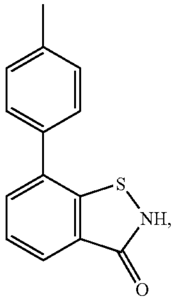
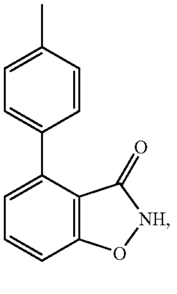
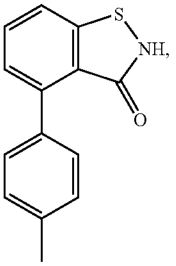
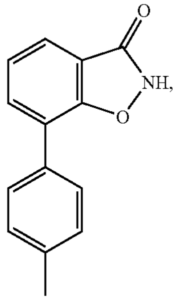
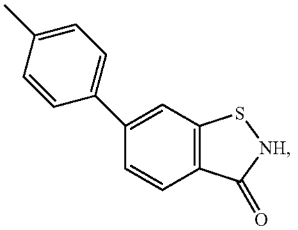
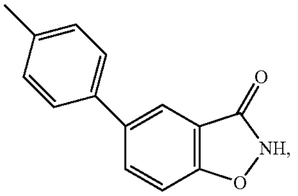
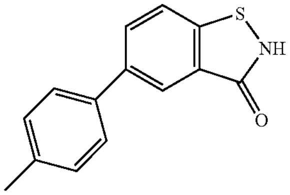
and
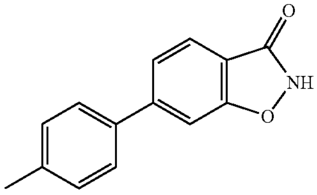

and the esters, amides and salts of said acidic moieties;

with the proviso that at least one of said $R^1$ through $R^{24}$ substituents contains a terminal primary or secondary amino moiety or a moiety convertible to a primary or secondary amino moiety;

or a tautomer thereof or a pharmaceutically-acceptable salt thereof.

A class of compounds of particular interest within the sub-class defined by Formula I consists of those compounds wherein m is one; wherein each of $R^1$ and $R^2$ is independently selected from amino, aminomethyl, aminoethyl, aminopropyl, $CH_2OH$, $CH_2OCOCH_3$, $CH_2Cl$, Cl, $CH_2OCH_3$, $CH_2OCH(CH_3)_2$, I, CHO, $CH_2CO_2H$, $CH(CH_3)CO_2H$, $NO_2$, Cl,

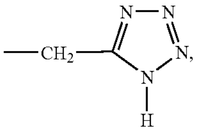
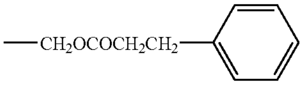

$-CO_2CH_3$, $-CONH_2$, $-CONHCH_3$, $CON(CH_3)_2$, $-CH_2-NHCO_2C_2H_5$,

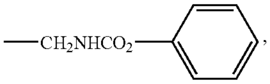

$-CH_2NHCO_2CH_3$, $-CH_2NHCO_2C_3H_7$, $-CH_2NHCO_2CH_2(CH_3)_2$, $-CH_2NHCO_2C_4H_9$, $CH_2NHCO_2$-adamantyl, $-CH_2NHCO_2$-(1-napthyl), $-CH_2NHCONHCH_3$, $-CH_2NHCONHC_2H_5$, $-CH_2NHCONHC_3H_7$, $-CH_2NHCONHC_4H_9$, $-CH_2NHCONHCH(CH_3)_2$, $-CH_2NHCONH$(1-napthyl), $-CH_2NHCONH$(1-adamantyl), $CO_2H$,

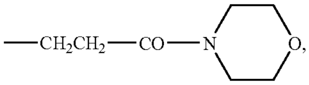
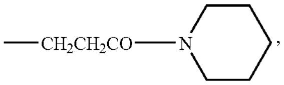

$-CH_2CH_2CH_2CO_2H$, $-CH_2CH_2F$, $-CH_2OCONHCH_3$, $-CH_2OCSNHCH_3$, $-CH_2NHCSOC_3H_7$, $-CH_2CH_2CH_2F$, $-CH_2ONO_2$,

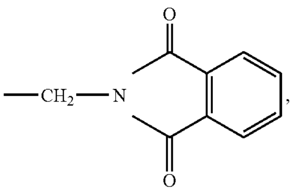
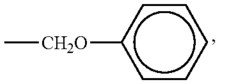

$-CH_2SH$,

H, Cl, $NO_2$, $CF_3$, $CH_2OH$, Br, F, I, methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, 1-oxoethyl, 1-oxopropyl, 1-oxobutyl, 1-oxopentyl, 1,1-dimethoxypropyl, 1,1-dimethoxybutyl, 1,1-dimethoxypentyl, hydroxyalkyl, halo, difluoromethyl, 1,1-difluoroethyl, 1,1-difluoropropyl, 1,1-difluorobutyl and 1,1-difluoropentyl; wherein each of $R^3$ through $^{11}$ is hydrido, with the proviso that at least one of $R^5$, $R^6$, $R^8$ and $R^9$ is an acidic group selected from $CO_2H$, SH, $PO_3H_2$, $SO_3H$, $CONHNH_2$, $CONHNHSO_2CF_3$, OH,

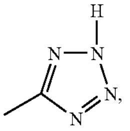 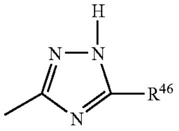 and

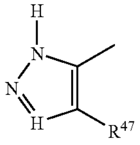

wherein each of $R^{46}$ and $R^{47}$ is independently selected from Cl, CN, $NO_2$, $CF_3$, $CO_2CH_3$ and $SO_2CF_3$;

with the proviso that at least one of said $R^1$ through $R^{11}$ substituents contains a terminal primary or secondary amino moiety or a moiety convertible to a primary or secondary amino moiety;

or a tautomer thereof or a pharmaceutically-acceptable salt thereof.

A class of compounds of more particular interest within the sub-class defined by Formula I consists of those compounds wherein m is one; wherein $R^1$ is selected from amino, aminomethyl, aminoethyl, aminopropyl, methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, 1-oxoethyl, 1-oxopropyl, 1-oxobutyl, 1-oxopentyl, 1,1-dimethoxypropyl, 1,1-dimethoxybutyl, 1,1-dimethoxypentyl, hydroxyalkyl, halo, difluoromethyl, 1,1-difluoroethyl, 1,1-difluoropropyl, 1,1-difluorobutyl and 1,1-difluoropentyl; wherein $R^2$ is selected from ethyl, n-propyl, isopropyl, n-butyl, sec-butyl, isobutyl, 4-methylbutyl, tert-butyl, n-pentyl and neopentyl; wherein each of $R^3$, $R^4$, $R^6$, $R^7$, $R^8$, $R^{10}$, and $R^{11}$ is hydrido; wherein one of $R^5$ and $R^9$ is hydrido and the other of $R^5$ and $R^9$ is an acidic group selected from $CO_2H$, SH, $PO_3H_2$, $SO_3H$, $CONHNH_2$, $CONHNHSO_2CF_3$, OH,

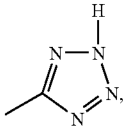 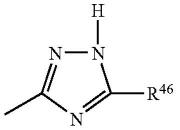 and 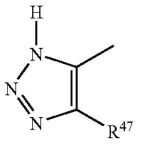

wherein each of $R^{46}$ and $R^{47}$ is independently selected from Cl, CN, $NO_2$, $CF_3$, $CO_2CH_3$ and $SO_2CF_3$;

with the proviso that at least one of said $R^1$ through $R^{11}$ substituents contains a terminal primary or secondary amino moiety or a moiety convertible to a primary or secondary amino moiety;

or a tautomer thereof or a pharmaceutically-acceptable salt thereof.

The second component of a conjugate of the invention is provided by a residue which forms a kidney-enzyme-cleavable amide bond with the residue of the first-component AII antagonist compound. Such residue is preferably selected from a class of compounds of Formula II:

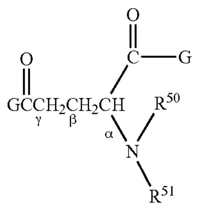

(II)

wherein each of $R^{50}$ and $R^{51}$ may be independently selected from hydrido, alkylcarbonyl, alkoxycarbonyl, alkoxyalkyl, hydroxyalkyl and haloalkyl; and wherein G is selected from hydroxyl, halo, mercapto, —$OR^{52}$, —$SR^{53}$ and

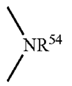

with each of $R^{52}$, $R^{53}$ and $R^{54}$ independently selected from alkyl; and wherein $R^{54}$ may be further selected from hydrido; with the proviso that said cleavable bond is within an amide group formed between said first and second residues, wherein said first residue has a terminal primary or second amino moiety provided by one of said $R^1$ through $R^{11}$ substituents of said Formula I compound or provided by a linker group attached to one of said $R^1$–$R^{11}$ substituents of said Formula I, and wherein said second residue has a carbonyl moiety attached at the gamma-position carbon of said Formula II compound, whereby said amide bond is formed from said first residue amino moiety and said second residue carbonyl moiety.

More preferred are compounds of Formula II wherein each G is hydroxy.

A more highly preferred class of compounds within Formula II consists of those compounds wherein each G is hydroxy; wherein $R^{50}$ is hydrido; and wherein $R^{51}$ is selected from

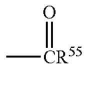

wherein $R^{55}$ is selected from methyl, ethyl, n-propyl, isopropyl, n-butyl, sec-butyl, iso-butyl, tert-butyl, n-pentyl, neopentyl, n-hexyl and chloromethyl.

A most highly preferred compound of Formula II is N-acetyl-γ-glutamic acid which provides a residue for the second component of a conjugate of the invention as shown below:

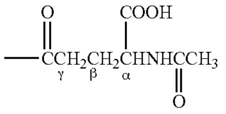

The phrase "terminal primary or secondary amino moiety or a moiety convertible to a primary or secondary amino terminal moiety" characterizes a structural requirement for selection of a suitable angiotensin II antagonist compound as the "active" first residue of a conjugate of the invention. Such terminal amino moiety must be available to react with a terminal carboxylic moiety of the cleavable second residue to form a kidney-enzyme-specific hydrolyzable bond.

In one embodiment of the invention, the first component used to form a conjugate of the invention provides a first residue derived from an AII antagonist compound containing a terminal primary or secondary amino moiety. Examples of such terminal amino moiety are amino and linear or branched aminoalkyl moieties containing linear or branched alkyl groups such as aminomethyl, aminoethyl, aminopropyl, aminoisopropyl, aminobutyl, aminosecbutyl, aminoisobutyl, aminotertbutyl, aminopentyl, aminoisopentyl and aminoneopentyl.

In another embodiment of the invention, the first component used to form the conjugate of the invention provides a first residue derived from an AII antagonist compound containing a moiety convertible to a primary or secondary amino terminal moiety. An example of a moiety convertible to an amino terminal moiety is a carboxylic acid group reacted with hydrazine so as to convert the acid moiety to carboxylic acid hydrazide. The hydrazide moiety thus contains the terminal amino moiety which may then be further reacted with the carboxylic acid containing residue of the second component to form a hydrolyzable amide bond. Such hydrazide moiety thus constitutes a "linker" group between the first and second components of a conjugate of the invention.

Suitable linker groups may be provided by a class of diamino-terminated linker groups based on hydrazine as defined by Formula III:

(III)

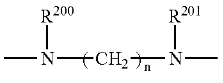

wherein each of $R^{200}$ and $R^{201}$ may be independently selected from hydrido, alkyl, cycloalkyl, cycloalkylalkyl, alkoxyalkyl, hydroxyalkyl, aralkyl, aryl, haloalkyl, amino, monoalkylamino, dialkylamino, cyanoamino, carboxyalkyl, alkylsulfino, alkylsulfonyl, arylsulfinyl and arylsulfonyl; and wherein n is zero or a number selected from three through seven, inclusive. In Table I there is shown a class of specific examples of diamino-terminated linker groups within Formula III, identified as Linker Nos. 1–73. These linker groups would be suitable to form a conjugate between a carbonyl moiety of an AII antagonist (designated as "I") and a carbonyl moiety of a carbonyl terminated second residue such as the carbonyl moiety attached to the gamma carbon of a glutamyl residue (designated as "T").

TABLE I

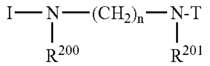

I = inhibitor
T = acetyl-γ-glutamyl

| LINKER NO. | n | $R^{200}$ | $R^{201}$ |
|---|---|---|---|
| 1 | 0 | H | H |
| 2 | 0 | $CH_3$ | H |
| 3 | 0 | $C_2H_5$ | H |
| 4 | 0 | $C_3H_7$ | H |
| 5 | 0 | $CH(CH_3)_2$ | H |
| 6 | 0 | $C_4H_9$ | H |
| 7 | 0 | $CH(CH_3)CH_2CH_3$ | H |
| 8 | 0 | $C(CH_3)_3$ | H |
| 9 | 0 | $C_5H_9$ | H |
| 10 | 0 | $C_6H_{11}$(cyclo) | H |
| 11 | 0 | $C_6H_5$ | H |
| 12 | 0 | $CH_2C_6H_5$ | H |
| 13 | 0 | H | $CH_3$ |
| 14 | 0 | H | $C_2H_5$ |
| 15 | 0 | H | $C_3H_7$ |
| 16 | 0 | H | $CH(CH_3)_2$ |
| 17 | 0 | H | $C_4H_9$ |
| 18 | 0 | H | $CH(CH_3)CH_2CH_3$ |
| 19 | 0 | H | $C(CH_3)_3$ |
| 20 | 0 | H | $C_5H_9$ |
| 21 | 0 | H | $C_6H_{13}$ |
| 22 | 0 | H | $C_6H_5$ |
| 23 | 0 | H | $CH_2C_6H_5$ |
| 24 | 0 | H | $C_6H_{11}$(cyclo) |
| 25 | 0 | $C_6H_{13}$ | H |
| 26 | 0 | $CH_3$ | $CH_3$ |
| 27 | 0 | $C_2H_5$ | $C_2H_5$ |
| 28 | 0 | $C_3H_7$ | $C_3H_7$ |
| 29 | 0 | $CH(CH_3)_2$ | $CH(CH_3)_2$ |
| 30 | 0 | $C_4H_9$ | $C_4H_9$ |
| 31 | 0 | $CH(CH_3)CH_2CH_3$ | $CH(CH_3)CH_2CH_3$ |
| 32 | 0 | $C(CH_3)_3$ | $C(CH_3)_3$ |
| 33 | 0 | $C_5H_9$ | $C_5H_9$ |
| 34 | 0 | $C_6H_{13}$ | $C_6H_{13}$ |
| 35 | 0 | $C_6H_{11}$(cyclo) | $C_6H_{11}$(cyclo) |
| 36 | 0 | $C_6H_5$ | $C_6H_5$ |
| 37 | 0 | $CH_2C_6H_5$ | $CH_2C_6H_5$ |
| 38 | 3 | H | H |
| 39 | 3 | $CH_3$ | H |
| 40 | 3 | H | $CH_3$ |
| 41 | 3 | $C_6H_5$ | H |
| 42 | 3 | H | $C_6H_5$ |
| 43 | 3 | $CH_3$ | $C_6H_5$ |
| 44 | 3 | $C_6H_5$ | $CH_3$ |
| 45 | 3 | $CH_2C_6H_5$ | H |
| 46 | 3 | H | $CH_2C_6H_5$ |
| 47 | 4 | H | H |
| 48 | 4 | $CH_3$ | H |
| 49 | 4 | H | $CH_3$ |
| 50 | 4 | $C_6H_5$ | H |
| 51 | 4 | H | $C_6H_5$ |
| 52 | 4 | $CH_3$ | $C_6H_5$ |
| 53 | 4 | $C_6H_5$ | $CH_3$ |
| 54 | 4 | $CH_2C_6H_5$ | H |
| 55 | 4 | H | $CH_2C_6H_5$ |
| 56 | 5 | H | H |
| 57 | 5 | $CH_3$ | H |
| 58 | 5 | H | $CH_3$ |
| 59 | 5 | $C_6H_5$ | H |
| 60 | 5 | H | $C_6H_5$ |
| 61 | 5 | $CH_3$ | $C_6H_5$ |
| 62 | 5 | $C_6H_5$ | $CH_3$ |
| 63 | 5 | $CH_2C_6H_5$ | H |
| 64 | 5 | H | $CH_2C_6H_5$ |
| 65 | 6 | H | H |
| 66 | 6 | $CH_3$ | H |
| 67 | 6 | H | $CH_3$ |
| 68 | 6 | $C_6H_5$ | H |

TABLE I-continued

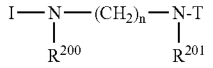

I = inhibitor
T = acetyl-γ-glutamyl

| LINKER NO. | n | $R^{200}$ | $R^{201}$ |
|---|---|---|---|
| 69 | 6 | H | $C_6H_5$ |
| 70 | 6 | $CH_3$ | $C_6H_5$ |
| 71 | 6 | $C_6H_5$ | $CH_3$ |
| 72 | 6 | $CH_2C_6H_5$ | H |
| 73 | 6 | H | $CH_2C_6H_5$ |

Another class of suitable diamino terminal linker groups is defined by Formula IV:

(IV)

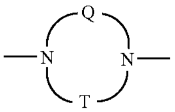

wherein each of Q and T is one or more groups independently selected from

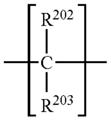
and
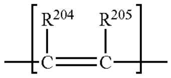

wherein each of $R^{202}$ through $R^{205}$ is independently selected from hydrido, hydroxy, alkyl, cycloalkyl, cycloalkylalkyl, aralkyl, aryl, alkoxy, aralkoxy, aryloxy, alkoxyalkyl, haloalkyl, hydroxyalkyl, halo, cyano, amino, monoalkylamino, dialkylamino, carboxy, carboxyalkyl, alkanoyl, alkenyl, cycloalkenyl and alkynyl.

A preferred class of linker groups within Formula IV is defined by Formula V:

(V)

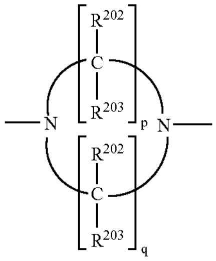

wherein each of $R^{202}$ and $R^{203}$ is independently selected from hydrido, hydroxy, alkyl, phenalkyl, phenyl, alkoxy, benzyloxy, phenoxy, alkoxyalkyl, hydroxyalkyl, halo, amino, monoalkylamino, dialkylamino, carboxy, carboxyalkyl and alkanoyl; and wherein each of p and q is a number independently selected from one through six, inclusive; with the proviso that when each of $R^{202}$ and $R^{203}$ is selected from halo, hydroxy, amino, monoalkylamino and dialkylamino, then the carbon to which $R^{202}$ or $R^{203}$ is attached in Formula V is not adjacent to a nitrogen atom of Formula V.

A more preferred class of linker groups of Formula V consists of divalent radicals wherein each of $R^{202}$ and $R^{203}$ is independently selected from hydrido, hydroxy, alkyl, alkoxy, amino, monoalkylamino, carboxy, carboxyalkyl and alkanoyl; and wherein each of p and q is a number independently selected from two through four, inclusive. Even more preferred are linker groups wherein each of $R^{202}$ and $R^{203}$ is independently selected from hydrido, amino, monoalkylamino and carboxyl; and wherein each of p and q is independently selected from the numbers two and three. Most preferred is a linker group wherein each of $R^{202}$ and $R^{203}$ is hydrido; and wherein each of p and q is two; such most preferred linker group is derived from a piperazinyl group and has the structure

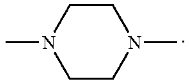

In Table II there is shown a class of specific examples of cyclized, diamino-terminated linker groups within Formula V. These linker groups, identified as Linker Nos. 74–95, would be suitable to form a conjugate between a carbonyl moiety of an AII antagonist (designated as "I") and a carbonyl moiety of carbonyl terminated second residue such as the carbonyl moiety attached to the gamma carbon of a glutamyl residue (designated as "T").

TABLE II

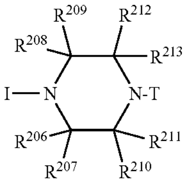

I = inhibitor
T = acetyl-γ-glutamyl

| LINKER NO. | $R^{206}$ | $R^{207}$ | $R^{208}$ | $R^{209}$ | $R^{210}$ | $R^{211}$ | $R^{212}$ | $R^{213}$ |
|---|---|---|---|---|---|---|---|---|
| 74 | H | H | H | H | H | H | H | H |
| 75 | $CH_3$ | H | H | H | H | H | H | H |

TABLE II-continued

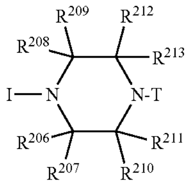

I = inhibitor
T = acetyl-γ-glutamyl

| LINKER NO. | $R^{206}$ | $R^{207}$ | $R^{208}$ | $R^{209}$ | $R^{210}$ | $R^{211}$ | $R^{212}$ | $R^{213}$ |
|---|---|---|---|---|---|---|---|---|
| 76 | H | H | H | H | $CH_3$ | H | H | H |
| 77 | $CH_3$ | H | H | H | $CH_3$ | H | H | H |
| 78 | $CH_3$ | H | $CH_3$ | H | H | H | H | H |
| 79 | $CH_3$ | H | H | H | H | H | $CH_3$ | H |
| 80 | $CH_3$ | $CH_3$ | H | H | H | H | H | H |
| 81 | H | H | H | H | $CH_3$ | $CH_3$ | H | H |
| 82 | $CH_3$ | $CH_3$ | H | H | $CH_3$ | $CH_3$ | H | H |
| 83 | $CH_3$ | $CH_3$ | $CH_3$ | $CH_3$ | H | H | H | H |
| 84 | $CH_3$ | $CH_3$ | H | H | H | H | $CH_3$ | $CH_3$ |
| 85 | H | H | H | H | $CH_3$ | $CH_3$ | $CH_3$ | $CH_3$ |
| 86 | $C_6H_5$ | H | H | H | H | H | H | H |
| 87 | H | H | H | H | $C_6H_5$ | H | H | H |
| 88 | $C_6H_5$ | H | H | H | $C_6H_5$ | H | H | H |
| 89 | $C_6H_5$ | H | H | H | H | H | $C_6H_{5H}$ | |
| 90 | $C_6H_5$ | H | $C_6H_5$ | H | H | H | H | H |
| 91 | $CH_2C_6H_5$ | H | H | H | H | H | H | H |
| 92 | H | H | H | H | $CH_2C_6H_5$ | H | H | H |
| 93 | $CH_2C_6H_5$ | H | H | H | $C_2C_6H_5$ | H | H | H |
| 94 | $CH_2C_6H_5$ | H | H | H | H | H | $CH_2C_6H_5$ | H |
| 95 | $CH_2C_6H_5$ | H | $CH_2C_6H_5$ | H | H | H | H | H |

Another class of suitable diamino terminal linker groups is defined by Formula VI:

(VI)

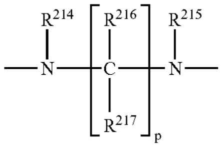

wherein each of $R^{214}$ through $R^{217}$ is independently selected from hydrido, alkyl, cycloalkyl, cycloalkylalkyl, hydroxyalkyl, alkoxyalkyl, aralkyl, aryl, haloalkyl, amino, monoalkylamino, dialkylamino, cyanoamino, carboxyalkyl, alkylsulfino, alkylsulfonyl, arylsulfinyl and arylsulfonyl; and wherein p is a number selected from one through six inclusive.

A preferred class of linker groups within Formula VI consists of divalent radicals wherein each of $R^{214}$ and $R^{215}$ is hydrido; wherein each of $R^{62}$ and $R^{63}$ is independently selected from hydrido, alkyl, phenalkyl, phenyl, alkoxyalkyl, hydroxyalkyl, haloalkyl and carboxyalkyl; and wherein p is two or three. A more preferred class of linker groups within Formula VI consists of divalent radicals wherein each of $R^{214}$ and $R^{215}$ is hydrido; wherein each of $R^{216}$ and $R^{217}$ is independently selected from hydrido and alkyl; and wherein p is two. A specific example of a more preferred linker within Formula VI is the divalent radical ethylenediamino. In Table III there is shown a class of specific examples of diamino-terminated linker groups within Formula VI. These linker groups, identified as Linker Nos. 96–134, would be suitable to form a conjugate between a carbonyl moiety of an AII antagonist (designated as "I") and a carbonyl moiety of carbonyl terminated second residue such as the carbonyl moiety attached to the gamma carbon of a glutamyl residue (designated as "T").

TABLE III

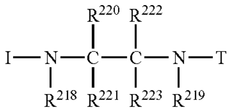

I = inhibitor
G = acetyl-γ- glutamyl

| LINKER NO. | $R^{218}$ | $R^{219}$ | $R^{220}$ | $R^{221}$ | $R^{222}$ | $R^{223}$ |
|---|---|---|---|---|---|---|
| 96 | H | H | H | H | H | H |
| 97 | H | H | H | H | H | $CH_3$ |

TABLE III-continued

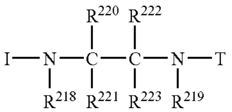

I = inhibitor

G = acetyl-γ- glutamyl

| LINKER NO. | $R^{218}$ | $R^{219}$ | $R^{220}$ | $R^{221}$ | $R^{222}$ | $R^{223}$ |
|---|---|---|---|---|---|---|
| 98 | H | H | H | $CH_3$ | H | H |
| 99 | H | H | H | $CH_3$ | H | $CH_3$ |
| 100 | $CH_3$ | H | H | H | H | H |
| 101 | H | $CH_3$ | H | H | H | H |
| 102 | H | H | H | H | $CH_3$ | $CH_3$ |
| 103 | H | H | $CH_3$ | $CH_3$ | H | H |
| 104 | $CH_3$ | $CH_3$ | H | H | H | H |
| 105 | H | H | H | H | H | $C_6H_5$ |
| 106 | H | H | H | $C_6H_5$ | H | H |
| 107 | H | H | H | $C_6H_5$ | H | $C_6H_5$ |
| 108 | $C_6H_5$ | H | H | H | H | H |
| 109 | H | $C_6H_5$ | H | H | H | H |
| 110 | H | H | H | H | $C_6H_5$ | $C_6H_5$ |
| 111 | H | H | $C_6H_5$ | $C_6H_5$ | H | H |
| 112 | $C_6H_5$ | $C_6H_5$ | H | H | H | H |
| 113 | H | H | H | H | H | $C_2H_5$ |
| 114 | H | H | H | $C_2H_5$ | H | H |
| 115 | H | H | H | $C_2H_5$ | H | $C_2H_5$ |
| 116 | $C_2H_5$ | H | H | H | H | H |
| 117 | H | $C_2H_5$ | H | H | H | H |
| 118 | H | H | H | H | $C_2H_5$ | $C_2H_5$ |
| 119 | H | H | $C_2H_5$ | $C_2H_5$ | H | H |
| 120 | $C_2H_5$ | $C_2H_5$ | H | H | H | H |
| 121 | $CH_3$ | H | $C_6H_5$ | H | H | H |
| 122 | $CH_3$ | H | H | H | $C_6H_5$ | H |
| 123 | H | $CH_3$ | $C_6H_5$ | H | H | H |
| 124 | H | $CH_3$ | H | H | $C_6H_5$ | H |
| 125 | $CH_3$ | $CH_3$ | H | $C_6H_5$ | H | H |
| 126 | $CH_3$ | $CH_3$ | H | H | H | $C_6H_5$ |
| 127 | H | H | H | H | H | $CH_2C_6H_5$ |
| 128 | H | H | H | $CH_2C_6H_5$ | H | H |
| 129 | $CH_2C_6H_5$ | H | H | H | H | H |
| 130 | H | $CH_2C_6H_5$ | H | H | H | H |
| 131 | $CH_3$ | H | $CH_2C_6H_5$ | H | H | H |
| 132 | $CH_3$ | H | H | H | $CH_2C_6H_5$ | H |
| 133 | H | $CH_3$ | $CH_2C_6H_5$ | H | H | H |
| 134 | H | $CH_3$ | H | H | $CH_2C_6H_5$ | H |

The term “hydrido” denotes a single hydrogen atom (H). This hydrido group may be attached, for example, to a carbon atom to form a

group or attached to an oxygen atom to form a hydroxyl group; or as another example, two hydrido groups may be attached to a carbon atom to form a $—CH_2—$ group. Where the term “alkyl” is used, either alone or within other terms such as “haloalkyl” and “hydroxyalkyl”, the term “alkyl” embraces linear or branched radicals having one to about twenty carbon atoms or, preferably, one to about twelve carbon atoms. More preferred alkyl radicals are “lower alkyl” radicals having one to about ten carbon atoms. Most preferred are lower alkyl radicals having one to about five carbon atoms. The term “cycloalkyl” embraces cyclic radicals having three to about ten ring carbon atoms, preferably three to about six carbon atoms, such as cyclopropyl and cyclobutyl. The term “haloalkyl” embraces radicals wherein any one or more of the alkyl carbon atoms is substituted with one or more halo groups, preferably selected from bromo, chloro and fluoro. Specifically embraced by the term “haloalkyl” are monohaloalkyl, dihaloalkyl and polyhaloalkyl groups. A monohaloalkyl group, for example, may have either a bromo, a chloro, or a fluoro atom within the group. Dihaloalkyl and polyhaloalkyl groups may be substituted with two or more of the same halo groups, or may have a combination of different halo groups. A dihaloalkyl group, for example, may have two fluoro atoms, such as difluoromethyl and difluorobutyl groups, or two chloro atoms, such as a dichloromethyl group, or one fluoro atom and one chloro atom, such as a fluoro-chloromethyl group. Examples of a polyhaloalkyl are trifluoromethyl, 1,1-difluoroethyl, 2,2,2-trifluoroethyl, perfluoroethyl and 2,2,3,3-tetrafluoropropyl groups. The term “difluoroalkyl” embraces alkyl groups having two fluoro atoms substituted on any one or two of the alkyl group carbon atoms. Preferably, when the difluoroalkyl group is attached at the triazole ring $R^1$ and $R^2$ positions of Formula I, the two fluoro atoms are substituted on the carbon atom which is attached directly to the triazole ring. Such preferred difluoroalkyl group may be characterized as an "alpha-carbon difluoro-substituted difluoroalkyl group" The terms "alkylol" and "hydroxyalkyl" embrace linear or branched alkyl groups having one to about ten carbon atoms any one of which may be substituted with one or more hydroxyl groups. The term "alkenyl" embraces linear or branched radicals having two to about twenty carbon atoms, preferably three to about ten carbon atoms, and containing at least one carbon-carbon double bond, which carbon-carbon double bond may have either cis or trans geometry within the alkenyl moiety. The term "alkynyl" embraces linear or branched radicals having two to about twenty carbon atoms, preferably-two to about ten carbon atoms, and containing at least one carbon-carbon triple bond. The term "cycloalkenyl" embraces cyclic radicals having three to about ten ring carbon atoms including one or more double bonds involving adjacent ring carbons. The terms "alkoxy" and "alkoxyalkyl" embrace linear or branched oxy-containing radicals each having alkyl portions of one to about ten carbon atoms, such as methoxy group. The term "alkoxyalkyl" also embraces alkyl radicals having two or more alkoxy groups attached to the alkyl radical, that is, to form monoalkoxyalkyl and dialkoxyalkyl groups. The "alkoxy" or "alkoxyalkyl" radicals may be further substituted with one or more halo atoms, such as fluoro, chloro or bromo, to provide haloalkoxy or haloalkoxyalkyl groups. The term "alkylthio" embraces radicals containing a linear or branched alkyl group, of one to about ten carbon atoms attached to a divalent sulfur atom, such as a methythio group. The term "aryl" embraces aromatic radicals such as phenyl, naphthyl and biphenyl. Preferred aryl groups are those consisting of one, two, or three benzene rings. The term "aralkyl" embraces aryl-substituted alkyl radicals such as benzyl, diphenylmethyl, triphenylmethyl, phenylethyl, phenylbutyl and diphenylethyl. The terms "benzyl" and "phenylmethyl" are interchangeable. The terms "aryloxy" and "arylthio" denote radical respectively, aryl groups having an oxygen or sulfur atom through which the radical is attached to a nucleus, examples of which are phenoxy and phenylthio. The terms "sulfinyl" and "sulfonyl", whether used alone or linked to other terms, denotes respectively divalent radicals SO and $SO_2$. The term "aralkoxy", alone or within another term, embraces an aryl group attached to an alkoxy group to form, for example, benzyloxy. The term "acyl" whether used alone, or within a term such as acyloxy, denotes a radical provided by the residue after removal of hydroxyl from an organic acid, examples of such radical being acetyl and benzoyl. The term "heteroaryl" embraces aromatic ring systems containing one or two hetero atoms selected from oxygen, nitrogen and sulfur in a ring system having five or six ring members, examples of which are thienyl, furanyl, pyridinyl, thiazolyl, pyrimidyl and isoxazolyl. Such heteroaryl may be attached as a substituent through a carbon atom of the heteroaryl ring system, or may be attached through a carbon atom of a moiety substituted on a heteroaryl ring-member carbon atom, for example, through the methylene substituent of imidazolemethyl moiety. Also, such heteroaryl may be attached through a ring nitrogen atom as long-as aromaticity of the heteroaryl moiety is preserved after attachment. The term "amido" denotes a radical consisting of a nitrogen atom attached to a carbonyl group, which radical may be further substituted in the manner described herein. The amido radical can be attached to the nucleus of a compound of the invention through the carbonyl moiety or the nitrogen atom of the amido radical. The term "alkenylalkyl" denotes a radical having a double-bond unsaturation site between two carbons, and which radical may consist of only two carbons or may be further substituted with alkyl groups which may optionally contain additional double-bond unsaturation. For any of the foregoing defined radicals, preferred radicals are those containing between one and about ten carbon atoms.

Specific examples of alkyl groups are methyl, ethyl, n-propyl, isopropyl, n-butyl, sec-butyl, isobutyl, tert-butyl, n-pentyl, isopentyl, methylbutyl, dimethylbutyl and neopentyl. Typical alkenyl and alkynyl groups may have one unsaturated bond, such as an allyl group, or may have a plurality or unsaturated bonds, with such plurality of bonds either adjacent, such as allene-type structures, or in conjugation, or separated by several saturated carbons.

Conjugates of the invention formed from compounds of Formula I have been found to inhibit the action of angiotensin II in mammals. Thus, conjugates of Formula I are therapeutically useful in methods for treating hypertension by administering to a hypertensive patient a therapeutically-effective amount of a conjugate containing a compound of Formula I, such that the conjugate is hydrolyzed by an enzyme found predominantly in the kidney so as to release an active angiotensin II antagonist species. The phrase "hypertensive patient" means, in this context, a mammalian subject suffering from the effects of hypertension or susceptible to a hypertensive condition if not treated to prevent or control such hypertension.

Included within the invention are conjugates of compounds of Formula I which are tautomeric forms of the described compounds, isomeric forms including diastereoisomers, and the pharmaceutically-acceptable salts thereof. The term "pharmaceutically-acceptable salts" embraces salts commonly used to form alkali metal salts and to form addition salts of free acids or free bases. The nature of the salt is not critical, provided that it is pharmaceutically-acceptable. Suitable pharmaceutically-acceptable acid addition salts of compounds of Formula I may be prepared from an inorganic acid or from an organic acid. Examples of such inorganic acids are hydrochloric, hydrobromic, hydroiodic, nitric, carbonic, sulfuric and phosphoric acid. Appropriate organic acids may be selected from aliphatic, cycloaliphatic, aromatic, araliphatic, heterocyclic, carboxylic and sulfonic classes of organic acids, example of which are formic, acetic, propionic, succinic, glycolic, gluconic, lactic, malic, tartaric, citric, ascorbic, glucuronic, maleic, fumaric, pyruvic, aspartic, glutamic, benzoic, anthranilic, p-hydroxybenzoic, salicyclic, phenylacetic, mandelic, embonic (pamoic), methansulfonic, ethanesulfonic, 2-hydroxyethanesulfonic, pantothenic, benzenesulfonic, toluenesulfonic, sulfanilic, mesylic, cyclohexylaminosulfonic, stearic, algenic, β-hydroxybutyric, malonic, galactaric and galacturonic acid. Suitable pharmaceutically-acceptable base addition salts of compounds of Formula I include metallic salts made from aluminium, calcium, lithium, magnesium, potassium, sodium and zinc or organic salts made from N,N'-dibenzylethylenediamine, chloroprocaine, choline, diethanolamine, ethylenediamine, meglumine (N-methylglucamine) and procaine. All of these salts may be prepared by conventional means from the corresponding compound of Formula I by reacting, for example, the appropriate acid or base with the compound of Formula I. Also, such pharmaceutical salts may be formed with either a compound of Formula I which is contained in the conjugate, or such salts may be formed with the conjugate itself.

Conjugates of the invention can possess one or more asymmetric carbon atoms and are thus capable of existing in the form of optical isomers as well as in the form of racemic or non-racemic mixtures thereof. The optical isomers can be obtained by resolution of the racemic mixtures according to conventional processes, for example by formation of diastereoisomeric salts by treatment with an optically active acid or base. Examples of appropriate acids are tartaric, diacetyltartaric, dibenzoyltartaric, ditoluoyltartaric and camphorsulfonic acid and then separation of the mixture of diastereoisomers by crystallization followed by liberation of the optically active bases from these salts. A different process for separation of optical isomers involves the use of a chiral chromatography column optimally chosen to maximize the separation of the enantiomers. Still another available method involves synthesis of covalent diastereoisomeric molecules by reacting conjugates with an optically pure acid in an activated form or an optically pure isocyanate. The synthesized diastereoisomers can be separated by conventional means such as chromatography, distillation, crystallization or sublimation, and then hydrolyzed to deliver the enantiomerically pure compound. The optically active conjugates can likewise be obtained by utilizing optically active starting materials. These isomers may be in the form of a free acid, a free base, an ester or a salt.

The first and second residues are provided by precursor compounds having suitable chemical moieties which react together to form a cleavable bond between the first and second residues. For example, the precursor compound of one of the residues will have a reactable carboxylic acid moiety and the precursor of the other residue will have a reactable amino moiety or a moiety convertible to a reactable amino moiety, so that a cleavable amide bond may be formed between the carboxylic acid moiety and the amino moiety.

Conjugates of the invention may be prepared using precursors of highly active angiotensin II antagonists of Formula I. Examples of lesser active, suitable precursors are acid chloride, esters and amides' of angiotensin II antagonists of Formula I. For example, ester precursors of angiotensin II antagonists may be reacted with hydrazine to provide an amino terminal moiety which then can be reacted with a glutamic acid derivative to form a conjugate of the invention. Such precursors or intermediates themselves may be relatively strong, relatively weak, or inactive as AII antagonists. Also, conjugates of the invention may be prepared using angiotensin II antagonists lacking a reactive terminal amino moiety. Such angiotensin II antagonists may be modified to contain a terminal acid moiety which then may be connected to a glutamyl residue through a diamino-terminated linker group, such as shown in Tables I–III.

A family of specific angiotensin II antagonist compounds of Formula I, from which a suitable first component of the conjugate may be selected, consists of biphenylmethyl 1H-substituted-1,2,4-triazole compounds listed below having a carboxylic acid terminal moiety or carboxylic acid moiety modified to be a hydrazide terminal moiety. All such compounds are characterized in having such carboxylic acid at one of the $R^5$ through $R^9$ positions of Formula I. Those compounds having a terminal carboxylic moiety may be reacted with one of the aforementioned linker groups, such as a hydrazine or a piperazine linker, to provide an amino terminal moiety which can then be reacted with the carboxylic acid moiety of a second component of the conjugate, such as a glutamic acid residue to form an enzyme-cleavable bond. Specific examples of these compounds are listed below:

4'-[(3,5-dibutyl-1H-1,2,4-triazol-1-yl)methyl][1,1'-biphenyl]-2-carboxylic acid, hydrazide;

4'-[(5-butyl-3-chloro-1H-1,2,4-triazol-1-yl)methyl][1,1'-biphenyl]-2-carboxylic acid;

4'-[(3-butyl-5-chloro-1H-1,2,4-triazol-1-yl)methyl][1,1'-biphenyl]-2-carboxylic acid;

4'-[(5-butyl-3-ethyl-1H-1,2,4-triazol-1-yl)methyl][1,1'-biphenyl]-2-carboxylic acid;

4'-[(5-butyl-3-propyl-1H-1,2,4-triazol-1-yl)methyl][1,1'-biphenyl]-2-carboxylic acid;

4'-[(5-butyl-3-isopropyl-1H-1,2,4-triazol-1-yl)methyl][1,1'-biphenyl]-2-carboxylic acid;

methyl 4'-[(3,5-dibutyl-1H-1,2,4-triazol-1-yl)methyl][1,1'-biphenyl]-2-carboxylate;

4'-[(3,5-dibutyl-1H-1,2,4-triazol-1-yl)methyl][1,1'-biphenyl]-2-carboxylic acid;

4'-[(5-butyl-3-secbutyl-1H-1,2,4-triazol-1-yl)methyl][1,1'-biphenyl]-2-carboxylic acid;

4'-[(5-butyl-3-isobutyl-1H-1,2,4-triazol-1-yl)methyl][1,1'-biphenyl]-2-carboxylic acid;

4'-[(5-butyl-3-tertbutyl-1H-1,2,4-triazol-1-yl)methyl][1,1'-biphenyl]-2-carboxylic acid;

4'-[(5-butyl-3-pentyl-1H-1,2,4-triazol-1-yl)methyl][1,1'-biphenyl]-2-carboxylic acid;

4'-[(5-butyl-3-isopentyl-1H-1,2,4-triazol-1-yl)methyl][1,1'-biphenyl]-2-carboxylic acid;

4'-[(5-butyl-3-mercapto-1H-1,2,4-triazol-1-yl)methyl][1,1'-biphenyl]-2-carboxylic acid;

4'-[(5-butyl-3-thiomethyl-1H-1,2,4-triazol-1-yl)methyl][1,1'-biphenyl]-2-carboxylic acid;

4'-[(5-butyl-3-thioethyl-1H-1,2,4-triazol-1-yl)methyl][1,1'-biphenyl]-2-carboxylic acid;

4'-[(5-butyl-3-thiopropyl-1H-1,2,4-triazol-1-yl)methyl][1,1'-biphenyl]-2-carboxylic acid;

4'-[(5-butyl-3-hydroxy-1H-1,2,4-triazol-1-yl)methyl][1,1'-biphenyl]-2-carboxylic acid;

4'-[(5-butyl-3-methoxy-1H-1,2,4-triazol-1-yl)methyl][1,1'-biphenyl]-2-carboxylic acid;

4'-[(5-butyl-3-ethoxy-1H-1,2,4-triazol-1-yl)methyl][1,1'-biphenyl]-2-carboxylic acid;

4'-[(5-butyl-3-propoxy-1H-1,2,4-triazol-1-yl)methyl][1,1'-biphenyl]-2-carboxylic acid;

4'-[(5-butyl-3-butoxy-1H-1,2,4-triazol-1-yl)methyl][1,1'-biphenyl]-2-carboxylic acid;

4'-[(5-butyl-3-cyclohexyl-1H-1,2,4-triazol-1-yl)methyl][1,1'-biphenyl]-2-carboxylic acid;

4'-[(5-butyl-3-cyclohexylmethyl-1H-1,2,4-triazol-1-yl)methyl][1,1'-biphenyl]-2-carboxylic acid;

4'-[[5-butyl-3-(2-cyclohexylethyl))-1H-1,2,4-triazol-1-yl]methyl][1,1'-biphenyl]-2-carboxylic acid;

4'-[(5-butyl-3-cyclohexanoyl-1,2,4,-triazol-1-yl)methyl][1,1'-biphenyl]-2-carboxylic acid;

4'-[[5-butyl-3-(1-oxo-2-cyclohexylethyl)-1H-1,2,4-triazol-1-yl]methyl][1,1'-biphenyl]-2-carboxylic acid;

4'-[(5-butyl-3-phenyl-1,2,4,-triazol-1-yl)methyl][1,1'-biphenyl]-2-carboxylic acid;

4'-[(5-butyl-3-phenylmethyl-1,2,4,-triazol-1-yl)methyl][1,1'-biphenyl]-2-carboxylic acid;

4'-[(5-butyl-1,2,4,-triazol-1-yl)methyl][1,1'-biphenyl)-2-carboxylic acid;

4'-[(3-butyl-1,2,4,-triazol-1-yl)methyl][1,1'-biphenyl]-2-carboxylic acid;

4'-[[5-butyl-3-(2-phenylethyl)-1H-1,2,4-triazol-1-yl]methyl][1,1'-biphenyl]-2-carboxylic acid;

4'-[(5-butyl-3-benzoyl-1,2,4,-triazol-1-yl)methyl][1,1'-biphenyl]-2-carboxylic acid;

4'-[[5-butyl-3-(1-oxo-2-phenylethyl)-1H-1,2,4-triazol-1-yl]methyl][1,1'-biphenyl]-2-carboxylic acid;

4'-[[5-butyl-3-(1,1-dimethoxypropyl)-1H-1,2,4-triazol-1-yl]methyl][1,1'-biphenyl]-2-carboxylic acid;

4'-[[5-butyl-3-(1,1-dimethoxybutyl)-1H-1,2,4-triazol-1-yl]methyl][1,1'-biphenyl]-2-carboxylic acid;

4'-[[5-butyl-3-(1,1-dimethoxypentyl)-1H-1,2,4-triazol-1-yl]methyl](1,1'-biphenyl]-2-carboxylic acid;

4'-[[5-butyl-3-(1-oxopropyl)-1H-1,2,4-triazol-1-yl]methyl][1,1'-biphenyl]-2-carboxylic acid;

4'-[[5-butyl-3-(1-oxobutyl)-1H-1,2,4-triazol-1-yl]methyl][1,1'-biphenyl]-2-carboxylic acid;

4'-[[5-butyl-3-(1-oxopentyl)-1H-1,2,4-triazol-1-yl]methyl][1,1'-biphenyl]-2-carboxylic acid;

4'-[[5-butyl-3-(1,1-difluoroethyl)-1H-1,2,4-triazol-1-yl]methyl][1,1'-biphenyl]-2-carboxylic acid;

4'-[[5-butyl-3-(1,1-difluoropropyl)-1H-1,2,4-triazol-1-yl]methyl][1,1'-biphenyl]-2-carboxylic acid;

4'-[[5-butyl-3-(1,1-difluorobutyl)-1H-1,2,4-triazol-1-yl]methyl][1,1'-biphenyl]-2-carboxylic acid;

4'-[[3-butyl-5-(1,1-difluorobutyl)-1H-1,2,4-triazol-1-yl]methyl][1,1'-biphenyl]-2-carboxylic acid;

4'-[[5-butyl-3-(1,1-difluoropentyl)-1H-1,2,4-triazol-1-yl]methyl][1,1'-biphenyl]-2-carboxylic acid;

4'-[(5-propyl-3-ethyl-1H-1,2,4-triazol-1-yl)methyl][1,1'-biphenyl]-2-carboxylic acid;

4'-[(3,5-dipropyl-1H-1,2,4-triazol-1-yl)methyl][1,1'-biphenyl]-2-carboxylic acid;

4'-[(3,5-isopropyl-1H-1,2,4-triazol-1-yl)methyl][1,1'-biphenyl]-2-carboxylic acid;

4'-[(5-propyl-3-isopropyl-1H-1,2,4-triazol-1-yl)methyl][1,1'-biphenyl]-2-carboxylic acid;

4'-[(5-propyl-3-butyl-1H-1,2,4-triazol-1-yl)methyl][1,1'-biphenyl]-2-carboxylic acid;

4'-[(5-propyl-3-secbutyl-1H-1,2,4-triazol-1-yl)methyl][1,1'-biphenyl]-2-carboxylic acid;

4'-[(5-propyl-3-isobutyl-1H-1,2,4-triazol-1-yl)methyl][1,1'-biphenyl]-2-carboxylic acid;

4'-[(5-propyl-3-tertbutyl-1H-1,2,4-triazol-1-yl)methyl][1,1'-biphenyl]-2-carboxylic acid;

4'-[(5-propyl-3-pentyl-1H-1,2,4-triazol-1-yl)methyl][1,1'-biphenyl]-2-carboxylic acid;

4'-[(5-propyl-3-isopentyl-1H-1,2,4-triazol-1-yl)methyl][1,1'-biphenyl]-2-carboxylic acid;

4'-[(5-propyl-3-mercapto-1H-1,2,4-triazol-1-yl)methyl][1,1'-biphenyl]-2-carboxylic acid;

4'-[(5-propyl-3-thiomethyl-1H-1,2,4-triazol-1-yl)methyl][1,1'-biphenyl]-2-carboxylic acid;

4'-[(5-propyl-3-thioethyl-1H-1,2,4-triazol-1-yl)methyl][1,1'-biphenyl]-2-carboxylic acid;

4'-[(5-propyl-3-thiopropyl-1H-1,2,4-triazol-1-yl)methyl][1,1'-biphenyl]-2-carboxylic acid;

4'-[(5-propyl-3-hydroxy-1H-1,2,4-triazol-1-yl)methyl][1,1'-biphenyl]-2-carboxylic acid;

4'-[(5-propyl-3-methoxy-1H-1,2,4-triazol-1-yl)methyl][1,1'-biphenyl]-2-carboxylic acid;

4'-[(5-propyl-3-ethoxy-1H-1,2,4-triazol-1-yl)methyl][1,1'-biphenyl]-2-carboxylic acid;

4'-[(5-propyl-3-propoxy-1H-1,2,4-triazol-1-yl)methyl][1,1'-biphenyl]-2-carboxylic acid;

4'-[(5-propyl-3-cyclohexyl-1H-1,2,4-triazol-1-yl)methyl][1,1'-biphenyl]-2-carboxylic acid;

4'-[(5-propyl-3-cyclohexylmethyl-1H-1,2,4-triazol-1-yl)methyl][1,1'-biphenyl]-2-carboxylic acid;

5-[4'-[[5-propyl-3-(2-cyclohexylethyl)-1H-1,2,4-triazol-1-yl]methyl][1,1'-biphenyl]-2-carboxylic acid;

4'-[(5-propyl-3-cyclohexanoyl-1H-1,2,4-triazol-1-yl)methyl][1,1'-biphenyl]-2-carboxylic acid;

5-[4'-[[5-propyl-3-(1-oxo-2-cyclohexylethyl)-1H-1,2,4-triazol-1-yl]methyl][1,1'-biphenyl]-2-carboxylic acid;

4'-[(5-propyl-3-phenyl-1H-1,2,4-triazol-1-yl)methyl][1,1'-biphenyl]-2-carboxylic acid;

4'-[(5-propyl-3-phenylmethyl-1H-1,2,4-triazol-1-yl)methyl][1,1'-biphenyl]-2-carboxylic acid;

4'-[[5-propyl-3-(2-phenylethyl)-1H-1,2,4-triazol-1-yl]methyl][1,1'-biphenyl]-2-carboxylic acid;

4'-[(5-propyl-3-benzoyl-1H-1,2,4-triazol-1-yl)methyl][1,1'-biphenyl]-2-carboxylic acid;

4'-[[5-propyl-3-(1-oxo-2-phenylethyl)-1H-1,2,4-triazol-1-yl]methyl][1,1'-biphenyl]-2-carboxylic acid;

4'-[[5-propyl-3-(1,1-dimethoxypropyl)-1H-1,2,4-triazol-1-yl]methyl][1,1'-biphenyl]-2-carboxylic acid;

4'-[[5-propyl-3-(1,1-dimethoxybutyl)-1H-1,2,4-triazol-1-yl]methyl][1,1'-biphenyl]-2-carboxylic acid;

4'-[[5-propyl-3-(1,1-dimethoxypentyl)-1H-1,2,4-triazol-1-yl]methyl][1,1'-biphenyl]-2-carboxylic acid;

4'-[[5-propyl-3-(1-oxopropyl)-1H-1,2,4-triazol-1-yl]methyl][1,1'-biphenyl]-2-carboxylic acid;

4'-[[5-propyl-3-(1-oxobutyl)-1H-1,2,4-triazol-1-yl]methyl][1,1'-biphenyl]-2-carboxylic acid;

4'-[[5-propyl-3-(1-oxopentyl)-1H-1,2,4-triazol-1-yl]methyl][1,1'-biphenyl]-2-carboxylic acid;

4'-[[5-propyl-3-(1,1-difluoroethyl)-1H-1,2,4-triazol-1-yl]methyl][1,1'-biphenyl]-2-carboxylic acid;

4'-[[3,5-bis(heptafluoropropyl)-1H-1,2,4-triazol-1-yl]methyl][1,1'-biphenyl]-2-carboxylic acid;

4'-[[5-propyl-3-(1,1-difluoropropyl)-1H-1,2,4-triazol-1-yl]methyl][1,1'-biphenyl]-2-carboxylic acid;

4'-[[5-propyl-3-(1,1-difluorobutyl)-1H-1,2,4-triazol-1-yl]methyl][1,1'-biphenyl]-2-carboxylic acid;

4'-[[5-propyl-3-(1,1-difluoropentyl)-1H-1,2,4-triazol-1-yl]methyl][1,1'-biphenyl]-2-carboxylic acid;

4'-[(3,5-diethyl-1H-1,2,4-triazol-1-yl)methyl][1,1'-biphenyl]-2-carboxylic acid;

4'-[(5-ethyl-3-propyl-1H-1,2,4-triazol-1-yl)methyl][1,1'-biphenyl]-2-carboxylic acid;

4'-[(5-ethyl-3-isopropyl-1H-1,2,4-triazol-1-yl)methyl][1,1'-biphenyl]-2-carboxylic acid;

4'-[(5-ethyl-3-butyl-1H-1,2,4-triazol-1-yl)methyl][1,1'-biphenyl]-2-carboxylic acid;

4'-[(5-ethyl-3-secbutyl-1H-1,2,4-triazol-1-yl)methyl][1,1'-biphenyl]-2-carboxylic acid;

4'-[(5-ethyl-3-isobutyl-1H-1,2,4-triazol-1-yl)methyl][1,1'-biphenyl]-2-carboxylic acid;

4'-[(5-ethyl-3-tertbutyl-1H-1,2,4-triazol-1-yl)methyl][1,1'-biphenyl]-2-carboxylic acid;

4'-[(5-ethyl-3-pentyl-1H-1,2,4-triazol-1-yl)methyl][1,1'-biphenyl]-2-carboxylic acid;

4'-[(5-ethyl-3-isopentyl-1H-1,2,4-triazol-1-yl)methyl][1,1'-biphenyl]-2-carboxylic acid;

4'-[(5-ethyl-3-mercapto-1H-1,2,4-triazol-1-yl)methyl][1,1'-biphenyl]-2-carboxylic acid;

4'-[(5-ethyl-3-thiomethyl-1H-1,2,4-triazol-1-yl)methyl][1,1'-biphenyl]-2-carboxylic acid;

4'-[(5-ethyl-3-thioethyl-1H-1,2,4-triazol-1-yl)methyl][1,1'-biphenyl]-2-carboxylic acid;

4'-[(5-ethyl-3-thiopropyl-1H-1,2,4-triazol-1-yl)methyl][1,1'-biphenyl]-2-carboxylic acid;

4'-[(5-ethyl-3-hydroxy-1H-1,2,4-triazol-1-yl)methyl][1,1'-biphenyl]-2-carboxylic acid;

4'-[(5-ethyl-3-methoxy-1H-1,2,4-triazol-1-yl)methyl][1,1'-biphenyl]-2-carboxylic acid;

4'-[(5-ethyl-3-ethoxy-1H-1,2,4-triazol-1-yl)methyl][1,1'-biphenyl]-2-carboxylic acid;

4'-[(5-ethyl-3-propoxy-1H-1,2,4-triazol-1-yl)methyl][1,1'-biphenyl]-2-carboxylic acid;

4'-[(5-ethyl-3-cyclohexyl-1H-1,2,4-triazol-1-yl)methyl][1,1'-biphenyl]-2-carboxylic acid;

4'-[(5-ethyl-3-cyclohexylmethyl-1H-1,2,4-triazol-1-yl)methyl][1,1'-biphenyl]-2-carboxylic acid;

4'-[[5-ethyl-3-(2-cyclohexylethyl)-1H-1,2,4-triazol-1-yl]methyl][1,1'-biphenyl]-2-carboxylic acid;

4'-[(5-ethyl-3-cyclohexanoyl-1H-1,2,4-triazol-1-yl)methyl][1,1'-biphenyl]-2-carboxylic acid;

4'-[[5-ethyl-3-(1-oxo-2-cyclohexylethyl)-1H-1,2,4-triazol-1-yl]methyl][1,1'-biphenyl]-2-carboxylic acid;

4'-[(5-ethyl-3-phenyl-1H-1,2,4-triazol-1-yl)methyl][1,1'-biphenyl]-2-carboxylic acid;

4'-[(5-ethyl-3-phenylmethyl-1H-1,2,4-triazol-1-yl)methyl][1,1'-biphenyl]-2-carboxylic acid;

4'-[[5-ethyl-3-(2-phenylethyl)-1H-1,2,4-triazol-1-yl]methyl][1,1'-biphenyl]-2-carboxylic acid;

4'-[(5-ethyl-3-benzoyl-1H-1,2,4-triazol-1-yl)methyl][1,1'-biphenyl]-2-carboxylic acid;

4'-[[5-ethyl-3-(1-oxo-2-phenylethyl)-1H-1,2,4-triazol-1-yl]methyl][1,1'-biphenyl]-2-carboxylic acid;

4'-[[5-ethyl-3-(1,1-dimethoxypropyl)-1H-1,2,4-triazol-1-yl]methyl][1,1'-biphenyl]-2-carboxylic acid;

4'-[[5-ethyl-3-(1,1-dimethoxybutyl)-1H-1,2,4-triazol-1-yl]methyl][1,1'-biphenyl]-2-carboxylic acid;

4'-[[5-ethyl-3-(1,1-dimethoxypentyl)-1H-1,2,4-triazol-1-yl]methyl][1,1'-biphenyl]-2-carboxylic acid;

4'-[[5-ethyl-3-(1-oxopropyl)-1H-1,2,4-triazol-1-yl]methyl][1,1'-biphenyl]-2-carboxylic acid;

4'-[[5-ethyl-3-(1-oxobutyl)-1H-1,2,4-triazol-1-yl]methyl][1,1'-biphenyl]-2-carboxylic acid;

4'-[[5-ethyl-3-(1-oxopentyl)-1H-1,2,4-triazol-1-yl]methyl][1,1'-biphenyl]-2-carboxylic acid;

4'-[[5-ethyl-3-(1,1-difluoroethyl)-1H-1,2,4-triazol-1-yl]methyl][1,1'-biphenyl]-2-carboxylic acid;

4'-[[5-ethyl-3-(1,1-difluoropropyl)-1H-1,2,4-triazol-1-yl]methyl][1,1'-biphenyl]-2-carboxylic acid;

4'-[[5-ethyl-3-(1,1-difluorobutyl)-1H-1,2,4-triazol-1-yl]methyl][1,1'-biphenyl]-2-carboxylic acid;

4'-[[5-ethyl-3-(1,1-difluoropentyl)-1H-1,2,4-triazol-1-yl]methyl][1,1'-biphenyl]-2-carboxylic acid;

4'-[(5-secbutyl-3-ethyl-1H-1,2,4-triazol-1-yl)methyl][1,1'-biphenyl]-2-carboxylic acid;

4'-[(5-secbutyl-3-propyl-1H-1,2,4-triazol-1-yl)methyl][1,1'-biphenyl]-2-carboxylic acid;

4'-[(5-secbutyl-3-isopropyl-1H-1,2,4-triazol-1-yl)methyl][1,1'-biphenyl]-2-carboxylic acid;

4'-[(5-secbutyl-3-butyl-1H-1,2,4-triazol-1-yl)methyl][1,1'-biphenyl]-2-carboxylic acid;

4'-[(3,5-disecbutyl-1H-1,2,4-triazol-1-yl)methyl][1,1'-biphenyl]-2-carboxylic acid;

4'-[(5-secbutyl-3-isobutyl-1H-1,2,4-triazol-1-yl)methyl][1,1'-biphenyl]-2-carboxylic acid;

4'-[(5-secbutyl-3-tertbutyl-1H-1,2,4-triazol-1-yl)methyl][1,1'-biphenyl]-2-carboxylic acid;

4'-[(5-secbutyl-3-pentyl-1H-1,2,4-triazol-1-yl)methyl][1,1'-biphenyl]-2-carboxylic acid;

4'-[(5-secbutyl-3-isopentyl-1H-1,2,4-triazol-1-yl)methyl][1,1'-biphenyl]-2-carboxylic acid;

4'-[(5-secbutyl-3-mercapto-1H-1,2,4-triazol-1-yl)methyl][1,1'-biphenyl]-2-carboxylic acid;

4'-[(5-secbutyl-3-thiomethyl-1H-1,2,4-triazol-1-yl)methyl][1,1'-biphenyl]-2-carboxylic acid;

4'-[(5-secbutyl-3-thioethyl-1H-1,2,4-triazol-1-yl)methyl][1,1'-biphenyl]-2-carboxylic acid;

4'-[(5-secbutyl-3-thiopropyl-1H-1,2,4-triazol-1-yl)methyl][1,1'-biphenyl]-2-carboxylic acid;

4'-[(5-secbutyl-3-hydroxy-1H-1,2,4-triazol-1-yl)methyl][1,1'-biphenyl]-2-carboxylic acid;

4'-[(5-secbutyl-3-methoxy-1H-1,2,4-triazol-1-yl)methyl][1,1'-biphenyl]-2-carboxylic acid;

4'-[(5-secbutyl-3-ethoxy-1H-1,2,4-triazol-1-yl)methyl][1,1'-biphenyl]-2-carboxylic acid;

4'-[(5-secbutyl-3-propoxy-1H-1,2,4-triazol-1-yl)methyl][1,1'-biphenyl]-2-carboxylic acid;

4'-[(5-secbutyl-3-cyclohexyl-1H-1,2,4-triazol-1-yl)methyl][1,1'-biphenyl]-2-carboxylic acid;

4'-[(5-secbutyl-3-cyclohexylmethyl-1H-1,2,4-triazol-1-yl)methyl][1,1'-biphenyl]-2-carboxylic acid;

4'-[[5-secbutyl-3-(2-cyclohexylethyl)-1H-1,2,4-triazol-1-yl]methyl][1,1'-biphenyl]-2-carboxylic acid;

4'-[(5-secbutyl-3-cyclohexanoyl-1H-1,2,4-triazol-1-yl)methyl][1,1'-biphenyl]-2-carboxylic acid;

4'-[[5-secbutyl-3-(1-oxo-2-cyclohexylethyl)-1H-1,2,4-triazol-1-yl]methyl][1,1'-biphenyl]-2-carboxylic acid;

4'-[(5-secbutyl-3-phenyl-1H-1,2,4-triazol-1-yl)methyl][1,1'-biphenyl]-2-carboxylic acid;

4'-[(5-secbutyl-3-phenylmethyl-1H-1,2,4-triazol-1-yl)methyl][1,1'-biphenyl]-2-carboxylic acid;

4'-[[5-secbutyl-3-(2-phenylethyl)-1H-1,2,4-triazol-1-yl]methyl][1,1'-biphenyl]-2-carboxylic acid;

4'-[(5-secbutyl-3-benzoyl-1H-1,2,4-triazol-1-yl)methyl][1,1'-biphenyl]-2-carboxylic acid;

4'-[[5-secbutyl-3-(1-oxo-2-phenylethyl)-1H-1,2,4-triazol-1-yl]methyl][1,1'-biphenyl]-2-carboxylic acid;

4'-[[5-secbutyl-3-(1,1-dimethoxypropyl)-1H-1,2,4-triazol-1-yl]methyl][1,1'-biphenyl]-2-carboxylic acid;

4'-[[5-secbutyl-3-(1,1-dimethoxybutyl)-1H-1,2,4-triazol-1-yl]methyl][1,1'-biphenyl]-2-carboxylic acid;

4'-[[5-secbutyl-3-(1,1-dimethoxypentyl)-1H-1,2,4-triazol-1-yl]methyl][1,1'-biphenyl]-2-carboxylic acid;

4'-[[5-secbutyl-3-(1-oxopropyl)-1H-1,2,4-triazol-1-yl]methyl][1,1'-biphenyl]-2-carboxylic acid;

4'-[[5-secbutyl-3-(1-oxobutyl)-1H-1,2,4-triazol-1-yl]methyl][1,1'-biphenyl]-2-carboxylic acid;

4'-[[5-secbutyl-3-(1-oxopentyl)-1H-1,2,4-triazol-1-yl]methyl][1,1'-biphenyl)-2-carboxylic acid;

4'-[[5-secbutyl-3-(1,1-difluoroethyl)-1H-1,2,4-triazol-1-yl]methyl][1,1'-biphenyl]-2-carboxylic acid;

4'-[[5-secbutyl-3-(1,1-difluoropropyl)-1H-112,4-triazol-1-yl]methyl][1,1'-biphenyl]-2-carboxylic acid;

4'-[[5-secbutyl-3-(1,1-difluorobutyl)-1H-1,2,4-triazol-1-yl]methyl][1,1'-biphenyl]-2-carboxylic acid;

4'-[[5-secbutyl-3-(1,1-difluoropentyl)-1H-1,2,4-triazol-1-yl]methyl][1,1'-biphenyl]-2-carboxylic acid;

4'-[(5-isobutyl-3-ethyl-1H-1,2,4-triazol-1-yl)methyl][1,1'-biphenyl]-2-carboxylic acid;

4'-[(5-isobutyl-3-propyl-1H-1,2,4-triazol-1-yl)methyl][1,1'-biphenyl]-2-carboxylic acid;

4'-[(5-isobutyl-3-isopropyl-1H-1,2,4-triazol-1-yl)methyl][1,1'-biphenyl]-2-carboxylic acid;

4'-[(5-isobutyl-3-butyl-1H-1,2,4-triazol-1-yl)methyl][1,1'-biphenyl]-2-carboxylic acid;

4'-[(5-isobutyl-3-secbutyl-1H-1,2,4-triazol-1-yl)methyl][1,1'-biphenyl]-2-carboxylic acid;

4'-[(3,5-diisobutyl-1H-1,2,4-triazol-1-yl)methyl][1,1'-biphenyl]-2-carboxylic acid;

4'-[(5-isobutyl-3-tertbutyl-1H-1,2,4-triazol-1-yl)methyl][1,1'-biphenyl]-2-carboxylic acid;

4'-[(5-isobutyl-3-pentyl-1H-1,2,4-triazol-1-yl)methyl][1,1'-biphenyl]-2-carboxylic acid;

4'-[(5-isobutyl-3-isopentyl-1H-1,2,4-triazol-1-yl)methyl][1,1'-biphenyl]-2-carboxylic acid;

4'-[(5-isobutyl-3-mercapto-1H-1,2,4-triazol-1-yl)methyl][1,1'-biphenyl]-2-carboxylic acid;

4'-[(5-isobutyl-0.3-thiomethyl-1H-1,2,4-triazol-1-yl)methyl][1,1'-biphenyl]-2-carboxylic acid;

4'-[(5-isobutyl-3-thioethyl-1H-1,2,4-triazol-1-yl)methyl][1,1'-biphenyl]-2-carboxylic acid;

4'-[(5-isobutyl-3-thiopropyl-1H-1,2,4-triazol-1-yl)methyl][1,1'-biphenyl]-2-carboxylic acid;

4'-[(5-isobutyl-3-hydroxy-1H-1,2,4-triazol-1-yl)methyl][1,1'-biphenyl]-2-carboxylic acid;

4'-[(5-isobutyl-3-methoxy-1H-1,2,4-triazol-1-yl)methyl)[1,1'-biphenyl]-2-carboxylic acid;

4'-[(5-isobutyl-3-ethoxy-1H-1,2,4-triazol-1-yl)methyl][1,1'-biphenyl]-2-carboxylic acid;

4'-[(5-isobutyl-3-propoxy-1H-1,2,4-triazol-1-yl)methyl][1,1'-biphenyl]-2-carboxylic acid;

4'-[(5-isobutyl-3-cyclohexyl-1H-1,2,4-triazol-1-yl)methyl][1,1'-biphenyl]-2-carboxylic acid;

4'-[(5-isobutyl-3-cyclohexylmethyl-1H-1,2,4-triazol-1-yl)methyl][1,1'-biphenyl]-2-carboxylic acid;

4'-[[5-isobutyl-3-(2-cyclohexylethyl)-1H-1,2,4-triazol-1-yl]methyl][1,1'-biphenyl]-2-carboxylic acid;

4'-[(5-isobutyl-3-cyclohexanoyl-1H-1,2,4-triazol-1-yl)methyl][1,1'-biphenyl]-2-carboxylic acid;

4'-[[5-isobutyl-3-(1-oxo-2-cyclohexylethyl)-1H-1,2,4-triazol-1-yl]methyl][1,1'-biphenyl]-2-carboxylic acid;

4'-[(5-isobutyl-3-phenyl-1H-1,2,4-triazol-1-yl)methyl][1,1'-biphenyl]-2-carboxylic acid;

4-[(5-isobutyl-3-phenylmethyl-1H-1,2,4-triazol-1-yl)methyl][1,1'-biphenyl]-2-carboxylic acid;

4'-[[5-isobutyl-3-(2-phenylethyl)-1H-1,2,4-triazol-1-yl]methyl][1,1'-biphenyl]-2-carboxylic acid;

4'-[(5-isobutyl-3-benzoyl-1H-1,2,4-triazol-1-yl)methyl][1,1'-biphenyl]-2-carboxylic acid;

4'-[[5-isobutyl-3-(1-oxo-2-phenylethyl)-1H-1,2,4-triazol-1-yl]methyl][1,1'-biphenyl]-2-carboxylic acid;

4'-[[5-isobutyl-3-(1,1-dimethoxypropyl)-1H-1,2,4-triazol-1-yl]methyl][1,1'-biphenyl]-2-carboxylic acid;

4'-[[5-isobutyl-3-(1,1-dimethoxybutyl)-1H-1,2,4-triazol-1-yl]methyl][1,1'-biphenyl]-2-carboxylic acid;

4'-[[5-isobutyl-3-(1,1-dimethoxypentyl)-1H-1,2,4-triazol-1-yl]methyl][1,1'-biphenyl]-2-carboxylic acid;

4'-[[5-isobutyl-3-(1-oxopropyl)-1H-1,2,4-triazol-1-yl]methyl][1,1'-biphenyl]-2-carboxylic acid;

4'-[[5-isobutyl-3-(1-oxobutyl)-1H-1,2,4-triazol-1-yl]methyl][1,1'-biphenyl]-2-carboxylic acid;

4'-[[5-isobutyl-3-(1-oxopentyl)-1H-1,2,4-triazol-1-yl]methyl][1,1'-biphenyl]-2-carboxylic acid;

4'-[[5-isobutyl-3-(1,1-difluoroethyl)-1H-1,2,4-triazol-1-yl]methyl][1,1'-biphenyl]-2-carboxylic acid;

4'-[[5-isobutyl-3-(1,1-difluoropropyl)-1H-1,2,4-triazol-1-yl]methyl][1,1'-biphenyl]-2-carboxylic acid;

4'-[[5-isobutyl-3-(1,1-difluorobutyl)-1H-1,2,4-triazol-1-yl]methyl][1,1'-biphenyl]-2-carboxylic acid;

4'-[[5-isobutyl-3-(1,1-difluoropentyl)-1H-1,2,4-triazol-1-yl]methyl][1,1'-biphenyl]-2-carboxylic acid;

4'-[(5-tertbutyl-3-ethyl-1H-1,2,4-triazol-1-yl)methyl][1,1'-biphenyl]-2-carboxylic acid;

4'-[(5-tertbutyl-3-propyl-1H-1,2,4-triazol-1-yl)methyl][1,1'-biphenyl]-2-carboxylic acid;

4'-[(5-tertbutyl-3-isopropyl-1H-1,2,4-triazol-1-yl)methyl][1,1'-biphenyl]-2-carboxylic acid;

4'-[(5-tertbutyl-3-butyl-1H-1,2,4-triazol-1-yl)methyl][1,1'-biphenyl]-2-carboxylic acid;

4'-[(5-tertbutyl-3-secbutyl-1H-1,2,4-triazol-1-yl)methyl][1,1'-biphenyl]-2-carboxylic acid;

4'-[(5-tertbutyl-3-isobutyl-1H-1,2,4-triazol-1-yl)methyl][1,1'-biphenyl]-2-carboxylic acid;

4'-[(3,5-ditertbutyl-1H-1,2,4-triazol-1-yl)methyl][1,1'-biphenyl]-2-carboxylic acid;

4'-[(5-tertbutyl-3-pentyl-1H-1,2,4-triazol-1-yl)methyl][1,1'-biphenyl]-2-carboxylic acid;

4'-[(5-tertbutyl-3-isopentyl-1H-1,2,4-triazol-1-yl)methyl][1,1'-biphenyl]-2-carboxylic acid;

4'-[(5-tertbutyl-3-mercapto-1H-1,2,4-triazol-1-yl)methyl][1,1'-biphenyl]-2-carboxylic acid;

4'-[(5-tertbutyl-3-thiomethyl-1H-1,2,4-triazol-1-yl)methyl][1,1'-biphenyl]-2-carboxylic acid;

4'-[(5-tertbutyl-3-thioethyl-1H-1,2,4-triazol-1-yl)methyl][1,1'-biphenyl]-2-carboxylic acid;

4'-[(5-tertbutyl-3-thiopropyl-1H-1,2,4-triazol-1-yl)methyl][1,1'-biphenyl]-2-carboxylic acid;

4'-[(5-tertbutyl-3-hydroxy-1H-1,2,4-triazol-1-yl)methyl][1,1'-biphenyl]-2-carboxylic acid;

4'-[(5-tertbutyl-3-methoxy-1H-1,2,4-triazol-1-yl)methyl][1,1'-biphenyl]-2-carboxylic acid;

4'-[(5-tertbutyl-3-ethoxy-1H-1,2,4-triazol-1-yl)methyl][1,1'-biphenyl]-2-carboxylic acid;

4'-[(5-tertbutyl-3-propoxy-1H-1,2,4-triazol-1-yl)methyl][1,1'-biphenyl]-2-carboxylic acid;

4'-[(5-tertbutyl-3-cyclohexyl-1H-1,2,4-triazol-1-yl)methyl][1,1'-biphenyl]-2-carboxylic acid;

4'-[(5-tertbutyl-3-cyclohexylmethyl-1H-1,2,4-triazol-1-yl)methyl][1,1'-biphenyl]-2-carboxylic acid;

4'-[[5-tertbutyl-3-(2-cyclohexylethyl)-1H-1,2,4-triazol-1-yl]methyl][1,1'-biphenyl]-2-carboxylic acid;

4'-[(5-tertbutyl-3-cyclohexanoyl-1H-1,2,4-triazol-1-yl)methyl][1,1'-biphenyl]-2-carboxylic acid;

4'-[[5-tertbutyl-3-(1-oxo-2-cyclohexylethyl)-1H-1,2,4-triazol-1-yl]methyl][1,1'-biphenyl]-2-carboxylic acid;

4'-[(5-tertbutyl-3-phenyl-1H-1,2,4-triazol-1-yl)methyl][1,1'-biphenyl]-2-carboxylic acid;

4'-[(5-tertbutyl-3-phenylmethyl-1H-1,2,4-triazol-1-yl)methyl][1,1'-biphenyl]-2-carboxylic acid;

4'-[[5-tertbutyl-3-(2-phenylethyl)-1H-1,2,4-triazol-1-yl]methyl][1,1'-biphenyl]-2-carboxylic acid;

4'-[(5-tertbutyl-3-benzoyl-1H-1,2,4-triazol-1-yl)methyl][1,1'-biphenyl]-2-carboxylic acid;

4'-[[5-tertbutyl-3-(1-oxo-2-phenylethyl)-1H-1,2,4-triazol-1-yl]methyl][1,1'-biphenyl]-2-carboxylic acid;

4'-[[5-tertbutyl-3-(1,1-dimethoxypropyl)-1H-1,2,4-triazol-1-yl]methyl](1,1'-biphenyl]-2-carboxylic acid;

4'-[[5-tertbutyl-3-(1,1-dimethoxybutyl)-1H-1,2,4-triazol-1-yl]methyl][1,1'-biphenyl]-2-carboxylic acid;

4'-[[5-tertbutyl-3-(1,1-dimethoxypentyl)-1H-1,2,4-triazol-1-yl]methyl][1,1'-biphenyl]-2-carboxylic acid;

4'-[[5-tertbutyl-3-(1-oxopropyl)-1H-1,2,4-triazol-1-yl]methyl][1,1'-biphenyl]-2-carboxylic acid;

4'-[[5-tertbutyl-3-(1-oxobutyl)-1H-1,2,4-triazol-1-yl]methyl][1,1'-biphenyl]-2-carboxylic acid;

4'-[[5-tertbutyl-3-(1-oxopentyl)-1H-1,2,4-triazol-1-yl]methyl][1,1'-biphenyl]-2-carboxylic acid;

4'-[[5-tertbutyl-3-(1,1-difluoroethyl)-1H-1,2,4-triazol-1-yl]methyl][1,1'-biphenyl]-2-carboxylic acid;

4'-[15-tertbutyl-3-(1,1-difluoropropyl)-1H-1,2,4-triazol-1-yl]methyl][1,1'-biphenyl]-2-carboxylic acid;

4'-[[5-tertbutyl-3-(1,1-difluorobutyl)-1H-1,2,4-triazol-1-yl]methyl][1,1'-biphenyl]-2-carboxylic acid;

4'-[[5-tertbutyl-3-(1,1-difluoropentyl)-1H-1,2,4-triazol-1-yl]methyl][1,1'-biphenyl]-2-carboxylic acid;

4'-[(5-pentyl-3-ethyl-1H-1,2,4-triazol-1-yl)methyl][1,1'-biphenyl]-2-carboxylic acid;

4'-[(5-pentyl-3-propyl-1H-1,2,4-triazol-1-yl)methyl][1,1'-biphenyl]-2-carboxylic acid;

4'[-(5-pentyl-3-isopropyl-1H-1,2,4-triazol-1-yl)methyl][1,1'-biphenyl]-2-carboxylic acid;

4'-[(5-pentyl-3-butyl-1H-1,2,4-triazol-1-yl)methyl][1,1'-biphenyl]-2-carboxylic acid;

4'-[(5-pentyl-3-secbutyl-1H-1,2,4-triazol-1-yl)methyl][1,1'-biphenyl]-2-carboxylic acid;

4'-[(5-pentyl-3-isobutyl-1H-1,2,4-triazol-1-yl)methyl][1,1'-biphenyl]-2-carboxylic acid;

4'-[(5-pentyl-3-tertbutyl-1H-1,2,4-triazol-1-yl)methyl][1,1'-biphenyl]-2-carboxylic acid;

4'-[(3,5-dipentyl-1H-1,2,4-triazol-1-yl)methyl][1,1'-biphenyl]-2-carboxylic acid;

4'-[(5-pentyl-3-isopentyl-1H-1,2,4-triazol-1-yl)methyl][1,1'-biphenyl]-2-carboxylic acid;

4'-[(5-pentyl-3-mercapto-1H-1,2,4-triazol-1-yl)methyl][1,1'-biphenyl]-2-carboxylic acid;

4'-[(5-pentyl-3-thiomethyl-1H-1,2,4-triazol-1-yl)methyl][1,1'-biphenyl]-2-carboxylic acid;

4'-[(5-pentyl-3-thioethyl-1H-1,2,4-triazol-1-yl)methyl][1,1'-biphenyl]-2-carboxylic acid;

4'-[(5-pentyl-3-thiopropyl-1H-1,2,4-triazol-1-yl)methyl][1,1'-biphenyl]-2-carboxylic acid;

4'-[(5-pentyl-3-hydroxy-1H-1,2,4-triazol-1-yl)methyl][1,1'-biphenyl]-2-carboxylic acid;

4'-[(5-pentyl-3-methoxy-1H-1,2,4-triazol-1-yl)methyl][1,1'-biphenyl]-2-carboxylic acid;

4'-[(5-pentyl-3-ethoxy-1H-1,2,4-triazol-1-yl)methyl][1,1'-biphenyl]-2-carboxylic acid;

4'-[(5-pentyl-3-propoxy-1H-1,2,4-triazol-1-yl)methyl][1,1'-biphenyl]-2-carboxylic acid;

4'-[(5-pentyl-3-cyclohexyl-1H-1,2,4-triazol-1-yl)methyl][1,1'-biphenyl]-2-carboxylic acid;

4'-[(5-pentyl-3-cyclohexylmethyl-1H-1,2,4-triazol-1-yl)methyl][1,1'-biphenyl]-2-carboxylic acid;

4'-[[5-pentyl-3-(2-cyclohexylethyl)'-1H-1,2,4-triazol-1-yl]methyl][1,1'-biphenyl]-2-carboxylic acid;

4'-[(5-pentyl-3-cyclohexanoyl-1H-1,2,4-triazol-1-yl)methyl][1,1'-biphenyl]-2-carboxylic acid;

4'-[[5-pentyl-3-(1-oxo-2-cyclohexylethyl)-1H-1,2,4-triazol-1-yl]methyl][1,1'-biphenyl]-2-carboxylic acid;

4'-[(5-pentyl-3-phenyl-1H-1,2,4-triazol-1-yl)methyl][1,1'-biphenyl]-2-carboxylic acid;

4'-[(5-pentyl-3-phenylmethyl-1H-1,2,4-triazol-1-yl)methyl][1,1'-biphenyl]-2-carboxylic acid;

4'-[[5-pentyl-3-(2-phenylethyl)-1H-1,2,4-triazol-1-yl]methyl][1,1'-biphenyl]-2-carboxylic acid;

4'-[(5-pentyl-3-benzoyl-1H-1,2,4-triazol-1-yl)methyl][1,1'-biphenyl]-2-carboxylic acid;

4'-[[5-pentyl-3-(1-oxo-2-phenylethyl)-1H-1,2,4-triazol-1-yl]methyl][1,1'-biphenyl]-2-carboxylic acid;

4'-[[5-pentyl-3-(1,1-dimethoxypropyl)-1H-1,2,4-triazol-1-yl]methyl][1,1'-biphenyl]-2-carboxylic acid;

4'-[[5-pentyl-3-(1,1-dimethoxybutyl)-1H-1,2,4-triazol-1-yl]methyl][1,1'-biphenyl]-2-carboxylic acid;

4'-[[5-pentyl-3-(1,1-dimethoxypentyl)-1H-1,2,4-triazol-1-yl]methyl][1,1'-biphenyl]-2-carboxylic acid;

4'-[[5-pentyl-3-(1-oxopropyl)-1H-1,2,4-triazol-1-yl]methyl][1,1'-biphenyl]-2-carboxylic acid;

4'-[[5-pentyl-3-(1-oxobutyl)-1H-1,2,4-triazol-1-yl]methyl][1,1'-biphenyl]-2-carboxylic acid;

4'-[[5-pentyl-3-(1-oxopentyl)-1H-1,2,4-triazol-1-yl]methyl][1,1'-biphenyl]-2-carboxylic acid;

4'-[[5-pentyl-3-(1,1-difluoroethyl)-1H-1,2,4-triazol-1-yl]methyl][1,1'-biphenyl]-2-carboxylic acid;

4'-[[5-pentyl-3-(1,1-difluoropropyl)-1H-1,2,4-triazol-1-yl]methyl][1,1'-biphenyl]-2-carboxylic acid;

4'-[[5-pentyl-3-(1,1-difluorobutyl)-1H-1,2,4-triazol-1-yl]methyl][1,1'-biphenyl]-2-carboxylic acid;

4'-[[5-pentyl-3-(1,1-difluoropentyl)-1H-1,2,4-triazol-1-yl]methyl][1,1'-biphenyl]-2-carboxylic acid;

4'-[(5-isopentyl-3-ethyl-1H-1,2,4-triazol-1-yl)methyl][1,1'-biphenyl]-2-carboxylic acid;

4'-[(5-isopentyl-3-propyl-1H-1,2,4-triazol-1-yl)methyl][1,1'-biphenyl]-2-carboxylic acid;

4'-[(5-isopentyl-3-isopropyl-1H-1,2,4-triazol-1-yl)methyl][1,1'-biphenyl]-2-carboxylic acid;

4'-[(5-isopentyl-3-butyl-1H-1,2,4-triazol-1-yl)methyl][1,1'-biphenyl]-2-carboxylic acid;

4'-[(5-isopentyl-3-secbutyl-1H-1,2,4-triazol-1-yl)methyl][1,1'-biphenyl]-2-carboxylic acid;

4'-[(5-isopentyl-3-isobutyl-1H-1,2,4-triazol-1-yl)methyl][1,1'-biphenyl]-2-carboxylic acid;

4'-[(5-isopentyl-3-tertbutyl-1H-1,2,4-triazol-1-yl)methyl][1,1'-biphenyl]-2-carboxylic acid;

4'-[(5-isopentyl-3-pentyl-1H-1,2,4-triazol-1-yl)methyl][1,1'-biphenyl]-2-carboxylic acid;

4'-[(3,5-diisopentyl-1H-1,2,4-triazol-1-yl)methyl][1,1'-biphenyl]-2-carboxylic acid;

4'-[(5-isopentyl-3-mercapto-1H-1,2,4-triazol-1-yl)methyl][1,1'-biphenyl]-2-carboxylic acid;

4'-[(5-isopentyl-3-thiomethyl-1H-1,2,4-triazol-1-yl)methyl][1,1'-biphenyl]-2-carboxylic acid;

4'-[(5-isopentyl-3-thioethyl-1H-1,2,4-triazol-1-yl)methyl][1,1'-biphenyl]-2-carboxylic acid;

4'-[(5-isopentyl-3-thiopropyl-1H-1,2,4-triazol-1-yl)methyl][1,1'-biphenyl]-2-carboxylic acid;

4'-[(5-isopentyl-3-hydroxy-1H-1,2,4-triazol-1-yl)methyl][1,1'-biphenyl]-2-carboxylic acid;

4'-[(5-isopentyl-3-methoxy-1H-1,2,4-triazol-1-yl)methyl][1,1'-biphenyl]-2-carboxylic acid;

4'-[(5-isopentyl-3-ethoxy-1H-1,2,4-triazol-1-yl)methyl][1,1'-biphenyl]-2-carboxylic acid;

4'-[(5-isopentyl-3-propoxy-1H-1,2,4-triazol-1-yl)methyl][1,1'-biphenyl]-2-carboxylic acid;

4'-[(5-isopentyl-3-cyclohexyl-1H-1,2,4-triazol-1-yl)methyl][1,1'-biphenyl]-2-carboxylic acid;

4'-[(5-isopentyl-3-cyclohexylmethyl-1H-1,2,4-triazol-1-yl)methyl][1,1'-biphenyl]-2-carboxylic acid;

4'-[[5-pentyl-3-(2-cyclohexylethyl)-1H-1,2,4-triazol-1-yl]methyl][1,1'-biphenyl]-2-carboxylic acid;

4'-[(5-isopentyl-3-cyclohexanoyl-1H-1,2,4-triazol-1-yl)methyl][1,1'-biphenyl]-2-carboxylic acid;

4'-[[5-isopentyl-3-(1-oxo-2-cyclohexylethyl)-1H-1,2,4-triazol-1-yl]methyl][1,1'-biphenyl]-2-carboxylic acid;

4'-[(5-isopentyl-3-phenyl-1H-1,2,4-triazol-1-yl)methyl][1,1'-biphenyl]-2-carboxylic acid;

4'-[(5-isopentyl-3-phenylmethyl-1H-1,2,4-triazol-1-yl)methyl][1,1'-biphenyl]-2-carboxylic acid;

4'-[[5-isopentyl-3-(2-phenylethyl)-1H-1,2,4-triazol-1-yl]methyl][1,1'-biphenyl]-2-carboxylic acid;

4'-[(5-isopentyl-3-benzoyl-1H-1,2,4-triazol-1-yl)methyl][1,1'-biphenyl]-2-carboxylic acid;

4'-[[5-isopentyl-3-(1-oxo-2-phenylethyl)-1H-1,2,4-triazol-1-yl]methyl][1,1'-biphenyl]-2-carboxylic acid;

4'-[[5-isopentyl-3-(1,1-dimethoxypropyl)-1H-1,2,4-triazol-1-yl]methyl][1,1'-biphenyl]-2-carboxylic acid;

4'-[[5-isopentyl-3-(1,1-dimethoxybutyl)-1H-1,2,4-triazol-1-yl]methyl][1,1'-biphenyl]-2-carboxylic acid;

4'-[[5-isopentyl-3-(1,1-dimethoxypentyl)-1H-1,2,4-triazol-1-yl]methyl][1,1'-biphenyl]-2-carboxylic acid;

4'-[[5-isopentyl-3-(1-oxopropyl)-1H-1,2,4-triazol-1-yl]methyl][1,1'-biphenyl]-2-carboxylic acid;

4'-[[5-isopentyl-3-(1-oxobutyl)-1H-1,2,4-triazol-1-yl]methyl][1,1'-biphenyl]-2-carboxylic acid;

4'-[[5-isopentyl-3-(1-oxopentyl)-1H-1,2,4-triazol-1-yl]methyl][1,1'-biphenyl]-2-carboxylic acid;

4'-[[5-isopentyl-3-(1,1-difluoroethyl)-1H-1,2,4-triazol-1-yl]methyl][1,1'-biphenyl]-2-carboxylic acid;

4'-[[5-isopentyl-3-(1,1-difluoropropyl)-1H-1,2,4-triazol-1-yl]methyl][1,1'-biphenyl]-2-carboxylic acid;

4'-[[5-isopentyl-3-(1,1-difluorobutyl)-1H-1,2,4-triazol-1-yl]methyl][1,1'-biphenyl]-2-carboxylic acid;

4'-[[5-isopentyl-3-(1,1-difluoropentyl)-1H-1,2,4-triazol-1-yl]methyl][1,1'-biphenyl]-2-carboxylic acid;

4'-[[5-(1-butenyl)-3-ethyl-1H-1,2,4-triazol-1-yl]methyl][1,1'-biphenyl]-2-carboxylic acid;

4'-[[5-(1-butenyl)-3-propyl-1H-1,2,4-triazol-1-yl]methyl][1,1'-biphenyl]-2-carboxylic acid;

4'-[[5-(1-butenyl)-3-isopropyl-1H-1,2,4-triazol-1-yl]methyl][1,1'-biphenyl]-2-carboxylic acid;

4'-[[5-(1-butenyl)-3-butyl-1H-1,2,4-triazol-1-yl]methyl][1,1'-biphenyl]-2-carboxylic acid;

4'-[[5-(1-butenyl)-3-secbutyl-1H-1,2,4-triazol-1-yl]methyl][1,1'-biphenyl]-2-carboxylic acid;

4'-[[5-(1-butenyl)-3-isobutyl-1H-1,2,4-triazol-1-yl]methyl][1,1'-biphenyl]-2-carboxylic acid;

4'-[[5-(1,1-butenyl)-3-tertbutyl-1H-1,2,4-triazol-1-yl]methyl][1,1'-biphenyl]-2-carboxylic acid;

4'-[[5-(1-butenyl)-3-pentyl-1H-1,2,4-triazol-1-yl]methyl][1,1'-biphenyl]-2-carboxylic acid;

4'-[[5-(1-butenyl)-3-isopentyl-1H-1,2,4-triazol-1-yl]methyl][1,1'-biphenyl]-2-carboxylic acid;

4'-[[5-(1-butenyl)-3-mercapto-1H-1,2,4-triazol-1-yl]methyl][1,1'-biphenyl]-2-carboxylic acid;

4'-[[5-(1-butenyl)-3-thiomethyl-1H-1,2,4-triazol-1-yl]methyl][1,1'-biphenyl]-2-carboxylic acid;

4'-[[5-(1-butenyl)-3-thioethyl-1H-1,2,4-triazol-1-yl]methyl][1,1'-biphenyl]-2-carboxylic acid;

4'-[[5-(1-butenyl)-3-thiopropyl-1H-1,2,4-triazol-1-yl]methyl][1,1'-biphenyl]-2-carboxylic acid;

4'-[[5-(1-butenyl)-3-hydroxy-1H-1,2,4-triazol-1-yl]methyl][1,1'-biphenyl]-2-carboxylic acid;

4'-[[5-(1-butenyl)-3-methoxy-1H-1,2,4-triazol-1-yl]methyl][1,1'-biphenyl]-2-carboxylic acid;

4'-[[5-(1-butenyl)-3-ethoxy-1H-1,2,4-triazol-1-yl]methyl][1,1'-biphenyl]-2-carboxylic acid;

4'-[[5-(1-butenyl)-3-propoxy-1H-1,2,4-triazol-1-yl]methyl][1,1'-biphenyl]-2-carboxylic acid;

4'-[[5-(1-butenyl)-3-cyclohexyl-1H-1,2,4-triazol-1-yl]methyl][1,1'-biphenyl]-2-carboxylic acid;

4'-[[5-(1-butenyl)-3-cyclohexylmethyl-1H-1,2,4-triazol-1-yl]methyl][1,1'-biphenyl]-2-carboxylic acid;

4'-[[5-(1-butenyl)-3-(2-cyclohexylethyl)-1H-1,2,4-triazol-1-yl]methyl][1,1'-biphenyl]-2-carboxylic acid;

4'-[[5-(1-butenyl)-3-cyclohexanoyl-1H-1,2,4-triazol-1-yl]methyl][1,1'-biphenyl]-2-carboxylic acid;

4'-[[5-(1-butenyl)-3-(1-oxo-2-cyclohexylethyl)-1H-1,2,4-triazol-1-yl]methyl][1,1'-biphenyl]-2-carboxylic acid;

4'-[[5-(1-butenyl)-3-phenyl-1H-1,2,4-triazol-1-yl]methyl][1,1'-biphenyl]-2-carboxylic acid;

4'-[[5-(1-butenyl)-3-phenylmethyl-1H-1,2,4-triazol-1-yl]methyl][1,1'-biphenyl]-2-carboxylic acid;

4'-[[5-(1-butenyl)-3-(2-phenylethyl)-1H-1,2,4-triazol-1-yl]methyl][1,1'-biphenyl]-2-carboxylic acid;

4'-[[5-(1-butenyl)-3-benzoyl-1H-1,2,4-triazol-1-yl]methyl][1,1'-biphenyl]-2-carboxylic acid;

4'-[[5-(1-butenyl)-3-(1-oxo-2-phenylethyl)-1H-1,2,4-triazol-1-yl]methyl][1,1'-biphenyl]-2-carboxylic acid;

4'-[[5-(1-butenyl)-3-(1,1-dimethoxypropyl)-1H-1,2,4-triazol-1-yl]methyl][1,1'-biphenyl]-2-carboxylic acid;

4'-[[5-(1-butenyl)-3-(1,1-dimethoxybutyl)-1H-1,2,4-triazol-1-yl]methyl][1,1'-biphenyl]-2-carboxylic acid;

4'-[[5-(1-butenyl)-3-(1,1-dimethoxypentyl)-1H-1,2,4-triazol-1-yl]methyl][1,1'-biphenyl]-2-carboxylic acid;

4'-[[5-(1-butenyl)-3-(1-oxopropyl)-1H-1,2,4-triazol-1-yl]methyl][1,1'-biphenyl]-2-carboxylic acid;

4'-[[5-(1-butenyl)-3-(1-oxobutyl)-1H-1,2,4-triazol-1-yl]methyl][1,1'-biphenyl]-2-carboxylic acid;

4'-[[5-(1-butenyl)-3-(1-oxopentyl)-1H-1,2,4-triazol-1-yl]methyl][1,1'-biphenyl]-2-carboxylic acid;

4'-[[5-(1-butenyl)-3-(1,1-difluoroethyl)-1H-1,2,4-triazol-1-yl]methyl][1,1'-biphenyl]-2-carboxylic acid;

4'-[[5-(1-butenyl)-3-(1,1-difluoropropyl)-1H-1,2,4-triazol-1-yl]methyl][1,1'-biphenyl]-2-carboxylic acid;

4'-[[5-(1-butenyl)-3-(1,1-difluorobutyl)-1H-1,2,4-triazol-1-yl]methyl][1,1'-biphenyl]-2-carboxylic acid;

4'-[[5-(1-butenyl)-3-(1,1-difluoropentyl)-1H-1,2,4-triazol-1-yl]methyl][1,1'-biphenyl]-2-carboxylic acid;

4'-[[5-(2-butenyl)-3-ethyl-1H-1,2,4-triazol-1-yl]methyl][1,1'-biphenyl]-2-carboxylic acid;

4'-[[5-(2-butenyl)-3-propyl-1H-1,2,4-triazol-1-yl]methyl][1,1'-biphenyl]-2-carboxylic acid;

4'-[[5-(2-butenyl)-3-isopropyl-1H-1,2,4-triazol-1-yl]methyl][1,1'-biphenyl]-2-carboxylic acid;

4'-[[5-(2-butenyl)-3-butyl-1H-1,2,4-triazol-1-yl]methyl][1,1'-biphenyl]-2-carboxylic acid;

4'-[[5-(2-butenyl)-3-secbutyl-1H-1,2,4-triazol-1-yl]methyl][1,1'-biphenyl]-2-carboxylic acid;

4'-[[5-(2-butenyl)-3-isobutyl-1H-1,2,4-triazol-1-yl]methyl][1,1'-biphenyl]-2-carboxylic acid;

4'-[[5-(2-butenyl)-3-tertbutyl-1H-1,2,4-triazol-1-yl]methyl][1,1'-biphenyl]-2-carboxylic acid;

4'-[[5-(2-butenyl)-3-pentyl-1H-1,2,4-triazol-1-yl]methyl][1,1'-biphenyl]-2-carboxylic acid;

4'-[[5-(2-butenyl)-3-isopentyl-1H-1,2,4-triazol-1-yl]methyl][1,1'-biphenyl]-2-carboxylic acid;

4'-[[5-(2-butenyl)-3-mercapto-1H-1,2,4-triazol-1-yl]methyl][1,1'-biphenyl]-2-carboxylic acid;

4'-[[5-(2-butenyl)-3-thiomethyl-1H-1,2,4-triazol-1-yl]methyl][1,1'-biphenyl]-2-carboxylic acid;

4'-[[5-(2-butenyl)-3-thioethyl-1H-1,2,4-triazol-1-yl]methyl][1,1'-biphenyl]-2-carboxylic acid;

4'-[[5-(2-butenyl)-3-thiopropyl-1H-1,2,4-triazol-1-yl]methyl][1,1'-biphenyl]-2-carboxylic acid;

4'-[[5-(2-butenyl)-3-hydroxy-1H-1,2,4-triazol-1-yl]methyl][1,1'-biphenyl]-2-carboxylic acid;

4'-[[5-(2-butenyl)-3-methoxy-1H-1,2,4-triazol-1-yl]methyl][1,1'-biphenyl]-2-carboxylic acid;

4'-[[5-(2-butenyl)-3-ethoxy-1H-1,2,4-triazol-1-yl]methyl][1,1'-biphenyl]-2-carboxylic acid;

4'-[[5-(2-butenyl)-3-propoxy-1H-1,2,4-triazol-1-yl]methyl][1,1'-biphenyl]-2-carboxylic acid;

4'-[[5-(2-butenyl)-3-cyclohexyl-1H-1,2,4-triazol-1-yl]methyl][1,1'-biphenyl]-2-carboxylic acid;

4'-[[5-(2-butenyl)-3-cyclohexylmethyl-1H-1,2,4-triazol-1-yl]methyl][1,1'-biphenyl]-2-carboxylic acid;

4'-[[5-(2-butenyl)-3-(2-cyclohexylethyl)-1H-1,2,4-triazol-1-yl]methyl][1,1'-biphenyl]-2-carboxylic acid;

4'-[[5-(2-butenyl)-3-cyclohexanoyl-1H-1,2,4-triazol-1-yl]methyl][1,1'-biphenyl]-2-carboxylic acid;

4'-[[5-(2-butenyl)-3-(1-oxo-2-cyclohexylethyl)-1H-1,2,4-triazol-1-yl]methyl][1,1'-biphenyl]-2-carboxylic acid;

4'-[[5-(2-butenyl)-3-phenyl-1H-1,2,4-triazol-1-yl]methyl][1,1'-biphenyl]-2-carboxylic acid;

4'-[[5-(2-butenyl)-3-phenylmethyl-1H-1,2,4-triazol-1-yl]methyl][1,1'-biphenyl]-2-carboxylic acid;

4'-[[5-(2-butenyl)-3-(2-phenylethyl)-1H-1,2,4-triazol-1-yl]methyl][1,1'-biphenyl]-2-carboxylic acid;

4'-[[5-(2-butenyl)-3-(1,1-dimethoxypropyl)-1H-1,2,4-triazol-1-yl]methyl][1,1'-biphenyl]-2-carboxylic acid;

4'-[[5-(2-butenyl)-3-(1,1-dimethoxybutyl)-1H-1,2,4-triazol-1-yl]methyl][1,1'-biphenyl]-2-carboxylic acid;

4'-[[5-(2-butenyl)-3-(1,1-dimethoxypentyl)-1H-1,2,4-triazol-1-yl]methyl][1,1'-biphenyl]-2-carboxylic acid;

4'-[[5-(2-butenyl)-3-(1-oxopropyl)-1H-1,2,4-triazol-1-yl]methyl][1,1'-biphenyl]-2-carboxylic acid;

4'-[[5-(2-butenyl)-3-(1-oxobutyl)-1H-1,2,4-triazol-1-yl]methyl][1,1'-biphenyl]-2-carboxylic acid;

4'-[[5-(2-butenyl)-3-(1-oxopentyl)-1H-1,2,4-triazol-1-yl]methyl][1,1'-biphenyl]-2-carboxylic acid;

4'-[[5-(2-butenyl)-3-(1,1-difluoroethyl)-1H-1,2,4-triazol-1-yl]methyl][1,1'-biphenyl]-2-carboxylic acid;

4'-[[5-(2-butenyl)-3-(1,1-difluoropropyl)-1H-1,2,4-triazol-1-yl]methyl][1,1'-biphenyl]-2-carboxylic acid;

4'-[[5-(2-butenyl)-3-(1,1-difluorobutyl)-1H-1,2,4-triazol-1-yl]methyl][1,1'-biphenyl]-2-carboxylic acid;

4'-[[5-(2-butenyl)-3-(1,1-difluoropentyl)-1H-1,2,4-triazol-1-yl]methyl][1,1'-biphenyl]-2-carboxylic acid;

4'-[[5-(3-butenyl)-3-ethyl-1H-1,2,4-triazol-1-yl]methyl][1,1'-biphenyl]-2-carboxylic acid;

4'-[[5-(3-butenyl)-3-propyl-1H-1,2,4-triazol-1-yl]methyl][1,1'-biphenyl]-2-carboxylic acid;

4'-[[5-(3-butenyl)-3-isopropyl-1H-1,2,4-triazol-1-yl]methyl][1,1'-biphenyl]-2-carboxylic acid;

4'-[[5-(3-butenyl)-3-butyl-1H-1,2,4-triazol-1-yl]methyl][1,1'-biphenyl]-2-carboxylic acid;

4'-[[5-(3-butenyl)-3-secbutyl-1H-1,2,4-triazol-1-yl]methyl][1,1'-biphenyl]-2-carboxylic acid;

4'-[[5-(3-butenyl)-3-isobutyl-1H-1,2,4-triazol-1-yl]methyl][1,1'-biphenyl]-2-carboxylic acid;

4'-[[5-(3-butenyl)-3-tertbutyl-1H-1,2,4-triazol-1-yl]methyl][1,1'-biphenyl]-2-carboxylic acid;

4'-[[5-(3-butenyl)-3-pentyl-1H-1,2,4-triazol-1-yl]methyl][1,1'-biphenyl]-2-carboxylic acid;

4'-[[5-(3-butenyl)-3-isopentyl-1H-1,2,4-triazol-1-yl]methyl][1,1'-biphenyl]-2-carboxylic acid;

4'-[[5-(3-butenyl)-3-mercapto-1H-1,2,4-triazol-1-yl]methyl][1,1'-biphenyl]-2-carboxylic acid;

4'-[[5-(3-butenyl)-3-thiomethyl-1H-1,2,4-triazol-1-yl]methyl][1,1'-biphenyl]-2-carboxylic acid;

4'-[[5-(3-butenyl)-3-thioethyl-1H-1,2,4-triazol-1-yl]methyl][1,1'-biphenyl]-2-carboxylic acid;

4'-[[5-(3-butenyl)-3-thiopropyl-1H-1,2,4-triazol-1-yl]methyl][1,1'-biphenyl]-2-carboxylic acid;

4'-[[5-(3-butenyl)-3-hydroxy-1H-1,2,4-triazol-1-yl]methyl][1,1'-biphenyl]-2-carboxylic acid;

4'-[[5-(3-butenyl)-3-methoxy-1H-1,2,4-triazol-1-yl]methyl][1,1'-biphenyl]-2-carboxylic acid;

4'-[[5-(3-butenyl)-3-ethoxy-1H-1,2,4-triazol-1-yl]methyl][1,1-'-biphenyl]-2-carboxylic acid;

4'-[[5-(3-butenyl)-3-propoxy-1H-1,2,4-triazol-1-yl]methyl][1,1'-biphenyl]-2-carboxylic acid;

4'-[[5-(3-butenyl)-3-cyclohexyl-1H-1,2,4-triazol-1-yl]methyl][1,1'-biphenyl]-2-carboxylic acid;

4'-[[5-(3-butenyl)-3-cyclohexylmethyl-1H-1,2,4-triazol-1-yl]methyl][1,1'-biphenyl]-2-carboxylic acid;

4'-[[5-(3-butenyl)-3-(2-cyclohexylethyl)-1H-1,2,4-triazol-1-yl]methyl][1,1'-biphenyl]-2-carboxylic acid;

4'-[[5-(3-butenyl)-3-cyclohexanoyl-1H-1,2,4-triazol-1-yl]methyl][1,1'-biphenyl]-2-carboxylic acid;

4'-[[5-(3-butenyl)-3-(1-oxo-2-cyclohexylethyl)-1H-1,2,4-triazol-1-yl]methyl][1,1'-biphenyl]-2-carboxylic acid;

4'-[[5-(3-butenyl)-3-phenyl-1H-1,2,4-triazol-1-yl]methyl][1,1'-biphenyl]-2-carboxylic acid;

4'-[[5-(3-butenyl)-3-phenylmethyl-1H-1,2,4-triazol-1-yl]methyl][1,1'-biphenyl]-2-carboxylic acid;

4'-[[5-(3-butenyl)-3-(2-phenylethyl)-1H-1,2,4-triazol-1-yl]methyl][1,1'-biphenyl]-2-carboxylic acid;

4'-[[5-(3-butenyl)-3-benzoyl-1H-1,2,4-triazol-1-yl]methyl][1,1'-biphenyl]-2-carboxylic acid;

4'-[[5-(3-butenyl)-3-(1-oxo-2-phenylethyl)-1H-1,2,4-triazol-1-yl]methyl][1,1'-biphenyl]-2-carboxylic acid;

4'-[[5-(3-butenyl)-3-(1,1-dimethoxypropyl)-1H-1,2,4-triazol-1-yl]methyl][1,1'-biphenyl]-2-carboxylic acid;

4'-[[5-(3-butenyl)-3-(1,1-dimethoxybutyl)-1H-1,2,4-triazol-1-yl]methyl][1,1'-biphenyl]-2-carboxylic acid;

4'-[[5-(3-butenyl)-3-(1,1-dimethoxypentyl)-1H-1,2,4-triazol-1-yl]methyl][1,1'-biphenyl]-2-carboxylic acid;

4'-[[5-(3-butenyl)-3-(1-oxopropyl)-1H-1,2,4-triazol-1-yl]methyl][1,1'-biphenyl]-2-carboxylic acid;

4'-[[5-(3-butenyl)-3-(1-oxobutyl)-1H-1,2,4-triazol-1-yl]methyl][1,1'-biphenyl]-2-carboxylic acid;

4'-[[5-(3-butenyl)-3-(1-oxopentyl)-1H-1,2,4-triazol-1-yl]methyl][1,1'-biphenyl]-2-carboxylic acid;

4'-[[5-(3-butenyl)-3-(1,1-difluoroethyl)-1H-1,2,4-triazol-1-yl]methyl][1,1'-biphenyl]-2-carboxylic acid;

4'-[[5-(3-butenyl)-3-(1,1-difluoropropyl)-1H-1,2,4-triazol-1-yl]methyl][1,1'-biphenyl]-2-carboxylic acid;

4'-[[5-(3-butenyl)-3-(1-difluorobutyl)-1H-1,2,4-triazol-1-yl]methyl][1,1'-biphenyl]-2-carboxylic acid;

4'-[[5-(3-butenyl)-3-(1-difluoropentyl)-1H-1,2,4-triazol-1-yl]methyl][1,1'-biphenyl]-2-carboxylic acid;

4'-[[5-(1-butynyl)-3-ethyl-1H-1,2,4-triazol-1-yl]methyl][1,1'-biphenyl]-2-carboxylic acid;

4'-[[5-(1-butynyl)-3-propyl-1H-1,2,4-triazol-1-yl]methyl][1,1'-biphenyl]-2-carboxylic acid;

4'-[[5-(1-butynyl)-3-butyl-1H-1,2,4-triazol-1-yl]methyl][1,1'-biphenyl]-2-carboxylic acid;

4'-[[5-(1-butynyl)-3-secbutyl-1H-1,2,4-triazol-1-yl]methyl][1,1'-biphenyl]-2-carboxylic acid;

4'-[[5-(1-butynyl)-3-isobutyl-1H-1,2,4-triazol-1-yl]methyl][1,1'-biphenyl]-2-carboxylic acid;

4'-[[5-(1-butynyl)-3-tertbutyl-1H-1,2,4-triazol-1-yl]methyl][1,1'-biphenyl]-2-carboxylic acid;

4'-[[5-(1-butynyl)-3-pentyl-1H-1,2,4-triazol-1-yl]methyl][1,1'-biphenyl]-2-carboxylic acid;

4'-[[5-(1-butynyl)-3-isopentyl-1H-1,2,4-triazol-1-yl]methyl][1,1'-biphenyl]-2-carboxylic acid;

4'-[[5-(1-butynyl)-3-mercapto-1H-1,24-triazol-1-yl]methyl][1,1'-biphenyl]-2-carboxylic acid;

4'-[[5-(1-butynyl)-3-thiomethyl-1H-1,2,4-triazol-1-yl]methyl][1,1'-biphenyl]-2-carboxylic acid;

4'-[[5-(1-butynyl)-3-thioethyl-1H-1,2,4-triazol-1-yl]methyl][1,1'-biphenyl]-2-carboxylic acid;

4'-[[5-(1-butynyl)-3-thiopropyl-1H-1,2,4-triazol-1-yl]methyl][1,1'-biphenyl]-2-carboxylic acid;

4'-[[5-(1-butynyl)-3-hydroxy-1H-1,2,4-triazol-1-yl]methyl][1,1'-biphenyl]-2-carboxylic acid;

4'-[[5-(1-butynyl)-3-methoxy-1H-1,2,4-triazol-1-yl]methyl][1,1'-biphenyl]-2-carboxylic acid;

4'-[[5-(1-butynyl)-3-ethoxy-1H-1,2,4-triazol-1-yl]methyl][1,1'-biphenyl]-2-carboxylic acid;

4'-[[5-(1-butynyl)-3-propoxy-1H-1,2,4-triazol-1-yl]methyl][1,1'-biphenyl]-2-carboxylic acid;

4'-[[5-(1-butynyl)-3-cyclohexyl-1H-1,2,4-triazol-1-yl]methyl][1,1'-biphenyl]-2-carboxylic acid;

4'-[[5-(1-butynyl)-3-cyclohexylmethyl-1H-1,2,4-triazol-1-yl]methyl][1,1'-biphenyl]-2-carboxylic acid;

4'-[[5-(1-butynyl)-3-(2-cyclohexylethyl)-1H-1,2,4-triazol-1-yl]methyl][1,1'-biphenyl]-2-carboxylic acid;

4'-[[5-(1-butynyl)-3-cyclohexanoyl-1H-1,2,4-triazol-1-yl]methyl][1,1'-biphenyl]-2-carboxylic acid;

4'-[[5-(1-butynyl)-3-(1-oxo-2-cyclohexylethyl)-1H-1,2,4-triazol-1-yl]methyl][1,1'-biphenyl]-2-carboxylic acid;

4'-[[5-(1-butynyl)-3-phenyl-1H-1,2,4-triazol-1-yl]methyl][1,1'-biphenyl]-2-carboxylic acid;

4'-[[5-(1-butynyl)-3-phenylmethyl-1H-1,2,4-triazol-1-yl]methyl][1,1'-biphenyl]-2-carboxylic acid;

4'-[[5-(1-butynyl)-3-(2-phenylethyl)-1H-1,2,4-triazol-1-yl]methyl][1,1'-biphenyl]-2-carboxylic acid;

4'-[[5-(1-butynyl)-3-benzoyl-1H-1,2,4-triazol-1-yl]methyl][1,1'-biphenyl]-2-carboxylic acid;

4'-[[5-(1-butynyl)-3-(1-oxo-2-phenylethyl)-1H-1,2,4-triazol-1-yl]methyl][1,1'-biphenyl]-2-carboxylic acid;

4'-[[5-(1-butynyl)-3-(1,1-dimethoxypropyl)-1H-1,2,4-triazol-1-yl]methyl][1,1'-biphenyl]-2-carboxylic acid;

4'-[[5-(1-butynyl)-3-(1,1-dimethoxybutyl)-1H-1,2,4-triazol-1-yl]methyl][1,1'-biphenyl-2-carboxylic acid;

4'-[[5-(1-butynyl)-3-(1,1-dimethoxypentyl)-1H-1,2,4-triazol-1-yl]methyl][1,1'-biphenyl]-2-carboxylic acid;

4'-[[5-(1-butynyl)-3-(1-oxopropyl)-1H-1,2,4-triazol-1-yl]methyl][1,1'-biphenyl]-2-carboxylic acid;

4'-[[5-(1-butynyl)-3-(1-oxobutyl)-1H-1,2,4-triazol-1-yl]methyl][1,1'-biphenyl]-2-carboxylic acid;

4'-[[5-(1-butynyl)-3-(1-oxopentyl)-1H-1,2,4-triazol-1-yl]methyl][1,1'-biphenyl]-2-carboxylic acid;

4'-[[5-(1-butynyl)-3-(1,1-difluoroethyl)-1H-1,2,4-triazol-1-yl]methyl][1,1'-biphenyl]-2-carboxylic acid;

4'-[[5-(1-butynyl)-3-(1,1-difluoropropyl)-1H-1,2,4-triazol-1-yl]methyl][1,1'-biphenyl]-2-carboxylic acid;

4'-[[5-(1-butynyl)-3-(1,1-difluorobutyl)-1H-1,2,4-triazol-1-yl]methyl][1,1'-biphenyl]-2-carboxylic acid;

4'-[[5-(1-butynyl)-3-(1,1-difluoropentyl)-1H-1,2,4-triazol-1-yl]methyl][1,1'-biphenyl]-2-carboxylic acid;

4'-[[5-(2-butynyl)-3-ethyl-1H-1,2,4-triazol-1-yl]methyl][1,1'-biphenyl]-2-carboxylic acid;

4'-[[5-(2-butynyl)-3-propyl-1H-1,2,4-triazol-1-yl]methyl][1,1'-biphenyl]-2-carboxylic acid;

4'-[[5-(2-butynyl)-3-butyl-1H-1,2,4-triazol-1-yl]methyl][1,1'-biphenyl]-2-carboxylic acid;

4'-[[5-(2-butynyl)-3-secbutyl-1H-1,2,4-triazol-1-yl]methyl][1,1'-biphenyl]-2-carboxylic acid;

4'-[[5-(2-butynyl)-3-isobutyl-1H-1,2,4-triazol-1-yl]methyl][1,1'-biphenyl]-2-carboxylic acid;

4'-[[5-(2-butynyl)-3-tertbutyl-1H-1,2,4-triazol-1-yl]methyl][1,1'-biphenyl]-2-carboxylic acid;

4'-[[5-(2-butynyl)-3-pentyl-1H-1,2,4-triazol-1-yl]methyl][1,1'-biphenyl]-2-carboxylic acid;

4'-[[5-(2-butynyl)-3-isopentyl-1H-1,2,4-triazol-1-yl]methyl][1,1'-biphenyl]-2-carboxylic acid;

4'-[[5-(2-butynyl)-3-mercapto-1H-1,2,4-triazol-1-yl]methyl][1,1'-biphenyl]-2-carboxylic acid;

4'-[[5-(2-butynyl)-3-thiomethyl-1H-1,2,4-triazol-1-yl]methyl][1,1'-biphenyl]-2-carboxylic acid;

4'-[[5-(2-butynyl)-3-thioethyl-1H-1,2,4-triazol-1-yl]methyl][1,1'-biphenyl]-2-carboxylic acid;

4'-[[5-(2-butynyl)-3-thiopropyl-1H-1,2,4-triazol-1-yl]methyl][1,1'-biphenyl]-2-carboxylic acid;

4'-[[5-(2-butynyl)-3-hydroxy-1H-1,2,4-triazol-1-yl]methyl][1,1'-biphenyl]-2-carboxylic acid;

4'-[[5-(2-butynyl)-3-methoxy-1H-1,2,4-triazol-1-yl]methyl][1,1'-biphenyl]-2-carboxylic acid;

4'-[[5-(2-butynyl)-3-ethoxy-1H-1,2,4-triazol-1-yl]methyl][1,1'-biphenyl]-2-carboxylic acid;

4'-[[5-(2-butynyl)-3-propoxy-1H-1,2,4-triazol-1-yl]methyl][1,1'-biphenyl]-2-carboxylic acid;

4'-[[5-(2-butynyl)-3-cyclohexyl-1H-1,2,4-triazol-1-yl]methyl][1,1'-biphenyl]-2-carboxylic acid;

4'-[[5-(2-butynyl)-3-cyclohexylmethyl-1H-1,2,4-triazol-1-yl]methyl][1,1'-biphenyl]-2-carboxylic acid;

4'-[[5-(2-butynyl)-3-(2-cyclohexylethyl)-1H-1,2,4-triazol-1-yl]methyl][1,1'-biphenyl]-2-carboxylic acid;

4'-[[5-(2-butynyl)-3-cyclohexanoyl-1H-1,2,4-triazol-1-yl]methyl][1,1'-biphenyl]-2-carboxylic acid;

4'-[[5-(2-butynyl)-3-(1-oxo-2-cyclohexylethyl)-1H-1,2,4-triazol-1-yl]methyl][1,1'-biphenyl]-2-carboxylic acid;

4'-[[5-(2-butynyl)-3-phenyl-1H-1,2,4-triazol-1-yl]methyl][1,1'-biphenyl]-2-carboxylic acid;

4'-[[5-(2-butynyl)-3-phenylmethyl-1H-1,2,4-triazol-1-yl]methyl][1,1'-biphenyl]-2-carboxylic acid;

4'-[[5-(2-butynyl)-3-(2-phenylethyl)-1H-1,2,4-triazol-1-yl]methyl][1,1'-biphenyl]-2-carboxylic acid;

4'-[[5-(2-butynyl)-3-benzoyl-1H-1,2,4-triazol-1-yl]methyl][1,1'-biphenyl]-2-carboxylic acid;

4'-[[5-(2-butynyl)-3-(1-oxo-2-phenylethyl)-1H-1,2,4-triazol-1-yl]methyl][1,1'-biphenyl]-2-carboxylic acid;

4'-[[5-(2-butynyl)-3-(1,1-dimethoxypropyl)-1H-1,2,4-triazol-1-yl]methyl][1,1'-biphenyl]-2-carboxylic acid;

4'-[[5-(2-butynyl)-3-(1,1-dimethoxybutyl)-1H-1,2,4-triazol-1-yl]methyl][1,1'-biphenyl]-2-carboxylic acid;

4'-[[5-(2-butynyl)-3-(1,1-dimethoxypentyl)-1H-1,2,4-triazol-1-yl]methyl][1,1'-biphenyl]-2-carboxylic acid;

4'-[[5-(2-butynyl)-3-(1-oxopropyl)-1H-1,2,4-triazol-1-yl]methyl][1,1'-biphenyl]-2-carboxylic acid;

4'-[[5-(2-butynyl)-3-(1-oxobutyl)-1H-1,2,4-triazol-1-yl]methyl][1,1'-biphenyl]-2-carboxylic acid;

4'-[[5-(2-butynyl)-3-(1-oxopentyl)-1H-1,2,4-triazol-1-yl]methyl][1,1'-biphenyl]-2-carboxylic acid;

4'-[[5-(2-butynyl)-3-(1,1-difluoroethyl)-1H-1,2,4-triazol-1-yl]methyl][1,1'-biphenyl]-2-carboxylic acid;

4'-[[5-(2-butynyl)-3-(1,1-difluoropropyl)-1H-1,2,4-triazol-1-yl]methyl][1,1'-biphenyl]-2-carboxylic acid;

4'-[[5-(2-butynyl)-3-(1,1-difluorobutyl)-1H-1,2,4-triazol-1-yl]methyl][1,1'-biphenyl]-2-carboxylic acid;

4'-[[5-(2-butynyl)-3-(1,1-difluoropentyl)-1H-1,2,4-triazol-1-yl]methyl][1,1'-biphenyl]-2-carboxylic acid;

4'-[[5-(3-butynyl)-3-ethyl-1H-1,2,4-triazol-1-yl]methyl][1,1'-biphenyl]-2-carboxylic acid;

4'-[[5-(3-butynyl)-3-propyl-1H-1,2,4-triazol-1-yl]methyl][1,1'-biphenyl]-2-carboxylic acid;

4'-[[5-(3-butynyl)-3-isopropyl-1H-1,2,4-triazol-1-yl]methyl][1,1'-biphenyl]-2-carboxylic acid;

4'-[[5-(3-butynyl)-3-butyl-1H-1,2,4-triazol-1-yl]methyl][1,1'-biphenyl]-2-carboxylic acid;

4'-[[5-(3-butynyl)-3-secbutyl-1H-1,2,4-triazol-1-yl]methyl][1,1'-biphenyl]-2-carboxylic acid;

4'-[5[-(3-butynyl)-3-isobutyl-1H-1,2,4-triazol-1-yl]methyl][1,1'-biphenyl]-2-carboxylic acid;

4'-[[5-(3-butynyl)-3-tertbutyl-1H-1,2,4-triazol-1-yl]methyl][1,1'-biphenyl]-2-carboxylic acid;

4'-[[5-(3-butynyl)-3-isopentyl-1H-1,2,4-triazol-1-yl]methyl][1,1'-biphenyl]-2-carboxylic acid;

4'-[[5-(3-butynyl)-3-pentyl-1H-1,2,4-triazol-1-yl]methyl][1,1'-biphenyl]-2-carboxylic acid;

4'-[[5-(3-butynyl)-3-mercapto-1H-1,2,4-triazol-1-yl]methyl][1,1'-biphenyl]-2-carboxylic acid;

4'-[[5-(3-butynyl)-3-thiomethyl-1H-1,2,4-triazol-1-yl]methyl][1,1'-biphenyl]-2-carboxylic acid;

4'-[[5-(3-butynyl)-3-thioethyl-1H-1,2,4-triazol-1-yl]methyl][1,1'-biphenyl]-2-carboxylic acid;

4'-[[5-(3-butynyl)-3-thiopropyl-1H-1,2,4-triazol-1-yl]methyl][1,1'-biphenyl]-2-carboxylic acid;

4'-[[5-(3-butynyl)-3-hydroxy-1H-1,2,4-triazol-1-yl]methyl][1,1'-biphenyl]-2-carboxylic acid;

4'-[[5-(3-butynyl)-3-methoxy-1H-1,2,4-triazol-1-yl]methyl][1,1'-biphenyl]-2-carboxylic acid;

4'-[[5-(3-butynyl)-3-ethoxy-1H-1,2,4-triazol-1-yl]methyl][1,1'-biphenyl]-2-carboxylic acid;

4'-[[5-(3-butynyl)-3-propoxy-1H-1,2,4-triazol-1-yl]methyl][1,1'-biphenyl]-2-carboxylic acid;

4'-[[5-(3-butynyl)-3-cyclohexyl-1H-1,2,4-triazol-1-yl]methyl][1,1'-biphenyl]-2-carboxylic acid;

4'-[[5-(3-butynyl)-3-cyclohexylmethyl-1H-1,2,4-triazol-1-yl]methyl][1,1'-biphenyl]-2-carboxylic acid;

4'-[[5-(3-butynyl)-3-(2-cyclohexylethyl)-1H-1,2,4-triazol-1-yl]methyl][1,1'-biphenyl]-2-carboxylic acid;

4'-[[5-(3-butynyl)-3-cyclohexanoyl-1H-1,2,4-triazol-1-yl]methyl][1,1'-biphenyl]-2-carboxylic acid;

4'-[[5-(3-butynyl)-3-(1-oxo-2-cyclohexylethyl)-1H-1,2,4-triazol-1-yl]methyl][1,1'-biphenyl]-2-carboxylic acid;

4'-[[5-(3-butynyl)-3-phenyl-1H-1,2,4-triazol-1-yl]methyl][1,1'-biphenyl]-2-carboxylic acid;

4'-[[5-(3-butynyl)-3-phenylmethyl-1H-1,2,4-triazol-1-yl]methyl][1,1'-biphenyl]-2-carboxylic acid;

4'-[[5-(3-butynyl)-3-(2-phenylethyl)-1H-1,2,4-triazol-1-yl]methyl][1,1'-biphenyl]-2-carboxylic acid;

4'-[[5-(3-butynyl)-3-benzoyl-1H-1,2,4-triazol-1-yl]methyl][1,1'-biphenyl]-2-carboxylic acid;

4'-[[5-(3-butynyl)-3-(1-oxo-2-phenylethyl)-1H-1,2,4-triazol-1-yl]methyl][1,1'-biphenyl]-2-carboxylic acid;

4'-[[5-(3-butynyl)-3-(1,1-dimethoxypropyl)-1H-1,2,4-triazol-1-yl]methyl][1,1'-biphenyl]-2-carboxylic acid;

4'-[[5-(3-butynyl)-3-(1,1-dimethoxybutyl)-1H-1,2,4-triazol-1-yl]methyl][1,1'-biphenyl]-2-carboxylic acid;

4'-[[5-(3-butynyl)-3-(1,1-dimethoxypentyl)-1H-1,2,4-triazol-1-yl]methyl][1,1'-biphenyl]-2-carboxylic acid;

4'-[[5-(3-butynyl)-3-(1-oxopropyl)-1H-1,2,4-triazol-1-yl]methyl][1,1'-biphenyl]-2-carboxylic acid;

4'-[[5-(3-butynyl)-3-(1-oxobutyl)-1H-1,2,4-triazol-1-yl]methyl][1,1'-biphenyl]-2-carboxylic acid;

4'-[[5-(3-butynyl)-3-(1-oxopentyl)-1H-1,2,4-triazol-1-yl]methyl][1,1'-biphenyl]-2-carboxylic acid;

4'-[[5-(3-butynyl)-3-(1,1-difluoroethyl)-1H-1,2,4-triazol-1-yl]methyl][1,1'-biphenyl]-2-carboxylic acid;

4'-[[5-(3-butynyl)-3-(1,1-difluoropropyl)-1H-1,2,4-triazol-1-yl]methyl][1,1'-biphenyl]-2-carboxylic acid;

4'-[[5-(3-butynyl)-3-(1,1-difluorobutyl)-1H-1,2,4-triazol-1-yl]methyl][1,1'-biphenyl]-2-carboxylic acid;

4'-[[5-(3-butynyl)-3-(1,1-difluoropentyl)-1H-1,2,4-triazol-1-yl]methyl][1,1'-biphenyl]-2-carboxylic acid;

4'-[(3,5-diethoxy-1H-1,2,4-triazol-1-yl)methyl][1,1'-biphenyl]-2-carboxylic acid;

4'-[(3,5-dipropoxy-1H-1,2,4-triazol-1-yl)methyl][1,1'-biphenyl]-2-carboxylic acid;

4'-[(3,5-diisopropoxy-1H-1,2,4-triazol-1-yl)methyl][1,1'-biphenyl]-2-carboxylic acid;

4'-[(3,5-dibutoxy-1H-1,2,4-triazol-1-yl)methyl][1,1'-biphenyl]-2-carboxylic acid;

4'-[(3,5-dithiomethyl-1H-1,2,4-triazol-1-yl)methyl][1,1'-biphenyl]-2-carboxylic acid;

4'-[(3,5-dithioethyl-1H-1,2,4-triazol-1-yl)methyl][1,1'-biphenyl]-2-carboxylic acid;

4'-[(3,5-dithiopropyl-1H-1,2,4-triazol-1-yl)methyl][1,1'-biphenyl]-2-carboxylic acid;

4'-[(3,5-dithioisopropyl-1H-1,2,4-triazol-1-yl)methyl][1,1'-biphenyl]-2-carboxylic acid;

4'-[[3,5-di(1-butenyl)-1H-1,2,4-triazol-1-yl]methyl][1,1'-biphenyl]-2-carboxylic acid;

4'-[[3,5-di(2-butenyl)-1H-1,2,4-triazol-1-yl]methyl][1,1'-biphenyl]-2-carboxylic acid;

4'-[[3,5-di(3-butenyl)-1H-1,2,4-triazol-1-yl]methyl][1,1'-biphenyl]-2-carboxylic acid;

4'-[[3,5-di(1-butynyl)-1H-1,2,4-triazol-1-yl]methyl][1,1'-biphenyl]-2-carboxylic acid;

4'-[[3,5-di(2-butynyl)-1H-1,2,4-triazol-1-yl]methyl][1,1'-biphenyl]-2-carboxylic acid; and 4'-[[3,5-di(3-butynyl)-1H-1,2,4-triazol-1-yl]methyl][1,1'-biphenyl]-2-carboxylic acid.

Another family of specific angiotensin II antagonist compounds of Formula I, from which a suitable first component of the conjugate may be selected, consists of biphenylmethyl 1H-substituted-1,2,4-triazole compounds listed below having an amino terminal moiety attached at the $R^1$ or $R^2$ positions of Formula I. Such amino terminal moiety may be reacted directly with the carboxylic acid moiety of a second component of the conjugate, such as a glutamic acid residue to form an enzyme-cleavable bond. Specific examples of these compounds are listed below:

5-[4'-[(5-ethyl-3-amino-1H-1,2,4-triazol-1-yl)methyl][1,1'-biphenyl]-2-yl]-1H-tetrazole;

5-[4'-[(5-ethyl-3-aminomethyl-1H-1,2,4-triazol-1-yl)methyl][1,1'-biphenyl]-2-'yl]-1H-tetrazole;

5-[4'-[(5-ethyl-3-aminoethyl-1H-1,2,4-triazol-1-yl)methyl][1,1'-biphenyl]-2-yl]-1H-tetrazole;

5-[4'-[(5-ethyl-3-aminopropyl-1H-1,2,4-triazol-1-yl)methyl][1,1'-biphenyl]-2-yl]-1H-tetrazole;

5-[4'-[(5-ethyl-3-aminobutyl-1H-1,2,4-triazol-1-yl)methyl][1,1'-biphenyl]-2-yl]-1H-tetrazole;

5-[4'-[[3-ethyl-5-(4-aminophenyl)-1H-1,2,4-triazol-1-yl]methyl][1,1'-biphenyl]-2-yl]-1H-tetrazole;

5-[4'-[[3-ethyl-5-(4-aminophenylmethyl)-1H-1,2,4-triazol-1-yl]methyl][1,1'-biphenyl]-2-yl]-1H-tetrazole;

5-[4'-[[3-ethyl-5-(4-aminophenylethyl)-1H-1,2,4-triazol-1-yl]methyl][1,1'-biphenyl]-2-yl]-1H-tetrazole;

5-[4'-[[3-ethyl-5-(4-aminomethylphenylmethyl)-1H-1,2,4-triazol-1-yl]methyl][1,1'-biphenyl]-2-yl]-1H-tetrazole;

5-[4'-[[3-ethyl-5-(4-aminomethylphenyl)-1H-1,2,4-triazol-1-yl]methyl][1,1'-biphenyl]-2-yl]-1H-tetrazole;

5-[4'-[[3-ethyl-5-(4-aminoethylphenyl)-1H-1,2,4-triazol-1-yl]methyl][1,1'-biphenyl]-2-yl]-1H-tetrazole;

5-[4'-[[3-ethyl-5-(4-aminocyclohexyl)-1H-1,2,4-triazol-1-yl]methyl][1,1'-biphenyl]-2-yl]-1H-tetrazole;

5-[4'-[[3-ethyl-5-(4-aminocyclohexylmethyl)-1H-1,2,4-triazol-1-yl]methyl][1,1-biphenyl]-2-yl]-1H-tetrazole;

5-[4'-[[3-ethyl-5-(4-aminocyclohexylethyl)-1H-1,2,4-triazol-1-yl]methyl][1,1'-biphenyl]-2-yl]-1H-tetrazole;

5-[4'-[[3-ethyl-5-(4-aminomethylcyclohexylmethyl)-1H-1,2,4-triazol-1-yl]methyl][1,1'-biphenyl]-2-yl]-1H-tetrazole;

5-[4'-[[3-ethyl-5-(4-aminomethylcyclohexyl)-1H-1,2,4-triazol-1-yl]methyl][1,1'-biphenyl]-2-yl]-1H-tetrazole;

5-[4'-[[3-ethyl-5-(4-aminoethylcyclohexyl)-1H-1,2,4-triazol-1-yl]methyl][1,1'-biphenyl]-2-yl]-1H-tetrazole;

5-[4'-[(5-propyl-3-amino-1H-1,2,4-triazol-1-yl)methyl][1,1'-biphenyl]-2-yl]-1H-tetrazole;

5-[4'-[(5-propyl-3-aminomethyl-1H-1,2,4-triazol-1-yl)methyl][1,1'-biphenyl]-2-yl]-1H-tetrazole;

5-[4'-[(5-propyl-3-aminoethyl-1H-1,2,4-triazol-1-yl)methyl][1,1'-biphenyl]-2-yl]-1H-tetrazole;

5-[4'-[(5-propyl-3-aminopropyl-1H-1,2,4-triazol-1-yl)methyl][1,1'-biphenyl]-2-yl]-1H-tetrazole;

5-[4'-[(5-propyl-3-aminobutyl-1H-1,2,4-triazol-1-yl)methyl][1,1'-biphenyl]-2-yl]-1H-tetrazole;

5-[4'-[[3-propyl-5-(4-aminophenyl)-1H-1,2,4-triazol-1-yl]methyl][1,1'-biphenyl]-2-yl]-1H-tetrazole;

5-[4'-[[3-propyl-5-(4-aminophenylmethyl)-1H-1,2,4-triazol-1-yl]methyl][1,1'-biphenyl]-2-yl]-1H-tetrazole;

5-[4'-[[3-propyl-5-(4-aminophenylethyl)-1H-1,2,4-triazol-1-yl]methyl][1,1'-biphenyl]-2-yl]-1H-tetrazole;

5-[4'-[[3-propyl-5-(4-aminomethylphenylmethyl)-1H-1,2,4-triazol-1-yl]methyl][1,1'-biphenyl]-2-yl]-1H-tetrazole;

5-[4'-[[3-propyl-5-(4-aminomethylphenyl)-1H-1,2,4-triazol-1-yl]methyl][1,1'-biphenyl]-2-yl]-1H-tetrazole;

5-[4'-[[3-propyl-5-(4-aminoethylphenyl)-1H-1,2,4-triazol-1-yl]methyl][1,1'-biphenyl]-2-yl]-1H-tetrazole;

5-[4'-[[3-propyl-5-(4-aminocyclohexyl)-1H-1,2,4-triazol-1-yl]methyl][1,1'-biphenyl]-2-yl]-1H-tetrazole;

5-[4'-[[3-propyl-5-(4-aminocyclohexylmethyl)-1H-1,2,4-triazol-1-yl]methyl][1,1'-biphenyl]-2-yl]-1H-tetrazole;

5-[4'-[[3-propyl-5-(4-aminocyclohexylethyl)-1H-1,2,4-triazol-1-yl]methyl][1,1-biphenyl]-2-yl]-1H-tetrazole;

5-[4'-[[3-propyl-5-(4-aminomethylcyclohexylmethyl)-1H-1,2,4-triazol-1-yl]methyl][1,1'-biphenyl]-2-yl]-1H-tetrazole;

5-[4'-[[3-propyl-5-(4-aminomethylcyclohexyl)-1H-1,2,4-triazol-1-yl]methyl][1,1'-biphenyl]-2-yl]-1H-tetrazole;

5-[4'-[[3-propyl-5-(4-aminoethylcyclohexyl)-1H-1,2,4-triazol-1-yl]methyl][1,1'-biphenyl]-2-yl]-1H-tetrazole;

5-[4'-[(5-isopropyl-3-amino-1H-1,2,4-triazol-1-yl)methyl][1,1'-biphenyl]-2-yl]-1H-tetrazole;

5-[4'-[(5-isopropyl-3-aminomethyl-1H-1,2,4-triazol-1-yl)methyl][1,1'-biphenyl]-2-yl]-1H-tetrazole;

5-[4'-[(5-isopropyl-3-aminoethyl-1H-1,2,4-triazol-1-yl)methyl][1,1'-biphenyl]-2-yl]-1H-tetrazole;

5-[4'-[(5-isopropyl-3-aminopropyl-1H-1,2,4-triazol-1-yl)methyl][1,1'-biphenyl]-2-yl]-1H-tetrazole;

5-[4'-[(5-isopropyl-3-aminobutyl-1H-1,2,4-triazol-1-yl)methyl][1,1'-biphenyl]-2-yl]-1H-tetrazole;

5-[4'-[[3-isopropyl-5-(4-aminophenyl)-1H-1,2,4-triazol-1-yl]methyl][1,1'-biphenyl]-2-yl]-1H-tetrazole;

5-[4'-[[3-isopropyl-5-(4-aminophenylmethyl)-1H-1,2,4-triazol-1-yl]methyl][1,1'-biphenyl]-2-yl]-1H-tetrazole;

5-[4'-[[3-isopropyl-5-(4-aminophenylethyl)-1H-1,2,4-triazol-1-yl]methyl][1,1'-biphenyl]-2-yl]-1H-tetrazole;

5-[4'-[[3-isopropyl-5-(4-aminomethylphenylmethyl)-1H-1,2,4-triazol-1-yl]methyl][1,1'-biphenyl]-2-yl]-1H-tetrazole;

5-[4'-[[3-isopropyl-5-(4-aminomethylphenyl)-1H-1,2,4-triazol-1-yl]methyl][1,1'-biphenyl]-2-yl]-1H-tetrazole;

5-[4'-[[3-isopropyl-5-(4-aminoethylphenyl)-1H-1,2,4-triazol-1-yl]methyl][1,1'-biphenyl]-2-yl]-1H-tetrazole;

5-[4'-[[3-isopropyl-5-(4-aminocyclohexyl)-1H-1,2,4-triazol-1-yl]methyl][1,1'-biphenyl]-2-yl]-1H-tetrazole;

5-[4'-[[3-isopropyl-5-(4-aminocyclohexylmethyl)-1H-1,2,4-triazol-1-yl]methyl][1,1'-biphenyl]-2-yl]-1H-tetrazole;

5-[4'-[[3-isopropyl-5-(4-aminocyclohexylethyl)-1H-1,2,4-triazol-1-yl]methyl][1,1'-biphenyl]-2-yl]-1H-tetrazole;

5-[4'-[[3-isopropyl-5-(4-aminomethylcyclohexylmethyl)-1H-1,2,4-triazol-1-yl]methyl][1,1'-biphenyl]-2-yl]-1H-tetrazole;

5-[4-[[3-isopropyl-5-(4-aminomethylcyclohexyl)-1H-1,2,4-triazol-1-yl]methyl][1,1'-biphenyl]-2-yl]-1H-tetrazole;

5-[4'-[[3-isopropyl-5-(4-aminoethylcyclohexyl)-1H-1,2,4-triazol-1-yl]methyl][1,1'-biphenyl]-2-yl]-1H-tetrazole;

5-[4'-[(5-butyl-3-amino-1H-1,2,4-triazol-1-yl)methyl][1,1'-biphenyl]-2-yl]-1H-tetrazole;

5-[4'-[(5-butyl-3-aminomethyl-1H-1,2,4-triazol-1-yl)methyl][1,1'-biphenyl]-2-yl]-1H-tetrazole;

5-[4]-[(5-butyl-3-aminoethyl-1H-1,2,4-triazol-1-yl)methyl][1,1'-biphenyl]-2-yl]-1H-tetrazole;

5-[4'-[(5-butyl-3-aminopropyl-1H-1,2,4-triazol-1-yl)methyl][1,1'-biphenyl]-2-yl]-1H-tetrazole;

5-[4'-[(5-butyl-3-aminobutyl-1H-1,2,4-triazol-1-yl)methyl][1,1'-biphenyl]-2-yl]-1H-tetrazole;

5-[4'-[[3-butyl-5-(4-aminophenyl)-1H-1,2,4-triazol-1-yl]methyl][1,1'-biphenyl]-2-yl]-1H-tetrazole;

5-[4'-[[3-butyl-5-(4-aminophenylmethyl)-1H-1,2,4-triazol-1-yl]methyl][1,1'-biphenyl]-2-yl]-1H-tetrazole;

5-[4'-[[3-butyl-5-(4-aminophenylethyl)-1H-1,2,4-triazol-1-yl]methyl][1,1'-biphenyl]-2-yl)-1H-tetrazole;

5-[4'-[[3-butyl-5-(4-aminomethylphenylmethyl)-1H-1,2,4-triazol-1-yl]methyl][1,1'-biphenyl]-2-yl]-1H-tetrazole;

5-[4'-[[3-butyl-5-(4-aminomethylphenyl)-1H-1,2,4-triazol-1-yl]methyl][1,1'-biphenyl]-2-yl]-1H-tetrazole;

5-[4'-[[3-butyl-5-(4-aminoethylphenyl)-1H-1,2,4-triazol-1-yl]methyl][1,1'-biphenyl]-2-yl]-1H-tetrazole;

5-[4'-[[3-butyl-5-(4-aminocyclohexyl)-1H-1,2,4-triazol-1-yl]methyl][1,1'-biphenyl]-2-yl]-1H-tetrazole;

5-[4'-[[3-butyl-5-(4-aminocyclohexylmethyl)-1H-1,2,4-triazol-1-yl]methyl][1,1'-biphenyl]-2-yl]-1H-tetrazole;

5-[4'-[[3-butyl-5-(4-aminocyclohexylethyl)-1H-1,2,4-triazol-1-yl]methyl][1,1-biphenyl]-2-yl]-1H-tetrazole;

5-[4'-[[3-butyl-5-(4-aminomethylcyclohexylmethyl)-1H-1,2,4-triazol-1-yl]methyl][1,1-biphenyl]-2-yl]-1H-tetrazole;

5-[4'-[[3-butyl-5-(4-aminomethylcyclohexyl)-1H-1,2,4-triazol-1-yl]methyl][1,1-biphenyl]-2-yl]-1H-tetrazole;

5-[4'-[[3-butyl-5-(4-aminoethylcyclohexyl)-1H-1,2,4-triazol-1-yl]methyl][1,1'-biphenyl]-2-yl]-1H-tetrazole;

5-[4'-[(5-secbutyl-3-amino-1H-1,2,4-triazol-1-yl)methyl][1,1'-biphenyl]-2-yl]-1H-tetrazole;

5-[4'-[(5-secbutyl-3-aminomethyl-1H-1,2,4-triazol-1-yl)methyl][1,1'-biphenyl]-2-yl]-1H-tetrazole;

5-[4'-[(5-secbutyl-3-aminoethyl-1H-1,2,4-triazol-1-yl)methyl][1,1'-biphenyl]-2-yl]-1H-tetrazole;

5-[4'-[(5-secbutyl-3-aminopropyl-1H-1,2,4-triazol-1-yl)methyl][1,1'-biphenyl]-2-yl]-1H-tetrazole;

5-[4'-[(5-secbutyl-3-aminobutyl-1H-1,2,4-triazol-1-yl)methyl][1,1'-biphenyl]-2-yl]-1H-tetrazole;

5-[4'-[[3-secbutyl-5-(4-aminophenyl)-1H-1,2,4-triazol-1-yl]methyl][1,1'-biphenyl]-2-yl]-1H-tetrazole;

5-[4'-[[3-secbutyl-5-(4-aminophenylmethyl)-1H-1,2,4-triazol-1-yl]methyl][1,1'-biphenyl]-2-yl]-1H-tetrazole;

5-[4'-[[3-secbutyl-5-(4-aminophenylethyl)-1H-1,2,4-triazol-1-yl]methyl][1,1'-biphenyl]-2-yl]-1H-tetrazole;

5-[4'-[[3-secbutyl-5-(4-aminomethylphenylmethyl)-1H-1,2,4-triazol-1-yl]methyl][1,1'-biphenyl]-2-yl]-1H-tetrazole;

5-[4'-[[3-secbutyl-5-(4-aminomethylphenyl)-1H-1,2,4-triazol-1-yl]methyl][1,1'-biphenyl]-2-yl]-1H-tetrazole;

5-[4'-[[3-secbutyl-5-(4-aminoethylphenyl)-1H-1,2,4-triazol-1-yl]methyl][1,1'-biphenyl]-2-yl]-1H-tetrazole;

5-[4'-[[3-secbutyl-5-(4-aminocyclohexyl)-1H-1,2,4-triazol-1-yl]methyl][1,1'-biphenyl]-2-yl]-1H-tetrazole;

5-[4'-[[3-secbutyl-5-(4-aminocyclohexylmethyl)-1H-1,2,4-triazol-1-yl]methyl][1,1'-biphenyl]-2-yl]-1H-tetrazole;

5-[4'-[[3-secbutyl-5-(4-aminocyclohexylethyl)-1H-1,2,4-triazol-1-yl]methyl][1,1'-biphenyl]-2-yl]-1H-tetrazole;

5-[4'-[[3-secbutyl-5-(4-aminomethylcyclohexylmethyl)-1H-1,2,4-triazol-1-yl]methyl][1,1'-biphenyl]-2-yl]-1H-tetrazole;

5-[4'-[[3-secbutyl-5-(4-aminomethylcyclohexyl)-1H-1,2,4-triazol-1-yl]methyl][1,1'-biphenyl]-2-yl]-1H-tetrazole;

5-[4'-[[3-secbutyl-5-(4-aminoethylcyclohexyl)-1H-1,2,4-triazol-1-yl]methyl][1,1'-biphenyl]-2-yl]-1H-tetrazole;

5-[4'-[(5-isobutyl-3-amino-1H-1,2,4-triazol-1-yl)methyl][1,1'-biphenyl]-2-yl]-1H-tetrazole;

5-[4'-[(5-isobutyl-3-aminomethyl-1H-1,2,4-triazol-1-yl)methyl][1,1'-biphenyl]-2-yl]-1H-tetrazole;

5-[4'-[(5-isobutyl-3-aminoethyl-1H-1,2,4-triazol-1-yl)methyl][1,1'-biphenyl]-2-yl]-1H-tetrazole;

5-[4'-[(5-isobutyl-3-aminopropyl-1H-1,2,4-triazol-1-yl)methyl][1,1'-biphenyl]-2-yl]-1H-tetrazole;

5-[4'-[(5-isobutyl-3-aminobutyl-1H-1,2,4-triazol-1-yl)methyl][1,1'-biphenyl]-2-yl]-1H-tetrazole;

5-[4-'-[[3-isobutyl-5-(4-aminophenyl)-1H-1,2,4-triazol-1-yl]methyl][1,1'-biphenyl]-2-yl]-1H-tetrazole;

5-[4'-[[3-isobutyl-5-(4-aminophenylmethyl)-1H-1,2,4-triazol-1-yl]methyl][1,1'-biphenyl]-2-yl]-1H-tetrazole;

5-[4'-[[3-isobutyl-5-(4-aminophenylethyl)-1H-1,2,4-triazol-1-yl]methyl][1,1'-biphenyl]-2-yl]-1H-tetrazole;

5-[4'-[[3-isobutyl-5-(4-aminomethylphenylmethyl)-1H-1,2,4-triazol-1-yl]methyl][1,1'-biphenyl]-2-yl]-1H-tetrazole;

5-[4'-[[3-isobutyl-5-(4-aminomethylphenyl)-1H-1,2,4-triazol-1-yl]methyl][1,1'-biphenyl]-2-yl]-1H-tetrazole;

5-[4'-[[3-isobutyl-5-(4-aminoethylphenyl)-1H-1,2,4-triazol-1-yl]methyl][1,1'-biphenyl]-2-yl]-1H-tetrazole;

5-[4'-[[3-isobutyl-5-(4-aminocyclohexyl)-1H-1,2,4-triazol-1-yl]methyl][1,1'-biphenyl]-2-yl]-1H-tetrazole;

5-[4'-[[3-isobutyl-5-(4-aminocyclohexylmethyl)-1H-1,2,4-triazol-1-yl]methyl][1,1'-biphenyl]-2-yl]-1H-tetrazole;

5-[4'-[[3-isobutyl-5-(4-aminocyclohexylethyl)-1H-1,2,4-triazol-1-yl]methyl][1,1'-biphenyl]-2-yl]-1H-tetrazole;

5-[4'-[[3-isobutyl-5-(4-aminomethylcyclohexylmethyl)-1H-1,2,4-triazol-1-yl]methyl][1,1'-biphenyl]-2-yl]-1H-tetrazole;

5-[4'-[[3-isobutyl-5-(4-aminomethylcyclohexyl)-1H-1,2,4-triazol-1-yl]methyl][1,1'-biphenyl]-2-yl]-1H-tetrazole;

5-[4'-[[3-isobutyl-5-(4-aminoethylcyclohexyl)-1H-1,2,4-triazol-1-yl]methyl][1,1-biphenyl]-2-yl]-1H-tetrazole;

5-[4'-[(5-tertbutyl-3-amino-1H-1,2,4-triazol-1-yl)methyl][1,1'-biphenyl]-2-yl]-1H-tetrazole;

5-[4'-[(5-tertbutyl-3-aminomethyl-1H-1,2,4-triazol-1-yl)methyl][1,1'-biphenyl]-2-yl]-1H-tetrazole;

5-[4'-[(5-tertbutyl-3-aminoethyl-1H-1,2,4-triazol-1-yl)methyl][1,1'-biphenyl]-2-yl]-1H-tetrazole;

5-[4'-[(5-tertbutyl-3-aminopropyl-1H-1,2,4-triazol-1-yl)methyl][1,1'-biphenyl]-2-yl]-1H-tetrazole;

5-[4'-[(5-tertbutyl-3-aminobutyl-1H-1,2,4-triazol-1-yl)methyl][1,1'-biphenyl]-2-yl]-1H-tetrazole;

5-[4'-4[[3-tertbutyl-5-(4-aminophenyl)-1H-1,2,4-triazol-1-yl]methyl][1,1'-biphenyl]-2-yl]-1H-tetrazole;

5-[4'-[[3-tertbutyl-5-(4-aminophenylmethyl)-1H-1,2,4-triazol-1-yl]methyl][1,1'-biphenyl]-2-yl]-1H-tetrazole;

5-[4'-[[3-tertbutyl-5-(4-aminophenylethyl)-1H-1,2,4-triazol-1-yl]methyl][1,1'-biphenyl]-2-yl]-1H-tetrazole;

5-[4'-[[3-tertbutyl-5-(4-aminomethylphenylmethyl)-1H-1,2,4-triazol-1-yl]methyl][1,1'-biphenyl]-2-yl]-1H-tetrazole;

5-[4'-[[3-tertbutyl-5-(4-aminomethylphenyl)-1H-1,2,4-triazol-1-yl]methyl][1,1'-biphenyl]-2-yl]-1H-tetrazole;

5-[4'-[[3-tertbutyl-5-(4-aminoethylphenyl)-1H-1,2,4-triazol-1-yl]methyl][1,1'-biphenyl]-2-yl]-1H-tetrazole;

5-[4'-[[3-tertbutyl-5-(4-aminocyclohexyl)-1H-1,2,4-triazol-1-yl]methyl][1,1'-biphenyl]-2-yl]-1H-tetrazole;

5-[4'-[[3-tertbutyl-5-(4-aminocyclohexylmethyl)-1H-1,2,4-triazol-1-yl]methyl][1,1'-biphenyl]-2-yl]-1H-tetrazole;

5-[4'-[[3-tertbutyl-5-(4-aminocyclohexylethyl)-1H-1,2,4-triazol-1-yl]methyl][1,1'-biphenyl]-2-yl]-1H-tetrazole;

5-[4'-[[3-tertbutyl-5-(4-aminomethylcyclohexylmethyl)-1H-1,2,4-triazol-1-yl]methyl][1,1'-biphenyl]-2-yl]-1H-tetrazole;

5-[4'-[[3-tertbutyl-5-(4-aminomethylcyclohexyl)-1H-1,2,4-triazol-1-yl]methyl][1,1'-biphenyl]-2-yl]-1H-tetrazole;

5-[4'-[[3-tertbutyl-5-(4-aminoethylcyclohexyl)-1H-1,2,4-triazol-1-yl]methyl][1,1'-biphenyl]-2-yl]-1H-tetrazole;

5-[4'-[(5-pentyl-3-amino-1H-1,2,4-triazol-1-yl)methyl][1,1'-biphenyl]-2-yl]-1H-tetrazole;

5-[43-[(5-pentyl-3-aminomethyl-1H-1,2,4-triazol-1-yl)methyl][1,1'-biphenyl]-2-yl]-1H-tetrazole;

5-[4'-[(5-pentyl-3-aminoethyl-1H-1,2,4-triazol-1-yl)methyl][1,1'-biphenyl]-2-yl]-1H-tetrazole;

5-[4'-[(5-pentyl-3-aminopropyl-1H-1,2,4-triazol-1-yl)methyl][1,1'-biphenyl]-2-yl]-1H-tetrazole;

5-[4'-[(5-pentyl-3-aminobutyl-1H-1,2,4-triazol-1-yl)methyl][1,1'-biphenyl]-2-yl]-1H-tetrazole;

5-[4'-[[3-pentyl-5-(4-aminophenyl)-1H-1,2,4-triazol-1-yl]methyl][1,1'-biphenyl]-2-yl]-1H-tetrazole;

5-[4'-[[3-pentyl-5-(4-aminophenylmethyl)-1H-1,2,4-triazol-1-yl]methyl][1,1'-biphenyl]-2-yl]-1H-tetrazole;

5-[4'-[[3-pentyl-5-(4-aminophenylethyl)-1H-1,2,4-triazol-1-yl]methyl][1,1'-biphenyl]-2-yl]-1H-tetrazole;

5-[4'-[[3-pentyl-5-(4-aminomethylphenylmethyl)-1H-1,2,4-triazol-1-yl]methyl][1,1-biphenyl]-2-yl]-1H-tetrazole;

5-[4'-[[3-pentyl-5-(4-aminomethylphenyl)-1H-1,2,4-triazol-1-yl]methyl][1,1'-biphenyl]-2-yl]-1H-tetrazole;

5-[4'-[[3-pentyl-5-(4-aminoethylphenyl)-1H-1,2,4-triazol-1-yl]methyl][1,1'-biphenyl]-2-yl]-1H-tetrazole;

5-[4'-[[3-pentyl-5-(4-aminocyclohexyl)-1H-1,2,4-triazol-1-yl]methyl][1,1'-biphenyl]-2-yl]-1H-tetrazole;

5-[4'-[[3-pentyl-5-(4-aminocyclohexylmethyl)-1H-1,2,4-triazol-1-yl]methyl][1,1'-biphenyl]-2-yl]-1H-tetrazole;

5-[4'-[[3-pentyl-5-(4-aminocyclohexylethyl)-1H-1,2,4-triazol-1-yl]methyl][1,1'-biphenyl]-2-yl]-1H-tetrazole;

5-[4'-[[3-pentyl-5-(4-aminomethylcyclohexylmethyl)-1H-1,2,4-triazol-1-yl]methyl][1,1'-biphenyl]-2-yl]-1H-tetrazole;

5-[4'-[[3-pentyl-5-(4-aminomethylcyclohexyl)-1H-1,2,4-triazol-1-yl]methyl][1,1'-biphenyl]-2-yl]-1H-tetrazole;

5-[4'-[[3-pentyl-5-(4-aminoethylcyclohexyl)-1H-1,2,4-triazol-1-yl]methyl][1,1'-biphenyl]-2-yl]-1H-tetrazole;

5-[4'-[(5-isopentyl-3-amino-1H-1,2,4-triazol-1-yl)methyl][1,1'-biphenyl]-2-yl]-1H-tetrazole;

5-[4'-[(5-isopentyl-3-aminomethyl-1H-1,2,4-triazol-1-yl)methyl][1,1'-biphenyl]-2-yl]-1H-tetrazole;

5-[4'-[(5-isopentyl-3-aminoethyl-1H-1,2,4-triazol-1-yl)methyl][1,1'-biphenyl]-2-yl]-1H-tetrazole;

5-[4'-[(5-isopentyl-3-aminopropyl-1H-1,2,4-triazol-1-yl)methyl][1,1'-biphenyl]-2-yl]-1H-tetrazole;

5-[4'-[(5-isopentyl-3-aminobutyl-1H-1,2,4-triazol-1-yl)methyl][1,1'-biphenyl]-2-yl]-1H-tetrazole;

5-[4'-[[3-isopentyl-5-(4-aminophenyl)-1H-1,2,4-triazol-1-yl]methyl][1,1'-biphenyl]-2-yl]-1H-tetrazole;

5-[4'-[[3-isopentyl-5-(4-aminophenylmethyl)-1H-1,2,4-triazol-1-yl]methyl][1,1'-biphenyl]-2-yl]-1H-tetrazole;

5-[4'-[[3-isopentyl-5-(4-aminophenylethyl)-1H-1,2,4-triazol-1-yl]methyl][1,1'-biphenyl]-2-yl]-1H-tetrazole;

5-[4'-[[3-isopentyl-5-(4-aminomethylphenylmethyl)-1H-1,2,4-triazol-1-yl]methyl][1,1'-biphenyl]-2-yl]-1H-tetrazole;

5-[4'-[[3-isopentyl-5-(4-aminomethylphenyl)-1H-1,2,4-triazol-1-yl]methyl][1,1'-biphenyl]-2-yl]-1H-tetrazole;

5-[4'-[[3-isopentyl-5-(4-aminoethylphenyl)-1H-1,2,4-triazol-1-yl]methyl][1,1'-biphenyl]-2-yl]-1H-tetrazole;

5-[4'-[[3-isopentyl-5-(4-aminocyclohexyl)-1H-1,2,4-triazol-1-yl]methyl][1,1'-biphenyl]-2-yl]-1H-tetrazole;

5-[4'-[[3-isopentyl-5-(4-aminocyclohexylmethyl)-1H-1,2,4-triazol-1-yl]methyl][1,1'-biphenyl]-2-yl]-1H-tetrazole;

5-[4'-[[3-isopentyl-5-(4-aminocyclohexylethyl)-1H-1,2,4-triazol-1-yl]methyl][1,1'-biphenyl]-2-yl]-1H-tetrazole;

5-[4'-[[3-isopentyl-5-(4-aminomethylcyclohexylmethyl)-1H-1,2,4-triazol-1-yl]methyl][1,1'-biphenyl]-2-yl]-1H-tetrazole;

5-[4'-[[3-isopentyl-5-(4-aminomethylcyclohexyl)-1H-1,2,4-triazol-1-yl]methyl][1,1'-biphenyl]-2-yl]-1H-tetrazole;

5-[4'-[[3-isopentyl-5-(4-aminoethylcyclohexyl)-1H-1,2,4-triazol-1-yl]methyl][1,1'-biphenyl]-2-yl]-1H-tetrazole;

5-[4'-[(5-hexyl-3-amino-1H-1,2,4-triazol-1-yl)methyl][1,1'-biphenyl]-2-yl]-1H-tetrazole;

5-[4'-[(5-hexyl-3-aminomethyl-1H-1,2,4-triazol-1-yl)methyl][1,1'-biphenyl]-2-yl]-1H-tetrazole;

5-[4'-[(5-hexyl-3-aminoethyl-1H-1,2,4-triazol-1-yl)methyl][1,1'-biphenyl]-2-yl]-1H-tetrazole;

5-[4'-[(5-hexyl-3-aminopropyl-1H-1,2,4-triazol-1-yl)methyl][1,1'-biphenyl]-2-yl]-1H-tetrazole;

5-[4'-[(5-hexyl-3-aminobutyl-1H-1,2,4-triazol-1-yl)methyl][1,1'-biphenyl]-2-yl]-1H-tetrazole;

5-[4'-[[3-hexyl-5-(4-aminophenyl)-1H-1,2,4-triazol-1-yl]methyl][1,1'-biphenyl]-2-yl]-1H-tetrazole;

5-[4'-[[3-hexyl-5-(4-aminophenylmethyl)-1H-1,2,4-triazol-1-yl]methyl][1,1'-biphenyl]-2-yl]-1H-tetrazole;

5-[4'-[[3-hexyl-5-(4-aminophenylethyl)-1H-1,2,4-triazol-1-yl]methyl][1,1'-biphenyl]-2-yl]-1H-tetrazole;

5-[4'-[[3-hexyl-5-(4-aminomethylphenylmethyl)-1H-1,2,4-triazol-1-yl]methyl][1,1'-biphenyl]-2-yl]-1H-tetrazole;

5-[4'-[[3-hexyl-5-(4-aminomethylphenyl)-1H-1,2,4-triazol-1-yl]methyl][1,1'-biphenyl]-2-yl]-1H-tetrazole;

5-[4'-[[3-hexyl-5-(4-aminoethylphenyl)-1H-1,2,4-triazol-1-yl]methyl][1,1'-biphenyl]-2-yl]-1H-tetrazole;

5-[4'-[[3-hexyl-5-(4-aminocyclohexyl)-1H-1,2,4-triazol-1-yl]methyl][1,1'-biphenyl]-2-yl]-1H-tetrazole;

5-[4'-[[3-hexyl-5-(4-aminocyclohexylmethyl)-1H-1,2,4-triazol-1-yl]methyl][1,1'-biphenyl]-2-yl]-1H-tetrazole;

5-[4'-[[3-hexyl-5-(4-aminocyclohexylethyl)-1H-1,2,4-triazol-1-yl]methyl][1,1'-biphenyl]-2-yl]-1H-tetrazole;

5-[4'-[[3-hexyl-5-(4-aminomethylcyclohexylmethyl)-1H-1,2,4-triazol-1-yl]methyl][1,1'-biphenyl]-2-yl]-1H-tetrazole;

5-[4'-[[3-hexyl-5-(4-aminomethylcyclohexyl)-1H-1,2,4-triazol-1-yl]methyl][1,1'-biphenyl]-2-yl]-1H-tetrazole; and 5-[4'-[[3-hexyl-5-(4-aminoethylcyclohexyl)-1H-1,2,4-triazol-1-yl]methyl][1,1'-biphenyl]-2-yl]-1H-tetrazole.

Another family of specific angiotensin II antagonist compounds of Formula I, from which a suitable first component of the conjugate may be selected, consists of biphenylmethyl 1H-substituted-1,2,4-triazole compounds listed below having a terminal carboxylic acid moiety attached at the $R^1$ or $R^2$ positions of Formula I. Those compounds having a terminal carboxylic moiety may be reacted with one of the aforementioned linker groups, such as a hydrazine or a piperazine linker, to provide an amino terminal moiety which can then be reacted with the carboxylic acid moiety of a second component of the conjugate, such as a glutamic acid residue to form an enzyme-cleavable bond. Specific examples of these compounds are listed below:

5-[4'-[(5-ethyl-3-carboxy-1H-1,2,4-triazol-1-yl)methyl][1,1'-biphenyl]-2-yl]-1H-tetrazole;

5-[4'-[(5-ethyl-3-carboxymethyl-1H-1,2,4-triazol-1-yl)methyl][1,1'-biphenyl]-2-yl]-1H-tetrazole;

5-[4'-[(5-ethyl-3-carboxyethyl-1H-1,2,4-triazol-1-yl)methyl][1,1'-biphenyl]-2-yl]-1H-tetrazole;

5-[4'-[(5-ethyl-3-carboxypropyl-1H-1,2,4-triazol-1-yl)methyl][1,1'-biphenyl]-2-yl]-1H-tetrazole;

5-[4'-[(5-ethyl-3-carboxybutyl-1H-1,2,4-triazol-1-yl)methyl][1,1'-biphenyl]-2-yl]-1H-tetrazole;

5-[4'-[[3-ethyl-5-(4-carboxyphenyl)-1H-1,2,4-triazol-1-yl]methyl][1,1'-biphenyl]-2-yl]-1H-tetrazole;

5-[4'-[[3-ethyl-5-(4-carboxyphenylmethyl)-1H-1,2,4-triazol-1-yl]methyl][1,1'-biphenyl]-2-yl]-1H-tetrazole;

5-[4'-[[3-ethyl-5-(4-carboxyphenylethyl)-1H-1,2,4-triazol-1-yl]methyl][1,1'-biphenyl]-2-yl]-1H-tetrazole;

5-[4'-[[3-ethyl-5-(4-carboxymethylphenylmethyl)-1H-1,2,4-triazol-1-yl]methyl][1,1'-biphenyl]-2-yl]-1H-tetrazole;

5-[4'-[[3-ethyl-5-(4-carboxymethylphenyl)-1H-1,2,4-triazol-1-yl]methyl][1,1'-biphenyl]-2-yl]-1H-tetrazole;

5-[4'-[[3-ethyl-5-(4-carboxyethylphenyl)-1H-1,2,4-triazol-1-yl]methyl][1,1'-biphenyl]-2-yl]-1H-tetrazole;

5-[4'-[[3-ethyl-5-(4-carboxycyclohexyl)-1H-1,2,4-triazol-1-yl]methyl][1,1'-biphenyl]-2-yl]-1H-tetrazole;

5-[4'-[[3-ethyl-5-(4-carboxycyclohexylmethyl)-1H-1,2,4-triazol-1-yl]methyl][1,1'-biphenyl]-2-yl]-1H-tetrazole;

5-[4'-[[3-ethyl-5-(4-carboxycyclohexylethyl)-1H-1,2,4-triazol-1-yl]methyl][1,1'-biphenyl]-2-yl]-1H-tetrazole;

5-[4'-[[3-ethyl-5-(4-carboxymethylcyclohexylmethyl)-1H-1,2,4-triazol-1-yl]methyl][1,1'-biphenyl]-2-yl]-1H-tetrazole;

5-[4'-[[3-ethyl-5-(4-carboxymethylcyclohexyl)-1H-1,2,4-triazol-1-yl]methyl][1,1'-biphenyl]-2-yl]-1H-tetrazole;

5-[4'-[[3-ethyl-5-(4-carboxyethylcyclohexyl)-1H-1,2,4-triazol-1-yl]methyl][1,1'-biphenyl]-2-yl]-1H-tetrazole;

5-[4'-[(5-propyl-3-carboxy-1H-1,2,4-triazol-1-yl)methyl][1,1'-biphenyl]-2-yl]-1H-tetrazole;

5-[4'-[(5-propyl-3-carboxymethyl-1H-1,2,4-triazol-1-yl)methyl][1,1'-biphenyl]-2-yl]-1H-tetrazole;

5-[4'-[(5-propyl-3-carboxyethyl-1H-1,2,4-triazol-1-yl)methyl][1,1'-biphenyl]-2-yl]-1H-tetrazole;

5-[4'-[(5-propyl-3-carboxypropyl-1H-1,2,4-triazol-1-yl)methyl][1,1'-biphenyl]-2-yl]-1H-tetrazole;

5-[4'-[(5-propyl-3-carboxybutyl-1H-1,2,4-triazol-1-yl)methyl][1,1'-biphenyl]-2-yl]-1H-tetrazole;

5-[4'-[[3-propyl-5-(4-carboxyphenyl)-1H-1,2,4-triazol-1-yl]methyl][1,1'-biphenyl]-2-yl]-1H-tetrazole;

5-[4'-[[3-propyl-5-(4-carboxyphenylmethyl)-1H-1,2,4-triazol-1-yl]methyl][1,1'-biphenyl]-2-yl]-1H-tetrazole;

5-[4'-[[3-propyl-5-(4-carboxyphenylethyl)-1H-1,2,4-triazol-1-yl]methyl][1,1'-biphenyl]-2-yl]-1H-tetrazole;

5-[4'-[[3-propyl-5-(4-carboxymethylphenylmethyl)-1H-1,2,4-triazol-1-yl]methyl][1,1'-biphenyl]-2-yl]-1H-tetrazole;

5-[4'-[[3-propyl-5-(4-carboxymethylphenyl)-1H-1,2,4-triazol-1-yl]methyl][1,1'-biphenyl]-2-yl]-1H-tetrazole;

5-[4'-[[3-propyl-5-(4-carboxyethylphenyl)-1H-1,2,4-triazol-1-yl]methyl][1,1'-biphenyl]-2-yl]-1H-tetrazole;

5-[4'-[[3-propyl-5-(4-carboxycyclohexyl)-1H-1,2,4-triazol-1-yl]methyl][1,1'-biphenyl]-2-yl]-1H-tetrazole;

5-[4'-[[3-propyl-5-(4-carboxycyclohexylmethyl)-1H-1,2,4-triazol-1-yl]methyl][1,1-biphenyl]-2-yl]-1H-tetrazole;

5-[4'-[[3-propyl-5-(4-carboxycyclohexylethyl)-1H-1,2,4-triazol-1-yl]methyl][1,1'-biphenyl]-2-yl]-1H-tetrazole;

5-[4'-[[3-propyl-5-(4-carboxymethylcyclohexylmethyl)-1H-1,2,4-triazol-1-yl]methyl][1,1'-biphenyl]-2-yl]-1H-tetrazole;

5-[4'-[[3-propyl-5-(4-carboxymethylcyclohexyl)-1H-1,2,4-triazol-1-yl]methyl][1,1'-biphenyl]-2-yl]-1H-tetrazole;

5-[4'-[[3-propyl-5-(4-carboxyethylcyclohexyl)-1H-1,2,4-triazol-1-yl]methyl][1,1'-biphenyl]-2-yl]-1H-tetrazole;

5-[4'-[(5-isopropyl-3-carboxy-1H-1,2,4-triazol-1-yl)methyl][1,1'-biphenyl]-2-yl]-1H-tetrazole;

5-[4'-[(5-isopropyl-3-carboxymethyl-1H-1,2,4-triazol-1-yl)methyl][1,1'-biphenyl]-2-yl]-1H-tetrazole;

5-[4'-[(5-isopropyl-3-carboxyethyl-1H-1,2,4-triazol-1-yl)methyl][1,1'-biphenyl]-2-yl]-1H-tetrazole;

5-[4'-[(5-isopropyl-3-carboxypropyl-1H-1,2,4-triazol-1-yl)methyl][1,1'-biphenyl]-2-yl]-1H-tetrazole;

5-[4'-[(5-isopropyl-3-carboxybutyl-1H-1,2,4-triazol-1-yl)methyl][1,1'-biphenyl]-2-yl]-1H-tetrazole;

5-[4'-[[3-isopropyl-5-(4-carboxyphenyl)-1H-1,2,4-triazol-1-yl]methyl][1,1'-biphenyl]-2-yl]-1H-tetrazole;

5-[4'-[[3-isopropyl-5-(4-carboxyphenylmethyl)-1H-1,2,4-triazol-1-yl]methyl][1,1'-biphenyl]-2-yl]-1H-tetrazole;

5-[4'-[[3-isopropyl-5-(4-carboxyphenylethyl)-1H-1,2,4-triazol-1-yl]methyl][1,1'-biphenyl]-2-yl]-1H-tetrazole;

5-[4'-[[3-isopropyl-5-(4-carboxymethylphenylmethyl)-1H-1,2,4-triazol-1-yl]methyl][1,1'-biphenyl]-2-yl]-1H-tetrazole;

5-[4'-[[3-isopropyl-5-(4-carboxymethylphenyl)-1H-1,2,4-triazol-1-yl]methyl][1,1'-biphenyl]-2-yl]-1H-tetrazole;

5-[4'-[[3-isopropyl-5-(4-carboxyethylphenyl)-1H-1,2,4-triazol-1-yl]methyl][1,1'-biphenyl]-2-yl]-1H-tetrazole;

5-[4'-[[3-isopropyl-5-(4-carboxycyclohexyl)-1H-1,2,4-triazol-1-yl]methyl][1,1'-biphenyl]-2-yl]-1H-tetrazole;

5-[4'-[[3-isopropyl-5-(4-carboxycyclohexylmethyl)-1H-1,2,4-triazol-1-yl]methyl][1,1'-biphenyl]-2-yl]-1H-tetrazole;

5-[4'-[[3-isopropyl-5-(4-carboxycyclohexylethyl)-1H-1,2,4-triazol-1-yl]methyl][1,1'-biphenyl]-2-yl]-1H-tetrazole;

5-[4'-[[3-isopropyl-5-(4-carboxymethylcyclohexylmethyl)-1H-1,2,4-triazol-1-yl]methyl][1,1'-biphenyl]-2-yl]-1H-tetrazole;

5-(4'-[[3-isopropyl-5-(4-carboxymethylcyclohexyl)-1H-1,2,4-triazol-1-yl]methyl][1,1-biphenyl]-2-yl-1H-tetrazole;

5-[4'-[[3-isopropyl-5-(4-carboxyethylcyclohexyl)-1H-1,2,4-triazol-1-yl]methyl][1,1'-biphenyl]-2-yl]-1H-tetrazole;

5-[4'-[(5-butyl-3-carboxy-1H-1,2,4-triazol-1-yl)methyl][1,1'-biphenyl]-2-yl]-1H-tetrazole;

5-[4'-[(5-butyl-3-carboxymethyl-1H-1,2,4-triazol-1-yl)methyl][1,1'-biphenyl]-2-yl]-1H-tetrazole;

5-[4'-[(5-butyl-3-carboxyethyl-1H-1,2,4-triazol-1-yl)methyl][1,1'-biphenyl]-2-yl]-1H-tetrazole;

5-[4'-[(5-butyl-3-carboxypropyl-1H-1,2,4-triazol-1-yl)methyl][1,1'-biphenyl]-2-yl]-1H-tetrazole;

5-[4'-[(5-butyl-3-carboxybutyl-1H-1,2,4-triazol-1-yl)methyl][1,1'-biphenyl]-2-yl]-1H-tetrazole;

5-[4'-[[3-butyl-5-(4-carboxyphenyl)-1H-1,2,4-triazol-1-yl]methyl][1,1'-biphenyl]-2-yl]-1H-tetrazole;

5-[4'-[[3-butyl-5-(4-carboxyphenylmethyl)-1H-1,2,4-triazol-1-yl]methyl][1,1'-biphenyl]-2-yl]-1H-tetrazole;

5-[4'-[[3-butyl-5-(4-carboxyphenylethyl)-1H-1,2,4-triazol-1-yl]methyl][1,1'-biphenyl]-2-yl]-1H-tetrazole; 5-[4'-[[3-butyl-5-(4-carboxymethylphenylmethyl)-1H-1,2,4-triazol-1-yl]methyl][1,1'-biphenyl]-2-yl]-1H-tetrazole;

5-[4'-[[3-butyl-5-(4-carboxymethylphenyl)-1H-1,2,4-triazol-1-yl]methyl][1,1'-biphenyl]-2-yl]-1H-tetrazole;

5-[4'-[[3-butyl-5-(4-carboxyethylphenyl)-1H-1,2,4-triazol-1-yl]methyl][1,1'-biphenyl]-2-yl]-1H-tetrazole;

5-[4'-[[3-butyl-5-(4-carboxycyclohexyl)-1H-1,2,4-triazol-1-yl]methyl][1,1'-biphenyl]-2-yl]-1H-tetrazole;

5-[4'-[[3-butyl-5-(4-carboxycyclohexylmethyl)-1H-1,2,4-triazol-1-yl]methyl][1,1'-biphenyl]-2-yl]-1H-tetrazole;

5-[4'-[[3-butyl-5-(4-carboxycyclohexylethyl)-1H-1,2,4-triazol-1-yl]methyl][1,1'-biphenyl]-2-yl]-1H-tetrazole;

5-[4'-[[3-butyl-5-(4-carboxymethylcyclohexylmethyl)-1H-1,2,4-triazol-1-yl]methyl][1,1'-biphenyl]-2-yl]-1H-tetrazole;

5-[4'-[[3-butyl-5-(4-carboxymethylcyclohexyl)-1H-1,2,4-triazol-1-yl]methyl][1,1'-biphenyl]-2-yl]-1H-tetrazole;

5-[4'-[[3-butyl-5-(4-carboxyethylcyclohexyl)-1H-1,2,4-triazol-1-yl]methyl][1,1'-biphenyl]-2-yl]-1H-tetrazole;

5-[4'-[(5-secbutyl-3-carboxy-1H-1,2,4-triazol-1-yl)methyl][1,1'-biphenyl]-2-yl]-1H-tetrazole;

5-[4'-[(5-secbutyl-3-carboxymethyl-1H-1,2,4-triazol-1-yl)methyl][1,1'-biphenyl]-2-yl]-1H-tetrazole;

5-[4'-[(5-secbutyl-3-carboxyethyl-1H-1,2,4-triazol-1-yl)methyl][1,1'-biphenyl]-2-yl]-1H-tetrazole;

5-[4'-[(5-secbutyl-3-carboxypropyl-1H-1,2,4-triazol-1-yl)methyl][1,1'-biphenyl]-2-yl]-1H-tetrazole;

5-[4'-[(5-secbutyl-3-carboxybutyl-1H-1,2,4-triazol-1-yl)methyl][1,1'-biphenyl]-2-yl]-1H-tetrazole;

5-[4'-[[3-secbutyl-5-(4-carboxyphenyl)-1H-1,2,4-triazol-1-yl]methyl][1,1'-biphenyl]-2-yl]-1H-tetrazole;

5-[4'-[[3-secbutyl-5-(4-carboxyphenylmethyl)-1H-1,2,4-triazol-1-yl]methyl][1,1'-biphenyl]-2-yl]-1H-tetrazole;

5-[4'-[[3-secbutyl-5-(4-carboxyphenylethyl)-1H-1,2,4-triazol-1-yl]methyl][1,1'-biphenyl]-2-yl]-1H-tetrazole;

5-[4'-[[3-secbutyl-5-(4-carboxymethylphenylmethyl)-1H-1,2,4-triazol-1-yl]methyl][1,1'-biphenyl]-2-yl]-1H-tetrazole;

5-[4'-[[3-secbutyl-5-(4-carboxymethylphenyl)-1H-1,2,4-triazol-1-yl]methyl][1,1'-biphenyl]-2-yl]-1H-tetrazole;

5-[4'-[[3-secbutyl-5-(4-carboxyethylphenyl)-1H-1,2,4-triazol-1-yl]methyl][1,1'-biphenyl]-2-yl]-1H-tetrazole;

5-[4'-[[3-secbutyl-5-(4-carboxycyclohexyl)-1H-1,2,4-triazol-1-yl]methyl][1,1'-biphenyl]-2-yl]-1H-tetrazole;

5-[4'-[[3-secbutyl-5-(4-carboxycyclohexylmethyl)-1H-1,2,4-triazol-1-yl]methyl][1,1'-biphenyl]-2-yl]-1H-tetrazole;

5-[4'-[[3-secbutyl-5-(4-carboxycyclohexylethyl)-1H-1,2,4-triazol-1-yl]methyl][1,1'-biphenyl]-2-yl]-1H-tetrazole;

5-[4'-[[3-secbutyl-5-(4-carboxymethylcyclohexylmethyl)-1H-1,2,4-triazol-1-yl]methyl][1,1'-biphenyl]-2-yl]-1H-tetrazole;

5-[4'-[[3-secbutyl-5-(4-carboxymethylcyclohexyl)-1H-1,2,4-triazol-1-yl]methyl][1,1'-biphenyl]-2-yl]-1H-tetrazole;

5-[4'-[[3-secbutyl-5-(4-carboxyethylcyclohexyl)-1H-1,2,4-triazol-1-yl]methyl][1,1'-biphenyl]-2-yl]-1H-tetrazole;

5-[4'-[(5-isobutyl-3-carboxy-1H-1,2,4-triazol-1-yl)methyl][1,1'-biphenyl]-2-yl]-1H-tetrazole;

5-[4'-[(5-isobutyl-3-carboxymethyl-1H-1,2,4-triazol-1-yl)methyl][1,1'-biphenyl]-2-yl]-1H-tetrazole;

5-[4'-[(5-isobutyl-3-carboxyethyl-1H-1,2,4-triazol-1-yl)methyl][1,1'-biphenyl]-2-yl]-1H-tetrazole;

5-[4'-[(5-isobutyl-3-carboxypropyl-1H-1,2,4-triazol-1-yl)methyl][1,1'-biphenyl]-2-yl]-1H-tetrazole;

5-[4'-[(5-isobutyl-3-carboxybutyl-1H-1,2,4-triazol-1-yl)methyl][1,1'-biphenyl]-2-yl]-1H-tetrazole;

5-[4'-[[3-isobutyl-5-(4-carboxyphenyl)-1H-1,2,4-triazol-1-yl]methyl][1,1'-biphenyl]-2-yl]-1H-tetrazole;

5-[4'-[[3-isobutyl-5-(4-carboxyphenylmethyl)-1H-1,2,4-triazol-1-yl]methyl][1,1'-biphenyl)-2-yl]-1H-tetrazole;

5-[4'-[[3-isobutyl-5-(4-carboxyphenylethyl)-1H-1,2,4-triazol-1-yl]methyl][1,1'-biphenyl]-2-yl]-1H-tetrazole;

5-[4'-[[3-isobutyl-5-(4-carboxymethylphenylmethyl)-1H-1,2,4-triazol-1-yl]methyl][1,1'-biphenyl]-2-yl]-1H-tetrazole;

5-[4'-[[3-isobutyl-5-(4-carboxymethylphenyl)-1H-1,2,4-triazol-1-yl]methyl][1,1-biphenyl]-2-yl]-1H-tetrazole;

5-[4'-[[3-isobutyl-5-(4-carboxyethylphenyl)-1H-1,2,4-triazol-1-yl]methyl][1,1'-biphenyl]-2-yl]-1H-tetrazole;

5-[4'-[[3-isobutyl-5-(4-carboxycyclohexyl)-1H-1,2,4-triazol-1-yl]methyl][1,1'-biphenyl]-2-yl]-1H-tetrazole;

5-[4'-[[3-isobutyl-5-(4-carboxycyclohexylmethyl)-1H-1,2,4-triazol-1-yl]methyl][1,1'-biphenyl]-2-yl]-1H-tetrazole;

5-[4'-[[3-isobutyl-5-(4-carboxycyclohexylethyl)-1H-1,2,4-triazol-1-yl]methyl][1,1'-biphenyl]-2-yl]-1H-tetrazole;

5-[4'-[[3-isobutyl-5-(4-carboxymethylcyclohexylmethyl)-1H-1,2,4-triazol-1-yl]methyl][1,1'-biphenyl]-2-yl]-1H-tetrazole;

5-[4'-[[3-isobutyl-5-(4-carboxymethylcyclohexyl)-1H-1,2,4-triazol-1-yl]methyl][1,1'-biphenyl]-2-yl]-1H-tetrazole;

5-[4'-[[3-isobutyl-5-(4-carboxyethylcyclohexyl)-1H-1,2,4-triazol-1-yl]methyl][1,1'-biphenyl]-2-yl]-1H-tetrazole;

5-[4'-[(5-tertbutyl-3-carboxy-1H-1,2,4-triazol-1-yl)methyl][1,1'-biphenyl]-2-yl]-1H-tetrazole;

5-[4'-[(5-tertbutyl-3-carboxymethyl-1H-1,2,4-triazol-1-yl)methyl][1,1'-biphenyl]-2-yl]-1H-tetrazole;

5-[4'-[(5-tertbutyl-3-carboxyethyl-1H-1,2,4-triazol-1-yl)methyl][1,1'-biphenyl]-2-yl]-1H-tetrazole;

5-[4'-[(5-tertbutyl-3-carboxypropyl-1H-1,2,4-triazol-1-yl)methyl][1,1'-biphenyl]-2-yl]-1H-tetrazole;

5-[4'-[(5-tertbutyl-3-carboxybutyl-1H-1,2,4-triazol-1-yl)methyl][1,1'-biphenyl]-2-yl]-1H-tetrazole;

5-[4'-[[3-tertbutyl-5-(4-carboxyphenyl)-1H-1,2,4-triazol-1-yl]methyl][1,1'-biphenyl]-2-yl]-1H-tetrazole;

5-[4'-[[3-tertbutyl-5-(4-carboxyphenylmethyl)-1H-1,2,4-triazol-1-yl]methyl][1,1'-biphenyl]-2-yl]-1H-tetrazole;

5-[4'-[[3-tertbutyl-5-(4-carboxyphenylethyl)-1H-1,2,4-triazol-1-yl]methyl][1,1'-biphenyl]-2-yl]-1H-tetrazole;

5-[4'-[[3-tertbutyl-5-(4-carboxymethylphenylmethyl)-1H-1,2,4-triazol-1-yl]methyl][1,1'-biphenyl]-2-yl]-1H-tetrazole;

5-[4'-[[3-tertbutyl-5-(4-carboxymethylphenyl)-1H-1,2,4-triazol-1-yl]methyl][1,1'-biphenyl]-2-yl]-1H-tetrazole;

5-[4'-[[3-tertbutyl-5-(4-carboxyethylphenyl)-1H-1,2,4-triazol-1-yl]methyl][1,1'-biphenyl]-2-yl]-1H-tetrazole;

5-[4'-[[3-tertbutyl-5-(4-carboxycyclohexyl)-1H-1,2,4-triazol-1-yl]methyl][1,1'-biphenyl]-2-yl]-1H-tetrazole;

5-[4'-[[3-tertbutyl-5-(4-carboxycyclohexylmethyl)-1H-1,2,4-triazol-1-yl]methyl][1,1'-biphenyl]-2-yl]-1H-tetrazole;

5-[4'-[[3-tertbutyl-5-(4-carboxycyclohexylethyl)-1H-1,2,4-triazol-1-yl]methyl][1,1'-biphenyl]-2-yl]-1H-tetrazole;

5-[4'-[[3-tertbutyl-5-(4-carboxymethylcyclohexylmethyl)-1H-1,2,4-triazol-1-yl]methyl][1,1'-biphenyl]-2-yl]-1H-tetrazole;

5-[4'-[[3-tertbutyl-5-(4-carboxymethylcyclohexyl)-1H-1,2,4-triazol-1-yl]methyl][1,1'-biphenyl]-2-yl]-1H-tetrazole;

5-[4'-[[3-tertbutyl-5-(4-carboxyethylcyclohexyl)-1H-1,2,4-triazol-1-yl]methyl][1,1'-biphenyl]-2-yl]-1H-tetrazole;

5-[4'-[(5-pentyl-3-carboxy-1H-1,2,4-triazol-1-yl)methyl][1,1'-biphenyl]-2-yl]-1H-tetrazole;

5-[4'-[(5-pentyl-3-carboxymethyl-1H-1,2,4-triazol-1-yl)methyl][1,1'-biphenyl]-2-yl]-1H-tetrazole;

5-[14'-[(5-pentyl-3-carboxyethyl-1H-1,2,4-triazol-1-yl)methyl][1,1'-biphenyl]-2-yl]-1H-tetrazole;

5-[4'-[(5-pentyl-3-carboxypropyl-1H-1,2,4-triazol-1-yl)methyl][1,1'-biphenyl]-2-yl]-1H-tetrazole;

5-[4'-[(5-pentyl-3-carboxybutyl-1H-1,2,4-triazol-1-yl)methyl][1,1'-biphenyl]-2-yl]-1H-tetrazole;

5-[4'-[[3-pentyl-5-(4-carboxyphenyl)-1H-1,2,4-triazol-1-yl]methyl][1,1'-biphenyl]-2-yl]-1H-tetrazole;

5-[4'-[[3-pentyl-5-(4-carboxyphenylmethyl)-1H-1,2,4-triazol-1-yl]methyl][1,1'-biphenyl]-2-yl]-1H-tetrazole;

5-[4'-[[3-pentyl-5-(4-carboxyphenylethyl)-1H-1,2,4-triazol-1-yl]methyl][1,1'-biphenyl]-2-yl]-1H-tetrazole;

5-[4'-[[3-pentyl-5-(4-carboxymethylphenylmethyl)-1H-1,2,4-triazol-1-yl]methyl][1,1'-biphenyl]-2-yl]-1H-tetrazole;

5-[4'-[[3-pentyl-5-(4-carboxymethylphenyl)-1H-1,2,4-triazol-1-yl]methyl][1,1'-biphenyl]-2-yl]-1H-tetrazole;

5-[4'-[[3-pentyl-5-(4-carboxyethylphenyl)-1H-1,2,4-triazol-1-yl]methyl][1,1'-biphenyl]-2-yl]-1H-tetrazole;

5-[4'-[[3-pentyl-5-(4-carboxycyclohexyl)-1H-1,2,4-triazol-1-yl]methyl][1,1'-biphenyl]-2-yl]-1H-tetrazole;

5-[4'-[[3-pentyl-5-(4-carboxycyclohexylmethyl)-1H-1,2,4-triazol-1-yl]methyl][1,1'-biphenyl]-2-yl]-1H-tetrazole;

5-[4'-[[3-pentyl-5-(4-carboxycyclohexylethyl)-1H-1,2,4-triazol-1-yl]methyl][1,1'-biphenyl]-2-yl]-1H-tetrazole;

5-[4'-[[3-pentyl-5-(4-carboxymethylcyclohexylmethyl)-1H-1,2,4-triazol-1-yl]methyl][(1,1-biphenyl]-2-yl]-1H-tetrazole;

5-[4'-[[3-pentyl-5-(4-carboxymethylcyclohexyl)-1H-1,2,4-triazol-1-yl]methyl][1,1'-biphenyl]-2-yl]-1H-tetrazole;

5-[4'-[[3-pentyl-5-(4-carboxyethylcyclohexyl)-1H-1,2,4-triazol-1-yl]methyl][1,1'-biphenyl]-2-yl]-1H-tetrazole;

5-[4'-[(5-isopentyl-3-carboxy-1H-1,2,4-triazol-1-yl)methyl][1,1'-biphenyl]-2-yl]-1H-tetrazole;

5-[4'-[(5-isopentyl-3-carboxymethyl-1H-1,2,4-triazol-1-yl)methyl][1,1'-biphenyl]-2-yl]-1H-tetrazole;

5-[4'-[(5-isopentyl-3-carboxyethyl-1H-1,2,4-triazol-1-yl)methyl][1,1'-biphenyl]-2-yl]-1H-tetrazole;

5-[4'-[(5-isopentyl-3-carboxypropyl-1H-1,2,4-triazol-1-yl)methyl][1,1'-biphenyl]-2-yl]-1H-tetrazole;

5-[4'-[(5-isopentyl-3-carboxybutyl-1H-1,2,4-triazol-1-yl)methyl][1,1'-biphenyl]-2-yl]-1H-tetrazole;

5-[4'-[[3-isopentyl-5-(4-carboxyphenyl)-1H-1,2,4-triazol-1-yl]methyl][1,1'-biphenyl]-2-yl]-1H-tetrazole;

5-[4'-[[3-isopentyl-5-(4-carboxyphenylmethyl)-1H-1,2,4-triazol-1-yl]methyl][1,1-biphenyl)-2-yl]-1H-tetrazole;

5-[4'-[[3-isopentyl-5-(4-carboxyphenylethyl)-1H-1,2,4-triazol-1-yl]methyl][1,1'-biphenyl]-2-yl]-1H-tetrazole;

5-[4'-[[3-isopentyl-5-(4-carboxymethylphenylmethyl)-1H-1,2,4-triazol-1-yl]methyl][1,1'-biphenyl]-2-yl]-1H-tetrazole;

5-[4'-([3-isopentyl-5-(4-carboxymethylphenyl)-1H-1,2,4-triazol-1-yl]methyl][1,1'-biphenyl]-2-yl]-1H-tetrazole;

5-[4'-[[3-isopentyl-5-(4-carboxyethylphenyl)-1H-1,2,4-triazol-1-yl]methyl][1,1'-biphenyl]-2-yl]-1H-tetrazole;

5-[4'-[[3-isopentyl-5-(4-carboxycyclohexyl)-1H-1,2,4-triazol-1-yl]methyl][1,1'-biphenyl]-2-yl]-1H-tetrazole;

5-[4'-[[3-isopentyl-5-(4-carboxycyclohexylmethyl)-1H-1,2,4-triazol-1-yl]methyl][1,1'-biphenyl]-2-yl]-1H-tetrazole;

5-[4'-[[3-isopentyl-5-(4-carboxycyclohexylethyl)-1H-1,2,4-triazol-1-yl]methyl][1,1'-biphenyl]-2-yl]-1H-tetrazole;

5-[4'-[[3-isopentyl-5-(4-carboxymethylcyclohexylmethyl)-1H-1,2,4-triazol-1-yl]methyl][1,1'-biphenyl]-2-yl]-1H-tetrazole;

5-[4'-[[3-isopentyl-5-(4-carboxymethylcyclohexyl)-1H-1,2,4-triazol-1-yl]methyl][1,1'-biphenyl]-2-yl]-1H-tetrazole;

5-[4'-[[3-isopentyl-5-(4-carboxyethylcyclohexyl)-1H-1,2,4-triazol-1-yl]methyl][1,1'-biphenyl]-2-yl]-1H-tetrazole;

5-[4'-[(5-hexyl-3-carboxy-1H-1,2,4-triazol-1-yl)methyl][1,1'-biphenyl]-2-yl]-1H-tetrazole;

5-[4'-[(5-hexyl-3-carboxymethyl-1H-1,2,4-triazol-1-yl)methyl][1,1'-biphenyl]-2-yl]-1H-tetrazole;

5-[4'-[(5-hexyl-3-carboxyethyl-1H-1,2,4-triazol-1-yl)methyl][1,1'-biphenyl]-2-yl]-1H-tetrazole;

5-[4'-[(5-hexyl-3-carboxypropyl-1H-1,2,4-triazol-1-yl)methyl][1,1'-biphenyl]-2-yl]-1H-tetrazole;

5-[4'-[(5-hexyl-3-carboxybutyl-1H-1,2,4-triazol-1-yl)methyl][1,1'-biphenyl]-2-yl]-1H-tetrazole;

5-[4'-([3-hexyl-5-(4-carboxyphenyl)-1H-1,2,4-triazol-1-yl]methyl][1,1'-biphenyl]-2-yl]-1H-tetrazole;

5-[4'-[[3-hexyl-5-(4-carboxyphenylmethyl)-1H-1,2,4-triazol-1-yl]methyl][1,1'-biphenyl]-2-yl]-1H-tetrazole;

5-[4'-[[3-hexyl-5-(4-carboxyphenylethyl)-1H-1,2,4-triazol-1-yl]methyl][1,1'-biphenyl]-2-yl]-1H-tetrazole;

5-[4'-[[3-hexyl-5-(4-carboxymethylphenylmethyl)-1H-1,2,4-triazol-1-yl]methyl][1,1'-biphenyl]-2-yl]-1H-tetrazole;

5-[4'-[[3-hexyl-5-(4-carboxymethylphenyl)-1H-1,2,4-triazol-1-yl]methyl][1,1'-biphenyl]-2-yl]-1H-tetrazole;

5-[4'-[[3-hexyl-5-(4-carboxyethylphenyl)-1H-1,2,4-triazol-1-yl]methyl][1,1'-biphenyl]-2-yl]-1H-tetrazole;

5-[4'-[[3-hexyl-5-(4-carboxycyclohexyl)-1H-1,2,4-triazol-1-yl]methyl][1,1'-biphenyl]-2-yl]-1H-tetrazole;

5-[4'-[[3-hexyl-5-(4-carboxycyclohexylmethyl)-1H-1,2,4-triazol-1-yl]methyl][1,1'-biphenyl]-2-yl]-1H-tetrazole;

5-[4'-[[3-hexyl-5-(4-carboxycyclohexylethyl)-1H-1,2,4-triazol-1-yl]methyl][1,1'-biphenyl]-2-yl]-1H-tetrazole;

5-[4'-[[3-hexyl-5-(4-carboxymethylcyclohexylmethyl)-1H-1,2,4-triazol-1-yl]methyl][1,1'-biphenyl]-2-yl]-1H-tetrazole;

5-[4'-[[3-hexyl-5-(4-carboxymethylcyclohexyl)-1H-1,2,4-triazol-1-yl]methyl][1,1'-biphenyl]-2-yl]-1H-tetrazole; and 5-[4'-[[3-hexyl-5-(4-carboxyethylcyclohexyl)-1H-1,2,4-triazol-1-yl]methyl][1,1'-biphenyl]-2-yl]-1H-tetrazole.

A family of specific angiotensin II antagonist compounds of highest interest within Formula I from which a suitable first component of the conjugate may be selected, consists of amino-terminated biphenylmethyl 1H-substituted-1,2,4-triazole compounds as listed below. Such compounds would be suitable to form a conjugate with a carboxylic moiety of a second component of the conjugate, such as a glutamic acid residue, to form an enzyme-cleavable amide bond by direct reaction or by reaction through a diamino-containing linker of the type mentioned above. These Formula I angiotensin II antagonist compounds of highest interest are as follows:

methyl 4'-[(3,5-dibutyl-1H-1,2,4-triazol-1-yl)methyl][1,1'-biphenyl]-2-carboxylate;

4'-[(3,5-dibutyl-1H-1,2,4-triazol-1-yl)methyl][1,1'-biphenyl]-2-carboxylic acid;

4'-[(3,5-dibutyl-1H-1,2,4-triazol-1-yl)methyl][1,1'-biphenyl]-2-carboxylic acid, hydrazide;

4'-[(5-butyl-3-chloro-1H-1,2,4-triazol-1-yl)methyl][1,1'-biphenyl]-2-carboxylic acid;

4'-[(3-butyl-5-chloro-1H-1,2,4-triazol-1-yl)methyl][1,1'-biphenyl]-2-carboxylic acid;

4'-[(5-butyl-3-propyl-1H-1,2,4-triazol-1-yl)methyl][1,1'-biphenyl]-2-carboxylic acid;

4'-[(5-butyl-3-isopropyl-1H-1,2,4-triazol-1-yl)methyl][1,1'-biphenyl]-2-carboxylic acid;

4'-[(5-butyl-3-secbutyl-1H-1,2,4-triazol-1-yl)methyl][1,1'-biphenyl]-2-carboxylic acid;

4'-[(5-butyl-3-isobutyl-1H-1,2,4-triazol-1-yl)methyl) (1,1'-biphenyl]-2-carboxylic acid;

4'-[(5-butyl-3-tertbutyl-1H-1,2,4-triazol-1-yl)methyl][1,1'-biphenyl]-2-carboxylic acid;

4'-[(5-butyl-3-pentyl-1H-1,2,4-triazol-1-yl)methyl][1,1'-biphenyl]-2-carboxylic acid;

4'-[(5-butyl-3-isopentyl-1H-1,2,4-triazol-1-yl)methyl][1,1'-biphenyl]-2-carboxylic acid;

4'-[(5-butyl-3-cyclohexyl-1H-1,2,4-triazol-1-yl)methyl][1,1'-biphenyl]-2-carboxylic acid;

4'-[(5-butyl-3-cyclohexylmethyl-1H-1,2,4-triazol-1-yl)methyl][1,1'-biphenyl]-2-carboxylic acid;

4'-[[5-butyl-3-(2-cyclohexylethyl))-1H-1,2,4-triazol-1-yl]methyl][1,1'-biphenyl]-2-carboxylic acid;

4'-[(5-butyl-3-cyclohexanoyl-1,2,4,-triazol-1-yl)methyl][1,1'-biphenyl]-2-carboxylic acid;

4'-[[5-butyl-3-(1-oxo-2-cyclohexylethyl)-1H-1,2,4-triazol-1-yl]methyl][1,1'-biphenyl]-2-carboxylic acid;

4'-[(5-butyl-3-phenyl-1,2,4,-triazol-1-yl)methyl][1,1'-biphenyl]-2-carboxylic acid;

4'-[(5-butyl-3-phenylmethyl-1,2,4,-triazol-1-yl)methyl][1,1'-biphenyl]-2-carboxylic acid;

4'-[[5-butyl-3-(2-phenylethyl)-1H-1,2,4-triazol-1-yl]methyl][1,1'-biphenyl]-2-carboxylic acid;

4'-[(5-butyl-3-benzoyl-1,2,4,-triazol-1-yl)methyl][1,1'-biphenyl]-2-carboxylic acid;

4'-[[5-butyl-3-(1-oxo-2-phenylethyl)-1H-1,2,4-triazol-1-yl]methyl][1'-biphenyl]-2-carboxylic acid;

4'-[[5-butyl-3-(1,1-dimethoxypropyl)-1H-1,2,4-triazol-1-yl]methyl][1,1'-biphenyl]-2-carboxylic acid;

4'-[[5-butyl-3-(1,1-dimethoxybutyl)-1H-1,2,4-triazol-1-yl]methyl][1,1'-biphenyl]-2-carboxylic acid;

4'-[[5-butyl-3-(1-oxopropyl)-1H-1,2,4-triazol-1-yl]methyl][1,1'-biphenyl]-2-carboxylic acid;

4'-[[5-butyl-3-(1-oxobutyl)-1H-1,2,4-triazol-1-yl]methyl][1,1'-biphenyl]-2-carboxylic acid;

4'-[[5-butyl-3-(1-oxopentyl)-1H-1,2,4-triazol-1-yl]methyl][1,1'-biphenyl]-2-carboxylic acid;

4'-[[5-butyl-3-(1,1-difluoroethyl)-1H-1,2,4-triazol-1-yl]methyl][1,1'-biphenyl]-2-carboxylic acid;

4'-[[5-butyl-3-(1,1-difluoropropyl)-1H-1,2,4-triazol-1-yl]methyl][1,1'-biphenyl]-2-carboxylic acid;

4'-[[5-butyl-3-(1,1-difluorobutyl)-1H-1,2,4-triazol-1-yl]methyl][1,1'-biphenyl]-2-carboxylic acid;

4'-[[3-butyl-5-(1,1-'difluorobutyl)-1H-1,2,4-triazol-1-yl]methyl][1,1'-biphenyl]-2-carboxylic acid;

4'-[[5-butyl-3-(1,1-difluoropentyl)-1H-1,2,4-triazol-1-yl]methyl][1,1'-biphenyl]-2-carboxylic acid;

4'-[(3,5-dipropyl-1H-1,2,4-triazol-1-yl)methyl][1,1'-biphenyl]-2-carboxylic acid;

4'-[(3,5-isopropyl-1H-1,2,4-triazol-1-yl)methyl][1,1'-biphenyl]-2-carboxylic acid;

4'-[(3,5-disecbutyl-1H-1,2,4-triazol-1-yl)methyl][1,1'-biphenyl]-2-carboxylic acid;

4'-[(3,5-diisobutyl-1H-1,2,4-triazol-1-yl)methyl][1,1'-biphenyl]-2-carboxylic acid;

4'-[(3,5-ditertbutyl-1H-1,2,4-triazol-1-yl)methyl][1,1'-biphenyl]-2-carboxylic acid;

4'-[(3,5-dipentyl-1H-1,2,4-triazol-1-yl)methyl][1,1'-biphenyl]-2-carboxylic acid;

4'-[(3,5-diisopentyl-1H-1,2,4-triazol-1-yl)methyl][1,1'-biphenyl]-2-carboxylic acid;

5-[4'-[(5-butyl-3-amino-1H-1,2,4-triazol-1-yl)methyl][1,1'-biphenyl]-2-yl]-1H-tetrazole;

5-[4'-[(5-butyl-3-aminomethyl-1H-1,2,4-triazol-1-yl)methyl][1,1'-biphenyl]-2-yl]-1H-tetrazole;

5-[4'-[(5-butyl-3-aminoethyl-1H-1,2,4-triazol-1-yl)methyl][1,1'-biphenyl]-2-yl]-1H-tetrazole;

5-[4]-[(5-butyl-3-aminopropyl-1H-1,2,4-triazol-1-yl)methyl][1,1'-biphenyl]-2-yl]-1H-tetrazole;

5-[4'-[(5-butyl-3-aminobutyl-1H-1,2,4-triazol-1-yl)methyl][1,1'-biphenyl]-2-yl]-1H-tetrazole;

5-[4'-[[3-butyl-5-(4-aminophenyl)-1H-1,2,4-triazol-1-yl]methyl][1,1'-biphenyl]-2-yl]-1H-tetrazole;

5-[4'-[[3-butyl-5-(4-aminophenylmethyl)-1H-1,2,4-triazol-1-yl]methyl][1,1'-biphenyl]-2-yl]-1H-tetrazole;

5-[4'-[[3-butyl-5-(4-aminophenylethyl)-1H-1,2,4-triazol-1-yl]methyl][1,1'-biphenyl]-2-yl]-1H-tetrazole;

5-[4'-[[3-butyl-5-(4-aminomethylphenylmethyl)-1H-1,2,4-triazol-1-yl]methyl][1,1'-biphenyl]-2-yl]-1H-tetrazole;

5-[4'-[[3-butyl-5-(4-aminomethylphenyl)-1H-1,2,4-triazol-1-yl]methyl][1,1'-biphenyl]-2-yl]-1H-tetrazole;

5-[4'-[[3-butyl-5-(4-aminoethylphenyl)-1H-1,2,4-triazol-1-yl]methyl][1,1'-biphenyl]-2-yl]-1H-tetrazole;

5-[4'-[[3-butyl-5-(4-aminocyclohexyl)-1H-1,2,4-triazol-1-yl]methyl][1,1'-biphenyl]-2-yl]-1H-tetrazole;

5-[4'-[[3-butyl-5-(4-aminocyclohexylmethyl)-1H-1,2,4-triazol-1-yl]methyl][1,1'-biphenyl]-2-yl]-1H-tetrazole;

5-[4'-[[3-butyl-5-(4-aminocyclohexylethyl)-1H-1,2,4-triazol-1-yl]methyl][1,1-biphenyl]-2-yl]-1H-tetrazole;

5-[4'-[[3-butyl-5-(4-aminomethylcyclohexylmethyl)-1H-1,2,4-triazol-1-yl]methyl][1,1'-biphenyl]-2-yl]-1H-tetrazole;

5-[4'-[[3-butyl-5-(4-aminomethylcyclohexyl)-1H-1,2,4-triazol-1-yl]methyl][1,1'-biphenyl]-2-yl]-1H-tetrazole;

5-[4'-[[3-butyl-5-(4-aminoethylcyclohexyl)-1H-1,2,4-triazol-1-yl]methyl][1,1'-biphenyl]-2-yl]-1H-tetrazole;

5-[4'-[(5-butyl-3-carboxy-1H-1,2,4-triazol-1-yl)methyl][1,1'-biphenyl]-2-yl]-1H-tetrazole;

5-[4'-[(5-butyl-3-carboxymethyl-1H-1,2,4-triazol-1-yl)methyl][1,1'-biphenyl]-2-yl]-1H-tetrazole;

5-[4'-[(5-butyl-3-carboxyethyl-1H-1,2,4-triazol-1-yl)methyl][1,1'-biphenyl]-2-yl]-1H-tetrazole;

5-[4'-[(5-butyl-3-carboxypropyl-1H-1,2,4-triazol-1-yl)methyl][1,1'-biphenyl]-2-yl]-1H-tetrazole;

5-[4'-[(5-butyl-3-carboxybutyl-1H-1,2,4-triazol-1-yl)methyl][1,1'-biphenyl]-2-yl]-1H-tetrazole;

5-[4'-[[3-butyl-5-(4-carboxyphenyl)-1H-1,2,4-triazol-1-yl]methyl][1,1'-biphenyl]-2-yl]-1H-tetrazole;

5-[4'-[[3-butyl-5-(4-carboxyphenylmethyl)-1H-1,2,4-triazol-1-yl]methyl][1,1'-biphenyl]-2-yl]-1H-tetrazole;

5-[4'-[[3-butyl-5-(4-carboxyphenylethyl)-1H-1,2,4-triazol-1-yl]methyl][1,1'-biphenyl]-2-yl]-1H-tetrazole;

5-[4'-[[3-butyl-5-(4-carboxymethylphenylmethyl)-1H-1,2,4-triazol-1-yl]methyl][1,1'-biphenyl]-2-yl]-1H-tetrazole;

5-[4'-[[3-butyl-5-(4-carboxymethylphenyl)-1H-1,2,4-triazol-1-yl]methyl][1,1'-biphenyl]-2-yl]-1H-tetrazole;

5-[4'-[[3-butyl-5-(4-carboxyethylphenyl)-1H-1,2,4-triazol-1-yl]methyl][1,1'-biphenyl]-2-yl]-1H-tetrazole;

5-[4'-[[3-butyl-5-(4-carboxycyclohexyl)-1H-1,2,4-triazol-1-yl]methyl][1,1'-biphenyl]-2-yl]-1H-tetrazole;

5-[4'-[[3-butyl-5-(4-carboxycyclohexylmethyl)-1H-1,2,4-triazol-1-yl]methyl][1,1'-biphenyl]-2-yl]-1H-tetrazole;

5-[4'-[[3-butyl-5-(4-carboxycyclohexylethyl)-1H-1,2,4-triazol-1-yl]methyl][1,1'-biphenyl]-2-yl]-1H-tetrazole;

5-[4'-[[3-butyl-5-(4-carboxymethylcyclohexylmethyl)-1H-1,2,4-triazol-1-yl]methyl][1,1'-biphenyl]-2-yl]-1H-tetrazole;

5-[4'-[[3-butyl-5-(4-carboxymethylcyclohexyl)-1H-1,2,4-triazol-1-yl]methyl][1,1'-biphenyl]-2-yl]-1H-tetrazole; and

[4'-[[3-butyl-5-(4-carboxyethylcyclohexyl)-1H-1,2,4-triazol-1-yl]methyl][1,1'-biphenyl]-2-yl]-1H-tetrazole.

General Synthetic Procedures

Conjugates of the invention are synthesized by reaction between precursors of the first and second residues. One of such precursors must contain a reactive acid moiety, and the other precursor must contain a reactive amino moiety, so that a conjugate is formed having a cleavable bond. Either precursor of the first and second residues may contain such reactive acid or amino moieties. Preferably, the precursors of the first residue are angiotensin II antagonists and will contain a reactive amino moiety or a moiety convertible to a reactive amino moiety. Inhibitor compounds lacking a reactive amino moiety may be chemically modified to provide such reactive amino moiety. Chemical modification of these inhibitor compounds lacking a reactive amino group may be accomplished by reacting an acid or an ester group on an AII antagonist compound with an amino compound having at least one reactive amino moiety and another reactive hetero atom selected from O, S and N. A suitable amino compound would be a diamino compound such as hydrazine or urea. Hydrazine, for example, may be reacted with a carboxylic acid or ester moiety of an AII antagonist compound to form a hydrazide derivative of such AII antagonist compound.

The AII antagonist compound 4'-[(3,5-dibutyl-1H-1,2,4-triazol-1-yl)methyl][1,1'-biphenyl]-2-carboxylic acid may be used as a model compound to illustrate the chemical modification of a carboxylic acid-containing compound to make a reactive amino-containing precursor for synthesizing a conjugate of the invention. In the following General Synthetic Procedures, there are described firstly, in Schemes I–VI, methods for making suitable angiotensin II antagonists of Formula I for selection as the first component of the conjugate. Then, in Schemes VII–XII, there are described general methods for making a conjugate by reacting a first component AII antagonist of Formula I with a cleavable second component represented by N-acetyl-γ-glutamic acid.

Conjugates of the invention may be prepared using precursors of highly active angiotensin II antagonists of Formula I. Examples of lesser active, suitable precursors are acid chloride, esters and amides of angiotensin II antagonists of Formula I. For example, ester precursors of more active angiotensin II antagonists, such as ester-type AII antagonists of Example Nos. 1, 34, 35, 67 and 68, as well as AII antagonists containing carboxylic acid terminal moieties, of Example Nos. 2, 6, 8, 18–20, 36, 52, 63, 64, 71–72 and 75–78, may be reacted with hydrazine to provide an intermediate bearing an amino terminal moiety which then can be reacted with a glutamic acid derivative to form a conjugate of the invention. Such precursors or intermediates themselves may be relatively strong, relatively weak, or inactive as AII antagonists. Also, conjugates of the invention may be prepared using angiotensin II antagonists lacking a reactive terminal acidic or amino moiety. Such angiotensin II antagonists, as shown in Example Nos. 3, 5, 7, 9–16, 21–33, 37–40, 42–51, 53–62, 65, 66, 69–70, 73 and 74, lack a terminal amino moiety. These AII antagonist compounds may be modified to contain a terminal amino moiety which then may be connected to a glutamyl residue through a diamino-terminated linker group, such as shown in Tables I–III.

Scheme I

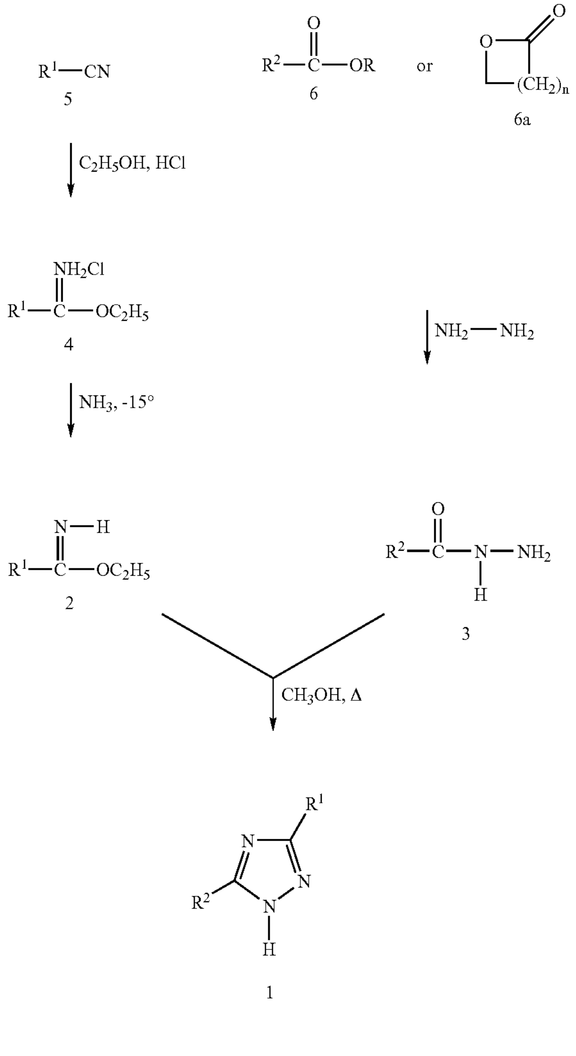

5 6 or 6a 4 2 3 1

R = H, $CH_3$, or $C_2H_5$

Synthetic Scheme I shows the preparation of 1H-1,2,4-triazoles 1 from ethyl iminoesters 2 and the corresponding hydrazide 3 via the general proceure outlined by H. Paul, G. Hilgetog and G. Jahnchen, *Chem. Ber.,* 101, 2033 (1968). The free, iminoesters 2 can be prepared from the corresponding iminoester hydrochlorides 4, which in turn can be prepared from the corresponding nitrile 5; the procedures for the preparation of 2 and 4 from 5 are outlined by P. Reynaud and R. D. Moreau, *Bull. Soc. Chim. France,* 2997 (1964). The hydrazides 3 can be either purchased or prepared from the corresponding alkyl esters 6 or lactones 6a and hydrazine.

Scheme II

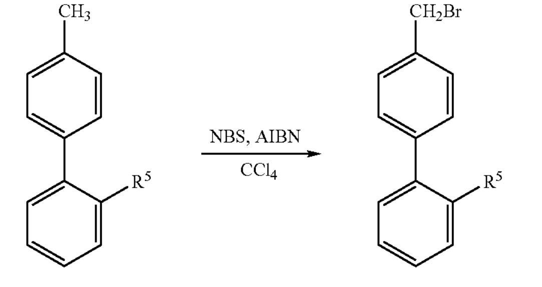

8 7

Synthetic Scheme II shows the preparation of the alkylating agent 7 from the corresponding precursor 8. When $R^5$ equals $CO_2CH_3$, 8 was purchased from Chemo Dynamics Inc.

Scheme III

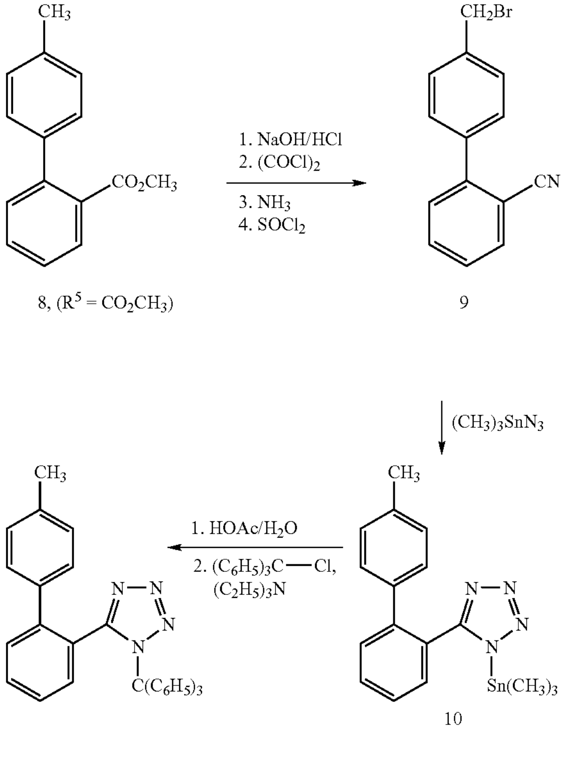

8, ($R^5 = CO_2CH_3$) 9

10

8, [$R^5 = CN_4C(C_6H_5)_3$]

Synthetic Scheme III shows the preparation of the alkylating agent precursor 8 where $R^5$ equal $CN_4C(C_6H_5)_3$ from the corresponding methyl ester 8 ($R^5$═$CO_2CH_3$). In step 1, the methyl ester is converted to the corresponding acid ($R^5$═$CO_2H$) by the action of sodium hydroxide/hydrochloric acid. In step 2, the acid is converted to the corresponding acid chloride ($R^5$═COCl) by the action of oxalyl chloride. In step 3, the acid chloride is converted to the corresponding primary amide ($R^5$═$CONH_2$) by the action of ammonia. In step 4, the amide is converted to the corresponding nitrile 9 by the action of thionyl chloride at reflux. The nitrile 9 is reacted with trimethyltinazide in toluene at reflux to give the corresponding trimethytin protected tetrazole 10; deprotection with acetic acid/water and reprotection with triphenylmethyl chloride/triethylamine gives the N-trityl tetrazole 8 ($R^5$=$CN_4C(C_6H_5)_3$).
Scheme IV
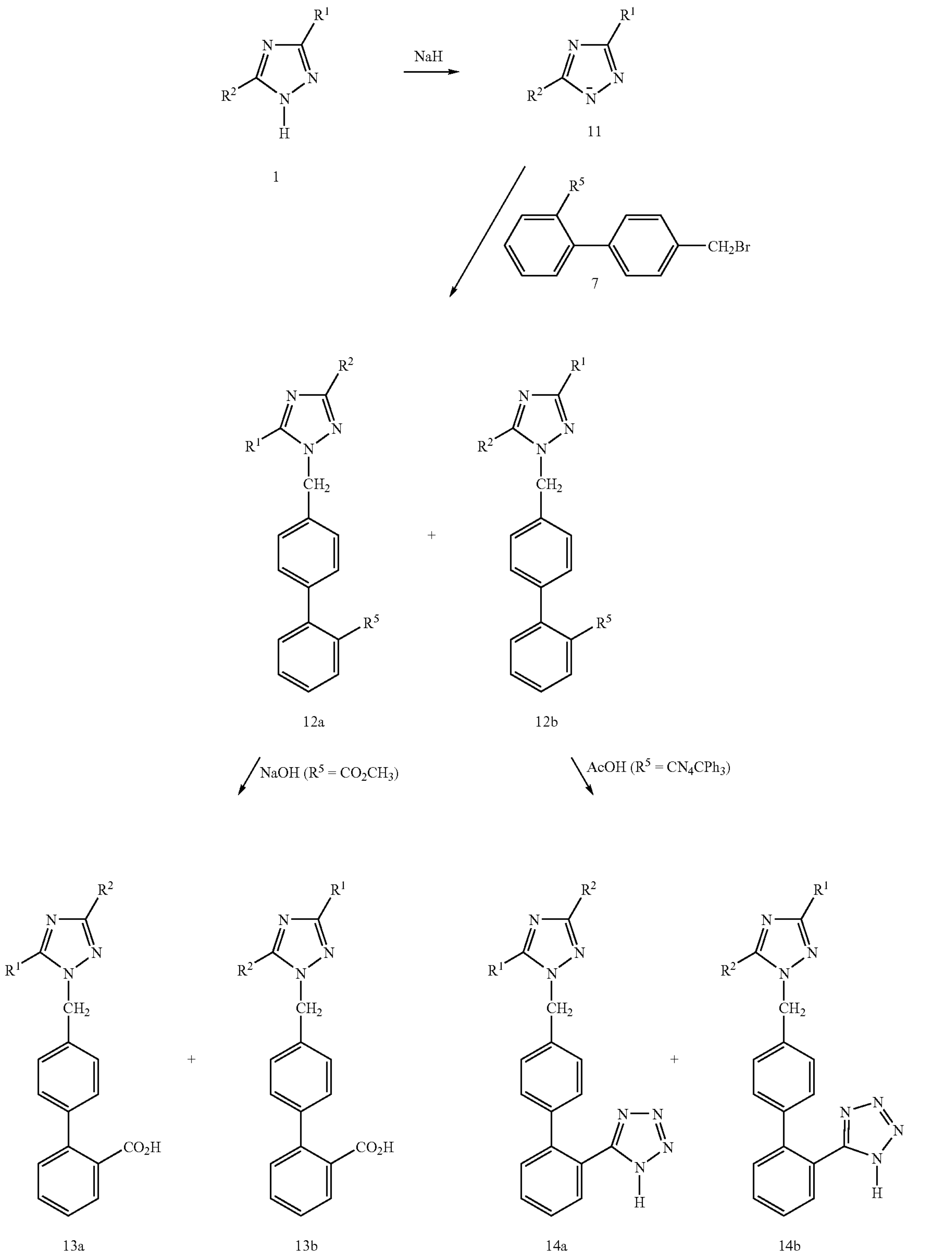

Synthetic Scheme IV shows the coupling reaction of the 1H-1,2,4-triazole 1 with the appropriate alkylating reagent 7. In the first step, 1 is treated with a base, such as sodium hydride, to generate the corresponding anion 11. Anion 11 is reacted with an alkylating agent 7 to give a mixture of regioisomers 12a and 12b. The isomer mixture may be converted to mixtures of the corresponding acids 13a and 13b or tetrazoles 14a and 14b by treatment with the appropriate reagent. Or, the isomers 12a and 12b may be separated by chromatographic methods, and each isomer may be reacted with the appropriate reagent to provide the acid- or tetrazole-substituted end product.

Scheme V

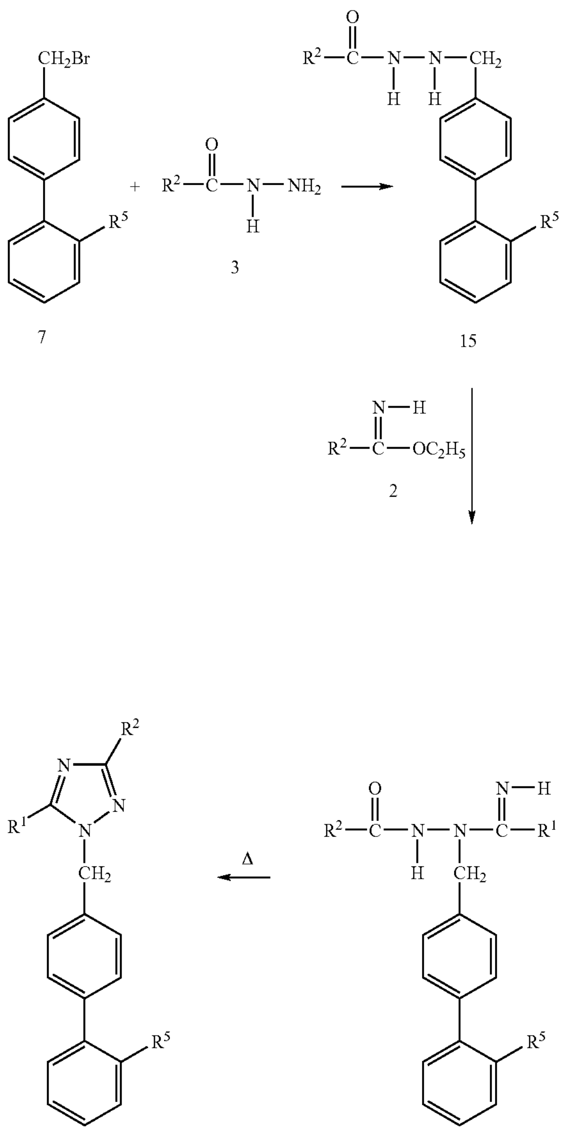

7 3 15 2 13a or 14a 16

Synthetic Scheme V shows the regioselective synthesis of isomer 13a or 14a from Scheme IV. In the first step of the reaction, an alkylating agent 7 is reacted with an appropriate hydrazide 3 to provide substituted hydrazide 15. An imidate 2 is reacted with hydrazide 15 to provide intermediate 16 which cyclizes upon heating to provide the corresponding product compound 13a or 14a.

Scheme VI

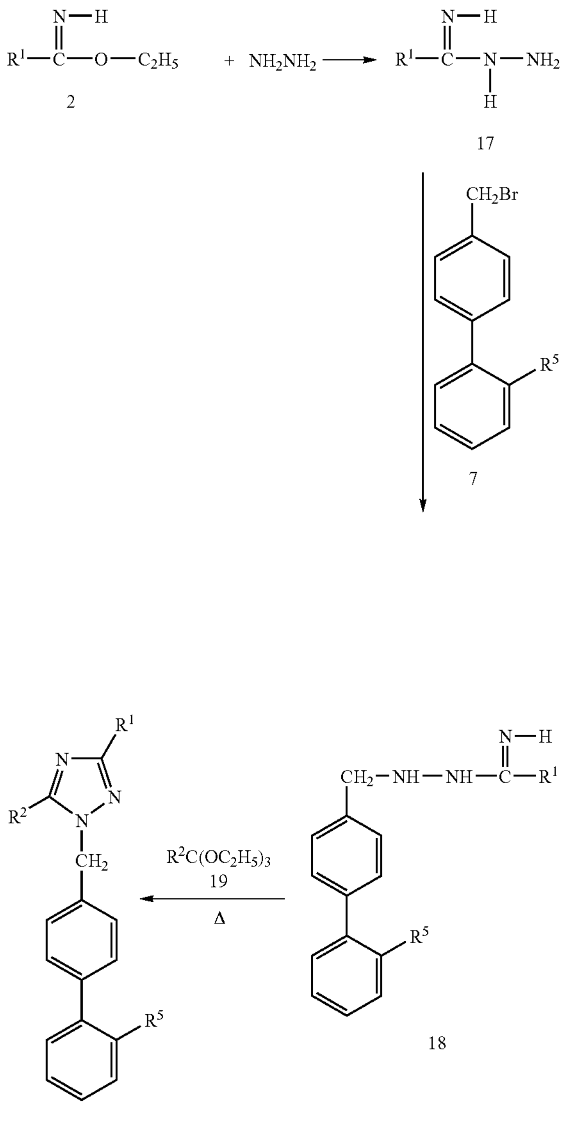

2 17 7 18 13b or 14b

Synthetic Scheme VI shows the regioselective synthesis of isomer 13b or 14b from Scheme IV. In the first step of the reaction, imidate 2 is reacted with hydrazine to give amidazone 17. This intermediate is reacted with alkylating agent 7 to give intermediate 18 which is then cyclized in the presence of heat and an appropriate orthoester 19 to yield the corresponding product compound 13b or 14b.

Scheme VII

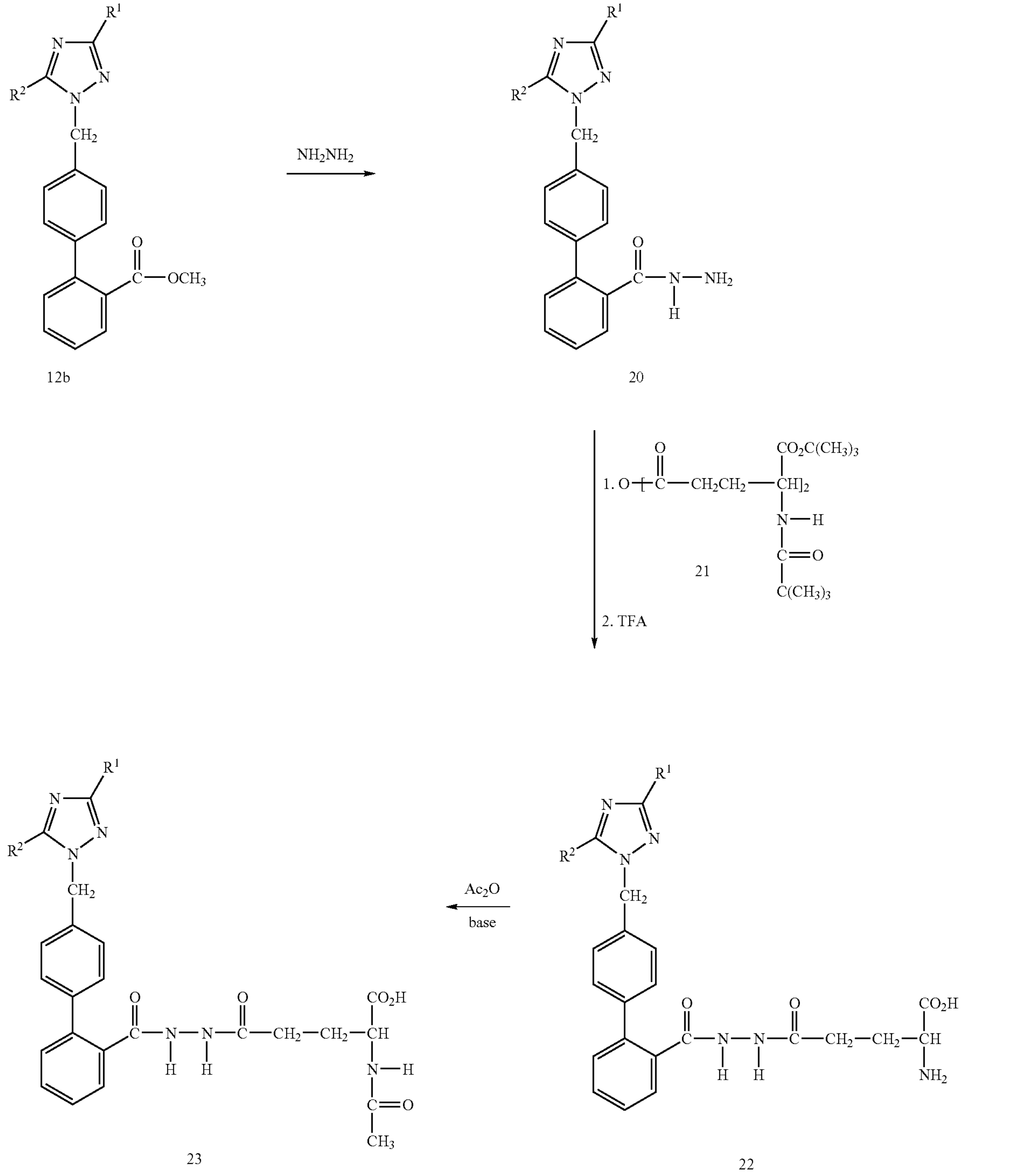

12b 20 21 22 23

Synthetic Scheme VII shows the preparation of renal-selective angiotensin II antagonists by coupling γ-glutamic acid with an angiotensin II antagonist; the biphenyl $R^5$ acid moiety of the AII antagonist is coupled to the γ-acid moiety of glutamic acid via an hydrazine linker. In step 1, the methyl ester of the AII antagonist 12b is converted to the hydrazide 20 by the action of hydrazine. In step 2, the hydrazide 20 is first reacted with the symmetrical anhydride of the protected γ-glutamic acid 21 and subsequently reacted with trifluoroacetic acid (TFA) to give the deprotected coupled material 22. In step 3, the free amino group of 22 is acetylated with acetic anhydride in the presence of base to give the renal-selective angiotensin II antagonists 23.

Scheme VIII
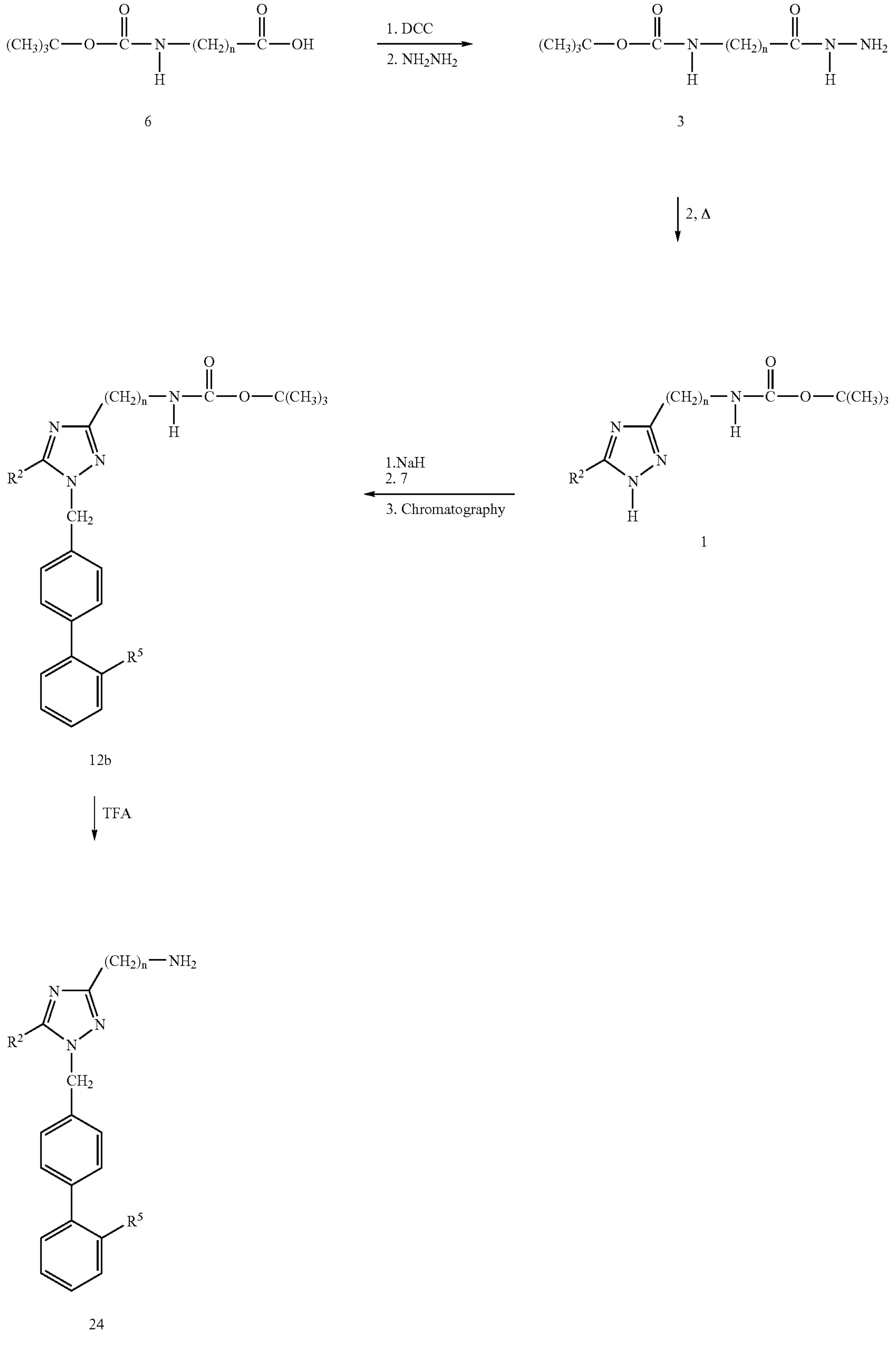
6
3
1
12b
24

Synthetic Scheme VIII shows the preparation of angiotensin II antagonists 24 which have an amino moiety incorporated in $R^1$. In step 1, a protected amino acid 6 is first reacted with dicyclohexylcarbodiimide (DCC) and subsequently reacted with hydrazine to give the hydrazide 3. In step 2, the hydrazide 3 is reacted with the iminoester 2 and subsequently cyclized to the corresponding 1H-1,2,4-triazole 1. In step 3, the anion of 1 is reacted with the appropriate alkylating agent 7 to give a mixture of regioisomers 12a and 12b which can be separated by chromatography. In step 4, the desired isomer 12b is deprotected with TFA to give the free amino AII antagonist 24.

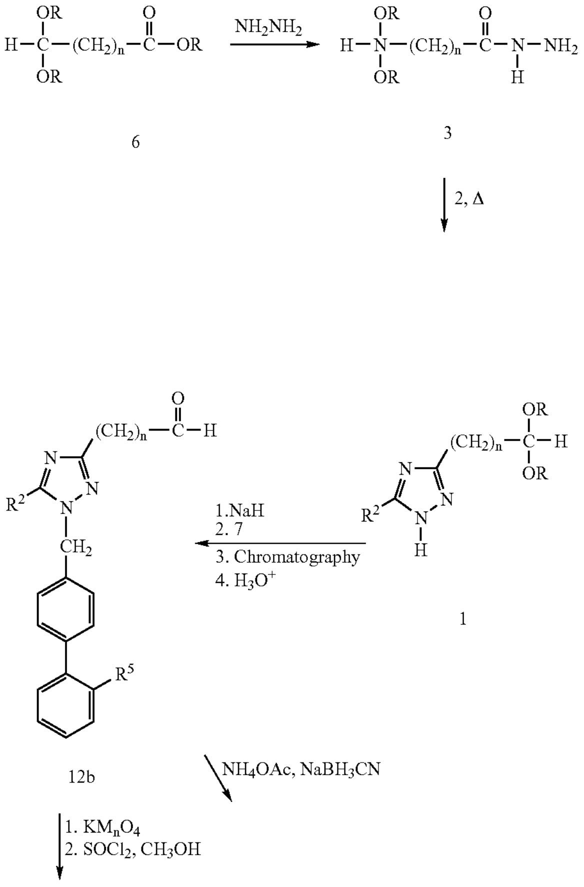

6

3

1

12b

-continued

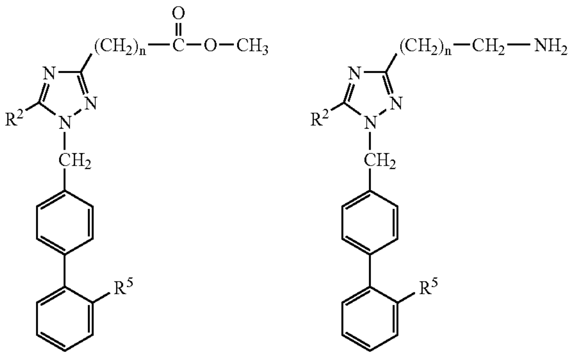

25

26

R = $CH_3$, $C_2H_5$

Synthetic Scheme IX shows the preparation of angiotensin II antagonists 25 and 26 which have a carbomethoxy moiety and an amino moiety, respectively, incorporated in $R^1$. In step 1, the dialkylacetal alkyl ester 6 is reacted with hydrazine to give the hydrazide 3. In step 2, the hydrazide 3 is reacted with the iminoester 2 and subsequently cyclized to the corresponding 1H-1,2,4-triazole 1. In step 3, the anion of 1 is reacted with the apropriate alkylating agent 7 to give a mixture of regioisomers which can be separated by chromatography prior to the generation of the free aldehyde 12b with aqueous acid. In step 4, the aldehyde 12b is oxidized to the corresponding acid with $KMnO_4$ and subsequently converted to the methyl ester 25 by $SOCl_2/CH_3OH$ at −10° or reduced to the corresponding aminomethyl analog 26 (homolog of 24) by $NH_4OAc/NaBH_3CN$.

Scheme X

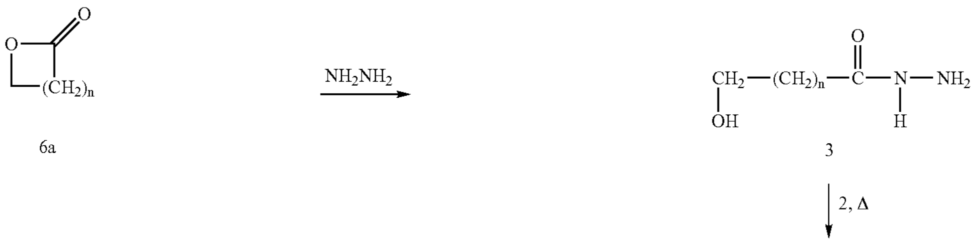

6a

3

-continued

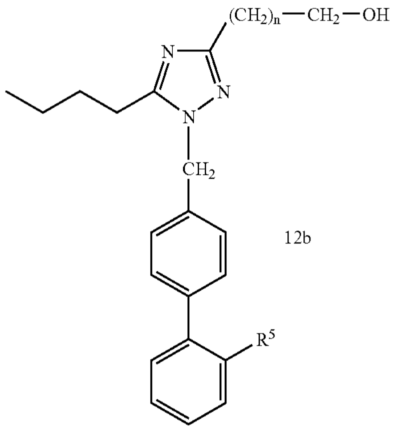

12b

1.NaH
2. 7
3. chromatography

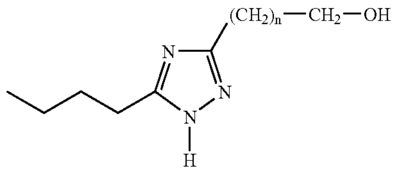

1

1. $KMnO_4$
2. $SOCl_2$, $CH_3OH$

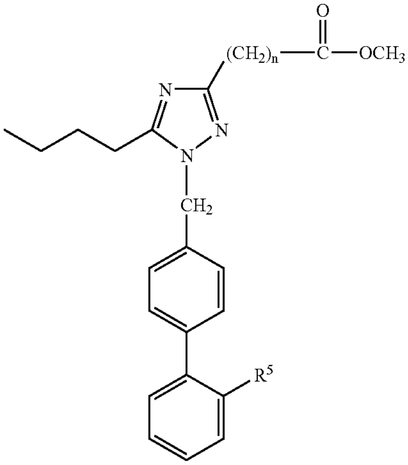

25

Synthetic Scheme X shows an alternate preparation of angiotensin II antagonists 25 which have a carbomethoxy moiety incorporated in $R^1$. In step 1, the lactone 6a is reacted with hydrazine to give the hydrazide 3. In step 2, the hydrazide 3 is reacted with the iminoester 2 and subsequently cyclized to the corresponding 1H-1,2,4-triazole 1. In step 3, the anion of 1 is reacted with the appropriate alkylating agent 7 to give a mixture of regioisomers which can be separated by chromatography to give 12b. In step 4, the primary alcohol 12b is oxidized to the corresponding acid with $KMnO_4$ and subsequently converted to the methyl ester 25 by $SOCl_2/CH_3OH$ at −10°.

Scheme XI

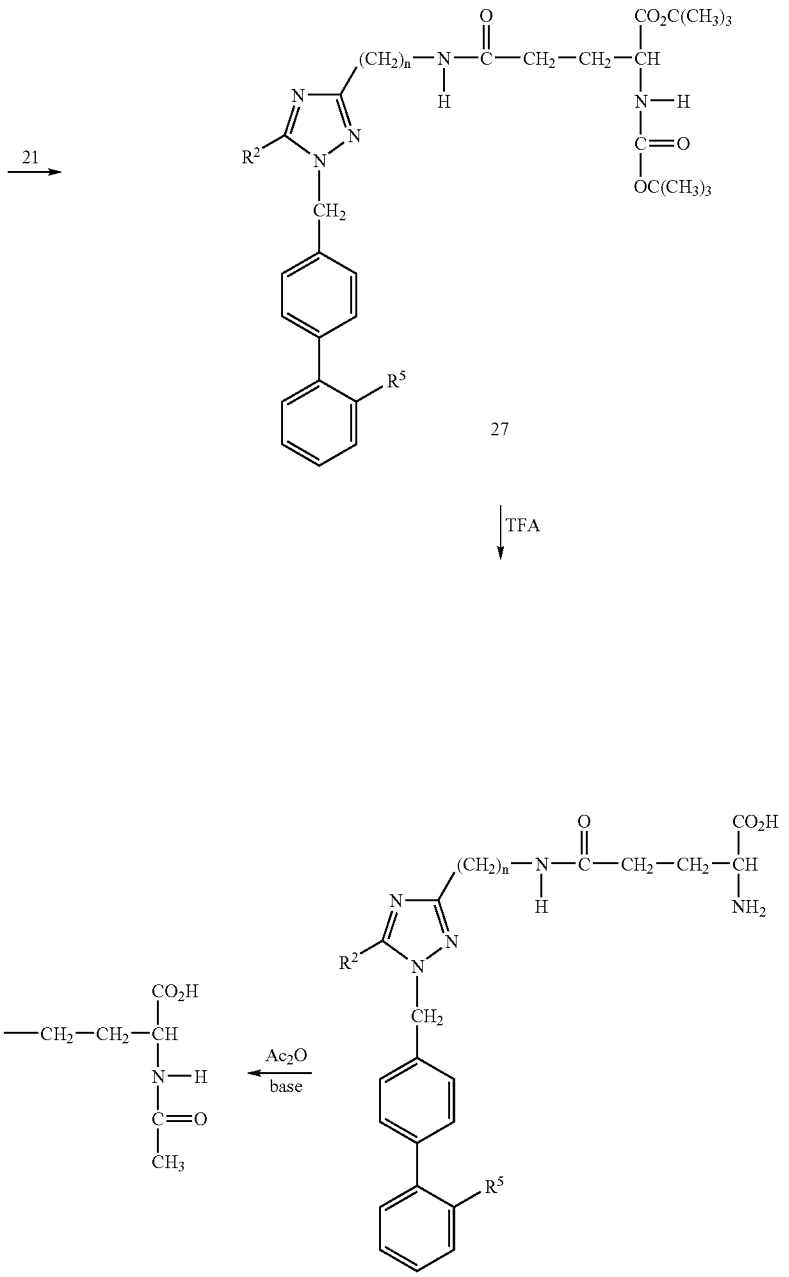

27

28

Synthetic Scheme XI shows the preparation of renal-selective angiotensin II antagonists by coupling amino containing AII antagonists 24 with γ-glutamic acid. In step 1, the AII antagonist is reacted with the symmetrical anhydride of the protected γ-glutamic acid 21 to give 27. In step 2, the protected material 27 is reacted with TFA to give the deprotected coupled material 28. In step 3, the free amino compound 28 is acetylated with acetic anhydride in the presence of base to give the renal-selective angiotensin II antagonists 29.

Scheme XII

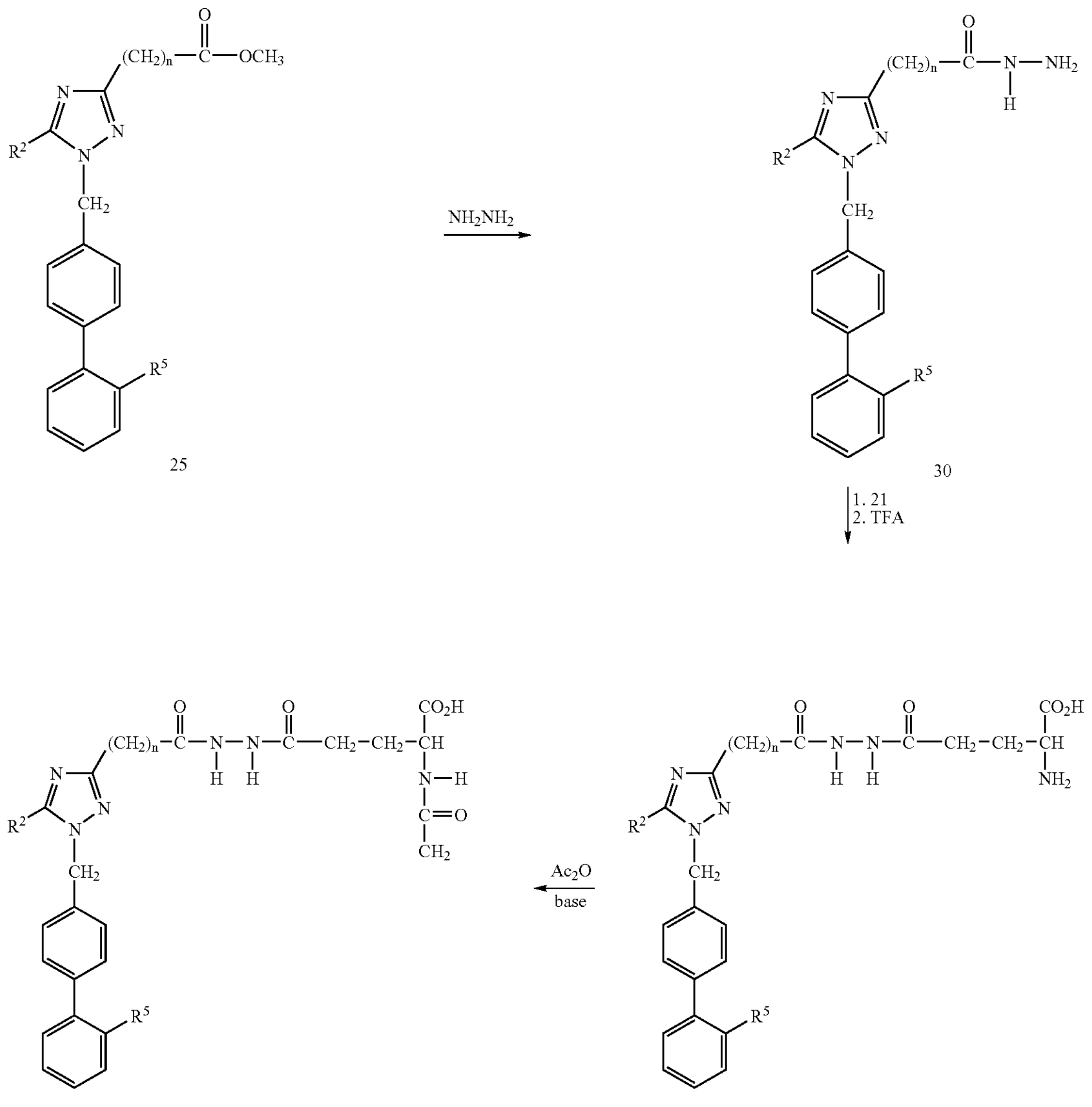

25

30

32

31

Synthetic Scheme XII shows the preparation of renal-selective angiotensin II antagonists by coupling γ-glutamic acid with an angiotensin II antagonist; the triazole $R^1$ acid moiety of the AII antagonist is coupled to the γ-acid moiety of glutamic acid via an hydrazine linker. In step 1, the methyl ester of the AII antagonist 5 is converted to the hydrazide 30 by the action of the hydrazine. In step 2, the hydrazide 30 is first reacted with the symmetrical anhydride of the protected γ-glutamic acid 21 and subsequently reacted with TFA to give the deprotected coupled material 31. In step 3, the free amino group of 31 is acetylated with acetic anhydride in the presence of base to give the renal-selective angiotensin II antagonists 32.

The following Examples 1–78 are detailed descriptions of the methods of preparation of specific angiotensin II antagonist compounds within Formula I. These detailed preparations fall within the scope of, and serve to exemplify, the above described General Synthetic Procedures which form part of the invention. These Examples #1–#78, as well as methods described in other preparatory examples which follow, are presented for illustrative purposes only and are not intended as a restriction on the scope of the invention. All parts are by weight and temperatures are given in centigrade degrees, unless otherwise indicated.

EXAMPLE 1

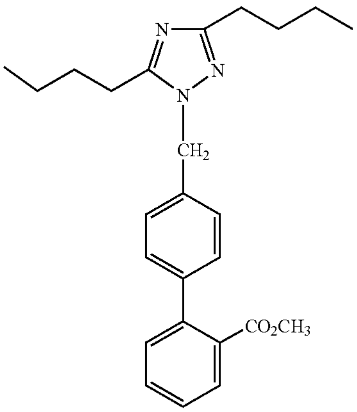

methyl 4'-[(3,5-dibutyl-1H-1,2,4-triazol-1-yl)methyl][1,1'-biphenyl]-2-carboxylate Step 1: Preparation of 4-bromomethyl-2'-methoxycarbonylbiphenyl A 47.46 g (210 mmol) sample of methyl 2-(p-tolyl) benzoate (Chemo Dynamics Inc.) was dissolved in 3 L of carbon tetrachloride and treated with 37.33 g (209 mmol) of N-bromosuccinimide (NBS) and 1.17 g (7.13 mmol) of azobisisobutyronitrile (AIBN) at reflux under nitrogen for 24 hours. The reaction mixture was treated again with 1.0 g (6.1 mmol) of AIBN and stirred at reflux for an additional 24 hours. The reaction was filtered and the solvent removed in in vacuo. Purification by silica gel chromatography (Waters Prep-500A) using ethyl acetate/hexane (5:95) as eluent provided 50.0 g (78%) of a colorless solid: mp 48–51° C.; NMR ($CDCl_3$) δ 3.64 (s, 3H), 4.54 (s, 2H), 7.23–7.63 (m, 7H), 7.81–7.89 (m, 1H). NMR indicated that this material was only 91% pure; it contained 9% of the corresponding dibromocompound (δ 6.70); however, no further attempts at purification were made and this mixture was used in all subsequent alkylation reactions.

Step 2: Preparation of 3,5-dibutyl-1H-1,2,4-triazole

A solution of 64.5 g (0.50 mol) of ethyl iminovalerate [P. Reynaud and R. C. Moreau, *Bull. Soc. Chim. France,* 2997 (1964)] in 100 mL of methanol was added slowly to 58.0 g (0.50 mol) of valeric acid hydrazide (Lancaster Synthesis) in 400 mL of methanol at 0° C. under a nitrogen atmosphere. After the addition was complete, the reaction was allowed to warm to ambient temperature and then stir at reflux for 2 days. The solvent was removed in vacuo; purification by silica gel chromatography (Waters Prep-500A) using ethyl acetate/hexane (80:20) gave 78.9 g (93%) of a colorless solid: mp 50.5–51.5° C.; NMR ($CDCl_3$) δ 0.88 (t, J=7 Hz, 6H), 1.28–1.33 (m, 4H), 1.63–1.77 (m, 4H), 2.72 (t, J=7 Hz, 4H); MS (FAB) m/e (rel intensity) 183 (12%), 182 (100), 181 (3), 180 (6), 152 (8), 139 (4); HRMS. Calcd for M+H: 182.1657. Found: 182.1661.

Step 3: Preparation of methyl 4'-[(3,5-dibutyl-1H-1,2,4-triazol-1-yl)methyl][1,1'-biphenyl]-2-carboxylate Under a static nitrogen atmosphere, 2.01 g (11.0 mmol) of solid 3,5-dibutyl-1H-1,2,4-triazole was added in small portions to 12 mmol of sodium hydride in 50 ml of dimethylformamide (DMF); stirring was continued until hydrogen evolution had ceased. The anion solution was cooled to −10° C. (ice/methanol) and treated with a solution of 3.37 g (11.0 mmol) of 4-bromomethyl-2'-methoxycarbonylbiphenyl in 20 ml of dry DMF. The reaction was allowed to warm to ambient temperature and stir overnight. Methanol (10 ml) was added to destroy any unreacted sodium hydride and the DMF was removed in vacuo. The residue was dissolved in ethyl acetate, washed with water, and dried ($MgSO_4$). Silica gel chromatography (Waters Prep-500A) using 40% ethyl acetate/hexane gave 2.0 g (4%) of compound as an oil: NMR ($CDCl_3$) δ 0.90 (t, J=7 HZ, 3H), 0.94 (t, J=7 Hz, 3H), 1.28–1.47 (m, 4H), 1.62–1.80 (m, 4H), 2.63–2.75 (m, 4H), 3.63 (s, 3H), 5.27 (s, 2H), 7.13–7.18 (m, 2H), 7.25–7.35 (m, 3H), 7.37–7.44 (m, 1H), 7.48–7.55 (m, 1H), 7.80–7.85 (m, 1H).

EXAMPLE 2

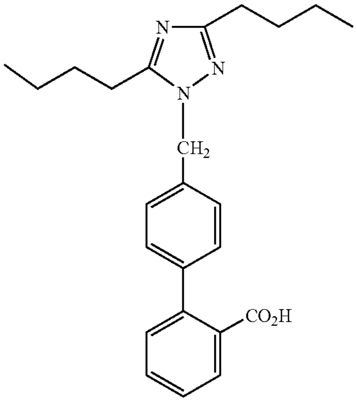

4'-[(3,5-dibutyl-1H-1,2,4-triazol-1-yl)methyl][1,1'-biphenyl]-2-carboxylic acid

A 2.0 g (4.9 mmol) sample of the methyl ester product compound from Example 1 was dissolved in 80 ml of ethanol and treated with 80 ml of 10% NaOH at ambient temperature for 3 days. The ethanol was removed in vacuo and the aqueous phase acidified to pH 1 with hydrochloric acid which caused the product to precipitate; filtration and drying in vacuo gave 1.65 g (86%) of colorless compound: mp 134–135° C.; NMR (DMSO-$d_6$) δ 0.85 (t, J=7 Hz, 3H), 0.90 (t, J=7 Hz, 3H), 1.23–1.39 (m, 4H), 1.53–1.68 (m, 4H), 2.59 (t, J=7 Hz, 2H), 2.78 (t, J=7 Hz, 2H), 5.37 (s, 2H), 5.37 (s, 2H), 7.18–7.26 (m, 2H), 7.28–7.37 (m, 3H), 7.42–7.48 (m, 1H), 7.53–7.60 (m, 1H), 7.70–7.75 (m, 1H).

EXAMPLE 3

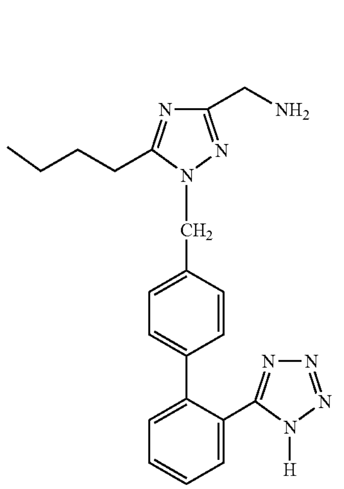

5-[4'-[(3-aminomethyl-5-butyl-1H-1,2,4-triazol-1-yl) methyl][1,1'-biphenyl]-2-yl]-1H-tetrazole Step 1: Preparation of N-Triphenylmethyl-5-[2-(4'-bromomethylbiphen-2-yl]tetrazole A 542.5 g (2.4 mol) sample of methyl 2-(p-tolyl)benzoate (Chemo Dynamics Inc.) was dissolved in 5.5 L of ethanol and treated with 3 L (7.5 mol) of 2.5 N sodium hydroxide. The reaction was stirred overnight at ambient temperature and treated with an additional 480 ml (6.0 mol) of sodium hydroxide; stirring was continued for an additional 24 h and the ethanol removed in vacuo. The remaining solution was cooled in ice and acidified to pH 1 with hydrochloric acid which caused the product to precipitate; filtration and drying in vacuo gave 510 g (100%) of crude 2-(p-tolyl)benzoic acid: mp 145.0–147.5° C.; NMR ($CDCl_3$) δ 2.40 (s, 3H), 7.17–7.28 (m, 4H), 7.35–7.45 (m, 2H), 7.51–7.59 (m, 1H), 7.90–7.97 (m, 1H). The crude acid was suspended in 1 L of toluene and slowly treated with 400 g (3.15 mol) of oxalyl chloride under nitrogen. The reaction was allowed to stir at ambient temperature for 4.5 h and concentrated in vacuo to remove excess oxalyl chloride. The residue was redissolved in 2 L of toluene and treated with 92.8 g (5.46 mol) of anhydrous ammonia. The reaction was filtered and the filtrate concentrated in vacuo producing 424 g (84%) of crude 2-(p-tolyl)benzamide: mp 128–130° C.; NMR ($CDCl_3$) δ 2.40 (s, 3H), 5.28 (br s, 1H), 5.77 (br s, 1H), 7.21–7.53 (m, 7H), 7.76–7.83 (m, 1H). The crude amide was treated with 1420 ml (19.5 mol) of thionyl chloride at reflux for 3.5 h. The reaction was filtered and the thionyl chloride removed in vacuo. The residue was dissolved in 800 ml of toluene and reconcentrated in vacuo. On standing overnight, the residue crystallized. The crystals were collected and washed with hexane to give 296 g (64%) of 2-(p-tolyl) benzonitrile: mp 50.5–52.0° C.; NMR ($CDCl_3$) δ 2.42 (s, 3H), 7.22–7.34 (m, 2H), 7.37–7.52 (m, 3H), 7.58–7.66 (m, 1H), 7.72–7.78 (m, 1H). A 286 g (1.48 mol) sample of the crude nitrile was dissolved in 1630 mL to toluene and treated with 377 g (1.8 mol) of trimethyltinazide at reflux for 24 h. The reaction was cooled; filtration gave 600 g of crude N-trimethylstannyl-5-[2-(4'-methylbiphen-2-yl]tetrazole: mp 271–272° C. (dec.); NMR (DMSO-$d_6$) δ 0.36 (br t, J=34 Hz, 9H), 2.24 (s, 3H), 6.89–7.06 (m, 4H), 7.35–7.55 (m, 4H). The crude N-trimethylstannyl tetrazole was suspended in 4270 mL of toluene and 287 mL of anhydrous tetrahydrofuran (THF) and treated with 63.4 g (173 mol) of anhydrous hydrogen chloride at ambient temperature under nitrogen with stirring. The reaction was allowed to stand overnight and filtered; recrystallization from toluene gave 217 g (62%) of 5-[2-(4'methylbiphen-2-yl)]tetrazole as a solid: mp 149–152° C.; NMR (DMSO-$d_6$) δ 2.28 (s, 3H), 6.94–7.02 (m, 2H), 7.08–7.15 (m, 2H), 7.50–7.59 (m, 2H), 7.62–7.72 (m, 2H). A 200 g (0.85 mol) sample of the tetrazole was suspended in 3.3 L of dichloromethane and treated with 262 g (0.91 mol) of triphenylmethyl chloride and 141 mL (1.0 mol) of anhydrous triethylamine. The reaction was stirred at reflux for 3 h under nitrogen, washed with water, dried ($MgSO_4$), and concentrated in vacuo. Recrystallization gave 338 g (83%) of N-triphenylmethyl-5-[2-(4'-methylbiphen-2-yl)]tetrazole as a colorless solid: mp 170–173° C.; NMR ($CDCl_3$) δ 2.27 (s, 3H), 6.86–6.96 (m, 8H), 6.98–7.04 (m, 2H), 7.09–7.52 (m, 12H), 7.86–7.94 (m, 1H). The N-triphenylmethyl tetrazole was dissolved in 4260 mL of carbon tetrachloride and treated with 126.4 g (0.71 mol) of N-bromosuccinimide (NBS) and 11.9 g (49 mmol) of benzoyl peroxide at reflux for 3.5 h. The reaction was filtered and the solvent removed in vacuo. Recrystallization from toluene gave 277 g (59%) of N-triphenylmethyl-5-[2-(4'-bromomethylbiphen-2-yl)]tetrazole as a colorless solid: mp 140–142° C.; NMR ($CDCl_3$) δ 4.39 (s, 2H), 6.85–6.95 (m, 7H), 7.06–7.15 (m, 4H), 7.22–7.43 (m, 9H), 7.45–7.55 (m, 2H), 7.94–8.01 (m, 1H). NMR indicated that this material was only 85% pure; it contained 7% of corresponding dibromo-compound (δ 6.50) and 8% of starting material (δ 2.27); however, no further attempts at purification were made and this mixture was used in all subsequent alkylation reactions.

Step 2: Preparation of 5-butyl-3-tert-butoxycarbonylaminomethyl-1H-1,2,4-triazole Under nitrogen, a solution of 5.0 g (15.6 mmol) of anhydrous hydrazine in 100 mL of methanol is cooled to −0° C. and treated with a solution of 25.0 g (13.2 mmol) of N-BOC glycine methyl ester (Chemical Dynamics Corporation) in 50 mL of methanol. The reaction is allowed to warm to ambient temperature and stirred overnight. Concentration in vacuo gives the crude hydrazide which is purified either by recrystallization or by silica gel chromatography (Waters Prep-500A). A 18.9 g (100 mol) sample of hydrazide is dissolved in 100 mL of methanol and is treated with 12.9 g (100 mmol) of ethyl iminovalerate under nitrogen. The reaction is stirred at reflux overnight and concentrated in vacuo. Purification by silica gel chromatography (Waters Prep-500A) gives 5-butyl-3-tert-butoxycarbonylaminomethyl-1H-1,2,4-triazole.

Step 3: Preparation at 5-[4'-[(3-aminomethyl-5-butyl-1H-1,2,4-triazol-1-yl)methyl][1,1'-biphenyl]-2-yl]-1H-tetrazole Under a static nitrogen atmosphere, 3.81 g (15.0 mmol) of 3-butyl-5-tert-butoxycarbonylamino-1H-1,2,4-triazole is added slowly to 15 mmol of sodium hydride in 50 ml of dimethylformamide (DMF); stirring is continued until hydrogen evolution has ceased. The anion solution is cooled to −10° C. (ice/methanol) and treated with a solution of 8.45 g (15.0 mmol) of N-triphenylmethyl-5-[2-(4'-bromomethyl-biphen-2-yl)]tetrazole in 20 ml of dry DMF. The reaction is allowed to warm to ambient temperature and stir overnight. Methanol (10 ml) is added to destroy any unreacted sodium hydride and the DMF is removed in vacuo. The residue is dissolved in ethyl acetate, washed with water, and dried ($MgSO_4$). Purification by silica gel chromatography gives the desired isomer which is dissolved in 100 mL of TFA and is stored at ambient temperature overnight. The reaction is cooled to 0° C., 50 mL of water is added, and is allowed to stir at ambient temperature overnight. The solvent is removed in vacuo and the residue is dissolved in acetonitrile/water. Purification by reverse phase chromatography (Waters Delta Prep.-3000) provides pure 5-[4'-[(3-aminomethyl-5-butyl-1H-1,2,4-triazol-1-yl][1,1'-biphenyl]-2-yl]-[1H-tetrazole as the TFA salt.

EXAMPLE 4

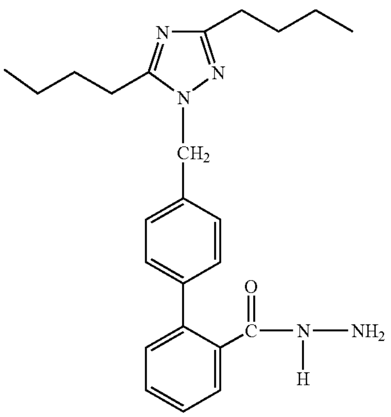

4'[(3,5-dibutyl-1H-1,2,4-triazol-1-yl)methyl][1,1'-biphenyl]-2 carboxylic acid, hydrazide A 7.10 g (17.5 mmol) sample of the methyl ester product compound of Example 1 was dissolved in 150 ml of methanol and treated with 22 ml (22.2 g 695 mmol) of anhydrous hydrazine under a static nitrogen atmosphere. The reaction was stirred at reflux for 2 days and concentrated in vacuo to give 7.03 g (99%) of compound which was a colorless glass: NMR ($CDCl_3$) δ 0.88 (t, J=7 Hz, 3H), 0.94 (t, J=7 Hz, 3H), 1.28–1.47 (m, 4H), 1.62–1.78 (m, 4H), 2.62–2.73 (m, 4H), 3.5–4.1 (br s, 2H), 5.26 (s, 2H), 6.53 (s, 1H), 7.13–7.63 (m, 8H).

EXAMPLE 5

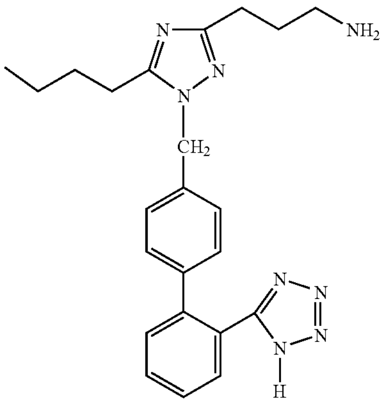

5-[4'-[[3-(3-aminopropyl)-5-butyl-1H-1,2,4-triazol-1-yl]methyl][1,1'-biphenyl]-2-yl]-1H-tetrazole Step 1: Preparation of 5-butyl-3-(3-tertbutoxycarbonylaminoprioyl)-1H-1,2,4-triazole Under nitrogen, 60.0 g (0.30 mol) of N-BOC-γ-aminobutyric acid (BACHEM) is dissolved in 1200 mL of methylene chloride and treated with 30.5 g (0.15 mol) of dicyclohexylcarbodiimide (DCC). The reaction is allowed to stir for 2 hours and filtered under nitrogen. The anhydride solution is then added to a solution of 1.58 g (98.5 mmol) of anhydrous hydrazine in 100 mL of methylene chloride at 0° C. The reaction is allowed to warm to ambient temperature and stirred overnight. Concentration in vacuo gives the crude hydrazide which is purified either by recrystallization or by silica gel chromatography (Waters Prep-500A). A 21.7 g (100 mmol) sample of hydrazide is dissolved in 100 mL of methanol and treated with 12.9 g (100 mmol) of ethyl iminovalerate under nitrogen. The reaction is stirred at reflux overnight and concentrated in invacuo. Purification by silica gel chromatography (Waters Prep-500A) gives 5-butyl-3-(3-tert-butoxycarbonylaminopropyl-1H-1,2,4-triazole.

Step 2: Preparation of 5-[4'-[[3-(3-aminopropyl)-5-butyl-1H-1,2,4-triazol-1-yl]methyl][1,1'-biphenyl]-2-yl]-1H-tetrazole Under a static nitrogen atmosphere, 14.4 g (46.0 mmol) of 3-(3-N-BOC-aminopropyl)-5-butyl-1H-1,2,4-triazole is added in small portions to 50 mmol of sodium hydride in 250 ml of dimethylformamide (DMF); stirring is continued until hydrogen evolution has ceased. The anion solution is cooled to −10° C. (ice/methanol) and is treated with a solution of 25.5 g (46.0 mmol) of N-triphenylmethyl-5-[2-(4'-bromomethylbiphen-2-yl)]tetrazole (from Step 1 of Example 3) in 100 ml of dry DMF. The reaction is allowed to warm to ambient temperature and stir overnight. Methanol (10 ml) is added to destroy any unreacted sodium hydride and the DMF is removed in vacuo; the residue is dissolved in ethyl acetate, washed with water, and dried ($MgSO_4$). Purification by silica gel chromatography gives the desired isomer which is dissolved in 200 mL of TFA and is stirred at ambient temperature overnight. The reaction is cooled to 0° C., 100 mL of water is added, and is allowed to stir at ambient temperature overnight. The solvent is removed in vacuo and the residue is dissolved in acetonitrile/water. Purification by reverse phase chromatography (Waters Delta Prep-3000) provided pure 5-[4'-[[3-(3-aminopropyl)-5-butyl-1H-1,2,4-triazol-1-yl]methyl][1,1'-bi-phenyl]-2-yl]-1H-tetrazole as the TFA salt.

EXAMPLE 6

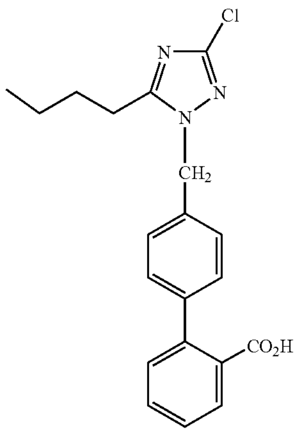

4'-[(5-butyl-3-chloro-1H-1,2,4-triazol-1-yl)methyl][1,1'-biphenyl]-2-carboxylic acid Step 1: Preparation of 3-butyl-5-chloro-1H-1,2,4-triazole A 10.0 g (80 mmol) sample of 3-butyl-1H-1,2,4-triazole [H. Paul, G. Hilgetag, and G. Jahnchen, *Chem. Ber.*, 101, 2033 (1968)] was dissolved in 320 mL of water containing 7.0 g (177 mmol) of sodium hydroxide. With stirring, the solution was cooled to 0° C. and chlorine was introduced over 3 h. The reaction was purged with nitrogen overnight and the solution extracted with chloroform. The extracts were combined, dried ($MgSO_4$), and concentrated in vacuo to give 16.8 g of a colorless oil which was placed in 200 mL of water and treated twice with 8.0 g (80 mmol) of sodium metabisulfite. The pH of the reaction medium was adjusted to 6 with 1M sodium carbonate prior to extraction with chloroform; the extracts were dried ($MgSO_4$) and concentrated in vacuo to give 14.9 g of crude product. Purification by silica gel chromatograph (Waters Prep-500A) using chloroform/methanol (95:5) gave 9.53 g (75%) of a colorless solid: mp 104–105° C.; NMR ($CDCl_3$) δ 0.94 (t, J=7 Hz, 3H), 1.33–1.47 (m, 2H), 1.68–1.83 μm, 2H), 2.80 (t, J=7 Hz, 2H); MS (FAB) m/e (rel intensity) 162 (28), 160 (100), 158 (10), 130 (5), 126 (10), 117 (5); HRMS. Calcd for M+H: 160.0642. Found: 160.0651.

Step 2: Preparation of 4'-[(5-butyl-3-chloro-1H-1,2,4-triazol-1-yl)methyl][1,1'-biphenyl]-2-carboxylic acid Under a static nitrogen atmosphere, 5.0 g (31.3 mmol) of solid 5-butyl-3-chloro-1H-1,2,4-triazole was added in small portions to 32 mmol of sodium hydride in 50 ml of dimethylformamide (DMF); stirring was continued until hydrogen evolution had ceased. The anion solution was cooled to −10° C. (ice/methanol) and treated with a solution of 9.55 g (31.3 mmol) of 4-bromomethyl-2'-methoxycarbonylbiphenyl in 20 ml of dry DMF. The reaction was allowed to warm to ambient temperature and stir overnight. Methanol (10 ml) was added to destroy any unreacted sodium hydride and the DMF was removed in vacuo. The residue was dissolved in ethyl acetate, washed with water, and dried ($MgSO_4$) to give 12.2 g of crude material was obtained which was a clear golden oil. A 4.81 g sample of this material was dissolved in 250 ml of methanol and treated with 250 ml of 10% NaOH at ambient temperature for 2 days. A portion of the isomer mixture of acids was separated by reverse phase chromatography (Waters Delta Prep-3000) using isocratic 45% acetronitrile/water (0.05% TFA). The faster moving isomer (250 mg) was identified as the 3-chloro isomer: NMR (DMSO-$d_6$) δ 0.86 (t, J=7 Hz, 3H), 1.23–1.36 (m, J=7 Hz, 2H), 1.54–1.65 (m, J=7 Hz, 1H), 2.80 (t, J=7 Hz, 2H), 5.40 (s, 2H), 7.23–7.58 (m, 7H), 7.72–7.77 9 m, 1H).

EXAMPLE 7

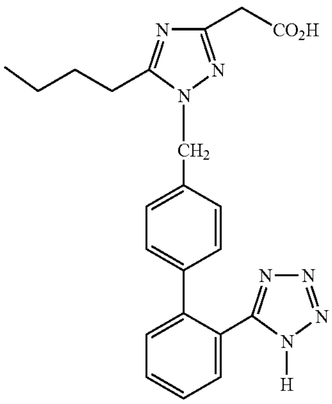

5-[4'-[(5-butyl-3-carboxymethyl-1H-1,2,4-triazol-1-yl)methyl][1,1'-biphenyl]-2-yl]-1H-tetrazole Step 1: Preparation of 5-butyl-3-(2,2-diethoxyethyl)-1H-1,2,4-triazole Under nitrogen, a solution of 38.4 g (1.2 mol) of anhydrous hydrazine in 500 mL of methanol is cooled to 0° C. and treated with a solution of 190.0 g (1.0 mol) of ethyl 3,3-diethoxypropionate (Aldrich) in 200 mL of methanol. The reaction is allowed to warm to ambient temperature and is stirred overnight at reflux. Concentration in vacuo gives the crude hydrazide which is purified either by recrystallization or by silica gel chromatography (Waters Prep-500A). A 17.6 g (100 mmol) sample of hydrazide is dissolved in 100 mL of methanol and is treated with 12.9 g (100 mmol) of ethyl iminovalerate under nitrogen. The reaction is stirred at reflux overnight and concentrated in vacuo. Purification by silica gel chromatography (Waters Prep-500A) gives 5-butyl-3-(2,2-di-ethoxyethyl)-1H-1,2,4-triazole.

Step 2: Preparation of 5-[4'-[(5-butyl-3-carboxymethyl-1H-1,2,4-triazol-1-yl)methyl][1,1'-biphenyl]-2-yl]-1H-tetrazole Under a static nitrogen atmosphere, 11.1 g (46.0 mmol) of 5-butyl-3-(2,2-diethoxyethyl)-1H-1,2,4-triazole is added in small portions to 50 mmol of sodium hydride in 250 ml of dimethylformamide (DMF); stirring is continued until hydrogen evolution has ceased. The anion solution is cooled to −10° C. (ice/methanol) and is treated with a solution of 25.5 g (9.2 mmol) of N-triphenylmethyl-5-[2-(4'-bromomethylbiphen-2-yl)]tetrazole (from Step 1 of Example 3) in 100 ml of dry DMF. The reaction is allowed to warm to ambient temperature and stir overnight. Methanol (10 ml) is added to destroy any unreacted sodium hydride and the DMF is removed in vacuo; the residue is dissolved in ethyl acetate, washed with water, and dried ($MgSO_4$). Purification by silica gel chromatography gives the desired isomer which is treated with 3N HCl/methanol (1:1) at reflux for 4 hours. The methanol is removed in vacuo and the pH is adjusted to 9 with NaOH. The solution is extracted with ethyl acetate twice to remove triphenylmethanol. The pH is readjusted to 3 with 6N HCl and the solution is extracted 3 times with ethyl acetate, the extracts are combined, washed with water, and dried ($MgSO_4$). Concentration in vacuo gives 5-[4'-[(5-butyl-3-formalmethyl-1H-1,2,4-triazole-1-yl)methyl][1,1'-biphenyl]-2-yl]-1H-tetrazole. A 4.01 g (10.0 mmol) sample of the free aldehyde is dissolved in 500 mL of acetone/water (1:1) and is treated with 1.65 g (10.4 mmol) of solid $KMnO_4$ over 6 hours at ambient temperature. The reaction is allowed to stir overnight and excess $KMnO_4$ is destroyed by the addition of 100 mL of methanol. The reaction is filtered and the acetone is removed in vacuo; the pH is adjusted to 3 with 6N HCl and the product is extracted with ethyl acetate. The extracts are combined, washed with water, and dried ($MgSO_4$). Concentration in vacuo gives the crude product which was dissolved in acetonitrile/water; purification by reverse phase chromatography (Waters Delta Prep-3000) provides pure 5-[4'-[5-butyl-3-caroxymethyl-1H-1,2,4-triazol-1-yl)methyl][1,1-biphenyl]-2-yl]-1H-tetrazole.

EXAMPLE 8

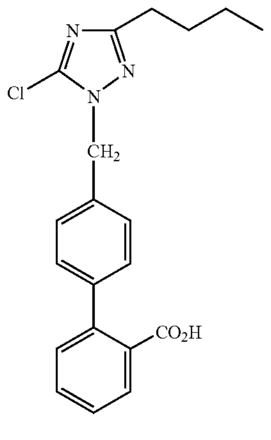

4'-[(3-butyl-5-chloro-1H-1,2,4-triazol-1-yl)methyl][1,1'-biphenyl]-2-carboxylic acid The slower moving isomer (120 mg) isolated in Example 6 was identified as the 5-chloro isomer: NMR (DMSO-$d_6$) δ 0.88 (t, =7 Hz, 3H), 1.25–1.35 (m, J=7 Hz, 2H), 1.56–1.67 (m, J=7 Hz, 2H), 2.49 (t, J=7 Hz, 2H), 5.37 (s, 2H), 7.23–7.58 (m, 7H), 7.72–7.77 (m, 1H).

EXAMPLE 9

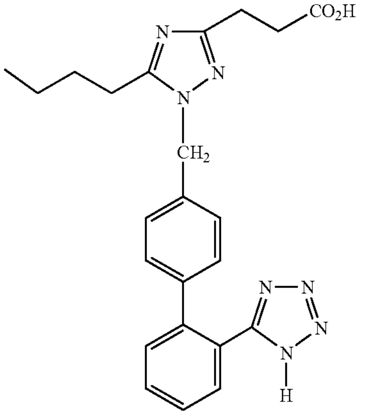

5-[4'-[[5-butyl-3-(2-carboxyethyl)-1H-1,2,4-triazol-1-yl]methyl][1,1'-biphenyl]-2-yl]-1H-tetrazole Step 1: Preparation of 5-butyl-3-(3-hydroxypropyl)-1H-1,2,4-triazole Under nitrogen, a solution 38.4 g (1.2 mol) of anhydrous hydrazine in 500 mL of methano is cooled to 0° C. and is treated with a solution of 86.0 g (1.0 mol) of γ-butyrolactone (Aldrich) in 100 mL of methanol. The reaction is allowed to warm to ambient temperature and stir overnight at reflux. Concentration in vacuo gives the crude hydrazide which is purified either by recrystallization or by silica gel chromatography (Waters Prep-500A). A 11.8 g (100 mmol) sample of hydrazide is dissolved in 100 mL of methanol and is treated with 12.9 g (190 mmol) of ethyl iminovalerate under nitrogen. The reaction is stirred at reflux overnight and concentrated in vacuo. Purification by silica gel chromatography (Waters Prep-500A) gives 5-butyl-3-(3-hydroxypropyl)-1H-1,2,4-triazole.

Step 2: Preparation of 5-[4'-[[5-butyl-3-(2-carboxyethyl)-1H-1,2,4-triazol-1-yl]methyl][1,1'-biphenyl]-2-yl]-1H-tetrazole Under a static nitrogen atmosphere, 8.4 g (46 mmol) of 5-butyl-3-(3-hydroxypropyl)-1H-1,2,4-triazole is added in small portions to 50 mol of sodium hydride in 250 ml of dimethylformamide (DMF); stirring is continued until hydrogen evolution has ceased. The anion solution is cooled to −10° C. (ice/methanol) and treated with a solution of 25.5 g (46 mmol) of N-triphenylmethyl-5-[2-(4'-bromomethylbiphen-2-yl)]tetrazole (from Step 1 of Example 3) in 100 ml of dry DMF. The reaction is allowed to warm to ambient temperature and stir overnight. Methanol (10 ml) is added to destroy any unreacted sodium hydride and the DMF is removed in vacuo; the residue is dissolved in ethyl acetate, washed with water, and dried ($MgSO_4$). Purification by silica gel chromatography gives a mixture of isomers which is treated with 3N HCl/methanol (1:1) at reflux for 4 hours. The methanol is removed in vacuo and the pH is adjusted to 9 with NaOH. The solution is extracted with ethyl acetate twice to remove triphenylmethanol. The pH is readjusted to 3 with 6 N HCl and the solution is extracted 3 times with ethyl acetate; the extracts are combined, washed with water, and dried ($MgSO_4$). Concentration in vacuo gives a mixture of 5-butyl-3-(3-hydroxypropyl)- and 3-butyl-5-(3-hydroxypropyl)-1H-1,2,4-triazol-1-yl]methyl][1,1'-biphenyl]-2-yl]-1H-tetrazole isomers. A 4.17 g (10.0 mmol) sample of the isomeric mixture of alcohols is dissolved in 500 mL of acetone/water (1:1) and is treated with 3.30 g (20.8 mmol) of solid $KMnO_4$ over 6 hours at ambient temperature. The reaction is allowed to stir overnight and excess $KMnO_4$ is destroyed by the addition of 100 mL of methanol. The reaction is filtered and the acetone is removed in vacuo; the pH is adjusted to 3 with 6N HCl and the product is extracted with ethyl acetate. The extracts are combined, washed with water, and dried ($MgSO_4$). Concentration in vacuo give the isomeric mixture of acids; purification by reverse phase chromatography (Waters Delta Prep-3000) provides pure 5-[4'-[[5-butyl-3-(2-carboxyethyl)-1H-1,2,4-triazol-1-yl]methyl][1,1'-biphenyl]-2-yl]-1H-tetrazole.

EXAMPLE 10

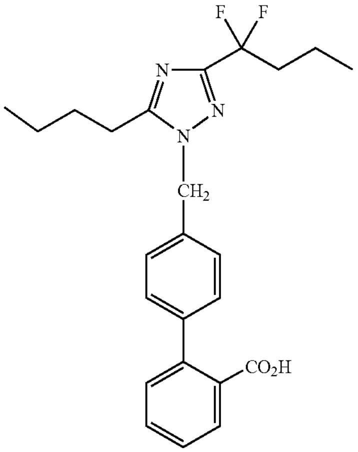

5-[4'-[[5-butyl-3-(1,1-difluorobutyl)-1H-1,2,4-triazol-1-yl]methyl][1,1'-biphenyl]-2-carboxylic acid Step 1: Preparation of 3-butyl-5-(1,1-difluorobutyl)-1H-1,2,4-triazole Under nitrogen, a stirred solution of 56.9 g (0.65 mol) of N-tert-butyl-N-methylamine (Fluka) and 66.1 g (0.65 mol) of triethylamine in 1 L of methylene chloride was cooled to 0° C. and treated with neat difluoroacetic anhydride [E. Sawicki, *J. Org. Chem.,* 21, 376 (1956)] at such a rate as to maintain the reaction temperature below 10° C. The reaction was allowed to warm to ambient temperature and stir overnight. All volitiles were removed in vacuo (bath temperature<35° C.) and the residue redissolved in methylene chloride; the solution was washed with saturated sodium bicarbonate, dried ($MgSO_4$), and concentrated to give 94 g (89%) of a yellow liquid. Vacuum distillation gave 86 g (81%) of colorless N-tert-butyl-N-methyldifluoroacetamide: bp 87–88° C. (22 mm); 'H NMR ($CDCl_3$) δ 1.37 (s, 9H), 2.93 (t, J=3 Hz, 3H), 5.97 (t, J=57 Hz, 1H); $^{19}F$ NMR. ($CDCl_3$) δ −122.20 (d, J=57 Hz, 2F). A 17.0 g (103 mmol) sample of the amide was dissolved in 50 mL of dry THF and added slowly to a solution of 145 mmol of lithium diisopropylamine (LDA) in 450 mL of dry THF at −78° C. The reaction was allowed to stir for 1 h at −78° C. prior to the addition of 17 mL (175 mmol) of 1-iodopropane by syringe. Stirring at −78° C. was continued for 1 hr and then the reaction was allowed to warm to ambient temperature overnight. Methanol (10 mL) was added and the reaction was concentrated in vacuo; the residue was dissolved in methylene chloride and washed with 1N hydrochloric acid, dried ($MgSO_4$) and reconcentrated to give 17.6 g (83%) of crude product. Purification by vacuum distillation gave 13.3 g (62%) of colorless N-tert-butyl-N-methyl-2,2-difluoro-valeramide: bp 125–130° C. (84 mm); 'H NMR ($CDCl_3$) δ 0.94 (t, J=7 Hz, 3H), 1.37 (s, 9H), 1.40–1.52 (m, 2H), 1.95–2.15 (m, 2H); $^{19}F$ NMR ($CDCl_3$) δ −100.29 (t, J=20 Hz, 2F). The difluorovaleramide was dissolved in 30 mL of trifluoroacetic acid (TFA) and stirred at reflux overnight under nitrogen. The solvent was removed in vacuo and the residue dissolved in methylene chloride; the solution was washed with water, dried ($MgSO_4$) and concentrated to give 9.7 g (100%) of crude N-methyl-2,2-difluorovaleramide: 'H NMR ($CDCl_3$) δ 0.92 (t, J=7 Hz, 3H), 1.36–1.51 (m, 2H), 1.90–2.11 (m, 2H), 2.84 (d, J=6 Hz, 3H), 6.60–6.85 (br s, 1H); $^{19}F$ NMR ($CDCl_3$) δ −106.98 (t, J=19 Hz, 2F). The crude N-methyl amide was dissolved in 40 mL of 6N hydrochloric acid and stirred at reflux for 24 hr. The reaction was cooled to ambient temperature and extracted with methylene chloride; the extracts were combined, dried ($MgSO_4$), and concentrated to give 8.0 g (56%) of crude 2,2-difluorovaleric acid: 'H NMR ($CDCl_3$) δ 1.00 (t, J=7 Hz, 3H), 1.46–1.63 (m, 2H), 1.97–2.17 (m, 2H); $^{19}F$ NMR ($CDCl_3$) δ 107.16 (t, J=18 Hz, 2F). A 4.83 g (35 mmol) sample of the crude acid was dissolved in 25 mL (35.2 g, 174 mmol) of phthaloyl chloride in a flask equipped with a reflux condenser and stirred under nitrogen in a 110° C. oil bath for 6 hrs. The condenser was replaced with a distillation head and 3.22 g (60%) of colorless 2,2-difluorovaleryl chloride was collected bp 96°; 'H NMR ($CDCl_3$) δ 1.03 (t, J=7 Hz, 3H), 1.48–1.65 (m, 2H), 2.03–2.23 (m, 2H); $^{19}F$ NMR ($CDCl_3$) δ −102.41 (t, J=18 Hz, 2F). The 2,2-difluorovaleryl chloride (20.6 mmol) was dissolved in 10 mL of methylene chloride and dropwise to a solution of 135 g (42 mmol) of anhydrous hydrazine in 20 mL of methylene chloride at 0° C. After the addition was complete, the reaction was stirred at ambient temperature for 1 h, washed with water, dried ($MgSO_4$), and concentrated to give 3.12 g (91%) of 2,2-difluorovaleric acid hydrazide: NMR ($CDCl_3$) δ 0.96 (t, J=7 Hz, 3H), 1.40–1.56 (m, 2H), 1.96–2.17 (m, 2H), 3.93 (br s, 2H), 7.67 (br s, 1H). A 2.84 g (18.7 mmol) sample of the crude hydrazide was dissolved in 50 mL of methanol and treated with 2.41 g (18.7 mmol) of ethyl iminovalerate. Under nitrogen, the reaction was stirred at reflux for 3 days and concentrated in vacuo. Purification by silica gel chromatography (Waters Prep-500A) using ethyl acetate/hexane (60:40) gave 3.0 g (74%) of 3-butyl-5-(1,1-difluoro)butyl-1H-1,2,4-triazole as a colorless solid: mp 92–93° C.; 'H NMR ($CDCl_3$) δ 0.97 (t, J=Hz, 3H), 0.92 (t, J=7 Hz, 3H), 1.30–1.45 (m, 2H), 1.47–1.62 (m, 2H), 1.66–1.81 (m, 2H), 2.18–2.38 (m, 2H), 2.83 (t, J=7 Hz, 2H); $^{19}F$ NMR ($CDCl_3$) δ −97.27 (t, J=18 Hz, 2F); MS (FAB) m/e (rel intensity) 218 (100), 198 (8), 188 (5), 178 (8), 170 (5); HRMS. Calcd for M+H: 218.1469. Found: 218.1461.

Step 2: Preparation of 5-[4'-[[5-butyl-3-(1,1-difluorobutyl)-1H-1,2,4-triazol-1-yl]methyl][1,1'-biphenyl]-2-carboxylic acid Under a static nitrogen atmosphere, 2.0 g (9.2 mmol) of solid 3-butyl-5-(1,1-difluorobutyl)-1H-1,2,4-triazole is added in small portions to 10 mmol of sodium hydride in 50 ml of dimethylformamide (DMF); stirring is continued until hydrogen evolution has ceased. The anion solution is cooled to −10° C. (ice/methanol) and is treated with a solution of 3.0 g (9.2 mmol) of 4-bromomethyl-2'-methoxycarbonylbiphenyl (from Step 1 of Example 1) in 20 ml of dry DMF. The reaction is allowed to warm to ambient temperature and stir overnight. Methanol (10 ml) is added to destroy any unreacted sodium hydride and the DMF is removed in vacuo; the residue is dissolved in ethyl acetate, washed with water, and dried ($MgSO_4$). Silica gel chromatography separates the two isomers; the more abundant isomer is dissolved in 80 ml of ethanol and is treated with 80 ml of 10% NaOH at ambient temperature for 3 days. The ethanol is removed in vacuo and the aqueous phase is acidified to pH 1 with hydrochloric acid which causes the product to precipitate; filtration and drying in vacuo gives 4'-[(5-butyl-3-(1,1-difluorobutyl)-1H-1,2,4-triazol-1-yl)methyl][1,1'-biphenyl)-2-carboxylic acid.

EXAMPLE 11

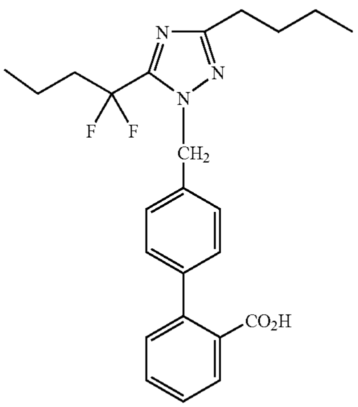

4'-[[3-butyl-5-(1,1-difluorobutyl)-1H-1,2,4-triazol-1-yl]methyl][1,1'-biphenyl]-2-carboxylic acid The less abundant isomer isolated in Example 10 is dissolved in 40 ml of ethanol and is treated with 40 ml of 10% NaOH at ambient temperature for 3 days. The ethanol is removed in vacuo and the aqueous phase is acidified to pH 1 with hydrochloric acid which causes the product to precipitate; filtration and drying in vacuo gives 4'-[(3-butyl-5-(1,1-difluorobutyl)-1H-1,2,4-triazol-1-yl)methyl][1,1'-biphenyl]-2-carboxylic acid.

EXAMPLE 12

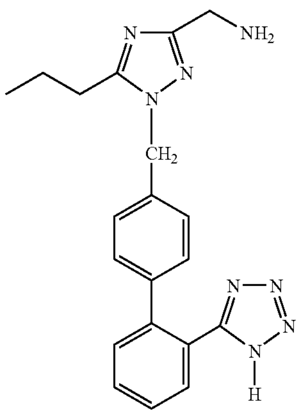

5-[4'-[(3-aminomethyl-5-propyl-1H-1,2,4-triazol-1-yl)methyl][1,1'-biphenyl]-2-yl]-1H-tetrazole Step 1: Preparation of 5-propyl-3-tert-butoxycarbonylamino-methyl-1H-1,2,4-triazole Under nitrogen, a solution of 18.9 g (100 mmol) of N-Boc glycine hydrazide (from step 2 of Example 3) in 100 mL of methanol is treated with 11.5 g (100 mmol) of ethyl iminobutyrate [P. Reynaud and R. C. Moreau, *Bull. Soc. Chim. France,* 2997 (1964)]. The reaction is stirred at reflux overnight and concentrated in vacuo. Purification by silica gel chromatography (Waters Prep-500A) gives 5-propyl-3-tert-butoxycarbonylaminomethyl-1H-1,2,4-triazole.

Step 2: Preparation of 5-[4'-[(3-aminomethyl-5-propyl-1H-1,2,4-triazol-1-yl)methyl][1,1'-biphenyl]-2-yl]-1H-tetrazole Under a static nitrogen atmosphere, 3.81 g (15.0 mmol) of 3-propyl-5-tert-butoxy-carbonylaminomethyl-1H-1,2,4-triazole is added to 15 mmol of sodium hydride in 50 mL of DMF; stirring is continued until hydrogen evolution has ceased. The anion solution is cooled to −10° C. (ice/methanol) and treated with a solution of 8.45 g (15 mmol) of N-triphenylmethyl-5-[2-(4'-bromomethylbiphen-2-yl)] tetrazole in 20 mL of dry DMF. The reaction is allowed to warm to ambient temperature and stir overnight. Methanol (10 mL) is added to destroy any unreacted sodium hydride and the DMF is removed in vacuo. The residue is dissolved in ethyl acetate, washed with water, and dried ($MgSO_4$). Purification by silica gel chromatography gives the desired isomer which is dissolved in 100 mL of TFA and is stirred at ambient temperature overnight. The reaction is cooled to 0° C., 50 mL of water is added and is allowed to stir at ambient temperature overnight. The solvent is removed in vacuo and the residue is dissolved in acetonitrile/water. Purification by reverse phase chromatography (Waters Delta Prep-3000) provides pure 5-[4'-[(3-aminomethyl-5-propyl-1H-1,2,4-triazole-1-yl][1,1'-biphenyl]-2-yl]-1H-tetrazole as the TFA salt.

EXAMPLE 13

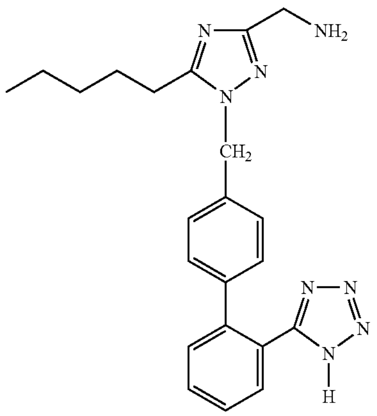

5-[4'-[(3-aminomethyl-5-pentyl-1H-1,2,4-triazol-1-yl)methyl][1,1'-biphenyl]-2-yl]-1H-tetrazole Step 1: Preparation of 5-pentyl-3-tert-butoxycarbonylamino-methyl-1H-1,2,4-triazole Under nitrogen, a solution of 18.9 g (100 mmol) of N-Boc glycine hydrazide (from step 2 of Example 3) in 100 mL of methanol is treated with 14.3 g (100 mmol) of ethyl iminocaproate [P. Reynaud and R. C. Moreau, *Bull. Soc. Chim. France,* 2997 (1964)]. The reaction is stirred at reflux overnight and concentrated in vacuo. Purification by silica gel chromatography (Waters Prep-500A) gives 5-pentyl-3-tert-butoxycarbonylaminomethyl-1H-1,2,4-triazole.

Step 2: Preparation of 5-[4'-[(3-aminomethyl-5-pentyl-1H-1,2,4-triazol-1-yl)methyl][1,1'-biphenyl]-2-yl]-1H-tetrazole Under a static nitrogen atmosphere, 4.02 g (15.0 mmol) of 3-pentyl-5-tert-butoxy-carbonylaminomethyl-1H-1,2,4-triazole is added to 15 mmol of sodium hydride in 50 mL of DMF; stirring is continued until hydrogen evolution has ceased. The anion solution is cooled to −10° C. (ice/methanol) and treated with a solution of 8.45 g (15 mmol) of N-triphenylmethyl-5-[2-(4'-bromomethylbiphen-2-yl)] tetrazole in 20 mL of dry DMF. The reaction is allowed to warm to ambient temperature and stir overnight. Methanol (10 mL) is added to destroy any unreacted sodium hydride and the DMF is removed in vacuo. The residue is dissolved in ethyl acetate, washed with water, and dried ($MgSO_4$). Purification by silica gel chromatography gives the desired isomer which is dissolved in 100 mL of TFA and is stirred at ambient temperature overnight. The reaction is cooled to 0° C., 50 mL of water is added and is allowed to stir at ambient temperature overnight. The solvent is removed in vacuo and the residue is dissolved in acetonitrile/water. Purification by reverse phase chromatography (Waters Delta Prep-3000) provides pure 5-[4'-[(3-aminomethyl-5-pentyl-1H-1,2,4-triazole-1-yl][1,1'-biphenyl]-2-yl]-1H-tetrazole as the TFA salt.

EXAMPLE 14

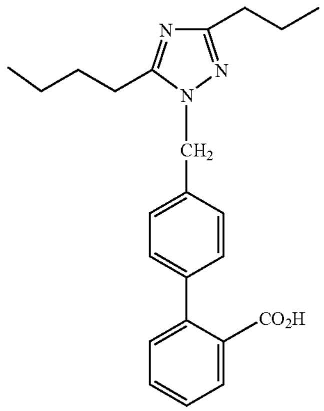

4'-[(5-butyl-3-propyl-1H-1,2,4-triazol-1-yl)methyl]-[1,1'-biphenyl]-2-carboxylic acid Step 1: Preparation of 5-butyl-3-propyl-1H-1,2,4-triazole A 3.95 g (38.7 mmol) sample of butyric acid hydrazide was dissolved in 30 mL of methanol and treated with 5.0 g (38.8 mmol) of ethyl iminovalerate under nitrogen. The reaction was stirred at reflux for 3 days and concentrated m vacuo. Purification by silica gel chromatography (Waters Prep-500A) using ethyl acetate/hexane (80:20) gave 5.51 g (85%) of 5-butyl-3-propyl-1H-1,2,4-triazole as a colorless solid: mp 48.5–50.0° C.; NMR ($CDCl_3$) δ 0.92 (t, J=7 Hz, 3H), 0.97 (t, J=7 Hz, 3H), 1.31–1.46 (m, 2H), 1.66–1.84 (m, 4H), 2.72 (t, J=7 Hz, 2H), 2.75 (t, J=7 Hz, 2H); MS (FAB) m/e (rel intensity) 168 (100), 166 (4), 152 (3), 138 (3), 125 (3); HRMS. Calcd for M+H: 168.1501. Found: 168.1534.

Step 2: Preparation of 4'-[(5-butyl-3-propyl-1H-1,2,4-triazol-1-yl)methyl][1,1'-biphenyl]-2-carboxylic acid Under a static nitrogen atmosphere, 2.0 g (12 mmol) of solid 5-butyl-3-propyl-1H-1,2,4-triazole is added in small portions to 12 mmol of sodium hydride in 50 ml of dimethylformamide (DMF); stirring is continued until hydrogen evolution has ceased. The anion solution is cooled to −10° C. (ice/methanol) and treated with a solution of 3.8 g (12 mmol) of 4-bromomethyl-2'-methoxycarbonylbiphenyl (from Step 1 of Example 1) in 20 ml of dry DMF. The reaction is allowed to warm to ambient temperature and stir overnight. Methanol (10 ml) is added to destroy any unreacted sodium hydride and the DMF is removed in vacuo. The residue is dissolved in ethyl acetate, washed with water, and dried ($MgSO_4$). Silica gel chromatography produces a mixture of the two isomers which is dissolved in 80 ml of ethanol and is treated with 80 ml of 10% nAOH at ambient temperature for 3 days. The ethanol is removed in vacuo and the aqueous phase is acidified to pH 1 with hydrochloric acid which causes the mixture of product isomers to precipitate.

Purification by reverse phase chromatography (Waters Delta Prep-3000) gives the 5-butyl-3-propyl isomer.

EXAMPLE 15

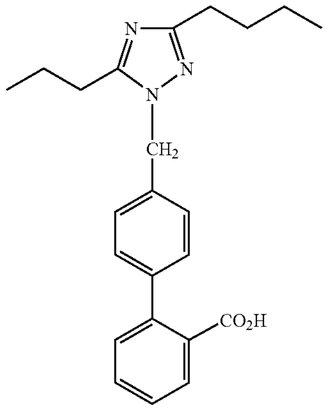

4'-[(3-butyl-5-propyl-1H-1,2,4-triazol-1-yl)methyl]-[1,1'-biphenyl]-2-carboxylic acid The other isomer for Example 14 is isolated in an identical manner and provides the 3-butyl-5-propyl isomer.

EXAMPLE 16

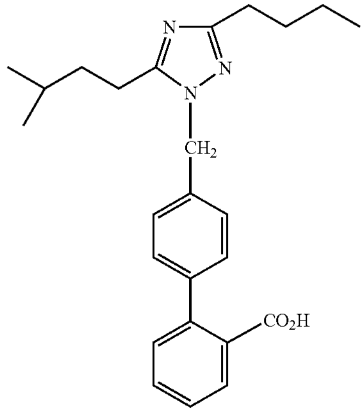

4'-[(3-butyl-5-isopentyl-1H-1,2,4-triazol-1-l)methyl]-1,1'-biphenyl]-2-carboxylic acid Step 1: Preparation at 3-butyl-5-isopentyl-1H-1,2,4-triazole Under nitrogen, a solution of 53.8 g (1.68 mol) of anhydrous hydrazine in 300 mL of methanol was cooled to 0° C. and treated with 186 g (1.4 mol) of methyl 4-methylvalerate. The reaction was allowed to warm to ambient temperature and stir overnight prior to stirring at reflux for 4 h. The reaction was concentrated in vacuo giving 166 g (93%) of 4-methylvaleric acid hydrazide as a colorless solid: 49–51° C.; NMR ($CDCl_3$) δ 0.89 (d, J=7 Hz, 6H), 1.48–1.64 (m, 3H), 2.15 (t, J=7 Hz, 2H), 3.91 (br s, 2H), 6.94 (br s, 1H). A 7.86 g (60 mmol) sample of the hydrazide was dissolved in 50 mL of methanol and treated with 7.8 g (60 mmol) of ethyl iminovalerate under nitrogen. The reaction was stirred at reflux overnight and concentrated in vacuo. Purification by silica gel chromatography (Waters Prep-500A) using ethyl acetate/hexane (40:60) gave 9.6 g (82.%) of 3-butyl-5-isopentyl-1H-1,2,4-triazole as a colorless solid which melts close to ambient temperature: NMR ($CDCl_3$) δ 0.81–0.90 (m, 9H), 1.25–1.40 (m, 2H), 1.47–1.74 (m, 5H), 2.70 (t, J=7 Hz, 4H); MS (FAB) m/e (rel intensity) 196 (100); HRMS. Calcd for M+H: 196.1814. Found: 196.1832.

Step 2: Preparation of 4'-[(3-butyl-5-isopentyl-1H-1,2,4-triazol-1-yl)methyl][1,1'-biphenyl]-2-carboxylic acid Under a static nitrogen atmosphere, 2.0 g (10.3 mmol) of solid 3-butyl-5-isopentyl-1H-1,2,4-triazole is added in small portions to 11 mmol of sodium hydride in 50 ml of dimethylformamide (DMF); stirring is continued until hydrogen evolution has ceased. The anion solution is cooled to −10° C. (ice/methanol) and is treated with a solution of 3.27 g (10.2 mmol) of 4-bromomethyl-2'-methoxycarbonylbiphenyl (from Step 1 of Example 1) in 20 ml of dry DMF. The reaction is allowed to warm to ambient temperature and stir overnight. Methanol (10 ml) is added to destroy any unreacted sodium hydride and the DMF is removed in vacuo. The residue is dissolved in ethyl acetate, washed with water, and dried ($MgSO_4$). The crude material is dissolved in 80 ml of ethanol and is treated with 80 ml of 10% NaOH at ambient temperature for 3 days. The ethanol is removed in vacuo and the aqueous phase is acidified to pH 1 with hydrochloric acid which causes the mixture of product isomers to precipitate purification by reverse phase chromatography (Waters Delta Prep-3000) give the 3-butyl-5-isopentyl isomer.

EXAMPLE 17

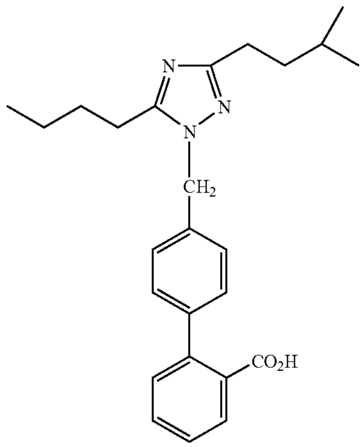

4'-[(5-butyl-3-isopentyl-1H-1,2,4-triazol-1-yl]methyl)-[1,1'-biphenyl]-2-carboxylic acid The other isomer from Example 16 is isolated in an identical manner and provides the 5-butyl-3-isopentyl isomer.

EXAMPLE 18

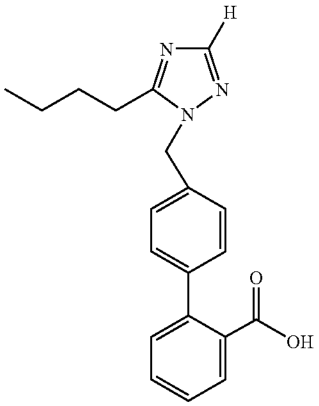

4'-[(5-butyl-1H-1,2,4-triazol-1-yl)methyl][1,1'-bi-phenyl]-2-carboxylic acid

Following General Procedure A, 5.0 g (39.9 mmol) of 5-butyl-1H-1,2,4-triazole was coupled with 12.2 g (39.9 mmol) of the alkylating reagent prepared in step 1 of Example 1 to give 3.1 g (22%) of a faster moving isomer: NMR ($CDCl_3$) δ 0.90 (t, J=8 Hz, 3H), 1.29–1.45 (m, 2H), 1.63–1.76 (m, 2H), 2.71 (t, J=8 Hz, 2H), 3.62 (s, 3H), 5.34 (s, 2H), 7.14–7.20 (m, 2H), 7.24–7.33 (m, 3H), 7.40 (dt, J=8 and 2 Hz, 1H), 7.50 (dt, J=8 and 2 Hz, 1H), 7.82 (dd, J=8 and 2 Hz, 1H), 7.85 (s, 1H) and 3.7 g (26%) of a slower moving isomer: NMR ($CDCl_3$) δ 0.92 (t, J=8 Hz, 3H), 1.31–1.46 (m, 2H), 1.66–1.79 (m, 2H), 2.73 (t, J=8 Hz, 2H), 3.62 (s, 3H), 5.28 (s, 2H), 7.21–7.34 (m, 5H), 7.39 (dt, J=8 and 2 Hz, 1H), 7.50 (dt, J=8 and 2 Hz, 1H), 7.83 (dd, J=8 and 2 Hz, 1H), 7.94 (s, 1H). The faster moving isomer was hydrolyzed to give 2.75 g (92%) of 4'-[(5-butyl-1H-1,2,4-triazol-1-yl)methyl]-[1,1'-biphenyl]-2-carboxylic acid as a colorless solid: NMR (DMSO-$d_6$) δ 0.85 (t, J=8 Hz, 3H), 1.23–1.38 (m, 2H), 1.52–1.65 (m, 2H), 2.76 (t, J=7 Hz, 2H), 5.41 (s, 2H), 7.16–7.24 (m, 2H), 7.27–7.37 (m, 3H), 7.44 (dt, J=8 and 2 Hz, 1H), 7.56 (dt, J=8 and 2 Hz, 1H), 7.72 (dd, J=8 and 2 Hz, 1H), 7.86 (s, 1H); MS (FAB) m/e (rel intensity) 336 (100), 307 (7), 289 (7), 224 (8), 211 (100), 193 (9).

EXAMPLE 19

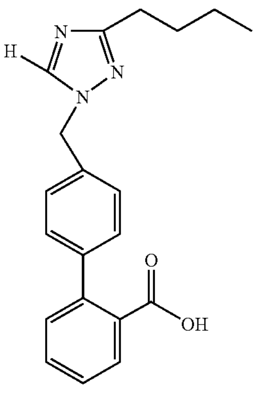

4'-[(3-butyl-1H-1,2,4-triazol-1-yl)methyl][1,1'-bi-phenyl]-2-carboxylic acid

The slower moving isomer from Example 18 was hydrolyzed to give 2.3 g (67%) of 4'-[(3-butyl-1H-1,2,4-triazol-1-yl)methyl][1,1'-biphenyl]-2-carboxylic acid as a colorless solid: NMR (DMSO-$d_6$) δ 0.87 (t, J=8 Hz, 3H), 1.23–1.38 (m, 2H), 1.54–1.67 (m, 2H), 2.58 (t, J=8 Hz, 2H), 5.36 (s, 2H), 7.23–7.38 (m, 5H), 7.44 (dt, J=8 and 2 Hz, 1H), 7.56 (dt, J=8 and 2 Hz, 1H), 7.72 (dd, J=8 and 2 Hz, 1H), 8.51 (s, 1H); MS (FAB) m/e (rel intensity) 336 (85), 211 (100), 165 (24), 126 (52).

EXAMPLE 20

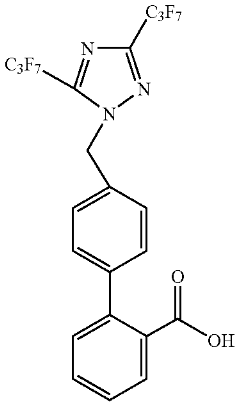

4'-[(3,5-di-perfluoropropyl-1H-1,2,4-triazol-1-yl)methyl][1,1'-biphenyl]-2-carboxylic acid Following General Procedure A, 11.0 g (27.2 mmol) of 3,5-bis(perfluoropropyl)-1H-1,2,4-triazole was coupled with 8.30 g (27.2 mmol) of the alkylating reagent prepared in step 1 of Example 1 to give 8.7 g (51%) of a colorless oil: NMR ($CDCl_3$) δ3.62 (s, 3H), 5.63 (s, 2H), 7.25–7.37 (m, 5H), 7.44 (dt, J=8 and 2 Hz, 1H), 7.54 (dt, J=8 and 2 Hz, 1H), 7.87 (dd, J=8 and 2 Hz, 1H). A 8.5 g (13.5 mmol) sample of this material was hydrolyzed to give 6.91 g (81%) of 4'-[(3,5-bis(1,1,2,2,3,3,3-heptafluoropropyl)-1H-1,2,4-triazol-1-yl]methyl][1,1'-biphenyl]-2-carboxlic acid as a colorless solid: NMR ($CDCl_3$) δ 5.62 (s, 2H), 7.27–7.37 (m, 5H), 7.44 (dt, J=8 and 2 Hz, 1H), 7.58 (dt, J=8 and 2 Hz, 1H), 7.98 (dd, J=8 and 2 Hz, 1H); MS (TSP) M+$NH_4$ (rel intensity) 633 (100), 211 (12); HRMS. Calc'd for M+Li: 622.0788. Found: 622.0759.

EXAMPLE 21

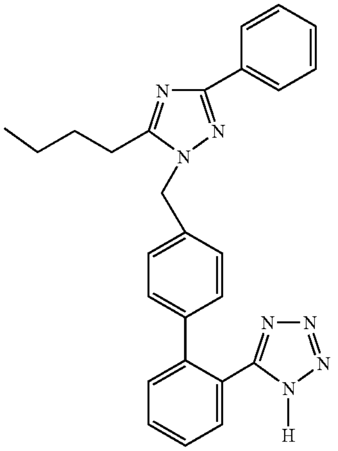

5-[4'-[(3-phenyl-5-butyl-1H-1,2,4-triazol-1-yl)methyl](1,1'-biphenyl)-2-yl]-1H-tetrazole Following General Procedure A, 2.0 g (9.9 mmol) of 5-butyl-3-phenyl-1H-1,2,4 triazole was coupled with 5.5 g (9.9 mmol) of the alkylating reagent prepared in step 1 of Example 3 to give 5.2 g (77%) of a faster moving isomer: NMR ($CDCl_3$) δ0.90 (t, J=8 Hz), 1.30–1.44 (m, 2H), 1.63–1.77 (m, 2H), 2.67 (t, J=8 Hz, 2H), 5.24 (s, 2H), 6.88–7.01 (m, 8H), 7.08–7.53 (m, 17H), 7.95 (dd, J=8 and 2 Hz, 1H), 8.12 (dd, J=8 and 2 Hz, 2H) and 420 mg (6.3%) of a slower moving isomer: NMR ($CDCl_3$) δ0.96 (t, J=8 Hz, 3H), 1.38–1.52 (m, 2H), 1.75–1.89 (m, 2H), 2.84 (t, J=8 Hz, 2H), 5.27 (s, 2H), 6.88–6.97 (m, 8H), 7.13 (d, J=8 Hz, 2H), 7.17–7.54 (m, 15H), 7.57 (d, J=8 Hz, 2H), 7.93 (dd, J=8 and 2 Hz, 1H). A 4.8 g (7.1 mmol) sample of the faster moving isomer was deportected to give 1.64 g (53%) of 5-[4'-[(3-phenyl-5-butyl-1H-1,2,4-triazol-1-yl)methyl] (1,1'-biphenyl-2-yl]-1H-tetrazole as a colorless solid: mp 113° C. (dec); NMR ($CDCl_3$) δ0.87 (t, J=8 Hz, 3H), 1.24–1.39 (m, 2H), 1.55–1.69 (m, 2H), 2.60 (t, J=8 2 Hz, 5.19 (s, 2H), 7.04<d, J=8 Hz, 2H), 7.11 (d, J=8 Hz, 2H), 7.27–7.39 (m, 4H), 7.47–7.60 (m, 2H), 7.87 (dd, J=8 and 2 Hz, 2H), 7.95 (dd, J=8 and 2 Hz, 1H); MS (FAB) m/e (rel intensity) 436 (100), 393 (8), 207 (60), 192 (20), 178 (13), 165 (8); HRMS. Calc'd for M+H: 436.2249. Found: 436.2240.

EXAMPLE 22

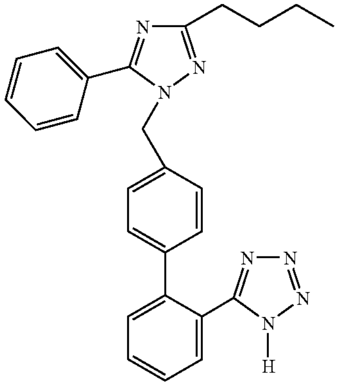

5-[4'-[(3-butyl-5-phenyl-1H-1,2,4-triazol-1-yl)methyl](1,1'-biphenyl)-2-yl]-1H-tetrazole The slower moving isomer from Example 21 was deprotected to give 251 mg (60%) of 5-[4'-[(3-butyl-5-phenyl-1H-1,2,4-triazol-1-yl)methyl][1,1'-biphenyl]-2-yl]-1H-tetrazole as a colorless solid: mp 205° C. (dec); NMR ($CDCl_3$) δ 0.88 (t, J=8 Hz, 3H), 1.23–1.38 (m, 2H), 1.55–1.68 (m, 2H), 2.52 (t, J=8 Hz, 2H), 5.32 (s, 2H), 6.99 (d, J=8 Hz, 2H), 7.08 (d, J=8 Hz, 2H), 7.31–7.61 (m, 8H), 7.90 (dd, J=8 and 2 Hz, 1H); MS (FAB) m/e (rel intensity) 436 (100), 393 (9), 374 (7), 277 (7), 247 (15), 207 (45); HRMS. Calc'd for M+H: 436.2249. Found: 436.2201.

EXAMPLE 23

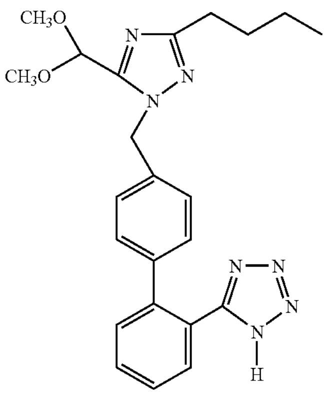

5-[4'-[[3-butyl-5-(dimethoxymethyl)-1H-1,2,4-triazol-1-yl]methyl][1,1'-biphenyl]-2-yl]-1H-tetrazole Following General Procedure A, 2.0 g (10 mmol) of 5-butyl-3-(dimethoxymethyl)-1H-1,2,4-triazole was coupled with 5.6 g (10 mmol) of the alkylating regagent prepared in step 1 of Example 3 to give 1.65 g (24%) of a faster moving isomer: NMR ($CDCl_3$) δ 0.92 (t, J=8 Hz, 3H), 1.31–1.45 (m, 2H), 1.66–1.78 (m, 2H), 2.69 (t, J=8 Hz, 2H), 3.33 (s, 6H), 5.30 (s, 2H), 5.42 (s, 1H), 6.90–6.96 (m, 5H), 7.02–7.12 (m, 4H), 7.21–7.38 (m, 11H), 7.41–7.52 (m, 2H), 7.86–7.92 (m, 1H) and 3.65 g (54.0%) of a slower moving isomer: NMR ($CDCl_3$) δ 0.85 (t, J=8 Hz, 3H), 1.22–1.36 (m, 2H), 1.57–1.70 (m, 2H), 2.59 (t, J=8 Hz, 2H), 3.45 (s, 6H), 5.20 (s, 2H), 5.55 (s, 1H), 6.89–6.97 (m, 5H), 7.08–7.19 (m, 4H), 7.21–7.37 (m, 11H), 7.41–7.52 (m, 2H), 7.90–7.95 (m, 1H). The faster moving isomer was deprotected to give 737 mg (70%) of 5-[4'-[[3-butyl-5-(dimethoxymethyl)-1H-1,2,4-triazol-1-yl]methyl][1,1'-biphenyl]-2-yl]-1H-tetrazole as a colorless solid: mp 152.5–153.5° C.; NMR ($CDCl_3$) δ 0.87 (t, J=8 Hz, 3H), 1.20–1.30 (m, 2H), 1.53–1.65 (m, 2H), 2.46 (t, J=8 Hz, 2H), 3.30 (s, 6H), 5.37 (s, 2H), 5.40 (s, 1H), 7.05–8.05 (m, 4H), 7.45 (dd, J=8 and 2 Hz, 1H), 7.51–7.65 (m, 2H), 8.02 (d, J=8 Hz, 1H); MS (FAB) m/e (rel intensity) 434 (65), 402 (40), 370 (11), 342 (46), 249 (85), 235 (18), 207 (100), 192 (89), 168 (70); HRMS. Calc'd for M+H: 434.2304. Found: 434.2332.

EXAMPLE 24

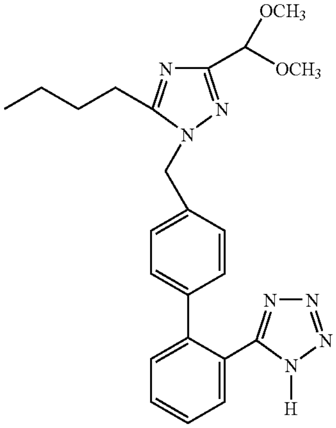

5-[4'-[(5-butyl-3-dimethoxymethyl-1H-1,2,4-triazol-1-yl)methyl](1,1'-biphenyl-2-yl]-1H-tetrazole A 3.65 g (5.4 mmol) sample of the slower moving isomer from Example 23 was deprotected to give 108 mg of colorless 5-[4'-[[5-butyl-3-(dimethoxymethyl)-1H-1,2,4-triazol-1-yl]methyl][1,1'-biphenyl]-2-yl]-1H-tetrazole after lyophilization: NMR ($CDCl_3$) δ 0.86 (t, J=8 Hz, 3H), 1.24–1.39 (m, 2H), 1.56–1.70 (m, 2H), 2.66 (t, J=8 Hz, 2H), 3.30 (s, 6H), 5.23 (s, 2H), 5.35 (s, 1H), 7.02 (d, J=8 Hz, 2H), 7.10 (d, J=8 Hz, 2H), 7.40 (dd, J=8 and 2 Hz, 1H), 7.51 (dt, J=8 and 2 Hz, 1H), 7.59 (dt, J=8 and 2 Hz, 1H), 7.89 (dd, J=8 and 2 Hz, 1H); MS (FAB) m/e (rel intensity) 434 (10), 402 (40), 249 (100), 207 (36), 192 (54), 168 (12); HRMS. Calc'd for M+H: 434.2304. Found: 434.2271.

EXAMPLE 25

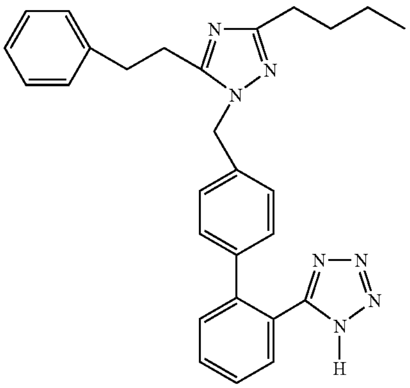

5-[4'-[(3-butyl-5-phenylethyl-1H-1,2,4-triazol-1-yl)methyl](1,1'-biphenyl-2-yl]-1H-tetrazole Following General Procedure A, 2.3 g (10 mmol) of 3-butyl-5-phenethyl-1H-1,2,4-triazole was coupled with 6.6 g (10 mmol) of the alkylating reagent prepared in step 1 of Example 3 to give 2.67 g (38%) of a faster moving isomer: NMR ($CDCl_3$) δ0.97 (t, J=8 Hz, 3H), 1.36–1.50 (m, 2H), 1.71–1.84 (m, 2H), 2.73 (t, J=8 Hz, 2H), 2.78–2.88 (m, 2H), 2.92–3.01 (m, 2H), 4.82 (s, 2H), 6.80–6.95 (m, 9H), 7.02–7.11 (m, 5H), 7.16–7.36 (m, 11H), 7.41–7.52 (m, 2H), 7.91–7.97 (m, 1H) and 2.94 g (42%) of a slower moving isomer: NMR ($CDCl_3$) δ 0.88 (t, J=8 Hz, 3H), 1.23–1.38 (m, 2H), 1.57–1.70 (m, 2H), 2.58 (t, J=8 Hz, 2H), 2.97–3.13 (m, 4H), 5.11 (s, 2H), 6.86 (d, J=8 Hz, 2H), 6.89–6.96 (m, 6H), 7.10 (d, J=8 Hz, 2H), 7.14–7.39 (m, 15H), 7.42–7.54 (m, 2H), 7.93 (dd, J=8 and 2 Hz, 1H). The faster moving isomer was deprotected to give 1.6 g (88%) of 5-[4'-[[3-butyl-5-(2-phenylethyl)-1H-1,2,4-triazol-1-yl)methyl][1,1'-biphenyl-2-yl]-1H-tetrazole a colorless solid: NMR ($CDCl_3$) δ0.86 (t, J=8 Hz, 3H), 1.17–1.31 (m, 2H), 1.48–1.51 (m, 2H), 2.42 (t, J=8 Hz, 2H), 2.76 (t, J=8 Hz, 2H), 2.92 (t, J=8 Hz, 2H), 4.80 (s, 2H), 6.83 (d, J=8, 2H), 6.92–7.00 (m, 2H), 7.08 (d, J=8 Hz, 2H), 7.17–71.32 (m, 3H), 7.42 (dd, J=8 and 2 Hz, 1H), 7.51–7.65 (m, 2H), 7.96 (dd, J=8 and 2 Hz, 1H); MS (FAB) m/e (rel intensity) 464 (37), 230 (25), 207 (100), 178 (17); HRMS. Calc'd for M+H: 464.2563. Found: 464.2532.

EXAMPLE 26

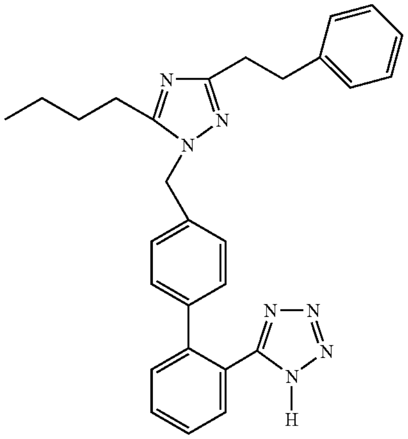

5-[4'[(5-butyl-3-phenylethyl-1H-1,2,4-triazol-1-yl)methyl](1,1'-biphenyl-2-yl]-1H-tetrazole The slower moving isomer from Example 25 was deprotected to give 1.5 g (77%) of 5-[4'-[[5-butyl-3-(2-phenylethyl)-1H-1,2,4-triazol-1-yl]methyl][1,1-biphenyl-2-yl]-1H-tetrazole as a colorless solid: mp 156.0–157.2° C.; NMR ($CDCl_3$) δ 0.84 (t, J=8 Hz, 3H), 1.19–1.34 (m, 2H), 1.47–1.61 (m, 2H), 2.52 (t, J=8 Hz, 2H), 2.66–2.77 (m, 2H), 2.85–2.95 (m, 2H), 5.15 (s, 2H), 6.88 (d, J=8 Hz, 2H), 7.05–7.11 (m, 4H), 7.12–7.28 (m, 5H), 7.41 (dd, J=8 and 2 Hz, 1H), 7.50 (dt, J=8 and 2 Hz, 1H), 7.59 (dt, J=8 and 2 Hz, 1H), 7.92 (dd, J=8 and 2 Hz, 1H); MS (FAB) m/e (rel intensity) 464 (83), 230 (22), 207 (92); HRMS. Calc'd for M+H: 464.2563. Found: 464.2560.

EXAMPLE 27

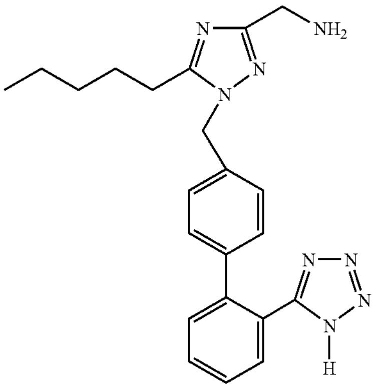

5-butyl-1-[2'-(1H-tetrazol-5-yl) [1,1'-biphenyl]-4-ylmethyl]-1H-1,2,4-triazole-3-methanamine A 1.5 g (3.5 mmol) sample of the diacetal compound of Example 24 was dissolved in 40 ml of ethanol and 40 ml of 3N HCl. The reaction was stirred at ambient temperature overnight and then at reflux for 50 min, the course of the reaction was followed by analytical reverse phase HPLC. The solvent was removed in vacuo. The residue was dissolved in ethyl acetate and extracted with saturated sodium bicarbonate solution until the water layer stayed basic. The water layer was acidified and extracted with an ethyl acetate/methylene chloride mixture. The organic layer was dried ($MgSO_4$) and removed in vacuo yielding 0.96 g of crude aldehyde: NMR ($CDCl_3$) δ 0.66 (t, J=8 Hz, 3H), 1.06–1.20 (m, 2H), 1.42–1.54 (m, 2H), 2.53 (t, J=8 Hz, 2H), 5.17 (s, 2H), 6.80–6.95 (m, 4H), 7.17–7.38 (m, 3H), 7.42–7.48 (m, 1H), 9.70 (s, 1H). Under a static nitrogen atmosphere, 0.91 g (2.3 mmol) of this material was dissolved in 10 ml of methanol and 1.77 g (23 mmol) ammonium acetate was added followed by 0.10 g (1.61 mmol) sodium cyanoborate. After stirring at ambient temperature for 3 days, analytical reverse phase HPLC indicated that the reaction was complete. Purification was accomplished by reverse phase chromatography (Waters Delta Prep 3000) using 25% acetonitrile/water (0.05% TFA). The solvent from the pure fractions was removed in vacuo and the residue dissolved in methanol and 3N HCl. After stirring for 30 min, the solvent was removed in vacuo and the residue lyophilized from acetonitrile/water providing 100 mg (10%) of 5-butyl-1-[2'-(1H-tetrazol-5-yl) [1,1'-biphenyl]-4-ylmethyl]-1H-1,2,4-triazole-3-methanamine as the colorless hydrochloride salt: NMR (DMSO-$d_6$) δ 0.85 (t, J=8 Hz, 3H), 1.22–1.38 (m, 2H), 1.51–1.64 (m, 2H), 2.77 (t, J=8 Hz, 2H), 4.00–4.09 (m, 2H), 5.40 (s, 2H), 7.01–7.25 (m, 4H), 7.39 (s, 1H), 7.48–7.73 (m, 3H); MS (FAB) m/e (rel intensity) 389 (100), 207 (65), 192 (17); HRMS. Calc'd for M+H: 389.2202. Found: 389.2170.

EXAMPLE 28

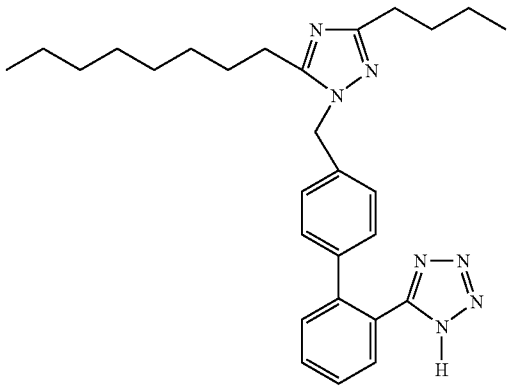

5-[4'-[(3-butyl-5-octyl-1H-1,2,4-triazol-1-yl)methyl] [1,1'-biphenyl]-2-yl]-1H-tetrazole Following General Procedure A, 2.0 g (8.4 mmol) of 3-butyl-5-octyl-1H-1,2,4-triazole was coupled with 5.5 g (8.4 mmol) of the alkylating reagent prepared in step 1 of Example 3. Silica gel chromatography (Waters Prep 500-A) using 25% ethyl acetate/hexane produced 4.5 g (75.4%) of a mixture of the two isomers which was dissolved in 40 ml of 10% water/acetic acid and stirred at ambient temperature overnight. The solvent was removed in vacuo. Purification of a sample of the isomeric product mix by reverse phase chromatography (Waters Delta Prep-3000) using 45% acetonitrile/water (0.05% TFA) for 30 minutes followed by 50% acetonitrile/water (0.05% TFA) provided two isomers. The faster moving isomer compound was dissolved in dilute base, the water was acidified (pH 4–5) with 1N HCl, and the product extracted with ethyl acetate. The ethyl acetate was dried ($MgSO_4$) and removed in vacuo yielding a solid which was recrystallized from acetonitrile providing 92 mg of 5-[4'-[(3-butyl-5-octyl-1H-1,2,4-triazol-1-yl)methyl][1,1'-biphenyl]-2-yl]-1H-tetrazole as a colorless solid: mp 136.5–138.0° C.; NMR ($CDCl_3$) δ 0.82 (t, J=8 Hz, 3H), 0.86 (t, J=8 Hz, 3H), 1.11–1.33 (m, 12H), 1.40–1.60 (m, 4H), 2.27 (t, J=8 Hz, 2H), 2.44 (t, J=8 Hz, 2H), 5.16 (s, 2H), 6.87 (d, t=8 Hz, 2H), 7.07 (d, J=8 Hz, 2H), 7.44 (dd, J=8 and 2 Hz, 1H), 7.50–7.66 (m, 2H), 7.90 (dd, J=8 and 2 Hz, 1H); MS (FAB) m/e (rel intensity) 472 (5), 207 (7); HRMS. Calc'd for M+H: 472.3189. Found: 472.3180.

EXAMPLE 29

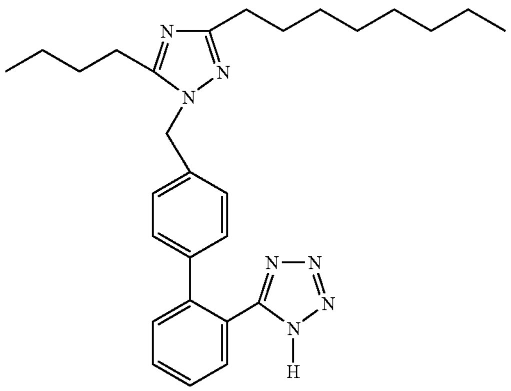

5-[4'-[(5-butyl-3-octyl-1H-1,2,4-triazol-1-yl)methyl] [1,1'-biphenyl]-2-yl]-1H-tetrazole The slower moving isomer from Example 28 was isolated in an identical manner and the product lyophilized from acetonitrile/water providing 53 mg of 5-[4'-[(5-butyl-3-octyl-1H-1,2,4-triazol-1-yl)methyl]1,1'-biphenyl]-2-yl]-1H-tetrazole as a colorless solid: NMR ($CDCl_3$) δ 0.83 (t, J=8 Hz, 3H), 0.86 (t, J=8 Hz, 3H), 1.12–1.37 (m, 12H), 1.46–1.63 (m, 4H), 2.35 (t, J=8 Hz, 2H), 2.51 (t, J=8 Hz, 2H), 5.19 (s, 2H), 6.92 (d, J=8 Hz, 2H), 7.09 (d, J=8 Hz, 2H), 7.40–7.48 (m, 1H), 7.51–7.66 (m, 2H), 7.91 (dd, J=8 and 2 Hz, 1H); MS (FAB) m/e (rel intensity) 472 (6), 207 (8); HRMS. Calc'd for M+H: 472.3189. Found: 472.3230.

EXAMPLE 30

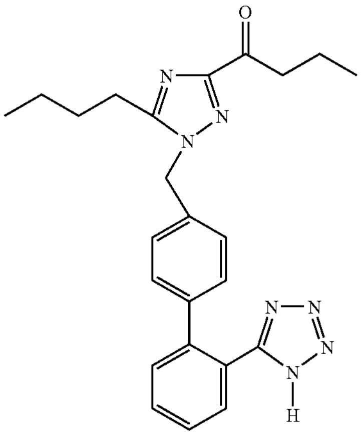

1-[[5-butyl-1-[2'-(1H-tetrazol-5-yl)[1,1'-biphenyl]-4-ylmethyl]-1H-1,2,4-triazol-3-yl]methyl]-1-butanone Under a static nitrogen atmosphere, 30.0 g (150 mmol) 5-butyl-3-dimethoxy-1H-1,2,4-triazole (from Step 1 of Example 23 was added in small portions to 165 mmol of sodium hydride in 300 ml anhydrous THF; stirring was continued for 1 h. The anion solution was cooled to −10° C. (methanol/ice) and treated with Sem-Cl dropwise. The reaction was allowed to warm to ambient temperature and stir overnight. The solvent was removed in vacuo. The residue was dissolved in methylene chloride, washed with water, dried ($MgSO_4$), and the solvent removed again in vacuo. Silica gel chromatography using 20% ethyl acetate/hexane followed by ethyl acetate provided 13.6 g of the faster moving isomer as an oil: NMR ($CDCl_3$) δ −0.07 (s, 9H), 0.82–0.92 (m, 5H), 1.26–1.40 (m, 2H), 1.62–1.74 (m, 2H), 2.67 (t, J=8 Hz, 2H), 3.38 (s, 6H), 3.53–3.62 (m, 2H), 5.47 (s, 2H), 5.55 (s, 1H). Under a static nitrogen atmosphere, 12.6 g (38.2 mmol) of the faster moving Sem-protected triazole isomer from above was dissolved in 630 ml of anhydrous THF, cooled to −78° C., and 45.8 mmol of sec-butyl lithium was added dropwise. The solution was stirred for 1 h and then the anion was quenched with 4.5 ml (45.8 mmol) of n-propyl iodide. The solution was stirred at −78° C. for 5 h and then allowed to warm to ambient temperature overnight. The solvent was removed in vacuo. The residue was dissolved in methylene chloride, washed with water, dried ($MgSO_4$) and the solvent removed providing 12.4 g of crude Sem-protected 5-butyl-3-(1,1-dimethoxybutane)-1H-1,2,4-triazole: NMR ($CDCl_3$) δ −0.04 (s, 9H), 0.75–0.93 (m, 8H), 0.98–1.11 (m, 2H), 1.25–1.41 (m, 2H), 1.62–1.74 (m, 2H), 1.99–2.08 (m, 2H), 2.68 (t, J=8 Hz, 2H), 3.20 (s, 6H), 3.62 (t, J=8 Hz, 2H), 5.56 (s, 2H). A 1.0 g (2.7 mmol) sample of the crude dimethoxybutyl compound was dissolved in 5 ml of ethanol and 5 ml of 3M HCl and stirred at reflux for 2.5 h. The solvent was removed in vacuo providing 560 mg of the crude HCl salt of 5-butyl-3-(1-butanone)-1H-1,2,4-triazole: NMR (DMSO-$d_6$) δ 0.83–0.94 (m, 6H), 1.21–1.36 (m, 2H), 1.55–1.75 (m, 4H), 2.83 (t, J=8 Hz, 2H), 2.97 (t, 7=8 Hz, 2H). The crude HCl salt of the triazole was dissolved in 20 ml of fresh methanol, 3 Å molecular sieves were added, and the mixture stirred at reflux under nitrogen overnight. The solution was filtered through celite and the solvent removed in vacuo. The residue was dissolved in ethyl acetate and washed with saturated sodium bicarbonate solution. The solvent was dried ($MgSO_4$) and removed in vacuo providing 390 mg of crude 5-butyl-3-(1,1-dimethoxybutyl)-1H-1,2,4-triazole: NMR ($CDCl_3$) δ 0.90 (t, J=8 Hz, 3H), 0.99 (t, J=8 Hz, 3H), 1.29–1.46 (m, 2H), 1.66–1.84 (m, 4H), 2.80 (t, J=8 Hz, 2H), 3.06 (t, J=8 Hz, 2H), 3.18 (s, 6H). Under a static nitrogen atmosphere, 380 mg (1.6 mmol) of this material in 5 ml of anhydrous dimethylformamide (DMF) was added to 1.9 mmol sodium hydride in 5 ml of DMF; stirring was continued for 1 h. The anion solution was cooled to 0° C. and 890 mg (1.6 mmol) of the alkylating reagent prepared in from step 1 of Example 3 was added as a solid. The reaction was allowed to warm to ambient temperature and stir overnight. Methanol (1 ml) was added to destroy any unreacted sodium hydride and the DMF was removed in vacuo. The residue was dissolved in ethyl acetate, washed with water, and dried ($MgSO_4$). The solvent was removed in vacuo providing 1.2 g of crude material which was dissolved in 10 ml ethanol and 10 ml 3N HCl and stirred at reflux for 2 h. The solvent was removed in vacuo. Purification by reverse phase chromatography (Water Delta Prep 3000) using isocratic 37% acetonitrile/water (0.05% TFA) for 40 minutes followed by 50% acetonitrile/water (0.05% TFA) provided the TFA salt. The salt was dissolved in basic water (pH 9–10), the water was acidified to pH 4 with 3N HCl, and the product extracted with ethyl acetate. The ethyl acetate was dried ($MgSO_4$) and removed in vacuo yielding a solid which was recrystallized from acetonitrile providing 146 mg (21%) of 1-[[5-butyl-1-[2'-(1H-tetrazol-5-yl)[1,1'-biphenyl]-4-ylmethyl]-1H-1,2,4-triazol-3-yl]methyl]-1-butanone mp 150.5–152.5° C.; NMR ($CDCl_3$) δ 0.85 (t, J=8 Hz, 3H), 0.96 (t, J=8 Hz, 3H), 1.23–1.39 (m, 2H), 1.54–1.77 (m, 4H), 2.67 (t, J=8 Hz, 2H), 2.97 (t, J=8 Hz, 2H), 5.28 (s, 2H), 7.02 (d, J=8 Hz, 2H), 7.10 (d, J=8 Hz, 2H), 7.37 (d, J=8 Hz, 1H), 7.43–7.62 (m, 2H), 7.86 (d, J=8 Hz, 1H); MS (FAB) m/e (rel intensity) 430 (6), 207 (12); HRMS. Calc'd for M+H: 430.2355. Found: 430.2404.

EXAMPLE 31

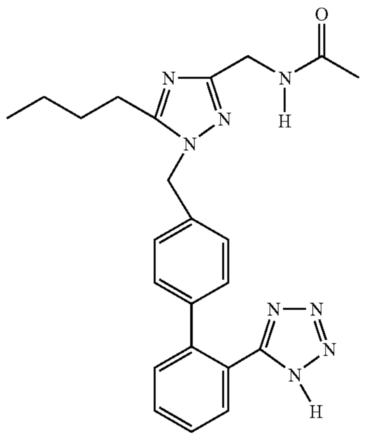

N-[[5-butyl-1-[2'-(1H-tetrazol-5-yl)[1,1'-biphenyl]-4-ylmethyl]-1H-1,2,4-triazol-3-yl]methyl]acetamide A 92.9 mg (0.22 mmol) sample of 5-[4'-[(5-butyl-3-methylamine-1H-1,2,4-triazol-1-yl)methyl]-(1,1'-biphenyl-2-yl]-1H-tetrazole hydrochloride from Example 27 was dissolved in 5 ml of water and the pH was adjusted to 9 with 1M potassium carbonate ($K_2CO_3$). The solution was cooled to 0° C. and 0.22 ml of 1M $K_2CO_3$ was added followed by 0.22 mmol of acetic anhydride. Additional $K_2CO_3$ was added as needed to maintain a pH of 9. At 30 min intervals, this addition was repeated until analytical reverse phase chromatography showed that all starting material has been consumed. The pH was adjusted to three with 1N HCl and extracted with ethyl acetate. The ethyl acetate was removed in vacuo and the product lyophilized from acetonitrile/water providing 36 mg (39%) of N-[[5-butyl-1-[2'-(1H-tetrazol-5-yl) [1,1'-biphenyl]-4-ylmethyl]-1H-1,2,4-triazol-3-yl]methyl]acetamide as a colorless solid: NMR ($CDCl_3$) δ0.80 (t, J=8 Hz, 3H), 1.18–1.37 (m, 2H), 1.47–1.64 (m, 2H), 1.94 (s, 3H), 2.63 (t, J=8 Hz, 2H), 4.22 (d, J=8 Hz, 2H), 5.18 (s, 2H), 6.95 (d, J=8 Hz, 2H), 7.04–7.21 (m, 2H), 7.44 (d, J=8 Hz, 1H), 7.50–7.66 (m, 2H), 7.90 (dd, J=8 and 2 Hz, 1H); MS (FAB) m/e (rel intensity) 431 (42), 207 (100); HRMS. Calc'd for M+H: 431.2308. Found: 431.2271.

EXAMPLE 32

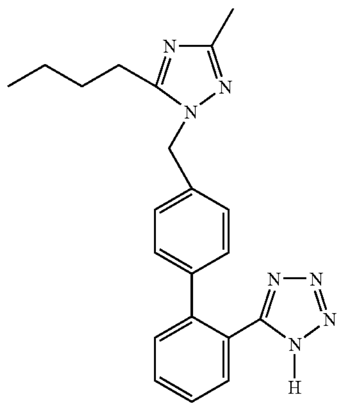

5-[4'-[(5-butyl-3-methyl-1H-1,2,4-triazol-1-yl)methyl][1,1'-biphenyl]-2-yl]-1H-tetrazole Following General Procedure A, 700 mg (5.0 mmol) of 5-butyl-3-methyl-1H-1,2,4-triazole was coupled with 2.8 g (5.0 mmol) of the alkylating reagent prepared in step 1 of Example 3. Silica gel chromatography using ethyl acetate/toluene (35:65) produced 2.75 g (90%) of a mixture of the two isomers which was dissolved in 30 ml 10% water/acetic acid and stirred at ambient temperature for 3 days. The solvent was removed in vacuo and the residue dissolved in dilute base, washed with toluene, acidified to pH 4 with 1N HCl and the product extracted with ethyl acetate. Purification of the isomeric product mixture by reverse phase chromatography (Water Delta Prep-3000) using isocratic acetonitrile/water (23:77) (0.05% TFA) provided two isomers. The faster moving isomer compound was dissolved in dilute base, acidified to pH 3–4 and extracted with ethyl acetate. The solvent was removed in vacuo; recrystallization from acetonitrile gave 199 mg (12%) of 5-[4'-[(5-butyl-3-propyl-1H-1,2,4-triazol-1-yl)methyl]-(1,1'-biphenyl]-2-yl]-1H-tetrazole as a colorless solid: mp 170.0–170.5° C.; NMR ($CDCl_3$) δ0.79 (t, J=8 Hz, 3H), 1.18–1.32 (m, 2H), 1.44–1.56 (m, 2H), 1.99 (s, 3H), 2.49 (t, J=8 Hz, 2H), 5.15 (s, 2H), 6.87 (d, J=8 Hz, 2H), 7.08 (d, J=8 Hz, 2H), 7.44 (dd, J=8 and 2 Hz, 1H), 7.51–7.65 (m, 2H), 7.90 (dd, J=8 and 2 Hz, 1H); MS (FAB) m/e (rel intensity) 374 (100), 235 (13), 207 (100), 140 (29); HRMS. Calc'd for M+H: 374.2093. Found: 374.2062.

EXAMPLE 33

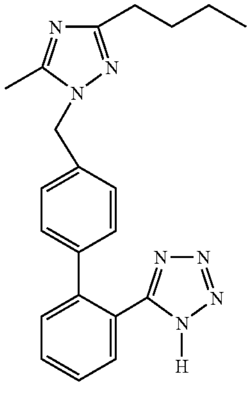

5-[4'-[(3-butyl-5-methyl-1H-1,2,4-triazol-1-yl)methyl][1,1'-biphenyl]-2-yl]-1H-tetrazole The slower moving isomer from Example 32 was dissolved in dilute base, acidified to pH 3–4, and extracted with ethyl acetate. The solvent was removed in vacuo and the product lyophilized from acetonitrile/water which gave 536 mg (33%) of 5-[4'-[(3-butyl-5-methyl-1H-1,2,4-triazol-1-yl)methyl]-[1,1'-biphenyl]-1-yl)-1H-tetrazole as a colorless solid: NMR ($CDCl_3$) δ 0.82 (t, J=8 Hz, 3H), 1.21–1.35 (m, 2H), 1.53–1.66 (m, 2H), 2.35 (s, 3H), 2.56 (t, J=8 Hz, 2H), 5.23 (s, 2H), 7.03 (d, J=8 Hz, 2H), 7.11 (d, J=8 Hz, 2H), 7.42 (dd, J=8 and 2 Hz, 1H), 7.47–7.63 (m, 2H), 7.88 (dd, J=8 and 2 Hz, 1H); MS (FAB) m/e (rel intensity) 374 (65), 331 (12), 235 (13), 207 (100), 192 (38), 140 (56); HRMS. Calc'd for M+H: 374.2093. Found: 374.2071.

EXAMPLE 34

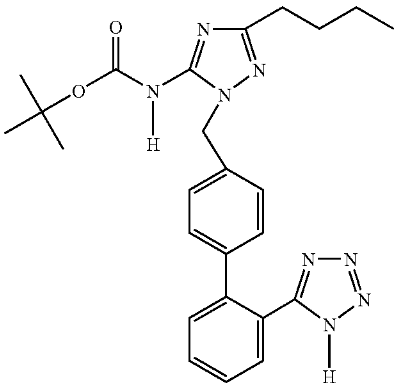

1,1-dimethylethyl [3-butyl-[1-2'-(1H-tetrazol-5-yl)[1,1'-biphenyl]-4-ylmethyl]-1H-1,2,4-triazol-5-yl]methylcarbamate Following General Procedure A, 6.0 g (25 mmol) of [(5-butyl-1H-1,2,4-triazol-3-yl)methyl]carbamate was coupled with 16.4 g (25 mmol) of the alkylating reagent prepared in step 1 of Example 3. Silica gel chromatography (Waters Prep 500A) using ethyl acetate/hexane (2:3) gave 4.29 g (24%) of a faster moving isomer: NMR ($CDCl_3$) δ 0.94 (t, J=8 Hz, 3H), 1.33–1.46 (m, 2H), 1.43 (s, 9H), 1.66–1.78 (m, 2H), 2.69 (t, J=8 Hz, 2H), 4.26 (d, J=8 Hz, 2H), 5.24 (s, 2H), 6.87–6.93 (m, 7H), 7.01 (d, J=8 Hz, 2H), 7.11 (d, J=8 Hz, 2H), 7.21–7.28 (m, 5H), 7.30–7.37 (m, 4H), 7.42–7.52 (m, 2H), 7.94 (dd, J=8 and 2 Hz, 1H) and 9.74 g (54%) of a slower moving isomer: NMR ($CDCl_3$) δ 0.87 (t, J=8 Hz, 3H), 1.24–1.36 (m, 2H), 1.44 (s, 9H), 1.57–1.69 (m, 2H), 2.58 (t, J=8 Hz, 2H), 4.38 (d, J=8 Hz, 2H), 5.12 (s, 2H), 6.91 (d, J=8 Hz, 8H), 7.11 (d, J=8 Hz, 2H), 7.21–7.28 (m, 6H), 7.30–7.37 (m, 4H), 7.42–7.52 (m, 2H), 7.91–7.96 (m, 1H). The faster moving isomer was dissolved in 30 ml of water/acetic acid (1:4) and stirred at ambient temperature overnight. The solvent was removed in vacuo; the residue dissolved in dilute base and washed with toluene. The water layer was acidified to pH 3–4 and extracted with ethyl acetate. Recrystallization from acetonitrile gave 2.53 g (88%) of 1,1-dimethylethyl[3-butyl-(1-(2-(1H-tetrazol-5-yl)[1,1'-biphenyl]-4-ylmethyl]-1H-1,2,4-triazol-5-yl]methylcarbamate as a colorless solid: mp 144–147° C.; NMR ($CDCl_3$) δ 0.88 (t, J=8 Hz, 3H), 1.22–1.45 (m, 2H), 1.36 (s, 9H), 1.54–1.66 (m, 2H), 2.56 (t, J=8 Hz, 2H), 4.05 (d, J=8 Hz, 2H), 5.38 (s, 2H), 5.50 (s, 1H), 7.06 (d, J=8 Hz, 2H), 7.12 (d, J=8 Hz, 2H), 7.45 (dd, J=8 and 2 Hz, 1H), 7.50–7.63 (m, 2H), 7.99 (d, J=8 Hz, 1H); MS (FAB) m/e (rel intensity) 495 (12), 395 (38), 367 (15), 207 (100), 178 (42); HRMS. Calc'd for M+Li: 495.2808. Found: 495.2771.

EXAMPLE 35

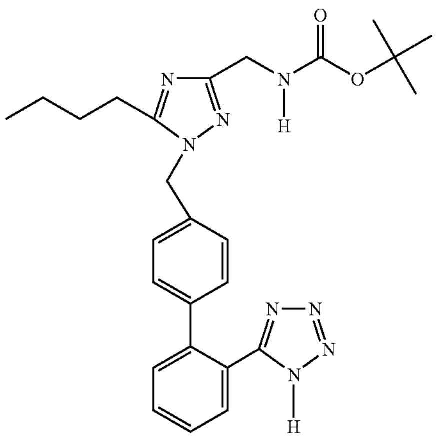

1,1-dimethylethyl[5-butyl-[1-[2'-(1H-tetrazol-5-yl) [1,1'-biphenyl]-4-ylmethyl]-1H-1,2,4-triazol-3-yl] methlycarbamate The slower moving isomer from Example 34 was dissolved in 70 ml of water/acetic acid (1:4) and stirred at ambient temperature overnight. The solvent was removed in vacuo; the residue dissolved in dilute base and washed with toluene. The water layer was acidified to pH 4 with 1N HCl and extracted with ethyl acetate. The ethyl acetate was dried ($MgSO_4$) and removed in vacuo. Lyophilization from acetonitrile/water gave 5.0 g (76%) of 1,1-dimethylethyl[5-butyl-[1-[2'-(1H-tetrazol-5-yl)[1,1'-biphenyl]-4-ylmethyl]-1H-1,2,4-triazol-3-yl]methylcarbamate as a colorless solid: NMR ($CDCl_3$) δ 0.77 (t, J=8 Hz, 3H), 1.16–1.30 (m, 2H), 1.40 (s, 9H), 1.42–1.56 (m, 2H), 2.57 (t, J=8 Hz, 2H), 4.12 (d, J=8 Hz, 2H), 5.19 (s, 2H), 5.59 (s, 1H), 6.94 (d, J=8 Hz, 2H), 7.08 (d, J=8 Hz, 2H), 7.43 (dd, J=8 and 2 Hz, 1H), 7.50–7.63 (m, 2H), 7.92 (dd, J=8 and 2 Hz, 1H); MS (FAB) m/e (rel intensity) 495 (29), 367 (38), 338 (21), 207 (100), 178 (48); HRMS. Calc'd for M+Li: 495.2808. Found: 495.2800.

EXAMPLE 36

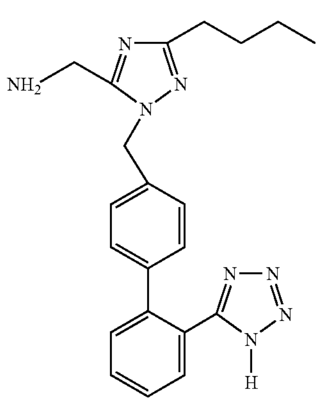

3-butyl-1-[2'-(1H-tetrazol-5-yl)[1,1'-biphenyl]-4-ylmethyl]-1H-1,2,4-triazole-5-methanamine Under nitrogen, 219 mg (0.45 mmol) of 1,1-dimethylethyl [3-butyl-[1-[2'-(1H-tetrazol-5-yl)[1,1'-biphenyl]-4-ylmethyl]-1H-1,2,4-triazol-5-yl]methylcarbamate from Example 34 was suspended in 10 ml of 4N HCl in dioxane. After 30 minutes, 10 ml of methylene chloride was added. The mixture was stirred at ambient temperature overnight. The solvent was removed in vacuo. Lyophilization from acetonitrile/water gave 201 mg (100%) of 3-butyl-1-[2'-(1H-tetrazol-5-yl) [1,1'-biphenyl]-4-ylmethyl]-1H-1,2,4-triazole-5-methanamine as the colorless hydrochloride salt: NMR ($CDCl_3$) δ 0.82 (t, J=8 Hz, 3H), 1.21–1.35 (m, 2H), 1.59–1.72 (m, 2H), 2.72 (t, J=8 Hz, 2H), 4.97 (s, 2H), 5.69 (s, 2H), 6.93 (d, J=8 Hz, 2H), 7.23 (d, J=8 Hz, 2H), 7.32 ((d, J=8 Hz, 1H), 7.39 (dt, J=8 and 2 Hz, 1H), 7.51 (dt, J=8 and 2 Hz, 1H), 7.74 (dd, J=8 and 2 Hz, 1H); MS (FAB) m/e (rel intensity) 389 (55), 207 (100), 192 (39), 178 (26); HRMS. Calc'd for M+H: 389.2202. Found: 389.2170.

EXAMPLE 37

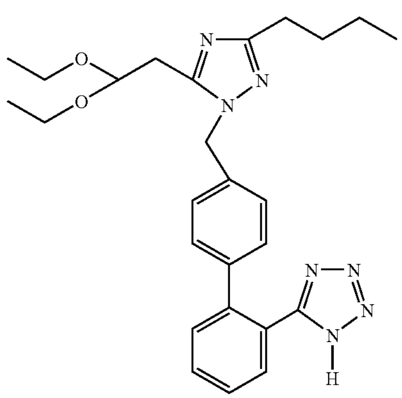

5-[4'-[[3-butyl-5-(2,2-diethyoxyethyl)-1H-1,2,4-triazol-1-yl]methyl][1,1'-biphenyl]-2-yl]-1H-tetrazole Following General Procedure A, 4.7 g (19.5 mmol) of 5-butyl-3-(2,2-diethoxyethyl)-1H-1,2,4-triazole was coupled with 19.5 mmol of the alkylating reagent prepared in step 1 of Example 3. Silica gel chromatography (Waters Prep 500A) using ethyl acetate/hexane (2:3) gave 5.98 g (43%) of a faster moving isomer: NMR ($CDCl_3$) δ 0.94 (t, J=8 Hz, 3H), 1.13 (t, J=8 Hz, 6H), 1.33–1.48 (m, 2H), 1.67–1.79 (m, 2H), 2.70 (t, J=8 Hz, 2H), 2.94 (d, J=8 Hz, 2H), 3.39–3.51 (m, 2H), 3.63–3.75 (m, 2H), 4.81 (t, J=7 Hz, 1H), 5.22 (s, 2H), 6.87–6.98 (m, 8H), 7.09 (d, J=8 Hz, 2H), 7.21–7.29 (m, 6H), 7.30–7.37 (m, 4H), 7.41–7.52 (m, 2H), 7.91–7.96 (m, 1H) and 6.3 g (45%) of a slower moving isomer: NMR ($CDCl_3$) δ 0.88 (t, J=8 Hz, 3H), 1.15 (t, J=7 Hz, 6H), 1.24–1.37 (m, 2H), 1.56–1.68 (m, 2H), 2.57 (t, J=8 Hz, 2H), 3.06 (d, J=7 Hz, 2H), 3.46–3.60 (m, 2H), 3.66–3.78 (m, 2H), 5.05 (t, J=7 Hz, 1H), 5.14 (s, 2H), 6.87–6.95 (m, 8H), 7.10 (d, J=8 Hz, 2H), 7.21–7.29 (m, 6H), 7.31–7.37 (m, 4H), 7.42–7.53 (m, 2H), 7.90–7.96 (m, 1H). The faster moving isomer was dissolved in 50 ml of acetic acid/water (4:1) and stirred at ambient temperature for 3 days. The solvent was removed in vacuo; the residue dissolve in dilute base and washed with toluene. The water layer was cooled to 0° C., acidified to pH 4–5 and extracted with ethyl acetate. Lyophilization from acetonitrile/water gave 3.8 g (98%) of 5-[4'-[[3-butyl-5-(2,2-diethyoxyethyl)-1H-1,2,4-triazol-1-yl]methyl][1,1'-biphenyl]-2-yl]-1H-tetrazole as a colorless solid: NMR ($CDCl_3$) δ 0.80 (t, J=8 Hz, 3H), 1.10 (t, J=8 Hz, 6H), 1.10–1.24 (m, 2H), 1.37–1.49 (m, 2H), 2.31 (t, J=8 Hz, 2H), 2.66 (d, J=7 Hz, 2H), 3.34–3.47 (m, 2H), 3.59–3.71 (m, 2H), 4.75 (t, J=7 Hz, 1H), 5.28 (s, 2H), 6.88 (d, J=8 Hz, 2H), 7.06 (d, J=8 Hz, 2H), 7.46 (dd, J=8 and 2 Hz, 1H), 7.55 (dt, J=8 and 2 Hz, 1H), 7.62 (dt, J=8 and 2 Hz, 1H), 7.91 (dd, J=8 and 2 Hz, 1H); MS (FAB) m/e (rel intensity) 476 (20), 430 (28), 356 (13), 235 (15), 207 (100), 192 (67); HRMS. Calc'd for M+H: 476.2773. Found: 476.2723.

EXAMPLE 38

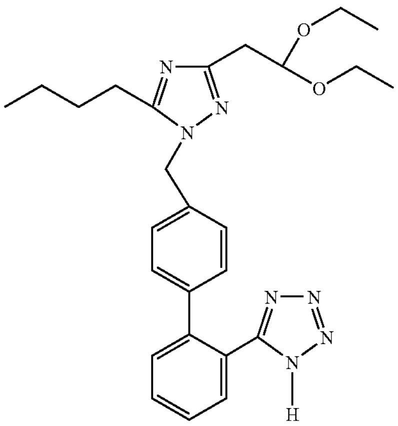

5-[4'-[[5-butyl-3-(2,2-diethyoxyethyl)-1H-1,2,4-triazol-1-yl]methyl][1,1'-biphenyl]-2-yl]-1H-tetrazole The 6.2 g (8.6 mmol) of the slower moving isomer from Example 37 was dissolved in 50 ml of acetic acid/water (4:1) and stirred at ambient temperature for 3 days. The solvent was removed in vacuo; the residue dissolved in dilute base, and washed with toluene. The water layer was cooled to 0° C., acidified with 1N HCl to pH 4–5, and extracted with ethyl acetate. Lyophilization from acetonitrile/water gave 3.7 g (92%) of 5-[4'-[[5-butyl-3-(2,2-diethyoxyethyl)-1H-1,2,4-triazol-1-yl]methyl][1,1'-biphenyl]-2-yl]-1H-tetrazole as colorless solid: NMR ($CDCl_3$) δ 0.85 (t, J=8 Hz, 3H), 1.09 (t, J=8 Hz, 6H), 1.24–1.38 (m, 2H), 1.51–1.63 (m, 2H), 2.55 (t, J=8 Hz, 2H), 2.75 (d, J=7 Hz, 2H), 3.38–3.50 (m, 2H), 3.54–3.66 (m, 2H), 4.87 (t, J=7 Hz, 1H), 5.19 (s, 2H), 6.99 (d, J=8 Hz, 2H), 7.12 (d, J=8 Hz, 2H), 7.42 (dd, J=8 and 2 Hz, 1H), 7.50–7.65 (m, 2H), 7.97 (dd, J=8 and 2 Hz, 1H); MS (FAB) m/e (rel intensity) 476 (3), 430 (28), 235 (10), 207 (100), 192 (61); HRMS. Calc'd for M+H: 476.2773. Found: 476.2760.

EXAMPLE 39

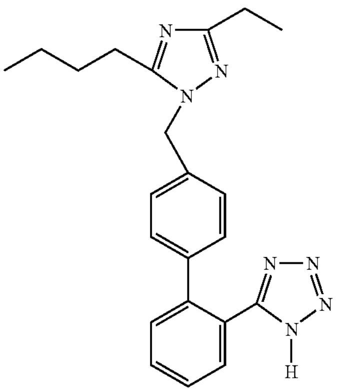

5-[4'-[(5-butyl-3-ethyl-1H-1,2,4-triazol-1-yl)methyl][1,1'-biphenyl]-2-yl]-1H-tetrazole Following General Procedure A, 770 mg (5 mmol) of 5-butyl-3-ethyl-1H-1,2,4-triazole was coupled with 2.8 g (5 mmol) of the alkylating reagent prepared in step 1 of Example 3. Silica gel chromatography (Waters Prep-500A) using ethyl acetate/hexane (2:3) gave 2.24 g (72%) of a mixture of the two isomers which was dissolved in 30 ml of acetic acid/water (9:1) and stirred at ambient temperature for 4 days. The solvent was removed in vacuo; the residue dissolved in dilute base, and washed with toluene. The water layer was acidified to pH 4 and extracted with ethyl acetate. The extracts were combined, dried ($MgSO_4$) and concentrated in vacuo. Purification of a 600 mg sample of the isomeric product mixture by reverse phase chromatography (Waters Delta Prep-3000) using isocratic acetonitrile/water (25:75) (0.05% TFA) provided two isomers. The faster moving isomer was dissolved in dilute base, acidified, extracted with ethyl acetate, dried ($MgSO_4$) and the ethyl acetate removed in vacuo. Lyophilization from acetonitrile/water gave 209 mg of 5-[4'-[(5-butyl-3-ethyl-1H-1,2,4-triazol-1-yl)methyl][1,1'-biphenyl]-2-yl]-1H-tetrazole as a colorless solid: NMR ($CDCl_3$) δ0.88 (t, J=8 Hz, 3H), 1.33–1.40 (m, 2H), 1.38 (t, J=8 Hz, 3H), 1.58–1.70 (m, 2H), 2.67–2.85 (m, 4H), 5.26 (s, 2H), 7.10 (s, 4H), 7.41 (dd, J=8 and 2 Hz, 1H), 7.74–7.62 (m, 2H), 7.86 (dd, J=8 and 2 Hz, 1H); MS (FAB) m/e (rel intensity) 388 (58), 207 (100), 192 (35); HRMS. Calc'd for M+H: 388.2249. Found: 388.2218.

EXAMPLE 40

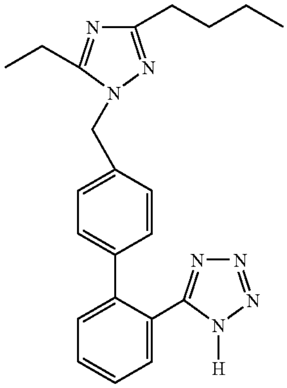

5-[4'-[(3-butyl-5-ethyl-1H-1,2,4-triazol-1-yl)methyl][1,1'-biphenyl]-2-yl]-1H-tetrazole The slower moving isomer from Example 39 was dissolved in dilute base, acidified to pH 3–4, extracted with ethyl acetate, dried ($MgSO_4$), and the ethyl acetate removed in vacuo. Lyophilization from acetonitrile/water gave 188 mg of 5-[4'-[(3-butyl-5-ethyl-1H-1,2,4-triazol-1-yl)methyl][1,1'-biphenyl]-2-yl]-1H-tetrazole as a colorless solid: NMR ($CDCl_3$) δ 0.87 (t, J=8 Hz, 3H), 1.16 (t, J=8 Hz, 3H), 1.21–1.35 (m, 2H), 1.52–1.65 (m, 2H), 2.50 (t, J=8 Hz, 2H), 2.67 (q, J=8 Hz, 2H), 5.23 (s, 2H), 7.02 (d, J=8 Hz, 2H), 7.12 (d, J=8 Hz, 2H), 7.43 (dd, J=8 and 2 Hz, 1H), 7.50–7.65 (m, 2H), 7.89 (dd, J=8 and 2 Hz, 1H); MS (FAB) m/e (rel intensity) 388 (35), 207 (100), 192 (47); HRMS. Calc'd for M+H: 388.2249. Found: 388.2222.

EXAMPLE 41

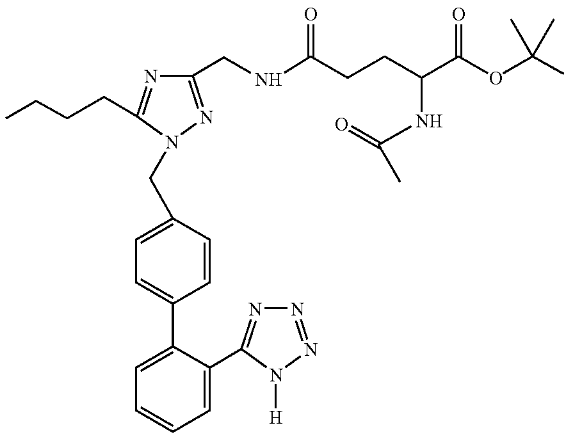

N2-acetyl-N-[[5-butyl-1-[[2-'(1H-tetrazol-5-yl)[1,1'-biphenyl]-4-yl]methyl]-1H-1,2,4-triazol-3-yl]methyl]-L-glutamine, 1,1-dimethylethyl ester Under nitrogen, 30 ml of TFA was added dropwise to a solution of 4.9 g (10 mmol) of 1,1dimethylethyl [5-butyl-[1-[2'-(1H-tetrazol-5-yl) [1,1'-biphenyl]-4-ylmethyl]-1H-1,2,4-triazol-3-yl]methyl]carbamate from Example 35 in 30 ml of methylene chloride at −10° C. (methanol/ice). The mixture was allowed to warm to ambient temperature and stir overnight. The solvent was removed in vacuo giving the TFA salt of the free amine. The TFA salt was dissolved in 35 ml of anhydrous DMF along with 8.7 ml (50 mmol) of anhydrous diisopropyl ethyl amine and treated with 20 mmol of the symmetrical anhydride of N-Boc-γglutamic acid t-butyl ester in 55 ml of anhydrous DMF. The reaction was stirred at ambient temperature overnight. The DMF was removed in vacuo; the residue dissolved in ethyl acetate, washed with cold 1M $K_2CO_3$ and water. The ethyl acetate was dried ($MgSO_4$) and the solvent removed in vacuo. Under nitrogen, 30 ml of TFA was added dropwise to a solution of this material in 30 ml of methylene chloride at −10° C. (methanol/ice). The reaction was allowed to warm to ambient temperature and stir overnight. The solvent was removed in vacuo giving the TFA salt of the free amine. The TFA salt was dissolved in 30 ml of water and cooled to 0° C. The pH was adjusted to nine with 1M $K_2CO_3$. The solution was cooled to 0° C., 0.94 ml (10 mmol) of acetic anhydride was added followed by 5 ml of 1M $K_2CO_3$, and the pH was adjusted to 9 with additional 1M $K_2CO_3$. At 30 minute intervals, this addition was repeated until 5 additions had been made. The pH was adjusted to 4 with 6N HCl and the solution extracted with ethyl acetate. The ethyl acetate was dried ($MgSO_4$) and removed in vacuo. Purification by silica gel chromatography (Waters Prep 500A) using isopropanol/acetic acid/chloroform (20:5:75) followed by lyophilization from acetonitrile/water gave 2.5 g (4'%) of N2-acetyl-N-[[5-butyl-1-[[2'-(1H-tetrazol-5-yl)[1,1'-biphenyl]-4-yl]methyl]-1H-1,2,4-triazol-3-yl]methyl]-L-glutamine, 1,1-dimethylethyl ester as a colorless solid: NMR ($CDCl_3$) δ 0.89 (t, J=8 Hz, 3H), 1.27–1.41 (m, 2H), 1.52–1.71 (m, 2H), 1.56 (s, 9H), 2.00 (s, 3H), 2.05–2.29 (m, 2H), 2.31–2.55 (m, 2H), 2.73 (t, J=8 Hz, 2H), 4.48–4.58 (m, 3H), 5.24 (s, 2H), 7.09 (d, J=8 Hz, 2H), 7.17 (d, J=8 Hz, 2H), 7.36–7.42 (m, 1H), 7.44–7.55 (m, 2H), 7.90 (dd, J=8 and 2 Hz, 1H); MS (FAB) m/e (rel intensity) 616 (20), 263 (23), 235 (26), 207 (100); HRMS. Calc'd for M+H: 616.3360. Found: 616.3353.

EXAMPLE 42

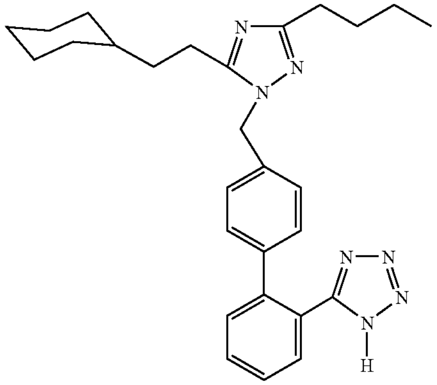

5-[4'-[[3-butyl-5-(2-cyclohexylethyl)-1H-1,2,4-triazol-1-yl]methyl][1,1'-biphenyl]-2-yl]-1H-tetrazole Following General Procedure A, 1.2 g (5 mmol) of 5-butyl-3-(2-cyclohexylethyl)-1H-1,2,4-triazole was coupled with 5 mmol of the alkylating reagent prepared in step 1 of Example 3. Silica gel chromatography (Waters Prep 500A) using ethyl acetate/hexane (1:3) gave 3.6 g (100%) of a mixture of the two isomers which was dissolved in 50 ml of acetic acid/water (9:1) and stirred at ambient temperature overnight. The solvent was removed in vacuo; the residue dissolved in dilute base, acidified and washed with ethyl acetate. The ethyl acetate was removed in vacuo. Purification of a small sample of the isomer product mixture by reverse phase chromatography (Water Delta Prep-3000) using isocratic acetonitrile/water (41:59) (0.05% TFA) provided two isomers. The faster moving isomer was dissolved in dilute base, acidified to pH 3–4, extracted with ethyl acetate, dried ($MgSO_4$) and the ethyl acetate removed in vacuo. Lyophilization from acetonitrile/water gave 58 mg of 5-[4'-[[3-butyl-5-(2-cyclohexylethyl)-1H-1,2,4-triazol-1-yl]methyl][1,1'-biphenyl]-2-yl]-1H-tetrazole as a colorless solid: NMR ($CDCl_3$) δ 0.78–0.95 (m, 5H), 1.07–1.40 (m, 6H), 1.48–1.74 (m, 9H), 2.66 (t, J=8 Hz, 2H), 2.78 (t, J=8 Hz, 2H), 5.24 (s, 2H), 7.10 (q, J=8 Hz, 4H), 7.41 (dd, J=8 and 2 Hz, 1H), 7.48–7.63 (m, 2H), 7.89 (dd, J=8 and 2 Hz, 1H); MS (FAB) m/e (rel intensity) 470 (45), 236 (35), 207 (100), 192 (33); HRMS. Calc'd for M+H: 470.3032. Found: 470.2990.

EXAMPLE 43

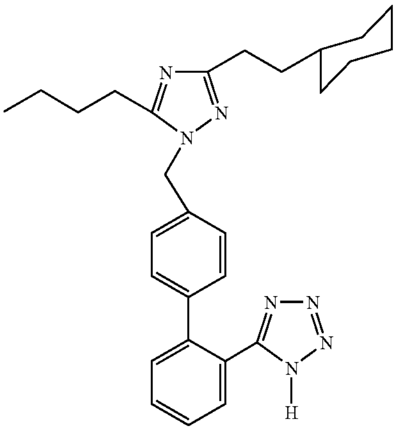

5-[4'-[[5-butyl-3-(2-cyclohexylethyl)-1H-1,2,4-triazol-1-yl]methyl][1,1'-biphenyl]-2-yl]-1H-tetrazole The slower moving isomer from Example 42 was dissolved in dilute base, acidified to pH 3–4, extracted with ethyl acetate, dried ($MgSO_4$), and the ethyl acetate removed in vacuo. Lyophilization from acetonitrile/water gave 29 mg of 5-[4'-[[5-butyl-3-(2-cyclohexylethyl)-1H-1,2,4-triazol-1-yl]methyl][1,1'-biphenyl]-2-yl]-1H-tetrazole as a colorless solid: NMR ($CDCl_3$) δ 0.95–1.00 (m, 5H), 1.10–1.43 (m, 6H), 1.59–1.77 (m, 9H), 2.83 (t, J=8 Hz, 2H), 2.92 (t, J=8 Hz, 2H), 5.31 (s, 2H) # 7.10–7.18 (m, 4H), 7.40 (dd, J=8 and 2 Hz, 1H), 7.47–7.61 (m, 2H), 7.89 (dd, J=8 and 2 Hz, 1H); MS (FAB) m/e (rel intensity) 470 (35), 236 (33), 207 (100), 192 (33); HRMS. Calc'd for M+H: 470.3032. Found: 470.2994.

EXAMPLE 44

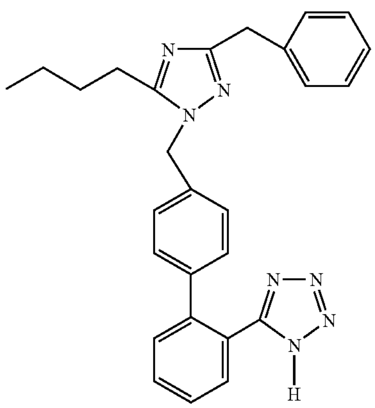

5-[4'-[[5-butyl-3-(phenylmethyl)-1H-1,2,4-triazol-1-yl]methyl][1,1'-biphenyl]-2-yl]-1H-tetrazole Under nitrogen, 0.74 g (2.2 mol) of N2-(4-[(2-cyanophenyl)phenyl)methyl] phenyl acetic acid hydrazide was dissolved in 5 ml of absolute ethanol and treated with 0.28 g (2.2 mmol) of ethyl iminovalerate. The reaction was stirred at relux for 3 days. The solvent was removed in vacuo, 5 ml of xylene was added and the reaction stirred at reflux under nitrogen for an additional 3 days. The solvent was removed in vacuo. Purification by silica gel chromatography (Chromatatron, 4 mm plate) using a step gradient of ethyl acetate/chloroform gave 410 g (31%) of 5-(4'-[[5-butyl-3-(phenylmethyl)-1H-1,2,4-triazol-1-yl]methyl][1,1'-biphenyl-2-yl] nitrile: NMR ($CDCl_3$) δ 0.88 (t, J=8 Hz, 3H), 1.27–1.41 (m, 2H), 1.59–1.72 (m, 2H), 2.67 (t, J=8 Hz, 2H), 4.06 (s, 2H), 5.30 (s, 2H), 7.14–7.37 (m, 8H), 7.39–7.50 (m, 3H), 7.53 (dt, J=8 and 2 Hz, 1H), 7.75 (dd, J=8 and 2 Hz, 1H). Under nitrogen, 230 mg (1.13 mmol) of trimethyl tin azide was added to a solution of the nitrile in 5 ml of xylene. The reaction was stirred at reflux for 3 days. The solvent was removed in vacuo and the residue dissolved in 10 ml of acetic acid/water (9:1) and stirred at ambient temperature overnight. The solvent was removed in vacuo. Reverse phase chromatography (Delta Prep 3000) using acetonitrile/water (35–45:65–55) gave the TFA salt. The salt was dissolved in dilute base, acidified to pH 3–4, extracted with ethyl acetate, dried ($MgSO_4$) and the ethyl acetate removed in vacuo. Lyophilization from acetonitrile/water gave 182 mg (45%) of 5-[4'-[[5-butyl-3-(phenylmethyl)-1H-1,2,4-triazol-1-yl]methyl][1,1'-biphenyl]-2-yl]-1H-tetrazole as a colorless solid: NMR ($CDCl_3$) δ 0.84 (t, J=8 Hz, 3H), 1.22–1.36 (m, 2H), 1.51–1.64 (m, 2H), 2.59 (t, J=8 Hz, 2H), 3.85 (s, 2H), 5.20 (s, 2H), 7.02 (d, J=8 Hz, 2H), 7.14 (d, J=8 Hz, 2H), 7.17–7.28 (m, 5H), 7.43 (dd, J=8 and 2 Hz, 1H), 7.51–7.65 (m, 2H), 7.96 (dd, J=8 and 2 Hz, 1H); MS (FAB) m/e (rel intensity) 450 (56), 207 (100), 192 (30), 178 (22); HRMS. Calc'd for M+H: 450.2406. Found: 450.2434.

EXAMPLE 45

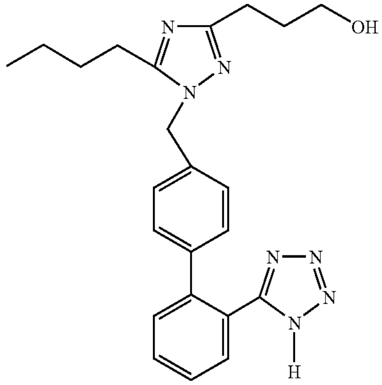

5-butyl-1-[2'-(1H-tetrazol-5-yl)[1,1'-biphenyl]-4-ylmethyl]-1H-1,2,4-triazole-3-propanol Following General Procedure A, 920 mg (5.0 mmol) of 5-butyl-1H-1,2,4-triazole-3-propanol was coupled with 5.0 mmol of the alkylating reagent prepared in step 1 of Example 3. Silica gel chromatography (Waters Prep 500A) using isopropanol/chloroform (5:95) gave a mixture of the two pure isomers which was dissolved in 40 ml acetic acid/water (9:1) and stirred at ambient temperature for 3 days. The solvent was removed in vacuo. Purification of an aliquot by reverse phase chromatography (Waters Delta Prep 3000) using acetonitrile/water (26:74) (0.05% TFA) provided two isomers. Lyophilization of the faster moving isomer from acetonitrile/water gave 124 mg of 5-butyl-1-[2'-(1H-tetrazol-5-yl)[1,1'-biphenyl]-4-ylmethyl]-1H-1,2,4-triazole-3-propanol as the colorless FTA salt: NMR ($CDCl_3$) δ 0.71 (t, J=8 Hz, 3H), 1.10–1.24 (m, 2H), 1.42–1.54 (m, 2H), 1.70–1.81 (m, 2H), 2.49 (t, J=8 Hz, 2H), 2.60 (t, J=8 Hz, 2H), 3.46 (t, J=6 Hz, 2H), 5.02 (s, 2H), 6.92 (q, J=8 Hz, 4H), 7.24–7.34 (m, 2H), 7.40 (dt, J=8 and 2 Hz, 1H), 7.52 (dd, J=8 and 2 Hz, 1H); MS (FAB) m/e (rel intensity) 418 (100), 207 (48), 184 (10); HRMS. Calc'd for M+H: 418.2355. Found: 418.2370.

EXAMPLE 46

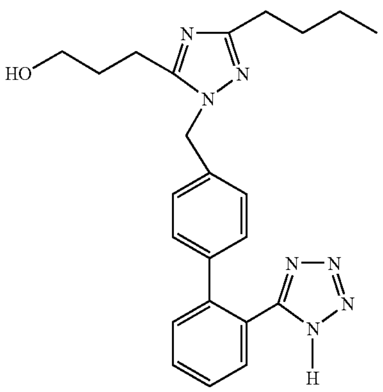

3-butyl-1-[2'-(1H-tetrazol-5-yl) [1,1'-biphenyl]-1 ylmethyl]-1H-1,2,4-triazole-5-propanol Lyophilization of the slower moving isomer from Example 45 gave 114 mg of 3-butyl-1-[2'-(1H-tetrazol-5-yl)[1,1-biphenyl]-1ylmethyl]-1H-1,2,4-triazole-5-propanol as the colorless TFA salt: NMR ($CDCl_3$) δ 0.75 (t, J=8 Hz, 3H), 1.13–1.27 (m, 2H), 1.48–1.60 (m, 2H), 1.64–1.75 (m, 2H), 2.52 (t, J=8 Hz, 2H), 2.66 (t, J=8 Hz, 2H), 3.39 (t, J=6 Hz, 2H), 5.12 (s, 2H), 6.94 (s, 4H), 7.25–7.35 (m, 2H), 7.40 (dt, J=8 and 2 Hz, 1H), 7.52 (d, J=8 Hz, 1H); MS (FAB) m/e (rel intensity) 418 (100), 207 (30); HRMS. Calc'd for M+H: 418.2355. Found: 418.2344.

EXAMPLE 47

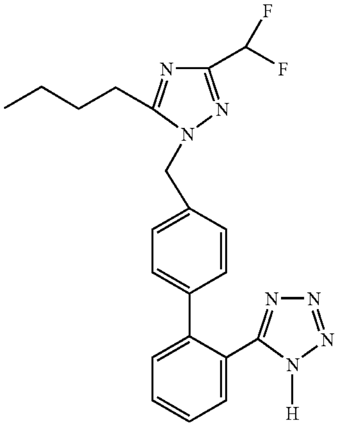

5-[4'-[[5-butyl-3-(difluoromethyl)-1H-1,2,4-triazol-1-yl]methyl][1,1'-biphenyl]-2-yl]-1H-tetrazole Following General Procedure A, 470 mg. (2.7 mmol) of 5-butyl-3-(difluoromethyl)-1H-1,2,4-triazole was coupled with 2.7 mmol of the alkylating reagent prepared in step 1 of Example 3. Purification by reverse phase chromatography (Waters Delta Prep 3000) using acetonitrile/water (36:64) (0.05% TFA) gave two isomers. The faster moving isomer was dissolved in dilute base, acidified to pH 3–4, extracted with ethyl acetate, dried ($MgSO_4$), and the ethyl acetate removed in vacuo. Lyophilization from acetonitrile/water gave 471 mg (27%) of 5-[4'-[[5-butyl-3-(difluoromethyl)-1H-1,2,4-triazol-1-yl]methyl][1,1'-biphenyl]-2-yl]-1H-tetrazole as a colorless solid: NMR ($CDCl_3$) δ 0.88 (t, J=8 Hz, 3H), 1.28–1.43 (m, 2H), 1.60–1.73 (m, 2H), 2.72 (t, J=8 Hz, 2H), 5.32° (s, 2H), 6.61 (t, J=54 Hz, 1H), 7.12 (d, J=8 Hz, 2H), 7.18 (d, J=8 Hz, 2H), 7.42 (dd, J=8 and 2 Hz, 1H), 7.51–7.65 (m, 2H), 8.00 (dd, J=8 and 2 Hz, 1H); MS (FAB) m/e (rel intensity) 410 (45), 235 (55), 207 (100), 192 (57); HRMS. Calc'd for M+H: 410.1905. Found: 410.1903.

EXAMPLE 48

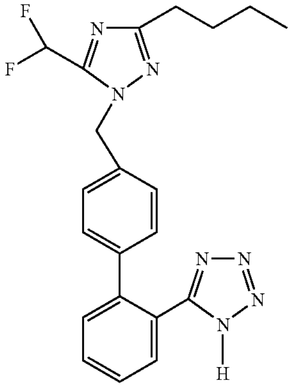

5-[4'-[[3-butyl-5-(difluoromethyl)-1H-1,2,4-triazol-1-yl]methyl][1,1'-biphenyl]-2-yl]-1H-tetrazole The slower moving isomer from Example 47 was dissolved in dilute base, acidified, extracted with ethyl acetate, dried ($MgSO_4$), and the ethyl acetate removed in vacuo. Lyophilization from acetonitrile/water gave 104 mg (6%) of 5-[4'-[[3-butyl-5-(difluoromethyl)-1H-1,2,4-triazol-1-yl] methyl][1,1'-biphenyl]-2-yl]-1H-tetrazole as a colorless solid: NMR ($CDCl_3$) δ 0.91 (t, J=8 Hz, 3H), 1.25–1.41 (m, 2H), 1.60–1.73 (m, 2H), 2.64 (t, J=8 Hz, 2H), 5.43 (s, 2H), 6.81 (t, J=52 Hz, 1H), 7.20 (d, J=8 Hz, 2H), 7.28 (d, J=8 Hz, 2H), 7.43 (dd, J=8 and 2 Hz, 1H), 7.52–7.65 (m, 2H), 8.10 (dd, J=8 and 2 Hz, 1H); MS (FAB) m/e (rel intensity) 410 (87), 235 (100), 207 (83); HRMS. Calc'd for M+H: 410.1905. Found: 410.1903.

EXAMPLE 49

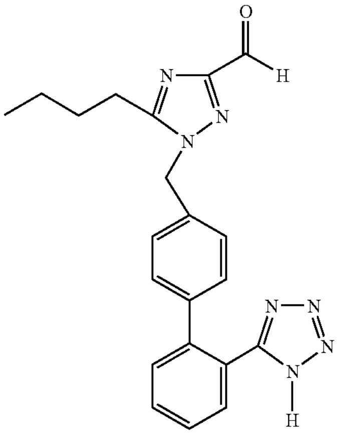

5-butyl-1-[2'-(1H-tetrazol-5-yl)[1,1'-biphenyl]-4-ylmethyl]-1H-1,2,4-triazole-3-carboxaldehyde A 92 mg sample of 5-[4'-[[5-butyl-3-(dimethoxymethyl)-1H-1,2,4-triazol-1-yl]methyl][1,1'-biphenyl]-2-yl]-1H-tetrazole from Example 24 was dissolved in 20 ml of ethanol and 2 ml of 3N HCl. The reaction was stirred at ambient temperature for 3 days. The solvent was removed in vacuo. Lyophilization from acetonitrile/water gave 70 mg (81%) of 5-butyl-1-[2'-(1H-tetrazol-5-yl)[1,1'-biphenyl]-4-ylmethyl]-1H-1,2,4-triazole-3-carboxaldehyde as the colorless hydrochloride salt: NMR ($CDCl_3$) δ 0.89 (t, J=8 Hz, 3H), 1.30–1.44 (m, 2H), 1.66–1.78 (m, 2H), 2.78 (t, J=8 Hz, 2H), 5.38 (s, 2H), 7.17 (q, J=8 Hz, 4H), 7.40 (d, J=8 Hz, 1H), 7.50–7.64 (m, 2H), 8.02 (d, J=8 Hz, 1H); MS (FAB) m/e (rel intensity) 388 (36), 235 (42), 207 (100), 192 (50); HRMS. Calc'd for M+Li: 395.2046. Found: 395.2049.

EXAMPLE 50

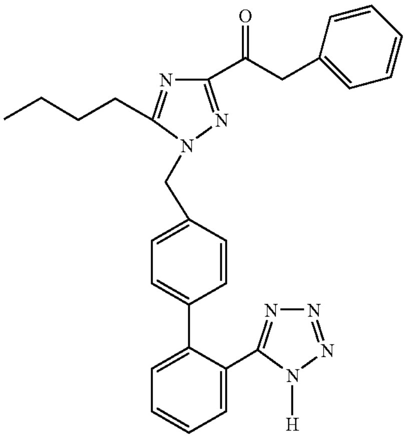

5-[4'-[[5-butyl-3-(phenylacetyl)-1H-1,2,4-triazol-1-yl]methyl][1,1'-biphenyl]-2-yl]-1H-tetrazole Under nitrogen, 7.3 mmol of sec-butyl lithium was added dropwise to 2.0 g (6.1 mmol) of the Sem-protected 5-butyl-3-(dimethoxymethyl)-1H-1,2,4-triazole from Example 30 in 100 ml of anhydrous THF at −78° C. The reaction was stirred for 1 h and then quenched with 0.87 ml (7.3 mmol) of benzyl bromide. The reaction was allowed to warm to ambient temperature and stir overnight. The THF was removed in vacuo; the residue dissolved in methylene chloride, washed with water and dried ($MgSO_4$). The methylene chloride was removed in vacuo. The residue was dissolved in 10 ml of ethanol and 10 ml of 3M HCl and stirred at reflux for 2.5 h. The solvents were removed in vacuo. The residue was dissolved in ethyl acetate, washed with saturated sodium bicarbonate solution, and dried ($MgSO_4$). Silica gel chromatography (Waters Prep 500A) using ethyl acetate/hexane (35:65) gave 460 mg (31%) of 5-butyl-3-(phenylacetyl)-1H-1,2,4-triazole: NMR ($CDCl_3$) δ 0.92 (t, J=8 Hz, 3H), 1.31–1.55 (m, 2H), 1.70–1.83 (m, 2H), 2.88 (t, J=8 Hz, 2H), 4.39 (s, 2H), 7.21–7.38 (m, 5H). Following General Procedure A, 440 mg (1.8 mmol) of this material was reacted with 1.8 mmol of the alkylating reagent prepared in step 1 of Example 3. The crude product was dissolved in 10 ml of acetic acid/water (9:1) and stirred at ambient temperature for 4 days. The solvent was removed in vacuo; the residue dissolved in dilute base and washed with toluene. The water was acidified and extracted with ethyl acetate. Purification by reverse phase chromatography (Waters Delta Prep 3000) using acetonitrile/water (45:55) gave 50 mg (5%) of 5-[4'-[[5-butyl-3-(phenylacetyl)-1H-1,2,4-triazol-1-yl]methyl][1,1'-biphenyl]-2-yl]-1H-tetrazole as the colorless TFA salt: NMR (DMSO-$d_6$) δ 0.86 (t, J=8 Hz, 3H), 1.23–1.38 (m, 2H), 1.52–1.65 (m, 2H), 2.80 (t, J=8 Hz, 2H), 4.32 (s, 2H), 5.52 (s, 2H), 7.11 (d, J=8 Hz, 2H), 7.19 (d, J=8 Hz, 2H), 7.23–7.35 (m, 5H), 7.52–7.63 (m, 2H), 7.65–7.74 (m, 2H); MS (FAB) m/e (rel intensity) 478 (100), 244 (8), 235 (8), 207 (34), 192 (12); HRMS. Calc'd for M+H: 478.2355. Found: 478.2414.

EXAMPLE 51

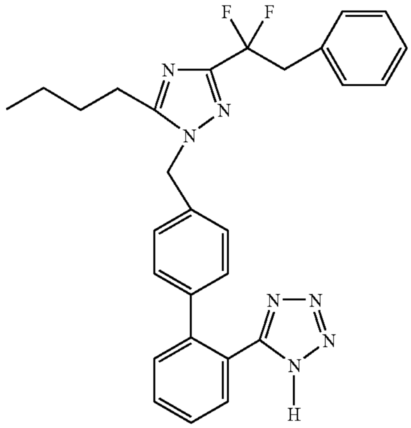

5-[4'-[[5-butyl-3-(1,1-difluoro-2-phenylethyl)-1H-1,2,4-triazol-1-yl]methyl][1,1'-biphenyl]-1-yl]-1H-tetrazole Under nitrogen, 8.5 g (48 mmol) of 5-butyl-3-(difluoromethyl)-1H-1,2,4-triazole from Example 47 was added in portions to 53 mmol of sodium hydride in 85 ml of anhydrous THF; stirring was continued for 1 h. The anion solution was cooled to 0° C. and treated dropwise with 8.9 ml (50 mmol) of Sem-Cl. The reaction was allowed to warm to ambient temperature and stir overnight. The THF was removed in vacuo; the residue dissolved in methylene chloride, washed with water, and dried ($MgSO_4$). Purification by silica gel chromatography (Waters Prep 500A) using ethyl acetate/hexane (1:9) gave 4.9 g 34% of the Sem-protected triazole as an oil: NMR ($CDCl_3$) δ −0.04 (s, 9H), 0.86–0.95 (m, 5H), 1.39–1.43 (m, 2H), 1.65–1.76 (m, 2H), 2.71 (t, J=8 Hz, 2H), 3.62 (t, J=8 Hz, 2H), 5.53 (s, 2H), 6.82 (t, J=52 Hz, 1H). Under nitrogen, 14.2 mmol of sec-butyllithium was added dropwise to 3.6 g (11.8 mmol) of the Sem-protected triazole in 200 ml of anhydrous THF at −78° C. The reaction was allowed to stir for 1 h prior to the addition of 1.7 ml (14.2 mmol) of benzyl bromide. After stirring at −78° C. for 2 h, the reaction was allowed to warm to ambient temperature and stir overnight. The solvent was removed in vacuo; the residue dissolved in methylene chloride, washed with water, and dried ($MgSO_4$). Silica gel chromatography (Waters Prep 500A) using ethyl acetate/hexane (5:95) gave 600 mg (10%) of the Sem protected 5-butyl-3-(1,1-difluoro-2-phenylethyl)-1H-1,2,4-triazole: NMR ($CDCl_3$) δ −0.04 (s, 9H), 0.85 (t, J=8 Hz, 2H), 0.94 (t, J=8 Hz, 3H), 1.30–1.44 (m, 2H), 1.67–1.79 (m, 2H), 2.73 (t, J=8 Hz, 2H), 3.54 (t, J=8 Hz, 2H), 3.70 (t, J=16 Hz, 2H), 5.34 (s, 2H), 7.21–7.31 (m, 5H). The Sem protected triazole was dissolved in 5 ml of ethanol and 5 ml of 3M HCl and allowed to stir at reflux for 3 h. The ethanol was removed in vacuo and the pH adjusted to nine with dilute sodium hydroxide. The resulting solution was extracted with methylene chloride; the extracts were combined, dried ($MgSO_4$), and concentrated in vacuo to provide 5-butyl-3-(1,1-difluoro-2-phenethyl-1H-1,2,4-triazole. Following General Procedure A, 1.4 mmol of this material was coupled with 1.4 mmol of the alkylating reagent prepared in step 1 of Example 3. The crude product was dissolved in 10 mL of acetic acid/water (9:1) and stirred at ambient temperature for 3 days. The solvent was removed in vacuo; the residue dissolved in dilute base and washed with toluene. The water was acidified to pH 3–4, extracted with ethyl acetate, and dried ($MgSO_4$). Purification by reverse phase chromatography (Waters Delta Prep 3000) using acetonitrile/water (47:53) (0.05% TFA) gave the TFA salt. The salt was dissolved in dilute base, acidified to pH 3–4, extracted with ethyl acetate, and dried ($MgSO_4$). Lyophilization from acetonitrile/water gave 290 mg (42%) of 5-[4'-[[5-butyl-3-(1,1-difluoro-2-phenylethyl)-1H-1,2,4-triazol-1-yl]methyl][1,1-biphenyl]-1-yl]-1H-tetrazole: NMR ($CDCl_3$) δ 0.86 (t, J=8 Hz, 3H), 1.21–1.36 (m, 2H), 1.54–1.68 (m, 2H), 2.64 (t, J=8 Hz, 2H), 3.57 (t, J=16 Hz, 2H), 5.23 (s, 2H), 6.92 (d, J=8 Hz, 2H), 7.10 (d, J=8 Hz, 2H), 7.16–7.25 (m, 5H), 7.39 (dd, J=8 and 2 Hz, 1H), 7.50–7.65 (m, 2H), 7.99 (dd, J=8 and 2 Hz, 1H); MS (FAB) m/e (rel intensity) 500(100), 266 (6), 235 (8), 207 (25), 192 (8); HRMS. Calc'd for M+H: 500.2374. Found: 500.2358.

EXAMPLE 52

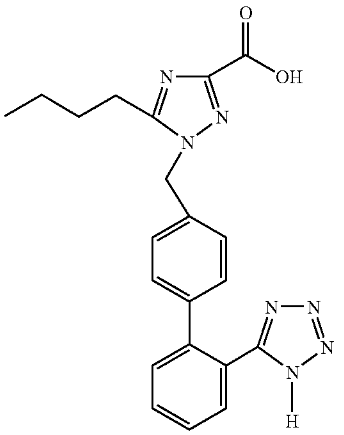

5-butyl-1-[2'-(1H-tetrazol-5-yl) [1,1'-biphenyl]-4-ylmethyl]-1H-1,2,4-triazole-3-carboxylic acid A 3.36 g (7.1 mmol) sample of 5-[4'-[[5-butyl-3-(2,2-diethyoxyethyl)-1H-1,2,4-triazol-1-yl]methyl][1,1'-biphenyl]-2-yl]-1H-tetrazole from Example 38 was dissolved in 15 ml of ethanol and 15 ml of 3M HCl. The reaction was stirred at ambient temperature overnight and then at reflux for 2 h. The solvent was removed in vacuo, the residue dissolved in 15 ml of THF and 15 ml of 3M HCl and stirred for 3 days at ambient temperature. The solvent was removed in vacuo; the residue dissolved in dilute base, acidified and extracted with ethyl acetate and methylene chloride. The solvents were combined and dried ($MgSO_4$). The solvents were removed in vacuo. The residue was dissolved in 70 ml of acetone and 35 ml of water. Potassium permanganate was added in 4 equal portions of 190 mg after each preceeding portion had reacted. The mixture was filtered through celite and the solvent removed in vacuo. Purification by reverse phase chromatography (Waters Delta Prep 3000) gave 88 mg (7%) of 5-butyl-1-[21-(1H-tetrazol-5-yl)[1,1'-biphenyl]-4-ylmethyl]-1H-1,2,4-triazole-3-carboxylic acid as the colorless TFA salt after lyophilization from acetonitrile/water: NMR (DMSO-$d_6$) δ 0.85 (t, J=8 Hz, 3H), 1.23–1.38 (m, 2H), 1.52–1.62 (m, 2H), 2.78 (t, J=8 Hz, 2H), 5.46 (s, 2H), 7.13 (q, J=8 Hz, 4H), 7.51–7.62 (m, 2H), 7.64–7.73 (m, 2H); MS (FAB) m/e (rel intensity) 404 (100), 235 (20), 207 (91), 192 (24); HRMS. Calc'd for M+H: 404.1835. Found: 404.1882.

EXAMPLE 53

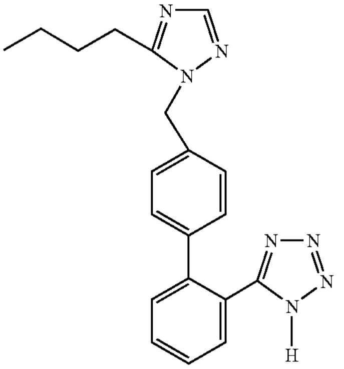

5-[4'-[(5-butyl-1H-1,2,4-triazol-1-yl)methyl][1,1'-biphenyl]-2-yl]-1H-tetrazole

Following general procedure A, 630 mg (5 mmol) of 3-butyl-1H-1,2,4-triazole was reacted with 5 mmol of the alkylating reagent prepared in step 1 of Example 3 to give 2.3 g (76%) of a mixture of the two isomers. Deprotection of the faster isomer provided 5-[4'-[(5-butyl-1H-1,2,4-triazol-1-yl)methyl][1,1'-biphenyl]-2-yl]1H-tetrazole: NMR ($CDCl_3$) δ 0.87 (t, J=8 Hz, 3H), 1.35–1.41 (m, 2H), 1.59–1.72 (m, 2H), 2.72 (t, J=8 Hz, 2H), 5.30 (s, 2H), 7.09 (d, J=8 Hz, 2H), 7.17 (d, J=8 Hz, 2H), 7.44 (dd, J=8 and 2 Hz, 1H), 7.52–7.66 (m, 2H), 7.72 (s, 1H), 8.01 (dd, J=8 and 2 Hz, 1H); MS (FAB) m/e (rel intensity) 360 (88), 235 (20), 207 (100), 192 (31), 178 (22); HRMS. Calc'd for M+H: 360.1936. Found: 360.1938.

EXAMPLE 54

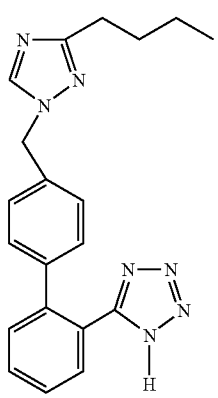

5-[4'-[(3-butyl-1H-1,2,4-triazol-1-yl)methyl][1,1-biphenyl]-2-yl]-1H-tetrazole

The slower moving isomer from Example 53 was deprotected to provide 5-[4'-[(3-butyl-1H-1,2,4-triazol-1-yl)methyl][1,1'-biphenyl]-2-yl]-1H-tetrazole: NMR ($CDCl_3$) δ 0.74 (t, J=8 Hz, 3H), 1.19–1.33 (m, 2H), 1.51–1.63 (m, 2H), 2.55 (t, J=8 Hz, 2H), 5.23 (s, 2H), 7.10 (q, J=8 Hz, 4H), 7.44 (dd, J=8 and 2 Hz, 1H), 7.50–7.64 (m, 2H), 7.92 (dd, J=8 and 2 Hz, 1H), 8.02 (s, 1H); MS (FAB) m/e (rel intensity) 360 (84), 135 (18), 207 (100), 192 (26), 178 (16), 126 (22); HRMS. Calc'd for M+H: 360.1936. Found: 360.1971.

EXAMPLE 55

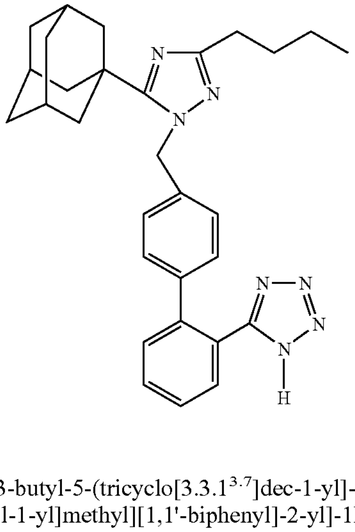

5-[4'-[[3-butyl-5-(tricyclo[3.3.1$^{3.7}$]dec-1-yl]-1H-1,2,4-triazol-1-yl]methyl][1,1'-biphenyl]-2-yl]-1H-tetrazole Following general procedure A, 1.3 g (5.0 mmol) of 5-butyl-3-adamantyl-1H-1,2,4-triazole was reacted with 5.0 mmol of the alkylating reagent prepared in step 1 of Example 3 to give 2.94 g (72%) of a mixture of the two isomers. Deprotection of the faster moving isomer-provided 5-[4'-[[3-butyl-5-(tricyclo[3.3.1$^{3.7}$]dec-1-yl]-1H-1,2,4-triazol-1-yl]methyl][1,1'-biphenyl]-2-yl]-1H-tetrazole: NMR ($CDCl_3$) δ 0.90 (t, J=8 Hz, 3H), 1.27–1.41 (m, 2H), 1.42–1.55 (m, 3H), 1.58–1.73 (m, 5H), 1.76–1.91 (m, 9H), 2.28–2.43 (m, 2H), 5.42 (s, 2H), 6.72–6.83 (m, 2H), 7.07 (d, J=8 Hz, 2H), 7.45–7.66 (m, 3H), 7.88 (t, J=8 Hz, 1H); MS (FAB) m/e (rel intensity) 494 (100), 260 (37), 207 (74), 178 (22); HRMS. Calc'd for M+H: 494.3032. Found: 494.3014.

EXAMPLE 56

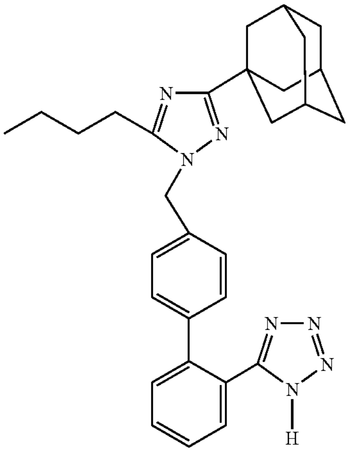

5-[4'-[[5-butyl-3-(tricyclo[3.3.1.1$^{3.7}$]dec-1-yl]-1H-1,2,4-triazol-1-yl]methyl][1,1'-biphenyl]-2-yl]-1H-tetrazole The slower moving isomer from Example 55 was deprotected to provide 5-[4'-[[5-butyl-3-(tricyclo[3.3.1.1$^{3.7}$]dec-1-yl]-1H-1,2,4-triazol-1-yl]methyl][1,1'-biphenyl]-2-yl]-1H-tetrazole: NMR ($CDCl_3$) δ 0.87 (t, J=8 Hz, 3H), 1.31–1.47 (m, 2H), 1.52–1.71 (m, 9H), 1.78 (s, 7H), 1.88 (s, 3H), 2.20–2.35 (m, 2H), 5.22 (s, 2H), 6.87 (d, J=8 Hz, 2H), 7.13 (d, J=8 Hz, 2H), 7.42 (dd, J=8 and 2 Hz, 1H), 7.49–7.63 (m, 2H), 7.93 (dd, J=8 and 2 Hz, 1H); MS (FAB) m/e (rel intensity) 494 (73), 451 (10), 260 (24), 207 (66), 178 (21); HRMS. Calc'd for M+H: 494.3032. Found: 494.3026.

EXAMPLE 57

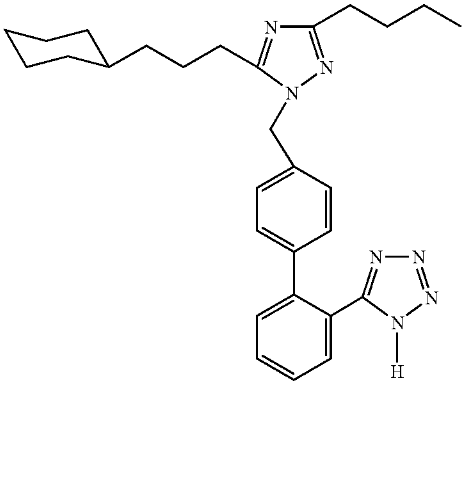

5-[4'-[[3-butyl-5-(3-cyclohexylpropyl)-1H-1,2,4-triazol-1-yl]-methyl][1,1'-biphenyl]-2-yl]-1H-tetrazole Following general procedure A, 1.25 g (5 mmol) of 5-butyl-3-(3-cyclohexylpropyl)-1H-1,2,4-triazole was reacted with 5 mmol of the alkylating reagent prepared in step 1 of Example 3 to give 3.1 g (85%) of a mixture of the two isomers. Deprotection of the faster moving isomer provided 5-[4'-[[3-butyl-5-(3-cyclohexylpropyl)-1H-1,2,4-triazol-1-yl]methyl][1,1-biphenyl]-2-yl]-1H-tetrazole: NMR ($CDCl_3$) δ 0.73–0.92 (m, 2H), 0.87 (t, J=8 Hz, 3H), 1.06–1.21 (m, 6H), 1.22–1.36 (m, 2H), 1.53–1.71 (m, 9H), 2.51 (t, J=8 Hz, 2H), 2.61 (t, J=8 Hz, 2H), 5.22 (s, 2H), 7.01 (d, J=8 Hz, 2H), 7.12 (d, J=8 Hz, 2H), 7.42 (dd, J=8 and 2 Hz, 1H), 7.51–7.64 (m, 2H), 7.94 (dd, J=8 and 2 Hz, 1H); MS (FAB) m/e (rel intensity) 484 (83), 250 (38), 207 (100), 178 (25); HRMS. Calc'd for M+H: 484.3189. Found: 484.3223.

EXAMPLE 58

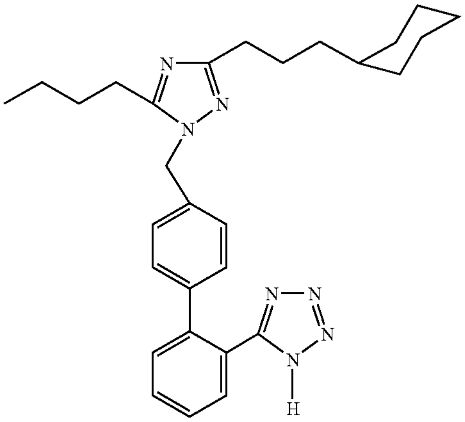

5-[4'-[[5-butyl-3-(3-cyclohexylpropyl)-1H-1,2,4-triazol-1-yl]methyl][1,1'-biphenyl]-2-yl]-1H-tetrazole The slower moving isomer from Example 57 was deprotected to provide 5-[4'-[[5-butyl-3-(3-cyclohexylpropyl)-1H-1,2,4-triazol-1-yl]methyl][1,1'-biphenyl]-2-yl]-1H-tetrazole: NMR ($CDCl_3$) δ 0.74–0.90 (m, 2H), 0.83 (t, J=8 Hz, 3H), 1.05–1.22 (m, 6H), 1.23–1.35 (m, 2H), 1.50–1.70 (m, 9H), 2.40 (t, J=8 Hz, 2H), 2.57 (t, J=8 Hz, 2H), 5.20 (s, 2H), 6.96 (d, J=8 Hz, 2H), 7.10 (d, J=8 Hz, 2H), 7.43 (dd, J=8 and 2 Hz, 2H), 7.50–7.64 (m, 2H), 7.92 (dd, J=8 and 2 Hz, 2H); MS (FAB) m/e (rel intensity) 484 (65), 250 (26), 207 (100), 178 (18); HRMS. Calc'd for M+H: 484.3189. Found: 484.3181.

EXAMPLE 59

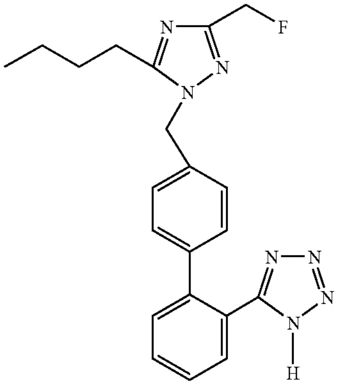

5-[4'-[[5-butyl-3-(fluoromethyl)-1H-1,2,4-triazol-1-yl]methyl][1,1'-biphenyl]-2-yl]-1H-tetrazole Following general procedure A, 790 mg (5.0 mmol) of 5-butyl-3-(fluoromethyl)-1H-1,2,4-triazole was reacted with 5 mmol of the alkylating reagent prepared in step 1 of Example 3 to give 1.3 g (42%) of a mixture of the two isomers. Deprotection of the faster moving isomer-provided 5-[4'-[[5-butyl-3-(fluoromethyl)-1H-1,2,4-triazol-1-yl]methyl][1,1'-biphenyl]-2-yl]-1H-tetrazole: NMR ($CDCl_3$) δ 0.86 (t, J=8 Hz, 3H), 1.26–1.40 (m, 2H), 1.56–1.69 (m, 2H), 2.67 (t, J=8 Hz, 2H), 5.16 (s, 1H), 5.27 (s, 2H), 5.32 (s, 1H), 7.06 (d, J=8 Hz, 2H), 7.16 (d, J=8 Hz, 2H), 7.43 (dd, J=8 and 2 Hz, 1H), 7.52–7.65 (m, 2H), 7.99 (dd, J=8 and 2 Hz, 1H); MS (FAB) m/e (rel intensity) 392 (100), 235 (22), 207 (66), 192 (18), 178 (14); HRMS. Calc'd for M+H: 392.1999. Found: 392.1932.

EXAMPLE 60

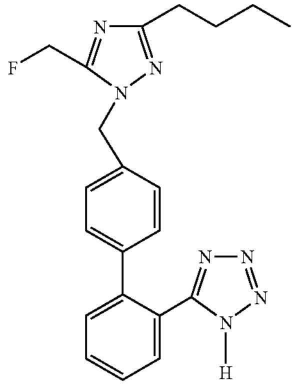

5-[4'-[[3-butyl-5-(fluoromethyl)-1H-1,2,4-triazol-1-yl]methyl][1,1-biphenyl]-2-yl]-1H-tetrazole The slower moving isomer from Example 59 was deprotected to provide 5-[4-[[3-butyl-5-(fluoromethyl)-1H-1,2,4-triazol-1-yl]methyl][1,1'-biphenyl]-2-yl]-1H-tetrazole: NMR ($CDCl_3$) δ 0.89 (t, J=8 Hz, 3H), 1.24–1.40 (m, 2H), 1.59 (m, 2H), 2.65 (t, J=8 Hz, 2H), 5.38 (s, 3H), 5.55 (s, 1H), 7.21 (s, 4H), 7.43 (d, J=8 Hz, 1H), 7.51–7.65 (m, 2H), 8.05 (d, J=8 Hz, 1H); MS (FAB) m/e (rel intensity) 392 (90), 235 (56), 207 (100), 192 (51), 178 (24); HRMS. Calc'd for M+H: 392.1999. Found: 392.1944.

EXAMPLE 61

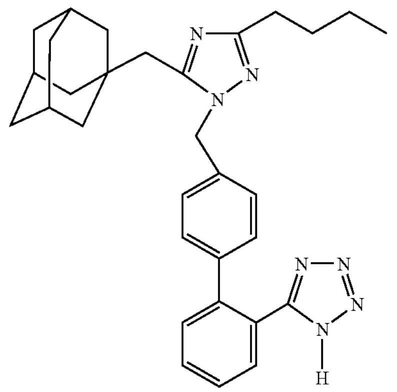

5-[4-[[13-butyl-5-(tricyclo[3.3.1.1$^{3.7}$]dec-1-ylmethyl]-1H-1,2,4-triazole-1-yl]methyl][1,1'-biphenyl]-2-yl]-1H-tetrazole Following general procedure A, 1.4 g (5.0 mmol) of 5-butyl-3-adamantyl-1H-1,2,4-triazole was reacted with 5.0 mmol of the alkylating reagent prepared in step 1 of Example 3 to give a mixture of the two isomers. Deprotection of the faster moving isomer provided 5-[4'-[[3-butyl-5-(tricyclo[3.3.1.1$^{3.7}$]dec-1-ylmethyl]-1H-1,2,4-triazole-1-yl] methyl][1,1-biphenyl]-2-yl]-1H-tetrazole: NMR ($CDCl_3$) δ 0.84 (t, J=8 Hz, 3H), 1.16–1.30 (m, 2H), 1.41 (s, 6H), 1.44–1.56 (m, 5H), 1.65 (d, J=12 Hz, 3H), 1.92 (s, 3H), 2.18 (s, 2H), 2.30 (t, J=8 Hz, 2H), 5.18 (s, 2H), 6.79 (d, J=8 Hz, 2H), 7.01 (d, J=8 Hz, 2H), 7.46 (d, J=8 Hz, 1H), 7.52 (m, 2H), 7.85 (dd, J=8 and 2 Hz, 1H); MS (FAB) m/e (rel intensity) 508 (45), 274 (25), 207 (100), 192 (31); HRMS. Calc'd for M+H: 508.3189. Found: 508.3162.

EXAMPLE 62

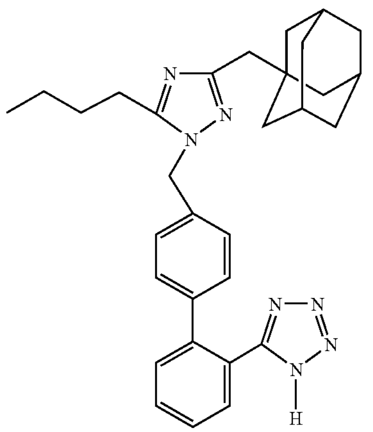

5-[4'-[[5-butyl-3-(tricyclo[3.3.1.1$^{3.7}$]dec-1-ylmethyl]-1H-1,2,4-triazol-1-yl]methyl][1,1'-biphenyl]-2-yl]-1H-tetrazole The slower moving isomer from Example 61 was deprotected to provide 5-[4'-[[5-butyl-3-(tricyclo[3.3.1.1$^{3.7}$]dec-1-ylmethyl]-1H-1,2,4-triazol-1-yl]methyl][1,1'-biphenyl]-2-yl]-1H-tetrazole: NMR ($CDCl_3$) δ 0.85 (t, J=8 Hz, 3H), 1.21–1.37 (m, 8H), 1.44–1.58 (m, 5H), 1.62 (d, J=10 Hz, 3H), 1.86 (s, 3H), 2.07 (s, 2H), 2.49 (t, J=8 Hz, 2H), 5.21 (s, 2H), 6.89 (d, J=8 Hz, 2H), 7.07 (d, J=8 Hz, 2H), 7.53 (dd, J=8 and 2 Hz, 1H), 7.52–7.65 (m, 2H), 7.91 (dd, J=8 and 2 Hz, 1H), MS (FAB) m/e (rel intensity) 508 (42), 274 (22), 207 (100), 192 (34); HRMS. Calc'd for M+H: 508.3189. Found: 508.3142°.

EXAMPLE 63

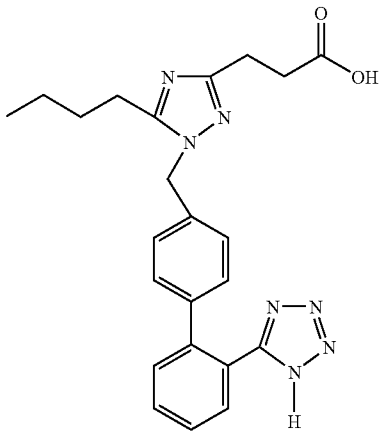

5-butyl-1-[2'-(1H-tetrazol-5-yl)[1,1'-biphenyl]-4-ylmethyl]-1H-1,2,4-triazole-3-propanoic acid A 2.18 g sample of the mixture of the two isomers from Example 45 was oxidized to the corresponding aldehydes with oxalyl chloride/dimethyl sulfoxide and subsequently oxidized to the acids with potassium permanganate to give 1.8 g of a mixture of the two propanoic isomers. Deprotection of the faster moving isomer provided 5-butyl-1-[2'-(1H-tetrazol-5-yl)[1,1'-biphenyl]-4-ylmethyl]-1H-1,2,4-triazole-3-propanoic acid: NMR ($CDCl_3$) δ 0.99 (t, J=8 Hz, 3H), 1.28–1.43 (m, 2H), 1.61–1.74 (m, 2H), 2.67–2.80 (m, 4H), 2.94 (t, J=6 Hz, 2H), 5.1.8 (s, 2H), 7.04–7.14 (m, 4H), 7.42 (dd, J=8 and 2 Hz, 1H), 7.50 (dt, J=8 and 2 Hz, 1H), 7.59 (dt, J=8 and 2 Hz, 1H), 7.90 (dd, J=8 and 2 Hz, 1H); MS (FAB) m/e (rel intensity) 432 (89), 389 (15), 237 (36), 198 (100); HRMS. Calc'd for M+H: 432.2148. Found: 432.2216.

EXAMPLE 64

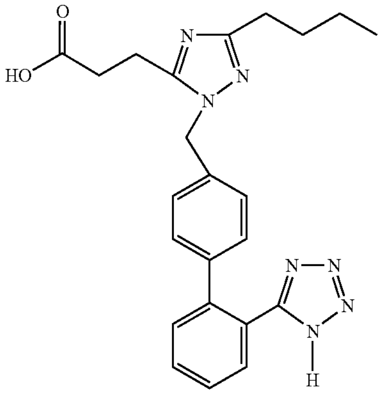

3-butyl-1-[2'-(1H-tetrazol-5-yl)[1,1'-biphenyl]-4-ylmethyl]-1H-1,2,4-triazole-5-propanoic acid The slower moving isomer from Example 63 was deprotected to give 3-butyl-1-[2'-(1H-tetrazol-5-yl)[1,1'-biphenyl]-4-ylmethyl]-1H-1,2,4-triazole-5-propanoic acid: NMR ($CDCl_3$) δ 0.92 (t, J=8 Hz, 3H), 1.30–1.40 (m, 2H), 1.65–1.78 (m, 2H), 2.70 (t, J=8 Hz, 2H), 2.84–2.91 (m, 2H), 2.93–3.00 (m, 2H), 5.40 (s, 2H), 7.20 (d, J=8 Hz, 2H), 7.34 (d, J=8 Hz, 2H), 7.37–7.42 (m, 1H), 7.51–7.62 (m, 2H), 8.30–8.36 (m, 1H); MS (FAB) m/e (rel intensity) 432 (100) 198 (45); HRMS. Calc'd for M+H: 432.2148. Found: 432.2214.

EXAMPLE 65

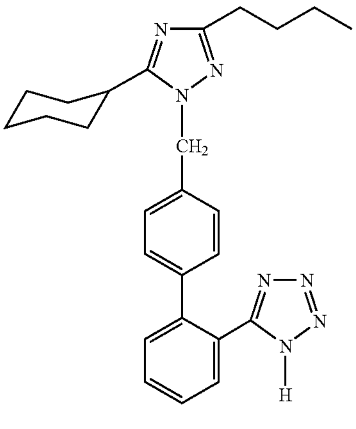

5-[4'-[(3-butyl-5-cyclohexyl-1H-1,2,4-triazol-1-yl) methyl][1,1'-biphenyl]-2-yl]-1H-tetrazole Following General Procedure A, 2.07 g (10 mmol) of 3-butyl-5-cyclohexyl-1H-1,2,4-triazole was reacted with 6.5 g (11.8 mmol) of the alkylating reagent prepared in step 1 of Example 3 to give 6.3 g (9.2 mmol) of a mixture of the two isomers. Deprotection of the faster moving isomer provided 33 mg of 5-[4'-[(3-butyl-5-cyclohexyl-1H-1,2,4-triazol-1-yl)methyl][1,1'-biphenyl]-2-yl]-1H-1,2,4-triazole as a colorless solid: mp 157.5–159.5° C.; NMR ($CDCl_3$) δ 0.87 (t, J=7 Hz, 3H), 1.11–1.36 (m, 6H), 1.45–1.70 (m, 6H), 1.70–1.80 (m, 2H), 2.50 (t, J=7 Hz, 2H), 2.64–2.78 (m, 1H), 5.23 (s, 2H), 6.98 (d, J=8 Hz, 2H), 7.08 (d, J=8 Hz, 2H), 7.41 (dd, J=5 and 1 Hz, 1H), 7.49 (dt, J=5 and 1 Hz, 1H), 7.57 (dt, J=5 and 1 Hz, 1H), 7.80 (dd, J=5 and 1 Hz, 1H): MS (FAB) m/e (rel intensity), 442 (100), 414 (10), 399 (20), 235 (8), 207 (65), 192 (18).

EXAMPLE 66

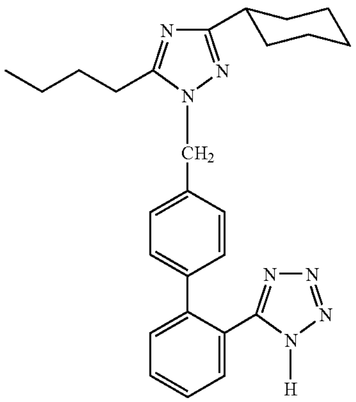

5-[4'-[(5-butyl-3-cyclohexyl-1H-1,2,4-triazol-1-yl) methyl][1,1'-biphenyl]-2-yl]-1H-tetrazole The slower moving isomer from Example 65 was deprotected to provide 135 mg of 5-[4'-[(5-butyl-3-cyclohexyl-1H-1,2,4-triazol-1-yl)methyl][1,1-biphenyl]-2-yl]-1H-tetrazole as a colorless solid: mp 125–127° C.; NMR ($CDCl_3$) δ 0.85 (t, J=7 Hz, 3H), 1.12–1.40 (m, J=8 Hz, 8H), 1.52–1.75 (m, J=8 Hz, 4H), 1.81 (d, J=8 Hz, 2H), 2.50 (t, J=8 Hz, 3H), 5.20 (s, 2H), 6.94 (d, J=8 Hz, 2H), 7.09 (d, J=8 Hz, 2H), 7.42 (dd, J=8 and 2 Hz, 1H), 7.50–7.64 (m, J=8 Hz, 2H), 7.88 (dd, J=8 and 2 Hz, 1H); MS (FAB) m/e (rel intensity) 442 (100), 414 (10), 399 (20), 235 (10), 207 (75), 192 (17).

EXAMPLE 67

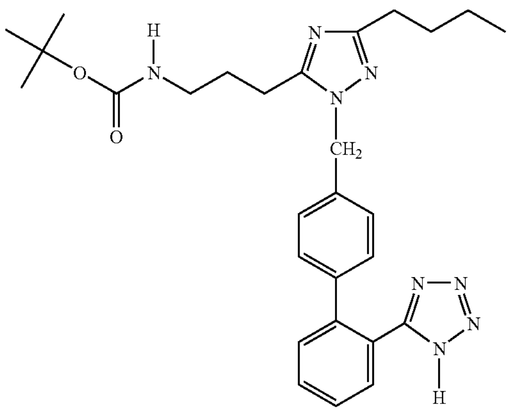

1,1-dimethylethyl 3-butyl-[1-[2'-(1H-tetrazol-5-yl)[1,1'-biphenyl]-4-ylmethyl]-1H-1,2,4-triazol-5-yl]propylcarbamate Following General Procedure A, 6.0 g (20 mmol) of 3-butyl-5-(N-Boc-3-aminopropyl)-1H-1,2,4-triazole was reacted with 13.1 g (24 mmol) of the alkylating reagent prepared in step 1 of Example 3. Deprotection of the faster moving isomer gave 3.52 g (33%) of 1,1-dimethylethyl 3-butyl-[1-[2'-(1H-tetrazol-5-yl)[1,1'-biphenyl]-4-ylmethyl]-1H-1,2,4-triazol-5-yl]propylcarbamate as a colorless solid: NMR (DMSO-$d_6$) δ 0.88 (t, J=8 Hz, 3H), 1.22–1.34 (m, J=8 Hz, 2H), 1.36 (s, 9H), 1.54–1.66 (m, J=7 Hz, 2H), 1.66–1.78 (m, J=7 Hz, 2H), 2.5 (t, J=8 Hz, 2H), 2.67 (t, J=8 Hz, 2H), 2.96 (q, J=8 Hz, 2H), 5.26 (s, 2H), 7.08 (s, 4H), 7.55 (q, J=8 Hz, 2H), 7.65 (d, J=8 Hz, 2H); MS (FAB) m/e (rel intensity) 517 (60), 489 (10), 461 (10), 439 (10), 417 (23), 389 (18), 357 (8), 323 (8), 305 (15), 283 (80), 227 (70), 207 (100), 183 (65); HRMS. Calc'd for M+H: 517.3039. Found 517.3001.

EXAMPLE 68

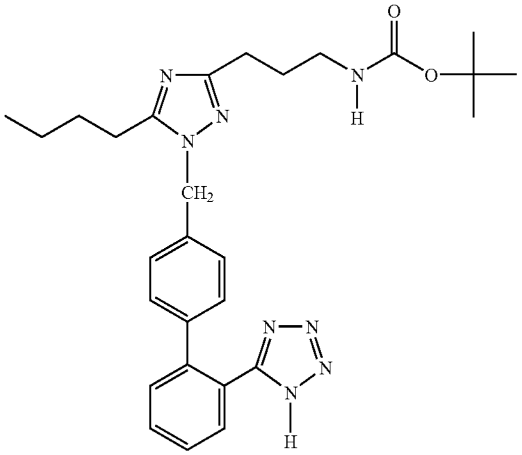

1,1-dimethylethyl 5-butyl-[1-[2'-(1H-tetrazol-5yl)[1,1'-biphenyl]-4-ylmethyl]-1H-1,2,4-triazol-3-yl]propylcarbamate The slower moving isomer from Example 67 was deprotected to give 3.43 g (33%) of 1,1-dimethylethyl 5-butyl-[1-[2'-(1H-tetrazol-5-yl)[1,1'-biphenyl]-4-ylmethyl]-1H-1,2,4-triazol-3-yl]propylcarbamate as a colorless solid: NMR (DMSO-$d_6$) δ 0.84 (t, J=7 Hz, 3H), 1.29 (q, J=8 Hz, 2H), 1.38 (s, 9H), 1.48–1.59 (m, J=8 Hz, 2H), 1.72 (t, J=8 Hz, 2H), 2.53 (t, J=7 Hz, 2H), 2.67 (t, J=8 Hz, 2H), 2.97 (q, J=8 Hz, 2H), 5.28 (s, 2H), 7.08 (s, 4H), 7.50 (d, J=8 Hz, 1H) 7.55 (d, J=8 Hz, 1H), 7.61–7.68 (m, J=7 Hz, 2H); MS (FAB) m/e (rel intensity) 517 (40), 439 (10) 417 (40), 390 (20), 357 (10), 207 (100), 192 (40); HRMS. Calc'd for M+H: 517.3039. Found: 517.3014.

EXAMPLE 69

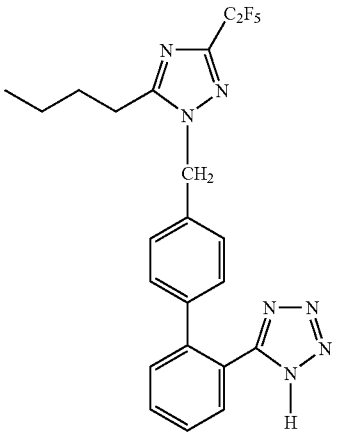

5-[4'-[[3-(1,1,2,2,2-pentafluorethyl)-5-butyl-1H-1,2,4-triazol-1-yl]methyl][1,1'-biphenyl]-2-yl]-1H-tetrazol Following General Procedure A, 1.21 g (5.0 mmol) of 3-perfluoroethyl-5-butyl-1H-1,2,4-triazole was reacted with 3.2 g (5.7 mmol) of the alkylating reagent prepared in step 1 of Example 3. Deprotection provided 409 mg of 5-[4'-[[3-(1,1,2,2,2-pentafluoroethyl)-5-butyl-1H-1,2,4-triazol-1-yl]methyl[1,1-biphenyl]-2-yl]-1H-tetrazole as a colorless oil: NMR ($CDCl_3$) δ 0.90 (t, J=7 Hz, 3H), 1.36 (q, J=7 Hz, 2H), 1.67 (t, J=7 Hz, 2H), 2.78 (t, J=7 Hz, 2H), 5.38 (s, 2H), 7.18 (s, 4H), 7.42 (d, J=8 Hz, 1H), 7.51–7.67 (m, J=8 Hz, 2H), 7.98 (d, J=8 Hz, 1H); MS (FAB) m/e (rel intensity) 478 (40), 452 (15), 235 (90), 207 (100), 178 (40), 152 (35); HRMS. Calc'd. for M+H: 478.1778. Found: 478.1807.

EXAMPLE 70

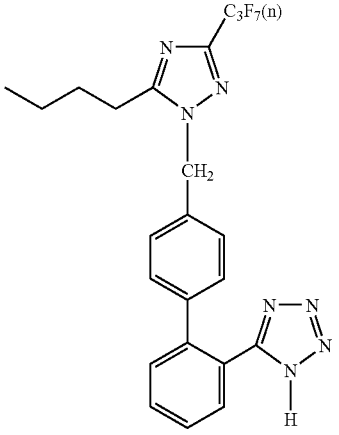

5-[4'-[[3-(1,1,2,2,3,3,3-heptafluoropropyl)-5-butyl-1H-1,2,4-triazol-1-yl]methyl][1,1'-biphenyl]-2-yl]-1H-tetrazole Following General Procedure A, 1.46 g (5.0 mmol) of 5-butyl-3-perfluoropropyl-1H-1,2,4-triazole was reacted with 3.20 g (5.7 mmol) of the alkylating reagent prepared in step 1 of Example 3. Deprotection provided 210 mg of 5-[4'-[[3-(1,1,2,2,3,3,3-heptafluoropropyl)-5-butyl-1H-1,2,4-triazol-1-yl]methyl][1,1'-biphenyl]-2-yl]-1H-tetrazole as a colorless oil: NMR ($CDCl_3$) δ 0.90 (t, J=7 Hz, 3H), 1.36 (q, J=8 Hz, 2H), 1.63–1.75 (m, J=8 Hz, 2H), 2.78 (t, J=8 Hz, 2H), 5.40 (s, 2H), 7.20 (q, J=7 Hz, 4H), 7.42 (dd, J=8 and 2 Hz, 1H), 7.52–7.65 (m, J=8 Hz, 2H), 8.04 (dd, J=8 and 2 Hz, 1H); MS (FAB) m/e (rel intensity) 528 (35), 502 (15), 294 (12), 235 (90), 207 (100), 136 (15); HRMS. Calc'd for M+H: 528.1747. Found: 528.1701.

EXAMPLE 71

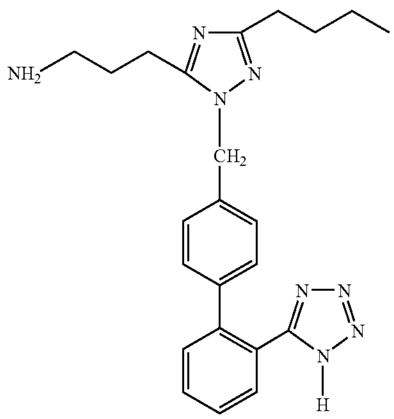

5-[4-[[3-butyl-5-(3-aminopropyl)-1H-1,2,4-triazol-1-yl]methyl][1,1'-biphenyl]-2-yl]-1H-tetrazole Under a static nitrogen atmosphere 2.40 g (4.7 mmol) of 5-[4'-[[3-butyl-5-(N-Boc-3-aminopropyl)-1H-1,2,4-triazol-1-yl]methyl][1,1'-biphenyl]-2-yl]-1H-tetrazole from Example 67 was dissolved in 30 mL of 4N HCl in dioxane at ambient temperature and allowed to stir overnight. The solvents were removed in vacuo; the residue was triturated with diethyl ether and filtered providing 2.08 g (98%) of 5-[4'-[[3-butyl-5-(3-aminopropyl)-1H-1,2,4-triazol-1-yl]methyl][1,1'-biphenyl]-2-yl]-1H-tetrazole as the hydrochloride salt: NMR (DMSO-$d_6$) δ 0.88 (t, J=7 Hz, 3H), 1.25–1.39 (m, 2H), 1.57–1.69 (m, 2H), 1.92–2.40 (m, 2H), 2.62 (t, J=7 Hz, 2H), 2.89 (q, J=8 Hz, 2H), 2.98 (t, J=8 Hz, 2H), 5.38 (s, 2H), 7.10 (d, J=8 Hz, 2H), 7.19 (d, J=8 Hz, 2H), 7.54 (d, J=8 Hz, 1H), 7.59 (dd, J=8 and 2 Hz, 1H), 7.66 (s, 1H), 7.70 (dd, J=8 and 2 Hz, 1H), 8.10 (br s, 2H); MS (FAB) m/e (rel intensity) 417 (38), 389 (10), 357 (10), 207 (100), 166 (50), 139 (10) 115 (10); HRMS. Calc'd for M+H: 417.2515. Found: 417.2563.

EXAMPLE 72

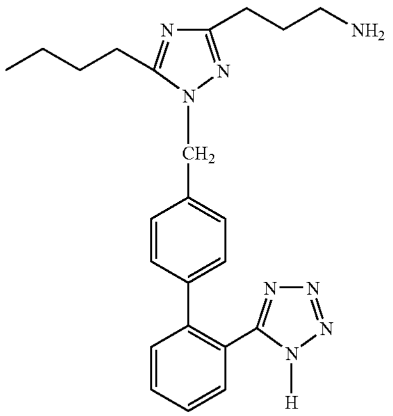

5-[4'-[[3-(3-aminopropyl)-5-butyl-1H-1,2,4-triazol-1-yl)methyl](1,1'-biphenyl)-2-yl]-1H-tetrazole Under a static nitrogen atmosphere 2.30 g (4.5 mmol) of 5-[4'-[[3-(N-Boc-3-aminopropyl)-5-butyl-1H-1,2,4-triazol-1-yl]methyl][1,1'-biphenyl]-2-yl]-1H-tetrazole from Example 68 was dissolved in 30 mL of 4N HCl in dioxane at ambient temperature and allowed to stir overnight. The solvents were removed in vacuo; the residue was triturated with diethyl ether and filtered providing 1.99 g (98%) of 5-[4'-[[3-(3-aminopropyl)-5-butyl-1H-1,2,4-triazol-1-yl]methyl] (1,1'-biphenyl)-2-yl]-1H-tetrazole as the hydrochloride salt: NMR (DMSO-$d_6$) δ 0.85 (t, J=7 Hz, 3H), 1.22–1.38 (m, 2H), 1.59 (t, J=8 Hz, 2H), 1.96 (t, J=8 Hz, 2H), 2.71–2.79 (m, 2H) 2.80–2.92 (m, 4H), 5.40 (s, 2H) 7.10 (d, J=8 Hz, 2H), 7.18 (d, J=8 Hz, 2H) 7.52 (d, J=8 Hz, 1H), 7.59 (d, J=8 Hz, 1H), 7.68 (d, J=8 Hz, 2H); MS (FAB) m/e (rel intensity) 417 (60), 389 (10), 357 (10), 263 (5), 235 (10), 207 (100), 166 (40), 136 (15); HRMS. Calc'd for M+H: 417.2515. Found: 417.2510.

EXAMPLE 73

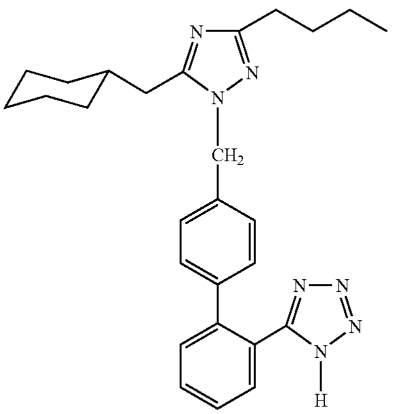

5-['-[(3-butyl-5-cyclohexylmethyl-1H-1,2,4-triazol-1-yl)methyl][1,1'-biphenyl]-2-yl]-1H-tetrazole Following General Procedure A, 2.21 g (10.0 mmol) of 3-butyl-7.5-cyclohexylmethyl-1H-1,2,4-triazole was reacted with 6.55 g (11.8 mmol) of the alkylating reagent prepared in step 1 of Example 3 to give 5.90 g (85%) of a mixture of the two isomers. The faster moving isomer was deprotected to provide 64 mg of 5-[4'-[(3-butyl-5-cyclohexylmethyl-1H-1,2,4-triazol-1-yl)methyl][1,1'-biphenyl]-2-yl]-1H-tetrazole as a colorless solid: NMR ($CDCl_3$) δ 0.92 (t, J=7 Hz, 3H) 0.94–1.05 (m, 2H) 1.08–1.25 (m, 3H), 1.25–1.41 (m, 2H), 1.55–1.80 (m, 8H), 2.65 (d, J=7 Hz, 2H), 2.68 (t, J=7 Hz, 2H), 5.27 (s, 2H), 7.11 (q, J=8 Hz, 4H), 7.42 (dd, J=8 and 2 Hz, 1H), 7.49–7.63 (m, 2H), 7.94 (dd, J=8 and 2 Hz, 1H); MS (FAB) m/e (rel intensity) 456 (100), 428 (10), 413 (20), 280 (10), 235 (10), 222 (25), 207 (80), 192 (30); HRMS. Calc'd for M+H: 456.2876. Found: 456.2839.

EXAMPLE 74

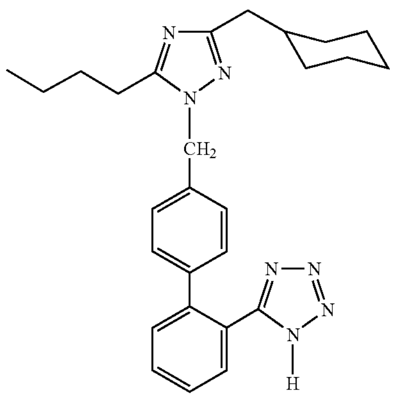

5-[4'-[(3-cyclohexylmethyl-5-butyl-1H-1,2,4-triazol-1-yl)methyl][1,1'-biphenyl]-2-yl]-1H-tetrazole The slower moving isomer from Example 73 was deprotected to provide 51 mg of 5-[4'-[(3-cyclohexylmethyl-5-butyl-1H-1,2,4-triazol-1-yl)methyl]([1,1-biphenyl]-2-yl]-1H-tetrazole as a colorless solid: NMR ($CDCl_3$) δ 0.84 (t, J=8 Hz, 3H), 0.92 (q, J=8 Hz, 2H), 1.05–1.22 (m, 3H), 1.22–1.36 (m, 2H), 1.52–1.69 (m, 8H), 2.5–0 (d, J=7 Hz, 2H), 2.63 (t, J=8 Hz, 2H), 5.18 (s, 2H), 7.05 (q, J=8 Hz, 4H), 7.35–7.55 (m, 3H), 7.68 (dd, J=8 and 2 Hz, 1H); MS (FAB) m/e (rel intensity) 456 (90), 413 (10), 281 (10), 243 (10), 222 (35), 207 (100), 192 (35); HRMS. Calc'd for M+H: 456.2876. Found: 456.2849.

EXAMPLE 75

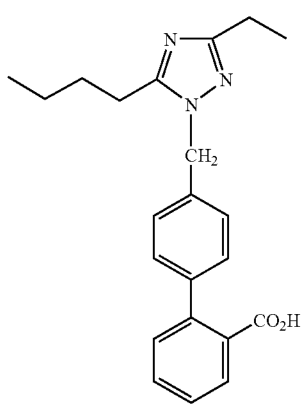

4'-[(3-ethyl-5-butyl-1H-1,2,4-triazol-1-yl)methyl][1,1'-biphenyl]-2-carboxylic acid Following General Procedure A, 1.0 g (6.0 mmol) of 3-ethyl-5-butyl-1H-1,2,4-triazole was reacted with 2.41 g (7.9 mmol) of the alkylating reagent prepared in step 1 of Example 1. Hydrolysis of the faster moving isomer provided 220 mg of 4'-[(3-ethyl-5-butyl-1H-1,2,4-triazol-1-yl)methyl][1,1'-biphenyl]-2-carboxylic acid as a colorless solid: NMR (DMSO-$d_6$) δ 0.85 (t, J=7 Hz, 3H), 1.19 (t, J=7 Hz, 3H), 1.27–1.38 (m, 2H), 1.52–1.63 (m, 2H), 2.59 (q, J=7 Hz, 2H), 2.74 (t, J=7 Hz, 2H), 5.35 (s, 2H), 7.21 (d, J=8 Hz, 2H), 7.31 (d, J=8 Hz, 2H), 7.35 (dd, J=8 and 2 Hz, 1H), 7.48 (dt, J=8 and 2 Hz, 1H), 7.57 (dt, J=8 and 2 Hz, 1H), 7.72 (dd, J=8 and 2 Hz, 1H).

EXAMPLE 76

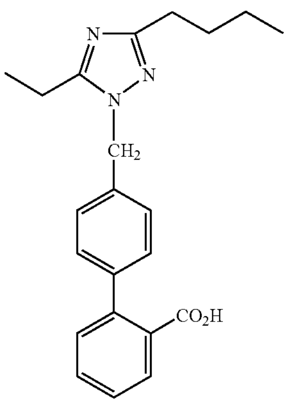

4'-[(3-butyl-5-ethyl-1H-1,2,4-triazol-1-yl)methyl][1,1-biphenyl]-2-carboxylic acid The slower moving isomer from Example 75 was hydrolyzed to provide 174 mg of 4'-[(3-butyl-5-ethyl-1H-1,2,4- triazol-1-yl)methyl][1,1'-biphenyl]-2-carboxylic acid as a colorless solid: NMR (DMSO-$d_6$) δ 0.89 (t, J=7 Hz, 3H), 1.17 (t, J=7 Hz, 3H), 1.27–1.40 (m, 2H), 1.56–1.68 (m, 2H), 2.58 (t, J=8 Hz, 2H) 2.77 (q, J=8 Hz, 2H), 5.35 s, 2H), 7.21 (d, J=8 Hz, 2H), 7.32 (d, J=8 Hz, 2H), 7.36 (dd, J=8 and 2 Hz, 1H), 7.46 (dt, J=8 and 2 Hz, 1H), 7.57 (dt, J=8 and 2 Hz, 1H), 7.73 (dd, J=8 and 2 Hz, 1H).

EXAMPLE 77

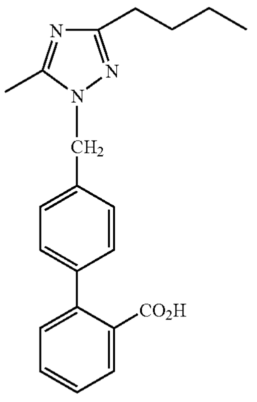

4'-[(3-butyl-5-methyl-1H-1,2,4-triazol-1-yl)methyl] [1,1'-biphenyl]-2-carboxylic acid Following General Procedure A, 1.0 g (7.2 mmol) of 3-butyl-5-methyl-1H-1,2,4-triazole was reacted with 2.89 g (9.5 mmol) of the alkylating reagent prepared in step 1 of Example 1. Hydrolysis of the slower moving isomer provided 220 mg of 4'-[(3-butyl-5-methyl-1H-1,2,4-triazol-1-yl)methyl][1,1'-biphenyl]-2-carboxylic acid as a colorless solid: NMR (DMSO-$d_6$) δ 0.88 (t, J=7 Hz, 3H), 1.25–1.38 (m, 2H), 1.54–1.67 (m, 2H), 2.39 (s, 3H), 2.54 (t, J=8 Hz, 2H), 5.32 (s, 2H), 7.21 (d, J=8 Hz, 2H), 7.32 (d, J=8 Hz, 2H), 7.36 (dd, J=8 and 2 Hz, 1H), 7.46 (dt, J=8 and 2 Hz, 1H), 7.56 (dt, J=8 and 2 Hz, 1H), 7.72 (dd, J=8 and 2 Hz, 1H).

EXAMPLE 78

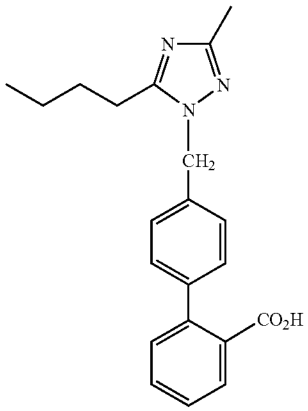

4'-[(3-methyl-5-butyl-1H-1,2,4-triazol-1-yl)methyl] [1,1'-biphenyl]-2-carboxylic acid The faster moving isomer from Example 77 was hydrolyzed to provide 19 mg of 4'-[(3-methyl-5-butyl-1H-1,2,4-triazol-1-yl)methyl][1,1'-biphenyl]-2-carboxylic acid as a colorless solid: NMR (DMSO-$d_6$) δ 0.86 (t, J=7 Hz, 3H), 1.25–1.38 (m, 2H), 1.52–1.64 (m, 2H), 2.21 (s, 3H), 2.72 (t, J=7 Hz, 2H), 5.32 (s, 2H), 7.21 (d, J=8 Hz, 2H), 7.32 (d, J=8 Hz, 2H), 7.35 (dd, J=8 and 2 Hz, 1H), 7.45 (dt, J=8 and 2 Hz, 1H), 7.57 (dt, J=8 and 2 Hz, 1H), 7.72 (dd, J=8 and 2 Hz, 1H).

A class of highly preferred specific conjugates of the invention is provided by conjugates formed from a biphenylmethyl 1H-substituted-1,2,4-triazole AII antagonist compound linked to a cleavable glutamyl residue. Each conjugate of this class contains a diamino linker moiety which connects a terminal carboxylic acid moiety on the biphenylmethyl portion of the AII antagonist compound with a terminal carboxylic acid moiety on the gamma carbon of the cleavable glutamyl residue. Example #79 is a detailed description of a conjugate of this class. Other specific conjugates of Examples #80–#144, as shown in Table IV, may be prepared generally in accordance with the procedures of Example #79.

EXAMPLE 79

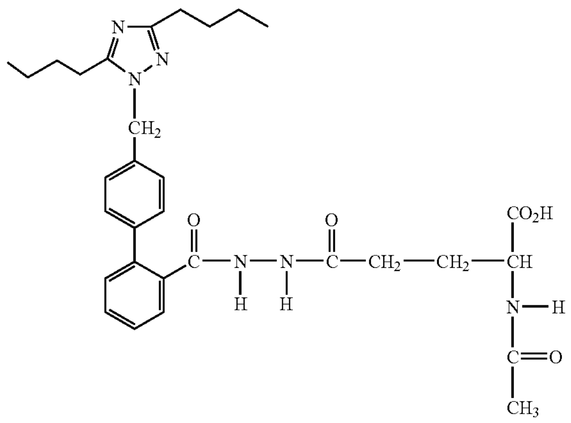

N-acetylglutamic acid, 5-[[4'-[(3,5-dibutyl-1H-1,2,4-triazol-1-yl)methyl][1,1'-biphenyl]-2-yl]]carbonylhydrazide To a solution of 10.45 g (34.5 mmol) of N-Boc-L-glutamic acid-α-tertbutyl ester (BACHEM) in 100 mL of methylene chloride under nitrogen was added 3.5 g (17.0 mmol) of solid dicyclohexylcarbodiimide (DCC). The reaction was allowed to stir for 2 h and filtered under nitrogen. The anhydride solution was then added to a solution of 6.03 g (14.9 mmol) of the compound of Example 4 in 75 mL of methylene chloride under nitrogen. The reaction was stirred overnight and concentrated in vacuo. Purification by silica gel chromatography (Waters Prep-500A) using ethyl acetate gave 7.90 g (77%) of pure material by thin-layer chromatography (TLC). This material was redissolved in 100 mL of methylene chloride under nitrogen and cooled to 0° C. prior to the addition of 135 mL of TFA. The stirred reaction was allowed to warm to ambient temperature overnight and concentrated in vacuo.

The crude product was dissolved in 80 mL of acetonitrile/water (1:1) and the pH adjusted to 9 with 1 M $K_2CO_3$. The solution was cooled to 0° C. and 1.1 mL (11 mmol) of acetic anhydride and 11 mL (11 mmol) of 1 M $K_2CO_3$ was added every 30 min for 5 h; during the course of this reaction the pH was maintained at 9 and the reaction temperature kept below 5° C. After the last addition, the reaction was allowed to warm to ambient temperature overnight. The pH was adjusted to 4 with 3 M HCl and the reaction concentrated to 300 mL. Purification by reverse phase chromatography (Waters Delta prep-3000) using isocratic 32% acetonitrile/water (0.05% TFA) gave 6.11 g (55%-overall yield from the compound of Example 4) of colorless product: NMR (DMSO-$d_6$) δ 0.85 (t, J=8 Hz, 3H), 0.88 (t, J=8 Hz, 3H), 1.23–1.39 (m, 4H), 1.53–1.68 (m, 6H), 1.84 (s, 3H), 2.15–2.24 (m, 2H), 2.55 (t, J=8 Hz, 2H), 2.70 (t, J=8 Hz, 2H), 4.10–4.20 (m, 1H), 5.31 (s, 2H), 7.11–7.19 (m, 2H), 7.37–7.57 (m, 6H); MS (FAB) m/e (rel intensity) 577 (42), 389 (10), 195 (82), 182 (100), 167 (63), 152 (28); HRMS. Calcd. for M+H: 577.3138. Found: 577.3160. Anal. Calcd. for $C_{31}H_{40}N_6O_5$.1.5 $CF_3CO_2H$: C, 54.65; H, 5.56; N, 11.25; F, 11.50. Found: C, 54.42; H, 5.75, N, 11.35, F, 11.85.

TABLE IV

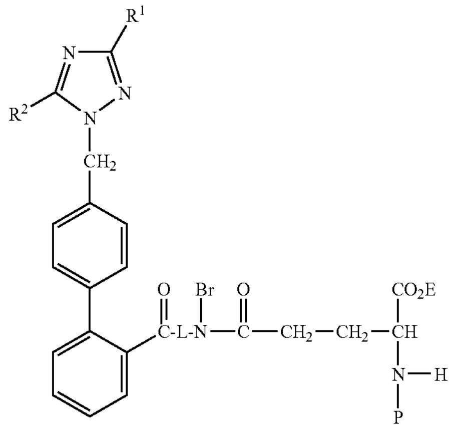

| Ex. # | $R^1$ | $R^2$ | L | B | E | P |
|---|---|---|---|---|---|---|
| 80 | $C_4H_9$(n) | $C_4H_9$(n) | —NH— | H | H | H |
| 81 | $C_4H_9$(n) | $C_4H_9$(n) | —NH— | H | $CH_3$ | H |
| 82 | $C_4H_9$(n) | $C_4H_9$(n) | —NH— | H | $CH_3$ | $COCH_3$ |
| 83 | $C_4H_9$(n) | $C_4H_9$(n) | —NH— | H | $C_2H_5$ | $COCH_3$ |
| 84 | $C_4H_9$(n) | $C_4H_9$(n) | —NH— | H | $C_2H_5$ | H |
| 85 | $C_4H_9$(n) | $C_4H_9$(n) | —NH— | H | H | $COCH_2Cl$ |
| 86 | $C_4H_9$(n) | $C_4H_9$(n) | —NH— | H | H | $COC_4H_9$(n) |
| 87 | Cl | $C_4H_9$(n) | —NH— | H | H | $COCH_3$ |
| 88 | Cl | $C_4H_9$(n) | —NH— | H | H | H |
| 89 | $C_4H_9$(n) | $C_4H_9$(n) | $—NHCH_2CH_2—$ | H | H | $COCH_3$ |
| 90 | $C_4H_9$(n) | $C_4H_9$(n) | $—NHCH_2CH_2—$ | H | H | H |
| 91 | $C_4H_9$(n) | $C_4H_9$(n) | $—NHCH_2CH_2—$ | H | $CH_3$ | H |
| 92 | $C_4H_9$(n) | $C_4H_9$(n) | $—NHCH_2CH_2—$ | H | $CH_3$ | $COCH_3$ |
| 93 | $C_4H_9$(n) | $C_4H_9$(n) | $—NHCH_2CH_2—$ | H | $C_2H_5$ | $COCH_3$ |
| 94 | $C_4H_9$(n) | $C_4H_9$(n) | $—NHCH_2CH_2—$ | H | $C_2H_5$ | H |
| 95 | $C_4H_9$(n) | $C_4H_9$(n) | $—NHCH_2CH_2—$ | H | H | $COCH_2Cl$ |
| 96 | $C_4H_9$(n) | $C_4H_9$(n) | $—NHCH_2CH_2—$ | H | H | $COC_4H_9$(n) |
| 97 | Cl | $C_4H_9$(n) | $—NHCH_2CH_2—$ | H | H | $COCH_3$ |
| 98 | Cl | $C_4H_9$(n) | $—NHCH_2CH_2—$ | H | H | H |
| 99 | $C_4H_9$(n) | $C_4H_9$(n) | 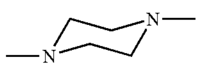 | * | H | $COCH_3$ |
| 100 | $C_4H_9$(n) | $C_4H_9$(n) | 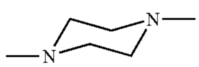 | * | H | H |
| 101 | $C_4H_9$(n) | $C_4H_9$(n) | 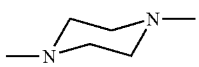 | * | $CH_3$ | H |
| 102 | $C_4H_9$(n) | $C_4H_9$(n) | 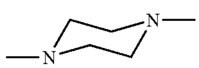 | * | $CH_3$ | $COCH_3$ |
| 103 | $C_4H_9$(n) | $C_4H_9$(n) | 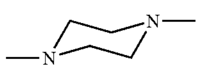 | * | $C_2H_5$ | $COCH_3$ |

TABLE IV-continued

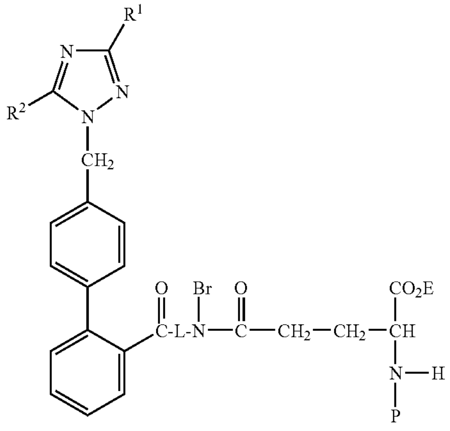

| Ex. # | $R^1$ | $R^2$ | L | B | E | P |
|---|---|---|---|---|---|---|
| 104 | $C_4H_9(n)$ | $C_4H_9(n)$ | 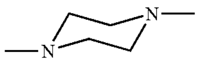 | * | $C_2H_5$ | H |
| 105 | $C_4H_9(n)$ | $C_4H_9(n)$ | 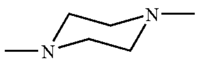 | * | H | $COC_4H_9(n))$ |
| 106 | $C_4H_9(n)$ | $C_4H_9(n)$ | 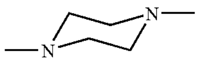 | H | H | $COC_4H_9(n))$ |
| 107 | Cl | $C_4H_9(n)$ | 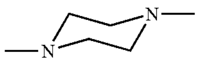 | * | H | $COCH_3$ |
| 108 | Cl | $C_4H_9(n)$ | 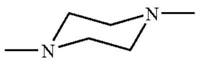 | * | H | H |
| 109 | $C_2H_5$ | $C_4H_9(n)$ | —NH— | H | H | $COCH_3$ |
| 110 | $C_2H_5$ | $C_4H_9(n)$ | —NH— | H | H | H |
| 111 | $C_3H_7(n)$ | $C_4H_9(n)$ | —NH— | H | H | $COCH_3$ |
| 112 | $C_3H_7(n)$ | $C_4H_9(n)$ | —NH— | H | H | H |
| 113 | $C_5H_{11}(n)$ | $C_4H_9(n)$ | —NH— | H | H | $COCH_3$ |
| 114 | $C_5H_{11}(n)$ | $C_4H_9(n)$ | —NH— | H | H | H |
| 115 | $C_6H_{13}(n)$ | $C_4H_9(n)$ | —NH— | H | H | $COCH_3$ |
| 116 | $C_6H_{13}(n)$ | $C_4H_9(n)$ | —NH— | H | H | H |
| 117 | $CF_2CH_2CH_2CH_3$ | $C_4H_9(n)$ | —NH— | H | H | $COCH_3$ |
| 118 | $CF_2CH_2CH_2CH_3$ | $C_4H_9(n)$ | —NH— | H | H | H |
| 119 | $CH_2CH_2CH(CH_2)_2$ | $C_4H_9(n)$ | —NH— | H | H | $COCH_3$ |
| 120 | $CH_2CH_2CH(CH_3)_2$ | $C_4H_9(n)$ | —NH— | H | H | H |
| 121 | $C_2H_5$ | $C_2H_5$ | —NH— | H | H | $COCH_3$ |
| 122 | $C_2H_5$ | $C_2H_5$ | —NH— | H | H | H |
| 123 | $C_3H_7(n)$ | $C_3H_7(n)$ | —NH— | H | H | $COCH_3$ |
| 124 | $C_3H_7(n)$ | $C_3H_7(n)$ | —NH— | H | H | $COCH_3$ |
| 125 | $C_5H_{11}(n)$ | $C_5H_{11}(n)$ | —NH— | H | H | $COCH_3$ |
| 126 | $C_5H_{11}(n)$ | $C_5H_{11}(n)$ | —NH | H | H | H |
| 127 | $C_6H_{13}(n)$ | $C_6H_{13}(n)$ | —NH— | H | H | $COCH_3$ |
| 128 | $C_6H_{13}(n)$ | $C_6H_{13}(n)$ | —NH— | H | H | H |
| 129 | $C_2H_5$ | $C_2H_5$ | $—NHCH_2CH_2—$ | H | H | $COCH_3$ |
| 130 | $C_2H_5$ | $C_2H_5$ | $—NHCH_2CH_2—$ | H | H | H |
| 131 | $C_3H_7(n)$ | $C_3H_7(n)$ | $—NHCH_2CH_2—$ | H | H | $COCH_3$ |
| 132 | $C_3H_7(n)$ | $C_3H_7(n)$ | $—NHCH_2CH_2—H$ | H | H | |
| 133 | $C_5H_{11}(n)$ | $C_5H_{11}(n)$ | $—NHCH_2CH_2—$ | H | H | $COCH_3$ |
| 134 | $C_5H_{11}(n)$ | $C_5H_{11}(n)$ | $—NHCH_2CH_2—$ | H | H | H |
| 135 | $C_6H_{13}(n)$ | $C_6H_{13}(n)$ | $—NHCH_2CH_2—$ | H | H | $COCH_3$ |
| 136 | $C_6H_{13}(n)$ | $C_6H_{13}(n)$ | $—NHCH_2CH_2—$ | H | H | H |

TABLE IV-continued

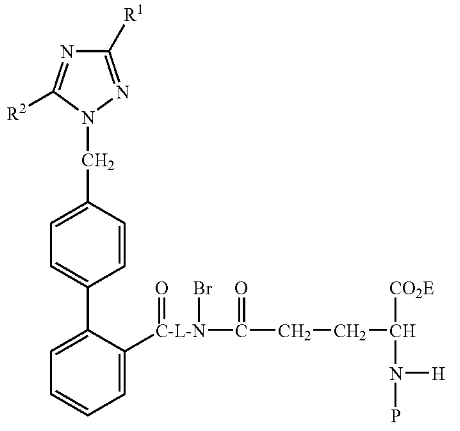

| Ex. # | $R^1$ | $R^2$ | L | B | E | P |
|---|---|---|---|---|---|---|
| 137 | $C_2H_5$ | $C_2H_5$ | 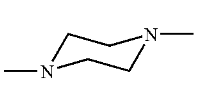 | * | H | $COCH_3$ |
| 138 | $C_2H_5$ | $C_2H_5$ | 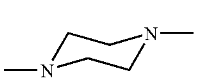 | * | H | H |
| 139 | $C_3H_7$(n) | $C_3H_7$(n) | 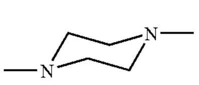 | * | H | $COCH_3$ |
| 140 | $C_3H_7$(n) | $C_3H_7$(n) | 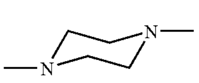 | * | H | $COCH_3$ |
| 141 | $C_5H_{11}$(n) $C_5H_{11}$(n) | $C_5H_{11}$(n) | 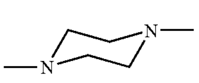 | * | H | $COCH_3$81 |
| 142 | $C_5H_{11}$(n) | $C_5H_{11}$(n) | 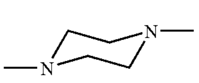 | * | H | H |
| 143 | $C_6H_{13}$(n) | $C_6H_{13}$(n) | 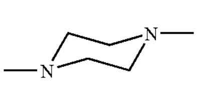 | * | H | $COCH_3$ |
| 144 | $C_6H_{13}$(n) | $C_6H_{13}$(n) | 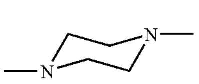 | * | H | H |

* B IS INCORPORATED IN A

Another preferred class of specific conjugates of the invention is provided by conjugates formed from a biphenylmethyl 1H-substituted-1,2,4-triazole AII antagonist compound linked to a cleavable glutamyl residue. Each conjugate of this class contains a terminal amino moiety on the triazole portion of the AII antagonist compound which is connected to a terminal carboxylic acid moiety on the gamma carbon of the cleavable glutamyl residue. Example #145 is a detailed description of a conjugate of this class. Other specific conjugates of Examples #146–#426, as shown in Table V, may be prepared generally in accordance with the procedures of Example #145.

Example 145

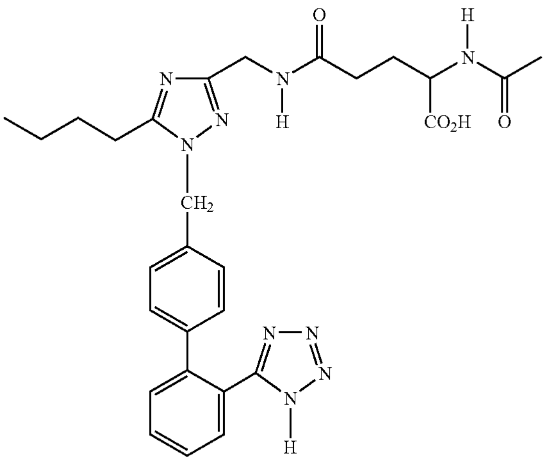

$N^2$-acetyl-N-[[5-butyl-1-[[2'-(1H-tetrazol-5-yl)[1,1'-biphenyl]-4-yl]methyl]-1H-1,2,4-triazol-3-yl]methyl]-L-glutamine To a solution of 10.45 g (34.5 mmol) of N-Boc-L-glutamic acid-α-tertbutyl ester (BACHEM) in 100 mL of methylene chloride under nitrogen is added 3.5 g (17.0 mmol) of solid dicyclohexylcarbodiimide (DCC). The reaction is allowed to stir for 2 h and filtered under nitrogen. The anhydride solution is then added to a solution of 5.78 g (14.9 mmol) of the compound of Example 3 in 75 mL of methylene chloride under nitrogen. The reaction is stirred overnight and concentrated in vacuo. Purification by silica gel chromatography (Waters Prep-500A) gives pure material by thin-layer chromatography (TLC). This material is redissolved in 100 mL of methylene chloride under nitrogen and is cooled to 0° C. prior to the addition of 135 mL of TFA. The stirred reaction is allowed to warm to ambient temperature overnight and is concentrated in vacuo. The crude product is dissolved in 80 mL of acetonitrile/water (1:1) and the pH is adjusted to 9 with 1 M $K_2CO_3$. The solution is cooled to 0° C. and 1.1 mL (11 mmol) of acetic anhydride and 11 mL (11 mmol) of 1 M $K_2CO_3$ is added every 30 min for 5 h; during the course of this reaction the pH is maintained at 9 and the reaction temperature is kept below 5° C. After the last addition, the reaction is allowed to warm to ambient temperature overnight. The pH is adjusted to 4 with 3 M HCl and the reaction is concentrated to 300 mL. Purification by reverse phase chromatography (Waters Delta prep-3000) gives $N^2$-acetyl-N-[[5-butyl-1-[[2'-(1H-tetrazol-5-yl)[1,1'-biphenyl]-4-yl]methyl]-1H-1,2,4-triazol-3-yl]methyl]-L-glutamine.

TABLE V

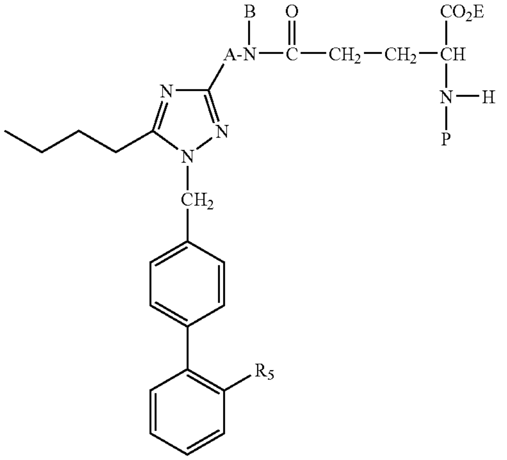

| Ex: # | $R_5$ | A | B | E | P |
|---|---|---|---|---|---|
| 146 | $CO_2H$ | single bond | H | H | $COCH_3$ |
| 147 | $CO_2H$ | single bond | H | H | $COCH_2Cl$ |
| 148 | $CO_2H$ | single bond | H | H | $COC_4H_9$ |
| 149 | $CO_2H$ | single bond | H | $CH_3$ | $COCH_3$ |
| 150 | $CO_2H$ | single bond | H | $C_2H_5$ | $COCH_3$ |
| 151 | $CN_4H$ | single bond | H | H | $COCH_3$ |
| 152 | $CN_4H$ | single bond | H | H | $COCH_2Cl$ |
| 153 | $CN_4H$ | single bond | H | H | $COC_4H_9$ |
| 154 | $CN_4H$ | single bond | H | CH3 | $COCH_3$ |
| 155 | $CN_4H$ | single bond | H | $C_2H_5$ | $COCH_3$ |
| 156 | $CO_2H$ | single bond | H | H | H |
| 157 | $CO_2H$ | single bond | H | $CH_3$ | H |
| 158 | $CO_2H$ | single bond | H | $C_2H_5$ | H |
| 159 | $CN_4H$ | single bond | H | H | H |
| 160 | $CN_4H$ | single bond | H | $CH_3$ | H |
| 161 | $CN_4H$ | single bond | H | $C_2H_5$ | H |
| 162 | $CO_2H$ | $-CH_2-$ | H | H | $COCH_3$ |
| 163 | $CO_2H$ | single bond | H | H | $COCH_2Cl$ |

TABLE V-continued

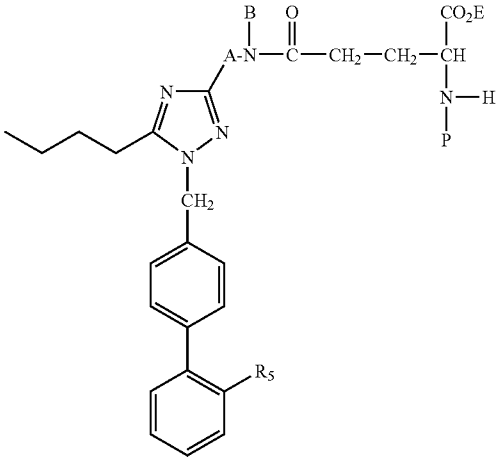

| Ex: # | $R_5$ | A | B | E | P |
|---|---|---|---|---|---|
| 164 | $CO_2H$ | single bond | H | H | $COC_4H_9$ |
| 165 | $CO_2H$ | single bond | H | $CH_3$ | $COCH_3$ |
| 166 | $CO_2H$ | single bond | H | $C_2H_5$ | $COCH_3$ |
| 167 | $CN_4H$ | single bond | H | H | $COCH_2Cl$ |
| 168 | $CN_4H$ | single bond | H | H | $COC_4H_9$ |
| 169 | $CN_4H$ | single bond | H | $CH_3$ | $COCH_3$ |
| 170 | $CN_4H$ | single bond | H | $C_2H_5$ | $COCH_3$ |
| 171 | $CO_2H$ | $—CH_2—$ | H | H | H |
| 172 | $CO_2H$ | single bond | H | $CH_3$ | H |
| 173 | $CO_2H$ | single bond | H | $C_2H_5$ | H |
| 174 | $CN_4H$ | $—CH_2—$ | H | H | H |
| 175 | $CN_4H$ | single bond | H | $CH_3$ | H |
| 176 | $CN_4H$ | single bond | H | $C_2H_5$ | H |
| 177 | $CN_4H$ | $—CH_2—$ | $CH_3$ | H | H |
| 178 | $CN_4H$ | $—CH_2—$ | $CH_3$ | H | $COCH_3$ |
| 179 | $CO_2H$ | $—CH_2CH_2—$ | H | H | $COCH_3$ |
| 180 | $CO_2H$ | single bond | H | H | $COCH_2Cl$ |
| 181 | $CO_2H$ | single bond | H | H | $COC_4H_9$ |
| 182 | $CO_2H$ | single bond | H | $CH_3$ | $COCH_3$ |
| 183 | $CO_2H$ | single bond | H | $C_2H_5$ | $COCH_3$ |
| 184 | $CN_4H$ | $—CH_2CH_2—$ | H | H | $COCH_3$ |
| 185 | $CN_4H$ | single bond | H | H | $COCH_2Cl$ |
| 186 | $CN_4H$ | single bond | H | H | $COC_4H_9$ |
| 187 | $CN_4H$ | single bond | H | $CH_3$ | $COCH_3$ |
| 188 | $CN_4H$ | single bond | H | $C_2H_5$ | $COCH_3$ |
| 189 | $CO_2H$ | $—CH_2CH_2—$ | H | H | H |
| 190 | $CO_2H$ | single bond | H | $CH_3$ | H |
| 191 | $CO_2H$ | single bond | H | $C_2H_5$ | |
| 192 | $CN_4H$ | $—CH_2CH_2—$ | H | H | H |
| 193 | $CN_4H$ | single bond | H | $CH_3$ | H |
| 194 | $CN_4H$ | single bond | H | $C_2H_5$ | H |
| 195 | $CO_2H$ | $C_3H_6(n)$ | H | H | $COCH_3$ |
| 196 | $CO_2H$ | single bond | H | H | $COCH_2Cl$ |
| 197 | $CO_2H$ | single bond | H | H | $COC_4H_9$ |
| 198 | $CO_2H$ | single bond | H | $CH_3$ | $COCH_3$ |
| 199 | $CO_2H$ | single bond | H | $C_2H_5$ | $COCH_3$ |
| 200 | $CN_4H$ | $C_3H_6(n)$ | H | H | $COCH_3$ |
| 201 | $CN_4H$ | single bond | H | H | $COCH_2Cl$ |
| 202 | $CN_4H$ | single bond | H | H | $COC_4H_9$ |
| 203 | $CN_4H$ | single bond | H | $CH_3$ | $COCH_3$ |
| 204 | $CN_4H$ | single bond | H | $C_2H_5$ | $COCH_3$ |
| 205 | $CO_2H$ | $C_3H_6(n)$ | H | H | H |
| 206 | $CO_2H$ | single bond | H | $CH_3$ | H |
| 207 | $CO_2H$ | single bond | H | $C_2H_5$ | H |
| 208 | $CN_4H$ | $C_3H_6(n)$ | H | H | H |
| 209 | $CN_4H$ | single bond | H | $CH_3$ | H |
| 210 | $CN_4H$ | single bond | H | $C_2H_5$ | H |
| 211 | $CO_2H$ | $C_4H_8(n)$ | H | H | $COCH_3$ |
| 212 | $CO_2H$ | single bond | H | H | $COCH_2Cl$ |
| 213 | $CO_2H$ | single bond | H | H | $COC_4H_9$ |
| 214 | $CO_2H$ | single bond | H | $CH_3$ | $COCH_3$ |
| 215 | $CO_2H$ | single bond | H | $C_2H_5$ | $COCH_3$ |
| 216 | $CN_4H$ | $C_4H_{8(n)}$ | H | H | $COCH_3$ |
| 217 | $CN_4H$ | single bond | H | H | $COCH_2Cl$ |

TABLE V-continued

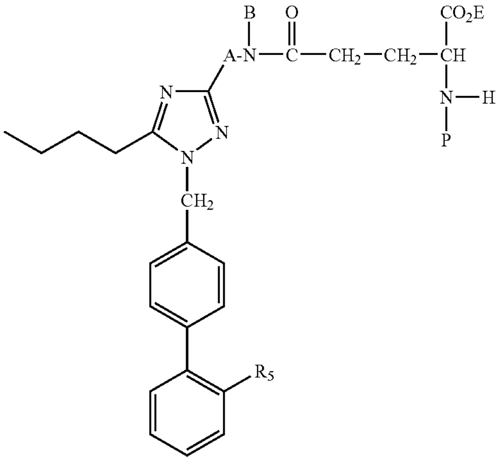

| Ex: # | $R_5$ | A | B | E | P |
|---|---|---|---|---|---|
| 218 | $CN_4H$ | single bond | H | H | $COC_4H_9$ |
| 219 | $CN_4H$ | single bond | H | $CH_3$ | $COCH_3$ |
| 220 | $CN_4H$ | single bond | H | $C_2H_5$ | $COCH_3$ |
| 221 | $CO_2H$ | $C_4H_8$(n) | H | H | H |
| 222 | $CO_2H$ | single bond | H | $CH_3$ | H |
| 223 | $CO_2H$ | single bond | H | $C_2H_5$ | H |
| 224 | $CN_4H$ | $C_4H_8$(n) | H | H | H |
| 225 | $CN_4H$ | single bond | H | $CH_3$ | H |
| 226 | $CN_4H$ | single bond | H | $C_2H_5$ | H |
| 227 | $CO_2H$ | 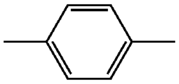 | H | H | $COCH_3$ |
| 228 | $CO_2H$ | single bond | H | H | $COCH_2Cl$ |
| 229 | $CO_2H$ | single bond | H | H | $COC_4H_9$ |
| 230 | $CO_2H$ | single bond | H | $CH_3$ | $COCH_3$ |
| 231 | $CO_2H$ | single bond | H | $C_2H_5$ | $COCH_3$ |
| 232 | $CN_4H$ | 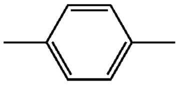 | H | H | $COCH_3$ |
| 233 | $CN_4H$ | single bond | H | H | $COCH_2Cl$ |
| 234 | $CN_4H$ | single bond | H | H | $COC_4H_9$ |
| 235 | $CN_4H$ | single bond | H | $CH_3$ | $COCH_3$ |
| 236 | $CN_4H$ | single bond | H | $C_2H_5$ | $COCH_3$ |
| 237 | $CO_2H$ | 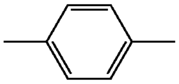 | H | H | H |
| 238 | $CO_2H$ | single bond | H | $CH_3$ | H |
| 239 | $CO_2H$ | single bond | H | $C_2H_5$ | H |
| 240 | $CN_4H$ | 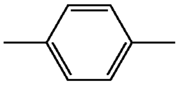 | H | H | H |
| 241 | $CN_4H$ | single bond | H | $CH_3$ | H |
| 242 | $CN_4H$ | single bond | H | $C_2H_5$ | H |
| 243 | $CO_2H$ | 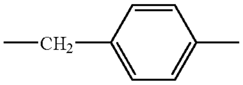 | H | H | $COCH_3$ |
| 244 | $CO_2H$ | single bond | H | H | $COCH_2Cl$ |
| 245 | $CO_2H$ | single bond | H | H | $COC_4H_9$ |
| 246 | $CO_2H$ | single bond | H | $CH_3$ | $COCH_3$ |
| 247 | $CO_2H$ | single bond | H | $C_2H_5$ | $COCH_3$ |

TABLE V-continued

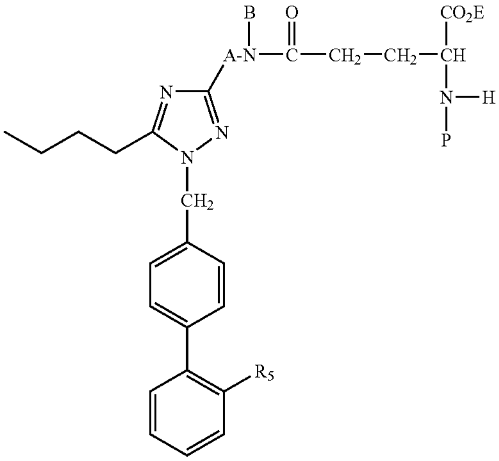

| Ex: # | $R_5$ | A | B | E | P |
|---|---|---|---|---|---|
| 248 | $CN_4H$ | 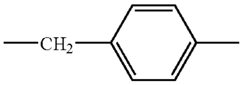 | H | H | $COCH_3$ |
| 249 | $CN_4H$ | single bond | H | H | $COCH_2Cl$ |
| 250 | $CN_4H$ | single bond | H | H | $COC_4H_9$ |
| 251 | $CN_4H$ | single bond | H | $CH_3$ | $COCH_3$ |
| 252 | $CN_4H$ | single bond | H | $C_2H_5$ | $COCH_3$ |
| 253 | $CO_2H$ | 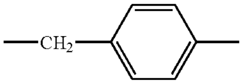 | H | H | H |
| 254 | $CO_2H$ | single bond | H | $CH_3$ | H |
| 255 | $CO_2H$ | single bond | H | $C_2H_5$ | H |
| 256 | $CN_4H$ | 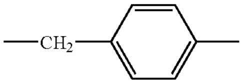 | H | H | H |
| 257 | $CN_4H$ | single bond | H | $CH_3$ | H |
| 258 | $CN_4H$ | single bond | H | $C_2H_5$ | H |
| 259 | $CO_2H$ | 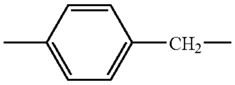 | H | H | $COCH_3$ |
| 260 | $CO_2H$ | single bond | H | H | $COCH_2Cl$ |
| 261 | $CO_2H$ | single bond | H | H | $COC_4H_9$ |
| 262 | $CO_2H$ | single bond | H | $CH_3$ | $COCH_3$ |
| 263 | $CO_2H$ | single bond | H | $C_2H_5$ | $COCH_3$ |
| 264 | $CN_4H$ | 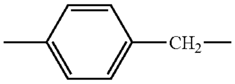 | H | H | $COCH_3$ |
| 265 | $CN_4H$ | single bond | H | H | $COCH_2Cl$ |
| 266 | $CN_4H$ | single bond | H | H | $COC_4H_9$ |
| 267 | $CN_4H$ | single bond | H | $CH_3$ | $COCH_3$ |
| 268 | $CN_4H$ | single bond | H | $C_2H_5$ | $COCH_3$ |
| 269 | $CO_2H$ | 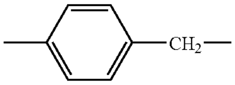 | H | H | H |
| 270 | $CO_2H$ | single bond | H | $CH_3$ | H |
| 271 | $CO_2H$ | single bond | H | $C_2H_5$ | H |

TABLE V-continued

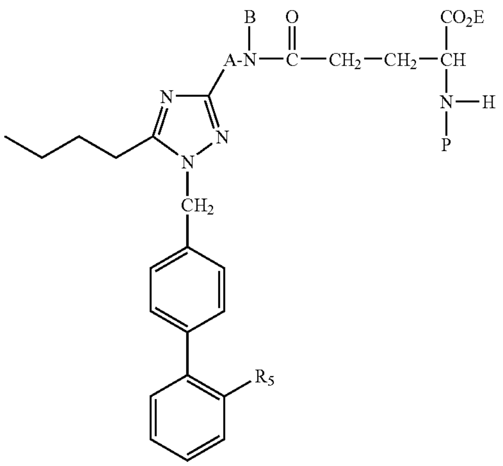

| Ex: # | $R_5$ | A | B | E | P |
|---|---|---|---|---|---|
| 272 | $CN_4H$ | 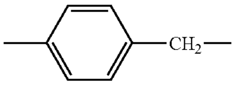 | H | H | H |
| 273 | $CN_4H$ | single bond | H | $CH_3$ | H |
| 274 | $CN_4H$ | single bond | H | $C_2H_5$ | H |
| 275 | $CO_2H$ | 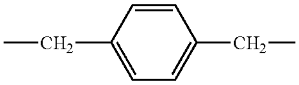 | H | H | $COCH_3$ |
| 276 | $CO_2H$ | single bond | H | H | $COCH_2Cl$ |
| 277 | $CO_2H$ | single bond | H | H | $COC_4H_9$ |
| 278 | $CO_2H$ | single bond | H | $CH_3$ | $COCH_3$ |
| 279 | $CO_2H$ | single bond | H | $C_2H_5$ | $COCH_3$ |
| 280 | $CN_4H$ | 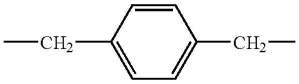 | H | H | $COCH_3$ |
| 281 | $CN_4H$ | single bond | H | H | $COCH_2Cl$ |
| 282 | $CN_4H$ | single bond | H | H | $COC_4H_9$ |
| 283 | $CN_2H$ | single bond | H | $CH_3$ | $COCH_3$ |
| 284 | $CN_4H$ | single bond | H | $C_2H_5$ | $COCH_3$ |
| 285 | $CO_2H$ | 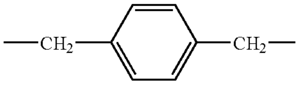 | H | H | H |
| 286 | $CO_2H$ | single bond | H | $CH_3$ | H |
| 287 | $CO_2H$ | single bond | H | $C_2H_5$ | H |
| 288 | $CN_4H$ | 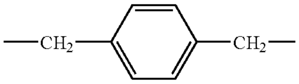 | H | H | H |
| 289 | $CN_4H$ | single bond | H | $CH_3$ | H |
| 290 | $CN_4H$ | single bond | H | $C_2H_5$ | H |
| 291 | $CN_4H$ | 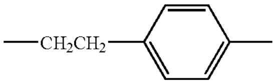 | H | H | $COCH_3$ |
| 292 | $CO_2H$ | single bond | H | H | $COCH_2Cl$ |
| 293 | $CO_2H$ | single bond | H | H | $COC_4H_9$ |
| 294 | $CO_2H$ | single bond | H | $CH_3$ | $COCH_3$ |
| 295 | $CO_2H$ | single bond | H | $C_2H_5$ | $COCH_3$ |

TABLE V-continued

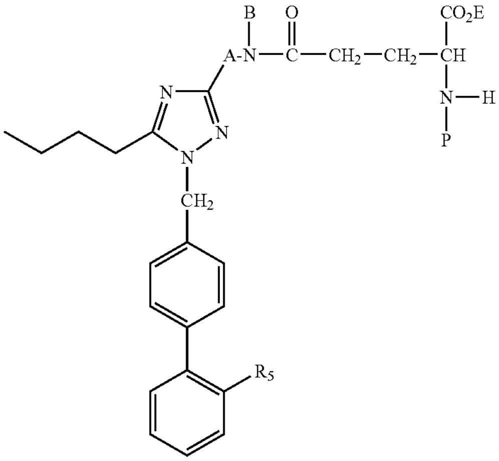

| Ex: # | $R_5$ | A | B | E | P |
|---|---|---|---|---|---|
| 296 | $CN_4H$ | 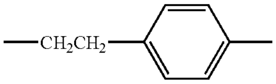 | H | H | H |
| 297 | $CN_4H$ | single bond | H | H | $COCH_2Cl$ |
| 298 | $CN_4H$ | single bond | H | H | $COC_4H_9$ |
| 299 | $CN_4H$ | single bond | H | $CH_3$ | $COCH_3$ |
| 300 | $CN_4H$ | single bond | H | $C_2H_5$ | $COCH_3$ |
| 301 | $CN_4H$ | 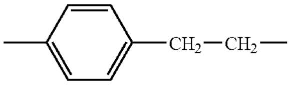 | H | H | $COCH_3$ |
| 302 | $CO_2H$ | single bond | H | $CH_3$ | H |
| 303 | $CO_2H$ | single bond | H | $C_2H_5$ | H |
| 304 | $CN_4H$ | 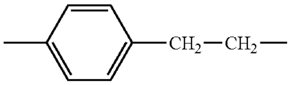 | H | H | H |
| 305 | $CN_4H$ | single bond | H | $CH_3$ | H |
| 306 | $CN_4H$ | single bond | H | $C_2H_5$ | H |
| 307 | $CO_2H$ | 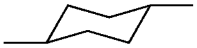 | H | H | $COCH_3$ |
| 308 | $CO_2H$ | single bond | H | H | $COCH_2Cl$ |
| 309 | $CO_2H$ | single bond | H | H | $COC_4H_9$ |
| 310 | $CO_2H$ | single bond | H | $CH_3$ | $COCH_3$ |
| 311 | $CO_2H$ | single bond | H | $C_2H_5$ | $COCH_3$ |
| 312 | $CN_4H$ | 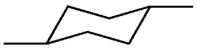 | H | H | $COCH_3$ |
| 313 | $CN_4H$ | single bond | H | H | $COCH_2Cl$ |
| 314 | $CN_4H$ | single bond | H | H | $COC_4H_9$ |
| 315 | $CN_4H$ | single bond | H | $CH_3$ | $COCH_3$ |
| 316 | $CN_4H$ | single bond | H | $C_2H_5$ | $COCH_3$ |
| 317 | $CO_2H$ | 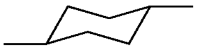 | H | H | H |
| 318 | $CO_2H$ | single bond | H | $CH_3$ | H |
| 319 | $CO_2H$ | single bond | H | $C_2H_5$ | H |
| 320 | $CN_4H$ | 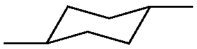 | H | H | H |
| 321 | $CN_4H$ | single bond | H | $CH_3$ | H |
| 322 | $CN_4H$ | single bond | H | $C_2H_5$ | H |

TABLE V-continued

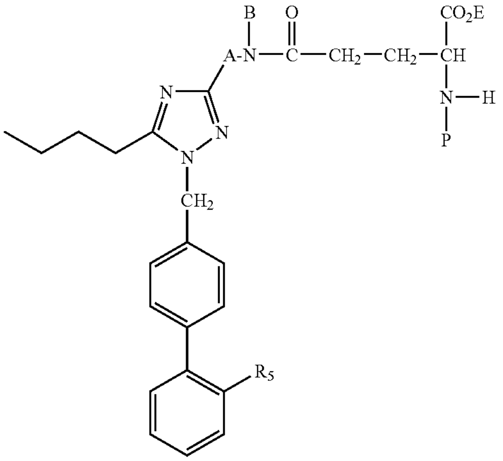

| Ex: # | $R_5$ | A | B | E | P |
|---|---|---|---|---|---|
| 323 | $CO_2H$ | 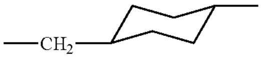 | H | H | $COCH_3$ |
| 324 | $CO_2H$ | single bond | H | H | $COCH_2Cl$ |
| 325 | $CO_2H$ | single bond | H | H | $COC_4H_9$ |
| 326 | $CO_2H$ | single bond | H | $CH_3$ | $COCH_3$ |
| 327 | $CO_2H$ | single bond | H | $C_2H_5$ | $COCH_3$ |
| 328 | $CN_4H$ | 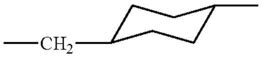 | H | H | $COCH_3$ |
| 329 | $CN_4H$ | single bond | H | H | $COCH_2Cl$ |
| 330 | $CN_4H$ | single bond | H | H | $COC_4H_9$ |
| 331 | $CN_4H$ | single bond | H | $CH_3$ | $COCH_3$ |
| 332 | $CN_4H$ | single bond | H | $C_2H_5$ | $COCH_3$ |
| 333 | $CO_2H$ | 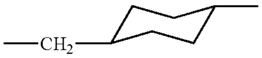 | H | H | H |
| 334 | $CO_2H$ | single bond | H | $CH_3$ | H |
| 335 | $CO_2H$ | single bond | H | $C_2H_5$ | H |
| 336 | $CN_4H$ | 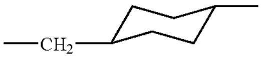 | H | H | H |
| 337 | $CN_4H$ | single bond | H | $CH_3$ | H |
| 338 | $CN_4H$ | single bond | H | $C_2H_5$ | H |
| 339 | $CO_2H$ | 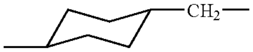 | H | H | $COCH_3$ |
| 340 | $CO_2H$ | single bond | H | H | $COCH_2Cl$ |
| 341 | $CO_2H$ | single bond | H | H | $COC_4H_9$ |
| 342 | $CO_2H$ | single bond | H | $CH_3$ | $COCH_3$ |
| 343 | $CO_2H$ | single bond | H | $C_2H_5$ | $COCH_3$ |
| 344 | $CN_4H$ | 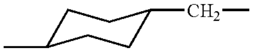 | H | H | $COCH_3$ |
| 345 | $CN_4H$ | single bond | H | H | $COCH_2Cl$ |
| 346 | $CN_4H$ | single bond | H | H | $COC_4H_9$ |
| 347 | $CN_4H$ | single bond | H | $CH_3$ | $COCH_3$ |
| 348 | $CN_4H$ | single bond | H | $C_2H_5$ | $COCH_3$ |
| 349 | $CO_2H$ | 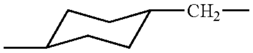 | H | H | H |
| 350 | $CO_2H$ | single bond | H | $CH_3$ | H |
| 351 | $CO_2H$ | single bond | H | $C_2H_5$ | H |

TABLE V-continued

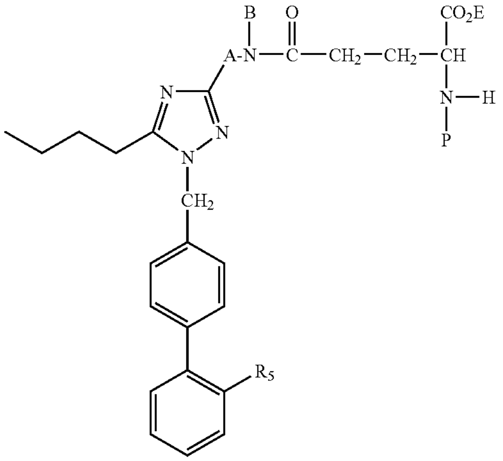

| Ex: # | $R_5$ | A | B | E | P |
|---|---|---|---|---|---|
| 352 | $CN_4H$ | 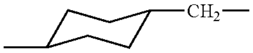 | H | H | H |
| 353 | $CN_4H$ | single bond | H | $CH_3$ | H |
| 354 | $CN_4H$ | single bond | H | $C_2H_5$ | H |
| 355 | $CO_2H$ | get,0016 | H | H | $COCH_3$ |
| 356 | $CO_2H$ | single bond | H | H | $COCH_2Cl$ |
| 357 | $CO_2H$ | single bond | H | H | $COC_4H_9$ |
| 358 | $CO_2H$ | single bond | H | $CH_3$ | $COCH_3$ |
| 359 | $CO_2H$ | single bond | H | $C_2H_5$ | $COCH_3$ |
| 360 | $CN_4H$ | 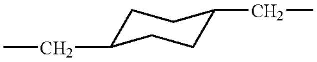 | H | H | $COCH_3$ |
| 361 | $CN_4H$ | single bond | H | H | $COCH_2Cl$ |
| 362 | $CN_4H$ | single bond | H | H | $COC_4H_9$ |
| 363 | $CN_4H$ | single bond | H | $CH_3$ | $COCH_3$ |
| 364 | $CN_4H$ | single bond | H | $C_2H_5$ | $COCH_3$ |
| 365 | $CO_2H$ | 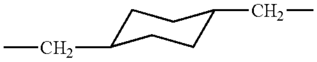 | H | H | H |
| 366 | $CO_2H$ | single bond | H | $CH_3$ | H |
| 367 | $CO_2H$ | single bond | H | $C_2H_5$ | H |
| 368 | $CN_4H$ | 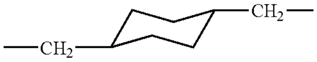 | H | H | H |
| 369 | $CN_4H$ | single bond | H | $CH_3$ | H |
| 370 | $CN_4H$ | single bond | H | $C_2H_5$ | H |
| 371 | $CN_4H$ | 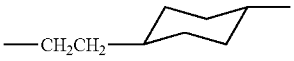 | H | H | $COCH_3$ |
| 372 | $CO_2H$ | single bond | H | H | $COCH_2Cl$ |
| 373 | $CO_2H$ | single bond | H | H | $COC_4H_9$ |
| 374 | $CO_2H$ | single bond | H | $CH_3$ | $COCH_3$ |
| 375 | $CO_2H$ | single bond | H | $C_2H_5$ | $COCH_3$ |
| 376 | $CN_4H$ | 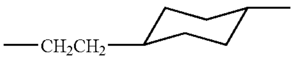 | H | H | H |
| 377 | $CN_4H$ | single bond | H | H | $COCH_2Cl$ |
| 378 | $CN_4H$ | single bond | H | H | $COC_4H_9$ |
| 379 | $CN_4H$ | single bond | H | $CH_3$ | $COCH_3$ |
| 380 | $CN_4H$ | single bond | H | $C_2H_5$ | $COCH_3$ |

TABLE V-continued

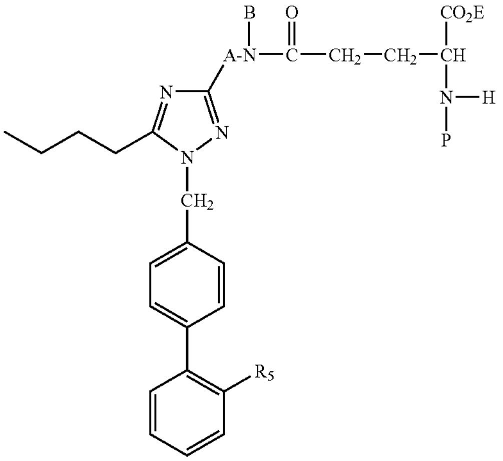

| Ex: # | $R_5$ | A | B | E | P |
|---|---|---|---|---|---|
| 381 | $CN_4H$ | 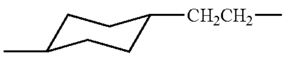 | H | H | $COCH_3$ |
| 382 | $CO_2H$ | single bond | H | $CH_3$ | H |
| 383 | $CO_2H$ | single bond | H | $C_2H_5$ | H |
| 384 | $CN_4H$ | 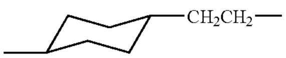 | H | H | H |
| 385 | $CN_4H$ | single bond | H | $CH_3$ | H |
| 386 | $CN_4H$ | single bond | H | $C_2H_5$ | H |
| 387 | $CN_4H$ | 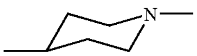 | * | H | $COCH_3$ |
| 388 | $CO_2H$ | single bond | H | H | $COCH_2Cl$ |
| 389 | $CO_2H$ | single bond | H | H | $COC_4H_9$ |
| 390 | $CO_2H$ | single bond | H | $CH_3$ | $COCH_3$ |
| 391 | $CO_2H$ | single bond | H | $C_2H_5$ | $COCH_3$ |
| 392 | $CN_4H$ | 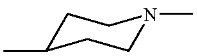 | * | H | H |
| 393 | $CN_4H$ | single bond | H | H | $COCH_2Cl$ |
| 394 | $CN_4H$ | single bond | H | H | $COC_4H_9$ |
| 395 | $CN_4H$ | single bond | H | $CH_3$ | $COCH_3$ |
| 396 | $CN_4H$ | single bond | H | $C_2H_5$ | $COCH_3$ |
| 397 | $CN_4H$ | 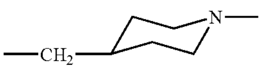 | * | H | $COCH_3$ |
| 398 | $CO_2H$ | single bond | H | $CH_3$ | H |
| 399 | $CO_2H$ | single bond | H | $C_2H_5$ | H |
| 400 | $CN_4H$ | 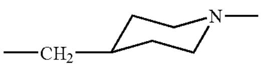 | * | H | H |
| 401 | $CN_4H$ | single bond | H | $CH_3$ | H |
| 402 | $CN_4H$ | single bond | H | $C_2H_5$ | H |
| 403 | $CN_4H$ | 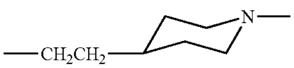 | * | H | $COCH_3$ |
| 404 | $CO_2H$ | single bond | H | H | $COCH_2Cl$ |
| 405 | $CO_2H$ | single bond | H | H | $COC_4H_9$ |
| 406 | $CO_2H$ | single bond | H | $CH_3$ | $COCH_3$ |
| 407 | $CO_2H$ | single bond | H | $C_2H_5$ | $COCH_3$ |

TABLE V-continued

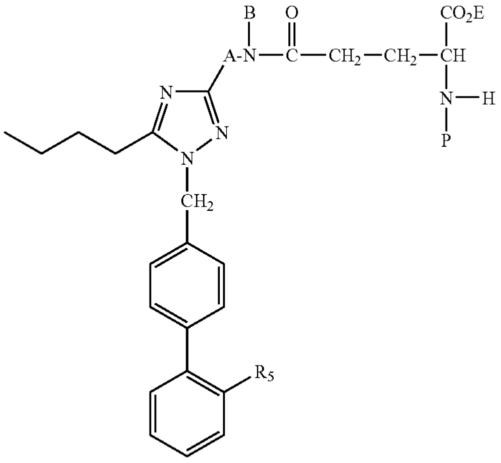

| Ex: # | $R_5$ | A | B | E | P |
|---|---|---|---|---|---|
| 408 | $CN_4H$ | 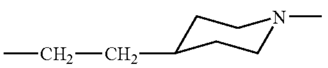 | * | H | H |
| 409 | $CN_4H$ | single bond | H | H | $COCH_2Cl$ |
| 410 | $CN_4H$ | single bond | H | H | $COC_4H_9$ |
| 411 | $CN_4H$ | single bond | H | $CH_3$ | $COCH_3$ |
| 412 | $CN_4H$ | single bond | H | $C_2H_5$ | $COCH_3$ |
| 413 | $CN_4H$ | 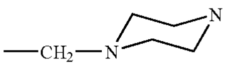 | * | H | $COCH_3$ |
| 414 | $CO_2H$ | single bond | H | $CH_3$ | H |
| 415 | $CO_2H$ | single bond | H | $C_2H_5$ | H |
| 416 | $CN_4H$ | 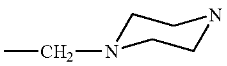 | * | H | H |
| 417 | $CN_4H$ | single bond | H | $CH_3$ | H |
| 418 | $CN_4H$ | single bond | H | $C_2H_5$ | H |
| 419 | $CN_4H$ | 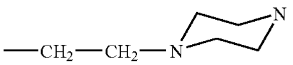 | * | H | $COCH_3$ |
| 420 | $CN_4H$ | single bond | H | H | $COCH_2Cl$ |
| 421 | $CN_4H$ | single bond | H | H | $COC_4H_9$ |
| 422 | $CN_4H$ | single bond | H | $CH_3$ | $COCH_3$ |
| 423 | $CN_4H$ | single bond | H | $C_2H_5$ | $COCH_3$ |
| 424 | $CN_4H$ | 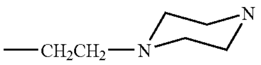 | * | H | H |
| 425 | $CN_4H$ | single bond | H | $CH_3$ | H |
| 426 | $CN_4H$ | single bond | H | $C_2H_5$ | H |

* B is incorporated in A

Another preferred class of specific conjugates of the invention is provided by conjugates formed from a biphenylmethyl 1H-substituted-1,2,4-triazole AII antagonist compound linked to a cleavable glutamyl residue. Each conjugate of this class contains a diamino linker moiety which connects a terminal carboxylic acid moiety on the triazole portion of the AII antagonist compound with a terminal carboxylic acid moiety on the gamma carbon of the cleavable glutamyl residue. Example #427 is a detailed description of a conjugate of this class. Other specific conjugates of Examples #428–#834, as shown in Table VI, may be prepared generally in accordance with the procedures of Example #427.

EXAMPLE 427

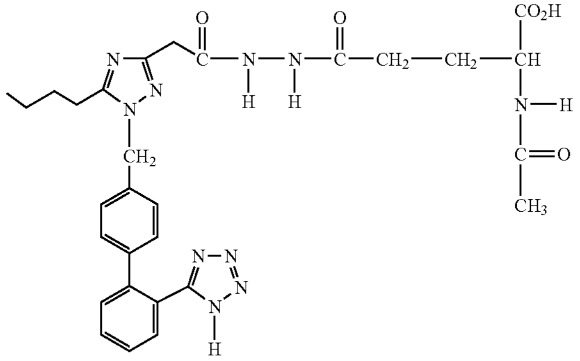

N-acetyl-L-glutamic acid, 5-[5-butyl-1-[[2'-(1H-tetrazol-5-yl)[1,1'-biphenyl]-4-yl]methyl-1H-1,2,4-triazol-3-yl]acetylhydrazide Step 1: Preparation of 5-[4'-[(5-butyl-3-hydrazinyl-carbonylmethyl-1,2,4-triazol-1-yl)methyl][1,1'-biphenyl]-2-yl]-1H-tetrazole Under nitrogen, 8.34 g (20 mmol) of the compound of Example 7 is dissolved in 200 mL of absolute methanol at −10° C. (ice/methanol) and is treated dripwise with 3.0 g (25 mmol) of thionyl chloride. After the addition is complete, the reaction is allowed to warm to ambient temperature for 2 h prior to stirring at reflux overnight. All volitiles are removed in vacuo and the residue redissolved in 100 mL of methanol. Under nitrogen, 20 g (625 mmol) of anhydrous hydrazine is added and the reaction is stirred at reflux overnight. Concentration in vacuo gives the crude product; purification by silica gel chromatography provides 5-[4'-[(5-butyl-3-hydrazinocarbonylmethyl-1H-1,2,4-triazol-1-yl) methyl][1,1'-biphenyl]-2-yl]-1H-tetrazole.

Step 2: Preparation of N-acetyl-L-glutamic acid 5-[5-butyl-1-[[2'-(1H-tetrazol-5-yl) [1,1'-biphenyl]-4-yl]methyl-1H-1,2,4-triazol-3-yl]acetylhydrazide To a solution of 10.45 g (34.5 mmol) of N-Boc-L-glutamic acid-α-tertbutyl ester (BACHEM) in 100 mL of methylene chloride under nitrogen is added 3.5 g (17.0 mmol) of solid dicyclohexylcarbodiimide (DCC). The reaction is allowed to stir for 2 h and filtered under nitrogen. The anhydride solution is then added to a solution of 6.42 g (14.9 mmol) of the compound of Example 20 in 75 mL of methylene chloride under nitrogen. The reaction is stirred overnight and is concentrated in vacuo. Purification by silica gel chromatography (Waters Prep-500A) gives pure material by thin-layer chromatography (TLC). This material is redissolved in 100 mL of methylene chloride under nitrogen and cooled to 0° C. prior to the addition of 135 mL of TFA. The stirred reaction is allowed to warm to ambient temperature overnight and is concentrated in vacuo. The crude product is dissolved in 80 mL of acetonitrile/water (1:1) and the pH is adjusted to 9 with 1 M $K_2CO_3$. The solution is cooled to 0° C. and 1.1 mL (11 mmol) of acetic anhydride and 11 mL (11 mmol) of 1 M $K_2CO_3$ is added every 30 min for 5 h; during the course of this reaction the pH is maintained at 9 and the reaction temperature is kept below 5° C. After the last addition, the reaction is allowed to warm to ambient temperature overnight. The pH was adjusted to 4 with 3 M HCl and the reaction concentrated to 300 mL. Purification by reverse phase chromatography (Waters Delta prep-3000) gives N-acetyl-L-glutamic acid, 5-[5-butyl-1-[[2'-(1H-tetrazol-5-yl) [1,1'-biphenyl]-4-yl]methyl-1H-1,2,4-traizol-3-yl] acetylhydrazide.

TABLE VI

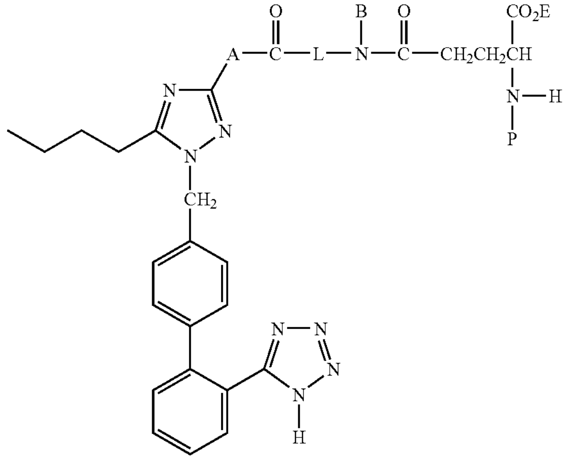

| Ex. # | A | L | B | E | P |
|---|---|---|---|---|---|
| 428 | single bond | —NH— | H | H | $COCH_3$ |
| 429 | single bond | —NH— | H | H | $COCH_2Cl$ |
| 430 | single bond | —NH— | H | H | $COC_4H_9$ |
| 431 | single bond | —NH— | H | $CH_3$ | $COCH_3$ |
| 432 | single bond | —NH— | H | $C_2H_5$ | $COCH_3$ |
| 433 | single bond | —NH— | H | H | H |
| 434 | single bond | —NH— | H | $CH_3$ | H |

TABLE VI-continued

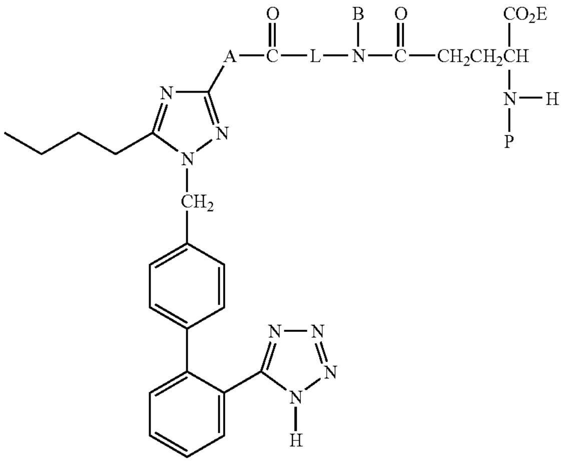

| Ex. # | A | L | B | E | P |
|---|---|---|---|---|---|
| 435 | single bond | —NH— | H | $C_2H_5$ | H |
| 436 | single bond | $—NHCH_2CH_2—$ | H | H | $COCH_3$ |
| 437 | single bond | $—NHCH_2CH_2—$ | H | H | $COCH_2Cl$ |
| 438 | single bond | $—NHCH_2CH_2—$ | H | H | $COC_4H_9$ |
| 439 | single bond | $—NHCH_2CH_2—$ | H | $CH_3$ | $COCH_3$ |
| 440 | single bond | $—NHCH_2CH_2—$ | H | $C_2H_5$ | $COCH_3$ |
| 441 | single bond | $—NHCH_2CH_2—$ | H | H | H |
| 442 | single bond | $—NHCH_2CH_2—$ | H | $CH_3$ | H |
| 443 | single bond | $—NHCH_2CH_2—$ | H | $C_2H_5$ | H |
| 444 | single bond | 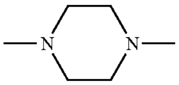 | * | H | $COCH_3$ |
| 445 | single bond | 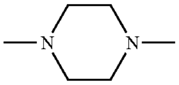 | H | H | $COCH_2Cl$ |
| 446 | single bond | 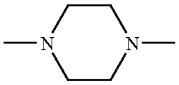 | H | H | $COC_4H_9$ |
| 447 | single bond | 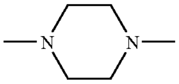 | H | $CH_3$ | $COCH_3$ |
| 448 | single bond | 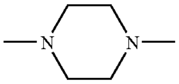 | H | $C_2H_5$ | $COCH_3$ |
| 449 | single bond | 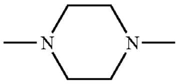 | * | H | H |
| 450 | single bond | 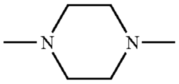 | H | $CH_3$ | H |
| 451 | single bond | 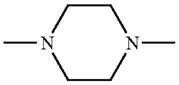 | H | $C_2H_5$ | H |
| 452 | $CH_2$ | —NH— | H | H | $COCH_2Cl$ |
| 453 | $CH_2$ | —NH— | H | H | $COC_4H_9$ |
| 454 | $CH_2$ | —NH— | H | $CH_3$ | $COCH_3$ |
| 455 | $CH_2$ | —NH— | H | $C_2H_5$ | $COCH_3$ |
| 456 | $CH_2$ | —NH— | H | H | H |

TABLE VI-continued

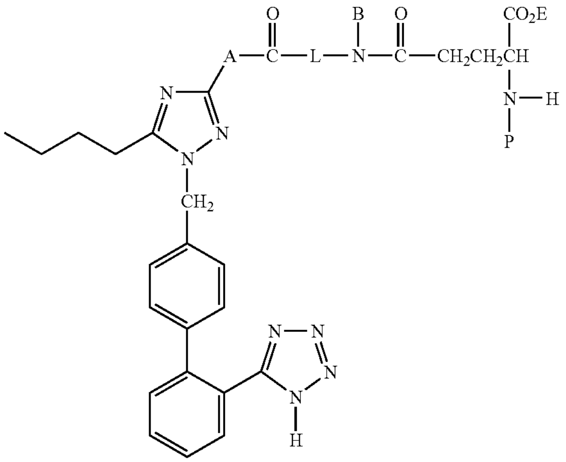

| Ex. # | A | L | B | E | P |
|---|---|---|---|---|---|
| 457 | $CH_2$ | —NH— | H | $CH_3$ | H |
| 458 | $CH_2$ | —NH— | H | $C_2H_5$ | H |
| 459 | $CH_2$ | $—NHCH_2CH_2—$ | H | H | $COCH_3$ |
| 460 | $CH_2$ | $—NHCH_2CH_2—$ | H | H | $COCH_2Cl$ |
| 461 | $CH_2$ | $—NHCH_2CH_2—$ | H | H | $COC_4H_9$ |
| 462 | $CH_2$ | $—NHCH_2CH_2—$ | H | $CH_3$ | $COCH_3$ |
| 463 | $CH_2$ | $—NHCH_2CH_2—$ | H | $C_2H_5$ | $COCH_3$ |
| 464 | $CH_2$ | $—NHCH_2CH_2—$ | H | H | |
| 465 | $CH_2$ | $—NHCH_2CH_2—$ | H | $CH_3$ | H |
| 466 | $CH_2$ | $—NHCH_2CH_2—$ | H | $C_2H_5$ | H |
| 467 | $CH_2$ | 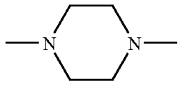 | * | H | $COCH_3$ |
| 468 | $CH_2$ | 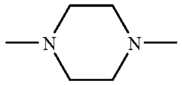 | H | H | $COCH_2Cl$ |
| 469 | $CH_2$ | 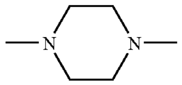 | H | H | $COC_4H_9$ |
| 470 | $CH_2$ | 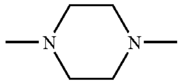 | H | $CH_3$ | $COCH_3$ |
| 471 | $CH_2$ | 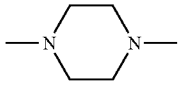 | H | $C_2H_5$ | $COCH_3$ |
| 472 | $CH_2$ | 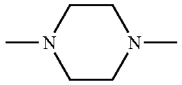 | * | H | H |
| 473 | $CH_2$ | 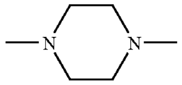 | H | $CH_3$ | H |
| 474 | $CH_2$ | 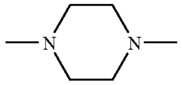 | H | $C_2H_5$ | H |
| 475 | $CH_2CH_2$ | —NH— | H | H | $COCH_3$ |
| 476 | $CH_2CH_2$ | —NH— | H | H | $COCH_2Cl$ |
| 477 | $CH_2CH_2$ | —NH— | H | H | $COC_4H_9$ |
| 478 | $CH_2CH_2$ | —NH— | H | $CH_3$ | $COCH_3$ |

TABLE VI-continued

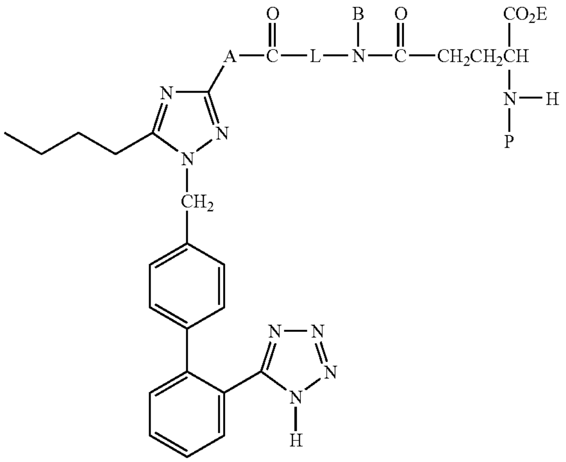

| Ex. # | A | L | B | E | P |
|---|---|---|---|---|---|
| 479 | $CH_2CH_2$ | —NH— | H | $C_2H_5$ | $COCH_3$ |
| 480 | $CH_2CH_2$ | —NH— | H | H | H |
| 481 | $CH_2CH_2$ | —NH— | H | $CH_3$ | H |
| 482 | $CH_2CH_2$ | —NH— | H | $C_2H_5$ | H |
| 483 | $CH_2CH_2$ | $—NHCH_2CH_2—$ | H | H | $COCH_3$ |
| 484 | $CH_2CH_2$ | $—NHCH_2CH_2—$ | H | H | $COCH_2Cl$ |
| 485 | $CH_2CH_2$ | $—NHCH_2CH_2—$ | H | H | $COC_4H_9$ |
| 486 | $CH_2CH_2$ | $—NHCH_2CH_2—$ | H | $CH_3$ | $COCH_3$ |
| 487 | $CH_2CH_2$ | $—NHCH_2CH_2—$ | H | $C_2H_5$ | $COCH_3$ |
| 488 | $CH_2CH_2$ | $—NHCH_2CH_2—$ | H | H | H |
| 489 | $CH_2CH_2$ | $—NHCH_2CH_2—$ | H | $CH_3$ | H |
| 490 | $CH_2CH_2$ | $—NHCH_2CH_2—$ | H | $C_2H_5$ | H |
| 491 | $CH_2CH_2$ | 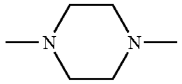 | * | H | $COCH_3$ |
| 492 | $CH_2CH_2$ | 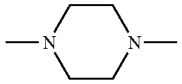 | H | H | $COCH_2Cl$ |
| 493 | $CH_2CH_2$ | 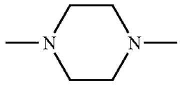 | H | H | $COC_4H_9$ |
| 494 | $CH_2CH_2$ | 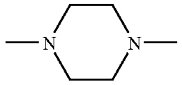 | H | $CH_3$ | $COCH_3$ |
| 495 | $CH_2CH_2$ | 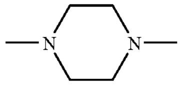 | H | $C_2H_5$ | $COCH_3$ |
| 496 | $CH_2CH_2$ | 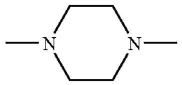 | * | H | H |
| 497 | $CH_2CH_2$ | 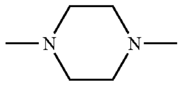 | H | $CH_3$ | H |
| 498 | $CH_2CH_2$ | 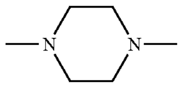 | H | $C_2H_5$ | H |
| 499 | $C_3H_6(n)$ | —NH— | H | H | $COCH_3$ |
| 500 | $C_3H_6(n)$ | —NH— | H | H | $COCH_2Cl$ |

TABLE VI-continued

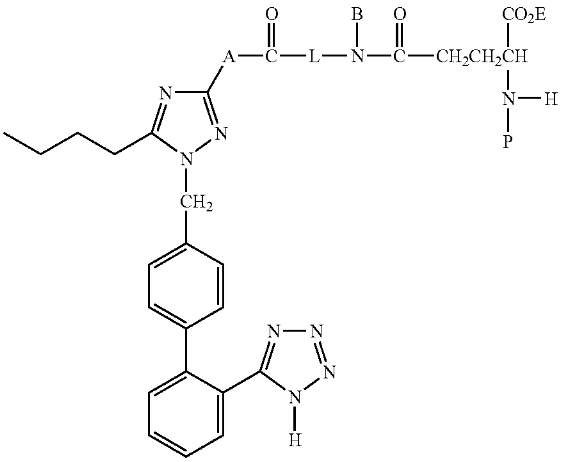

| Ex. # | A | L | B | E | P |
|---|---|---|---|---|---|
| 501 | $C_3H_6(n)$ | —NH— | H | H | $COC_4H_9$ |
| 502 | $C_3H_6(n)$ | —NH— | H | $CH_3$ | $COCH_3$ |
| 503 | $C_3H_6(n)$ | —NH— | H | $C_2H_5$ | $COCH_3$ |
| 504 | $C_3H_6(n)$ | —NH— | H | H | H |
| 505 | $C_3H_6(n)$ | —NH— | H | $CH_3$ | H |
| 506 | $C_3H_6(n)$ | —NH— | H | $C_2H_5$ | H |
| 507 | $C_3H_6(n)$ | $—NHCH_2CH_2—$ | H | H | $COCH_3$ |
| 508 | $C_3H_6(n)$ | $—NHCH_2CH_2—$ | H | H | $COCH_2Cl$ |
| 509 | $C_3H_6(n)$ | $—NHCH_2CH_2—$ | H | H | $COC_4H_9$ |
| 510 | $C_3H_6(n)$ | $—NHCH_2CH_2—$ | H | $CH_3$ | $COCH_3$ |
| 511 | $C_3H_6(n)$ | $—NHCH_2CH_2—$ | H | $C_2H_5$ | $COCH_3$ |
| 512 | $C_3H_6(n)$ | $—NHCH_2CH_2—$ | H | H | H |
| 513 | $C_3H_6(n)$ | $—NHCH_2CH_2—$ | H | $CH_3$ | H |
| 514 | $C_3H_6(n)$ | $—NHCH_2CH_2—$ | H | $C_2H_5$ | H |
| 515 | $C_3H_6(n)$ | 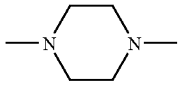 | * | H | $COCH_3$ |
| 516 | $C_3H_6(n)$ | 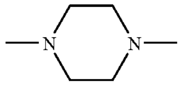 | H | H | $COCH_2Cl$ |
| 517 | $C_3H_6(n)$ | 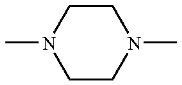 | H | H | $COC_4H_9$ |
| 518 | $C_3H_6(n)$ | 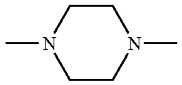 | H | $CH_3$ | $COCH_3$ |
| 519 | $C_3H_6(n)$ | 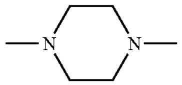 | H | $C_2H_5$ | $COCH_3$ |
| 520 | $C_3H_6(n)$ | 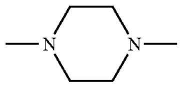 | * | H | H |
| 521 | $C_3H_6(n)$ | 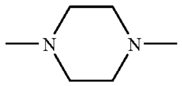 | H | $CH_3$ | H |
| 522 | $C_3H_6(n)$ | 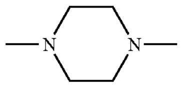 | H | $C_2H_5$ | H |

TABLE VI-continued

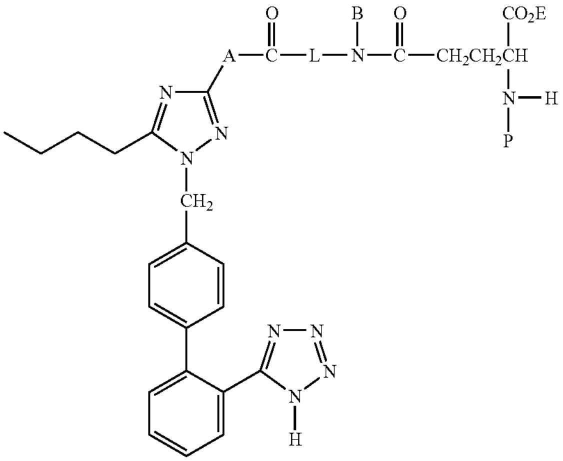

| Ex. # | A | L | B | E | P |
|---|---|---|---|---|---|
| 523 | $C_4H_8$(n) | —NH— | H | H | $COCH_3$ |
| 524 | $C_4H_8$(n) | —NH— | H | H | $COCH_2Cl$ |
| 525 | $C_4H_8$(n) | —NH— | H | H | $COC_4H_9$ |
| 526 | $C_4H_8$(n) | —NH— | H | $CH_3$ | $COCH_3$ |
| 527 | $C_4H_8$(n) | —NH— | H | $C_2H_5$ | $COCH_3$ |
| 528 | $C_4H_8$(n) | —NH— | H | H | H |
| 529 | $C_4H_8$(n) | —NH— | H | $CH_3$ | H |
| 530 | $C_4H_8$(n) | —NH— | H | $C_2H_5$ | H |
| 531 | $C_4H_8$(n) | $—NHCH_2CH_2—$ | H | H | $COCH_3$ |
| 532 | $C_4H_8$(n) | $—NHCH_2CH_2—$ | H | H | $COCH_2Cl$ |
| 533 | $C_4H_8$(n) | $—NHCH_2CH_2—$ | H | H | $COC_4H_9$ |
| 534 | $C_4H_8$(n) | $—NHCH_2CH_2—$ | H | $CH_3$ | $COCH_3$ |
| 535 | $C_4H_8$(n) | $—NHCH_2CH_2—$ | H | $C_2H_5$ | $COCH_3$ |
| 536 | $C_4H_8$(n) | $—NHCH_2CH_2—$ | H | H | H |
| 537 | $C_4H_8$(n) | $—NHCH_2CH_2—$ | H | $CH_3$ | H |
| 538 | $C_4H_8$(n) | $—NHCH_2CH_2—$ | H | $C_2H_5$ | H |
| 539 | $C_4H_8$(n) | 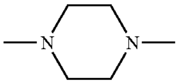 | * | H | $COCH_3$ |
| 540 | $C_4H_8$(n) | 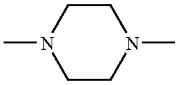 | H | H | $COCH_2Cl$ |
| 541 | $C_4H_8$(n) | 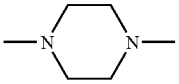 | H | H | $COC_4H_9$ |
| 542 | $C_4H_8$(n) | 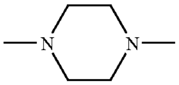 | H | $CH_3$ | $COCH_3$ |
| 543 | $C_4H_8$(n) | 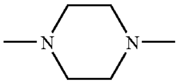 | H | $C_2H_5$ | $COCH_3$ |
| 544 | $C_4H_8$(n) | 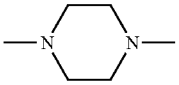 | * | H | H |
| 545 | $C_4H_8$(n) | 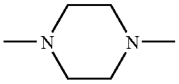 | H | $CH_3$ | H |

TABLE VI-continued
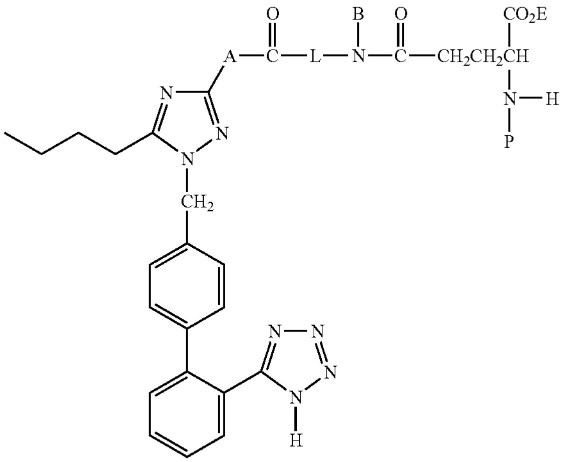
| Ex. # | A | L | B | E | P |
|---|---|---|---|---|---|
| 546 | $C_4H_8(n)$ | 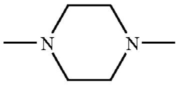 | H | $C_2H_5$ | H |
| 547 | 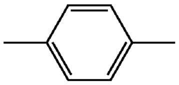 | —NH— | H | H | $COCH_3$ |
| 548 | 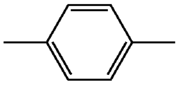 | —NH— | H | H | $COCH_2Cl$ |
| 549 | 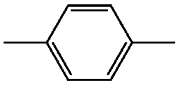 | —NH— | H | H | $COC_4H_9$ |
| 550 | 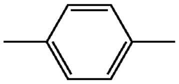 | —NH— | H | $CH_3$ | $COCH_3$ |
| 551 | 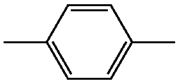 | —NH— | H | $C_2H_5$ | $COCH_3$ |
| 552 | 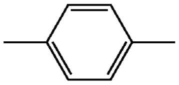 | —NH— | H | H | H |
| 553 | 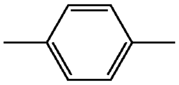 | —NH— | H | $CH_3$ | H |
| 554 | 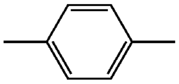 | —NH— | H | $C_2H_5$ | H |
| 555 | 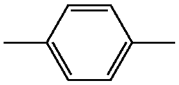 | $—NHCH_2CH_2—$ | H | H | $COCH_3$ |
| 556 | 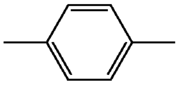 | $—NHCH_2CH_2—$ | H | H | $COCH_2Cl$ |

TABLE VI-continued
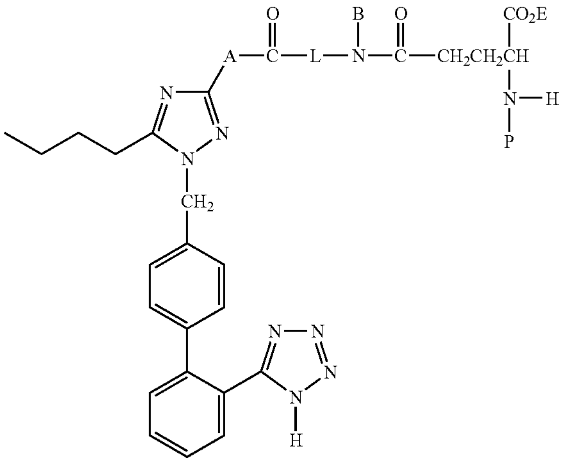
| Ex. # | A | L | B | E | P |
|---|---|---|---|---|---|
| 557 | 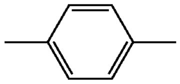 | —$NHCH_2CH_2$— | H | H | $COC_4H_9$ |
| 558 | 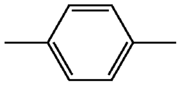 | —$NHCH_2CH_2$— | H | $CH_3$ | $COCH_3$ |
| 559 | 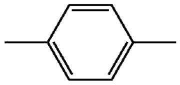 | —$NHCH_2CH_2$— | H | $C_2H_5$ | $COCH_3$ |
| 560 | 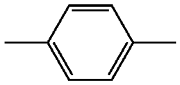 | —$NHCH_2CH_2$— | H | H | H |
| 561 | 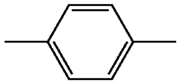 | —$NHCH_2CH_2$— | H | $CH_3$ | H |
| 562 | 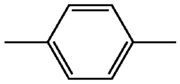 | —$NHCH_2CH_2$— | H | $C_2H_5$ | H |
| 563 | 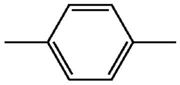 | 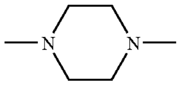 | * | H | $COCH_3$ |
| 564 | 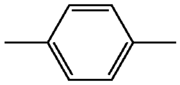 | 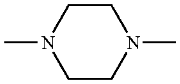 | H | H | $COCH_2Cl$ |
| 565 | 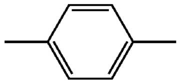 | 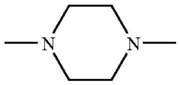 | H | H | $COC_4H_9$ |
| 566 | 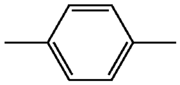 | 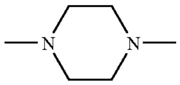 | H | $CH_3$ | $COCH_3$ |
| 567 | 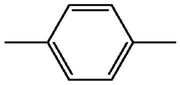 | 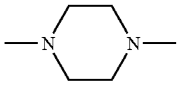 | H | $C_2H_5$ | $COCH_3$ |

TABLE VI-continued
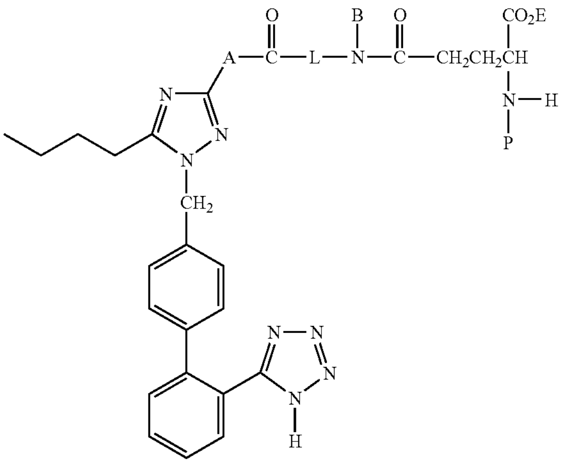
| Ex. # | A | L | B | E | P |
|---|---|---|---|---|---|
| 568 | 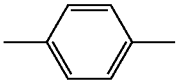 | 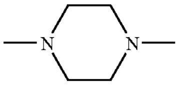 | * | H | H |
| 569 | 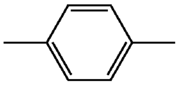 | 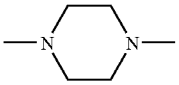 | H | $CH_3$ | H |
| 570 | 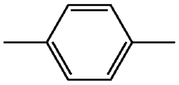 | 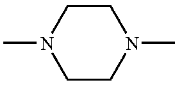 | H | $C_2H_5$ | H |
| 571 | 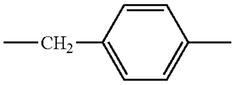 | —NH— | H | H | $COCH_3$ |
| 572 | 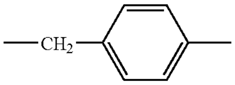 | —NH— | H | H | $COCH_2Cl$ |
| 573 | 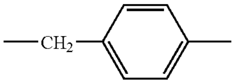 | —NH— | H | H | $COC_4H_9$ |
| 574 | 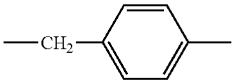 | —NH— | H | $CH_3$ | $COCH_3$ |
| 575 | 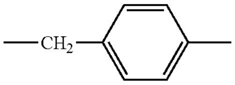 | —NH— | H | $C_2H_5$ | $COCH_3$ |
| 576 | 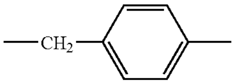 | —NH— | H | H | H |
| 577 | 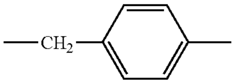 | —NH— | H | $CH_3$ | H |
| 578 | 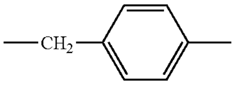 | —NH— | H | $C_2H_5$ | H |

TABLE VI-continued
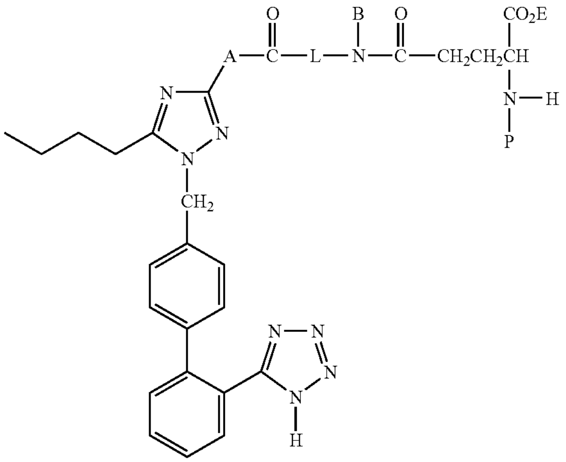
| Ex. # | A | L | B | E | P |
|---|---|---|---|---|---|
| 579 | 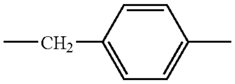 | —$NHCH_2CH_2$— | H | H | $COCH_3$ |
| 580 | 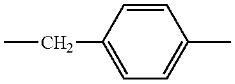 | —$NHCH_2CH_2$— | H | H | $COCH_2Cl$ |
| 581 | 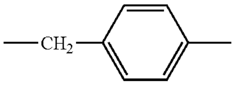 | —$NHCH_2CH_2$— | H | H | $COC_4H_9$ |
| 582 | 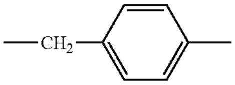 | —$NHCH_2CH_2$— | H | $CH_3$ | $COCH_3$ |
| 583 | 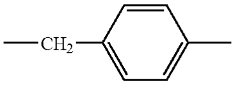 | —$NHCH_2CH_2$— | H | $C_2H_5$ | $COCH_3$ |
| 584 | 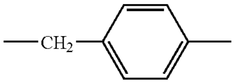 | —$NHCH_2CH_2$— | H | H | H |
| 585 | 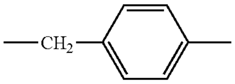 | —$NHCH_2CH_2$— | H | $CH_3$ | H |
| 586 | 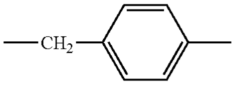 | —$NHCH_2CH_2$ | H | $C_2H_5$ | H |
| 587 | 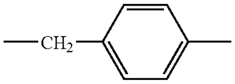 | 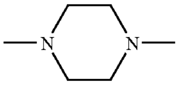 | * | H | $COCH_3$ |
| 588 | 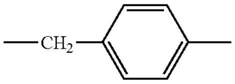 | 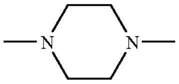 | H | H | $COCH_2Cl$ |
| 589 | 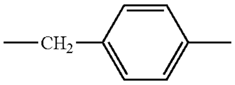 | 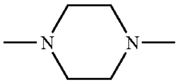 | H | H | $COC_4H_9$ |

TABLE VI-continued
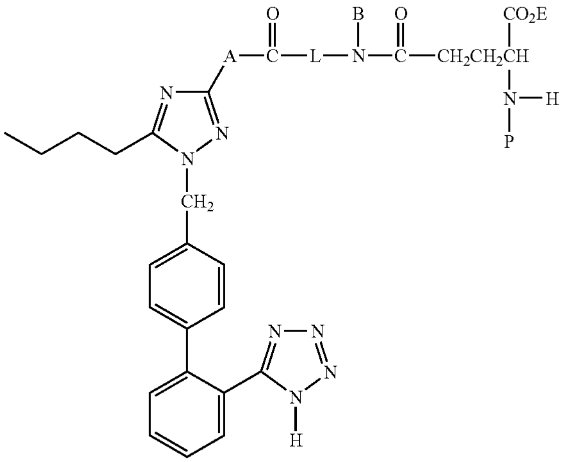
| Ex. # | A | L | B | E | P |
|---|---|---|---|---|---|
| 590 | 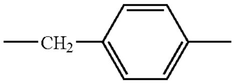 | 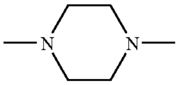 | H | $CH_3$ | $COCH_3$ |
| 591 | 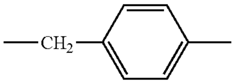 | 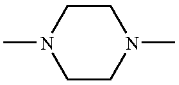 | H | $C_2H_5$ | $COCH_3$ |
| 592 | 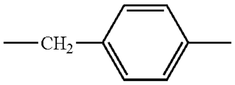 | 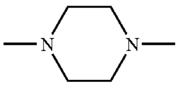 | * | H | H |
| 593 | 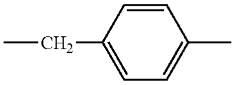 | 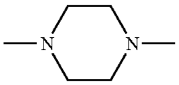 | H | $CH_3$ | H |
| 594 | 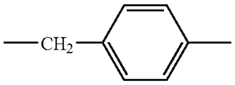 | 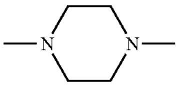 | H | $C_2H_5$ | H |
| 595 | 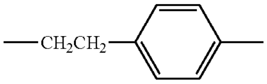 | —NH— | H | H | $COCH_3$ |
| 596 | 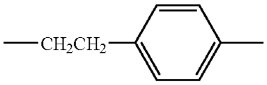 | —NH— | H | H | $COCH_2Cl$ |
| 597 | 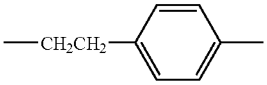 | —NH— | H | H | $COC_4H_9$ |
| 598 | 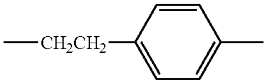 | —NH— | H | $CH_3$ | $COCH_3$ |
| 599 | 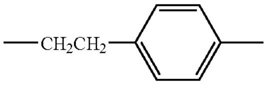 | —NH— | H | $C_2H_5$ | $COCH_3$ |
| 600 | 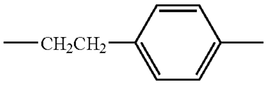 | —NH— | H | H | H |

TABLE VI-continued
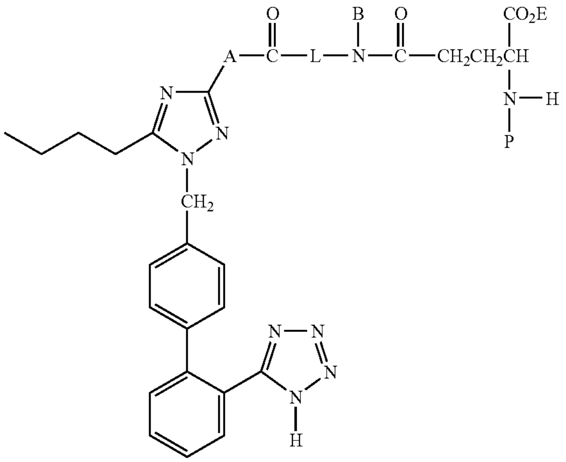
| Ex. # | A | L | B | E | P |
|---|---|---|---|---|---|
| 601 | 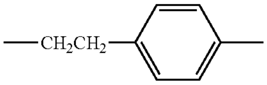 | —NH— | H | $CH_3$ | H |
| 602 | 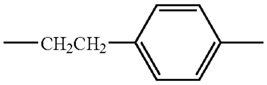 | —NH— | H | $C_2H_5$ | H |
| 603 | 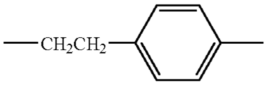 | —$NHCH_2CH_2$— | H | H | $COCH_3$ |
| 604 | 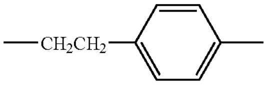 | —$NHCH_2CH_2$— | H | H | $COCH_2Cl$ |
| 605 | 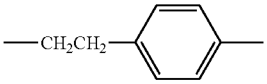 | —$NHCH_2CH_2$— | H | H | $COC_4H_9$ |
| 606 | 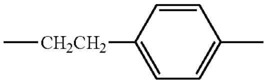 | —$NHCH_2CH_2$— | H | $CH_3$ | $COCH_3$ |
| 607 | 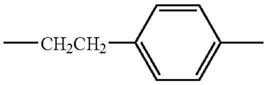 | —$NHCH_2CH_2$— | H | $C_2H_5$ | $COCH_3$ |
| 608 | 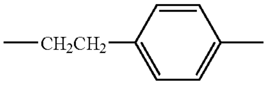 | —$NHCH_2CH_2$— | H | H | H |
| 609 | 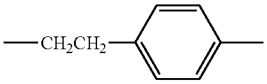 | —$NHCH_2CH_2$— | H | $CH_3$ | H |
| 610 | 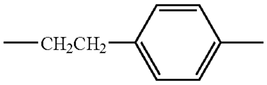 | —$NHCH_2CH_2$— | H | $C_2H_5$ | H |
| 611 | 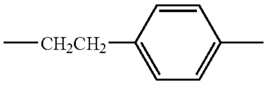 | 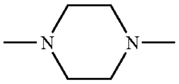 | * | H | $COCH_3$ |

TABLE VI-continued
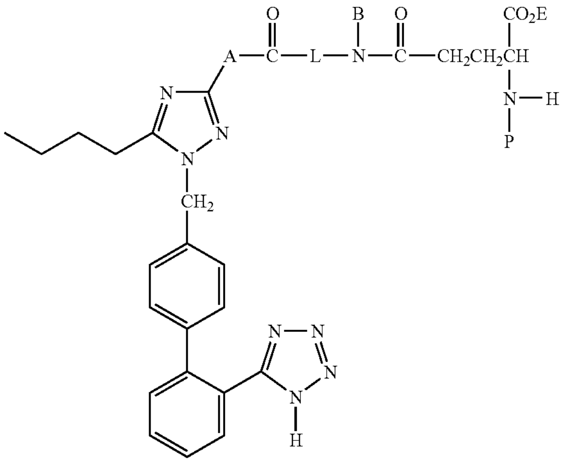
| Ex. # | A | L | B | E | P |
|---|---|---|---|---|---|
| 612 | 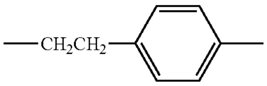 | 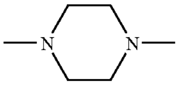 | H | H | $COCH_2Cl$ |
| 613 | 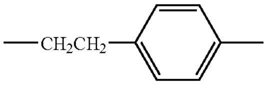 | 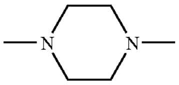 | H | H | $COC_4H_9$ |
| 614 | 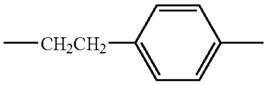 | 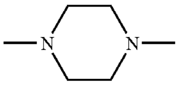 | H | $CH_3$ | $COCH_3$ |
| 615 | 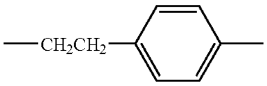 | 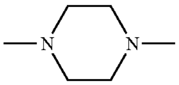 | H | $C_2H_5$ | $COCH_3$ |
| 616 | 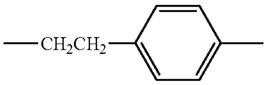 | 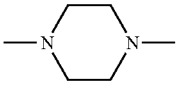 | * | H | H |
| 617 | 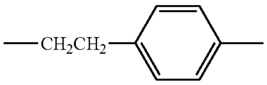 | 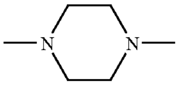 | H | $CH_3$ | H |
| 618 | 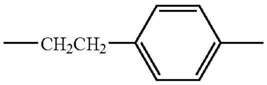 | 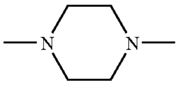 | H | $C_2H_5$ | H |
| 619 | 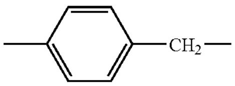 | —NH— | H | H | $COCH_3$ |
| 620 | 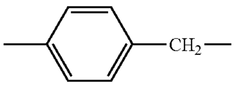 | —NH— | H | H | $COCH_2Cl$ |
| 621 | 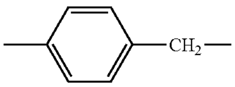 | —NH— | H | H | $COC_4H_9$ |
| 622 | 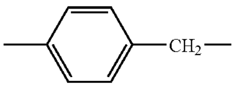 | —NH— | H | $CH_3$ | $COCH_3$ |

TABLE VI-continued
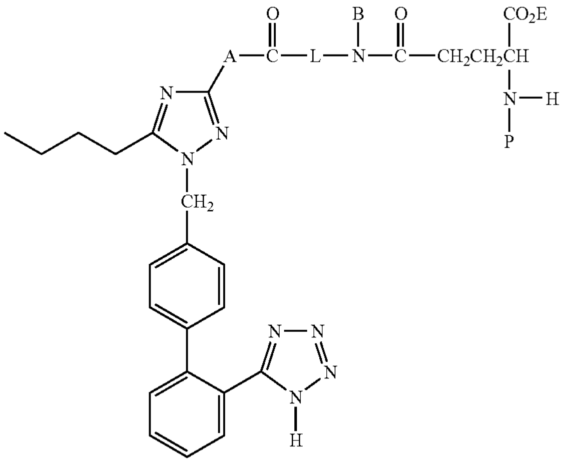
| Ex. # | A | L | B | E | P |
|---|---|---|---|---|---|
| 623 | 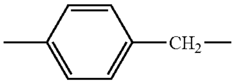 | —NH— | H | $C_2H_5$ | $COCH_3$ |
| 624 | 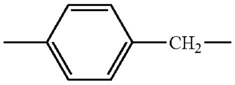 | —NH— | H | H | H |
| 625 | 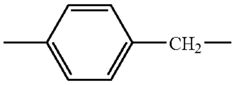 | —NH— | H | $CH_3$ | H |
| 626 | 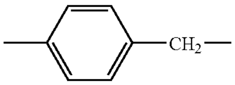 | —NH— | H | $C_2H_5$ | H |
| 627 | 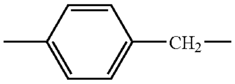 | $—NHCH_2CH_2—$ | H | H | $COCH_3$ |
| 628 | 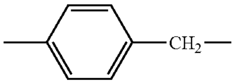 | $—NHCH_2CH_2—$ | H | H | $COCH_2Cl$ |
| 629 | 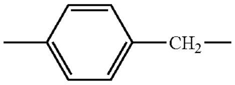 | $—NHCH_2CH_2—$ | H | H | $COC_4H_9$ |
| 630 | 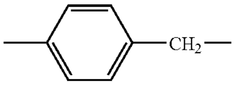 | $—NHCH_2CH_2—$ | H | $CH_3$ | $COCH_3$ |
| 631 | 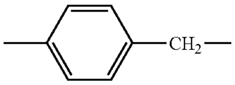 | $—NHCH_2CH_2—$ | H | $C_2H_5$ | $COCH_3$ |
| 632 | 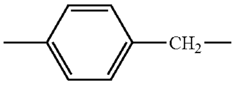 | $—NHCH_2CH_2—$ | H | H | H |
| 633 | 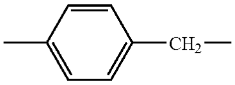 | $—NHCH_2CH_2—$ | H | $CH_3$ | H |

TABLE VI-continued
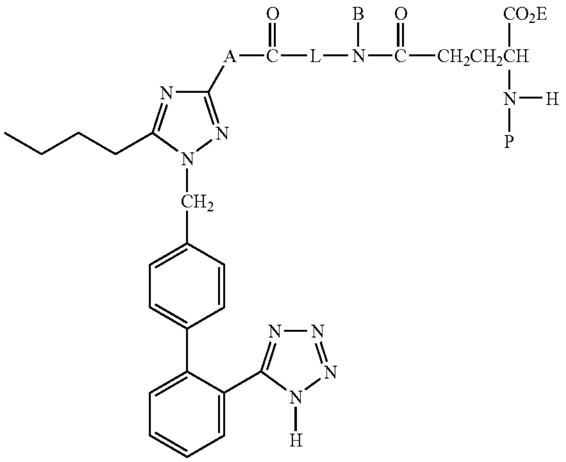
| Ex. # | A | L | B | E | P |
|---|---|---|---|---|---|
| 634 | 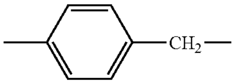 | —$NHCH_2CH_2$— | H | $C_2H_5$ | H |
| 635 | 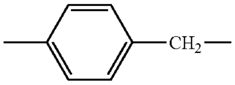 | 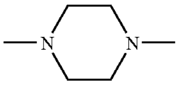 | * | H | $COCH_3$ |
| 636 | 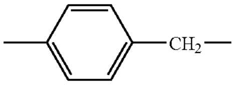 | 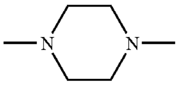 | H | H | $COCH_2Cl$ |
| 637 | 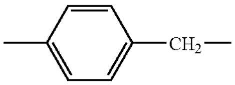 | 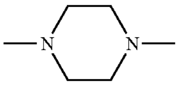 | H | H | $COC_4H_9$ |
| 638 | 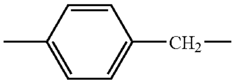 | 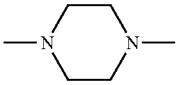 | H | $CH_3$ | $COCH_3$ |
| 639 | 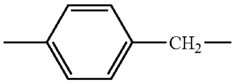 | 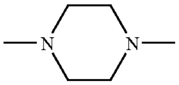 | H | $C_2H_5$ | $COCH_3$ |
| 640 | 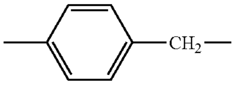 | 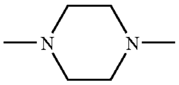 | * | H | H |
| 641 | 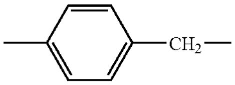 | 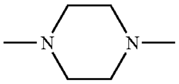 | H | $CH_3$ | H |
| 642 | 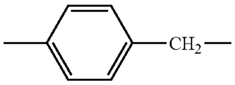 | 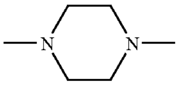 | H | $C_2H_5$ | H |
| 643 | 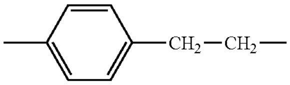 | —NH— | H | H | $COCH_3$ |
| 644 | 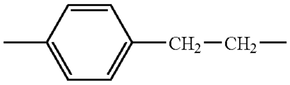 | —NH— | H | H | $COCH_2Cl$ |

TABLE VI-continued
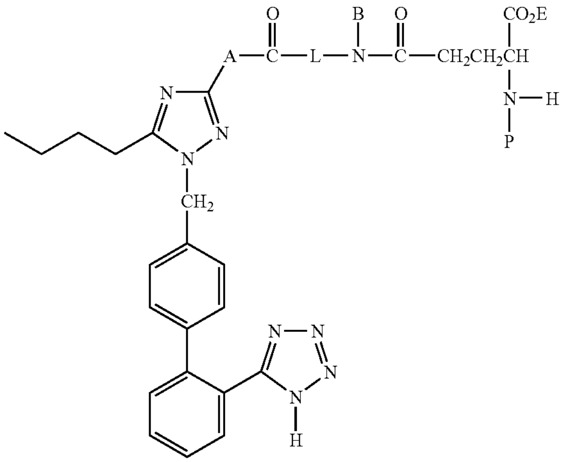
| Ex. # | A | L | B | E | P |
|---|---|---|---|---|---|
| 645 | 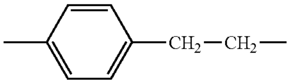 | —NH— | H | H | $COC_4H_9$ |
| 646 | 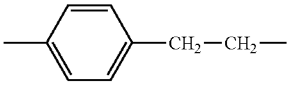 | —NH— | H | $CH_3$ | $COCH_3$ |
| 647 | 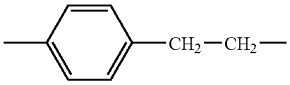 | —NH— | H | $C_2H_5$ | $COCH_3$ |
| 648 | 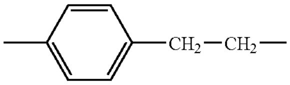 | —NH— | H | H | H |
| 649 | 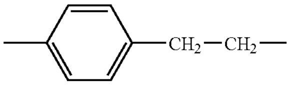 | —NH— | H | $CH_3$ | H |
| 650 | 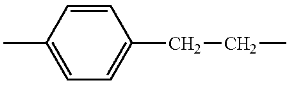 | —NH— | H | $C_2H_5$ | H |
| 651 | 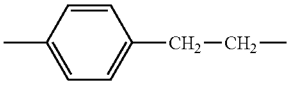 | $—NHCH_2CH_2—$ | H | H | $COCH_3$ |
| 652 | 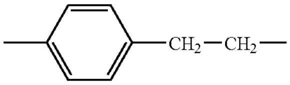 | $—NHCH_2CH_2—$ | H | H | $COCH_2Cl$ |
| 653 | 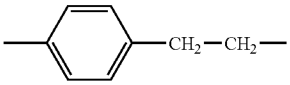 | $—NHCH_2CH_2—$ | H | H | $COC_4H_9$ |
| 654 | 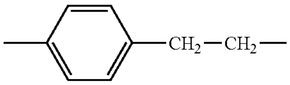 | $—NHCH_2CH_2—$ | H | $CH_3$ | $COCH_3$ |
| 655 | 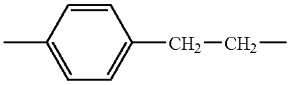 | $—NHCH_2CH_2—$ | H | $C_2H_5$ | $COCH_3$ |

TABLE VI-continued
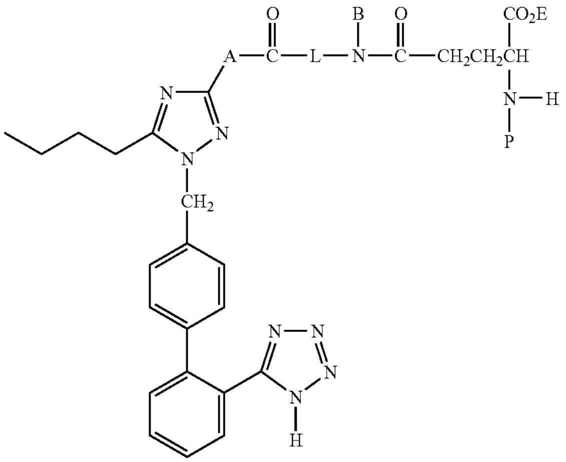
| Ex. # | A | L | B | E | P |
|---|---|---|---|---|---|
| 656 | 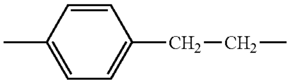 | $—NHCH_2CH_2—$ | H | H | H |
| 657 | 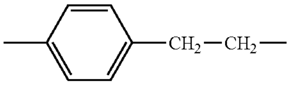 | $—NHCH_2CH_2—$ | H | $CH_3$ | H |
| 658 | 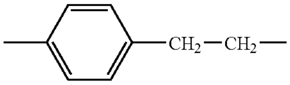 | $—NHCH_2CH_2—$ | H | $C_2H_5$ | H |
| 659 | 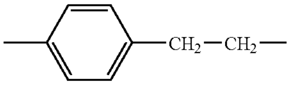 | 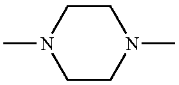 | * | H | $COCH_3$ |
| 660 | 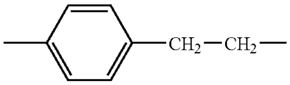 | 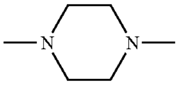 | H | H | $COCH_2Cl$ |
| 661 | 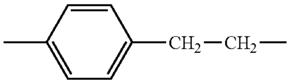 | 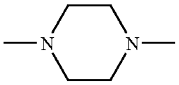 | H | H | $COC_4H_9$ |
| 662 | 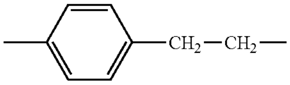 | 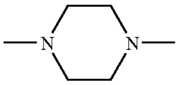 | H | $CH_3$ | $COCH_3$ |
| 663 | 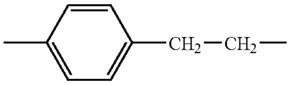 | 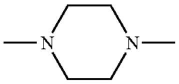 | H | $C_2H_5$ | $COCH_3$ |
| 664 | 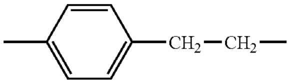 | 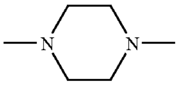 | * | H | H |
| 665 | 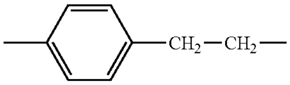 | 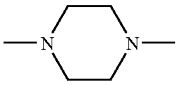 | H | $CH_3$ | H |
| 666 | 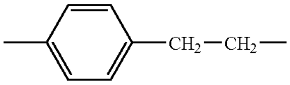 | 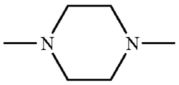 | H | $C_2H_5$ | H |

TABLE VI-continued
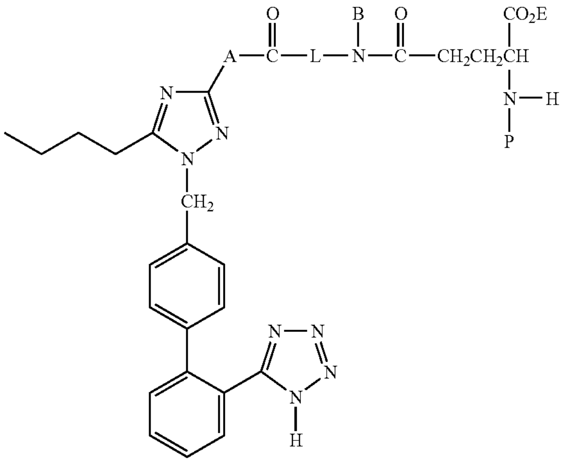
| Ex. # | A | L | B | E | P |
|---|---|---|---|---|---|
| 667 | 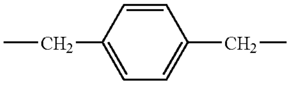 | —NH— | H | H | $COCH_3$ |
| 668 | 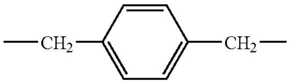 | —NH— | H | H | $COCH_2Cl$ |
| 669 | 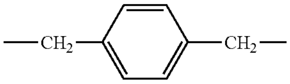 | —NH— | H | H | $COC_4H_9$ |
| 670 | 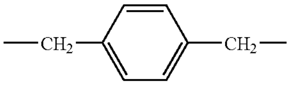 | —NH— | H | $CH_3$ | $COCH_3$ |
| 671 | 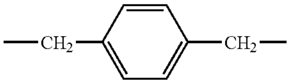 | —NH— | H | $C_2H_5$ | $COCH_3$ |
| 672 | 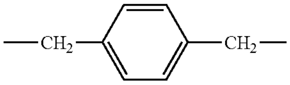 | —NH— | H | H | H |
| 673 | 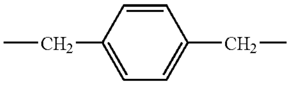 | —NH— | H | $CH_3$ | H |
| 674 | 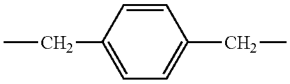 | —NH— | H | $C_2H_5$ | H |
| 675 | 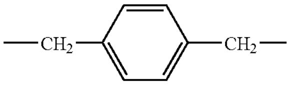 | $—NHCH_2CH_2—$ | H | H | $COCH_3$ |
| 676 | 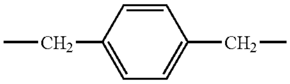 | $—NHCH_2CH_2—$ | H | H | $COCH_2Cl$ |
| 677 | 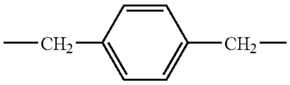 | $—NHCH_2CH_2—$ | H | H | $COC_4H_9$ |

TABLE VI-continued
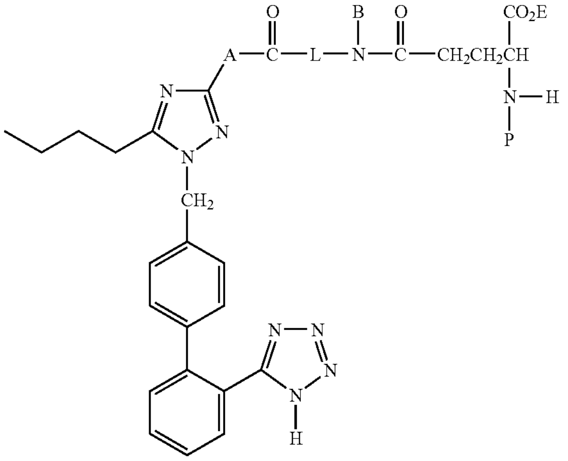
| Ex. # | A | L | B | E | P |
|---|---|---|---|---|---|
| 678 | 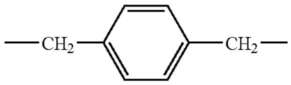 | —$NHCH_2CH_2$— | H | $CH_3$ | $COCH_3$ |
| 679 | 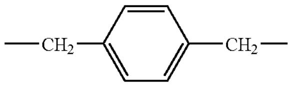 | —$NHCH_2CH_2$— | H | $C_2H_5$ | $COCH_3$ |
| 680 | 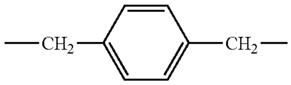 | —$NHCH_2CH_2$— | H | H | H |
| 681 | 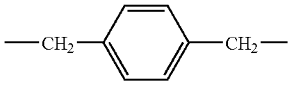 | —$NHCH_2CH_2$— | H | $CH_3$ | H |
| 682 | 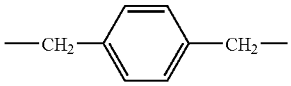 | —$NHCH_2CH_2$— | H | $C_2H_5$ | H |
| 683 | 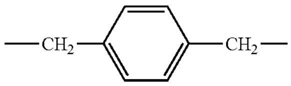 | 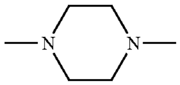 | * | H | $COCH_3$ |
| 684 | 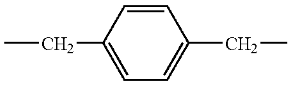 | 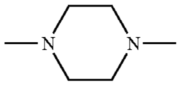 | H | H | $COCH_2Cl$ |
| 685 | 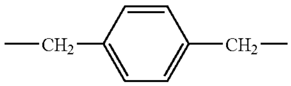 | 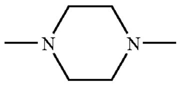 | H | H | $COC_4H_9$ |
| 686 | 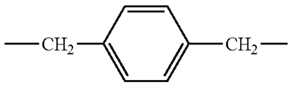 | 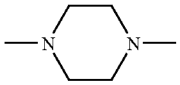 | H | $CH_3$ | $COCH_3$ |
| 687 | 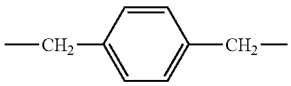 | 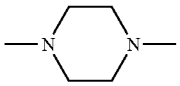 | H | $C_2H_5$ | $COCH_3$ |

TABLE VI-continued
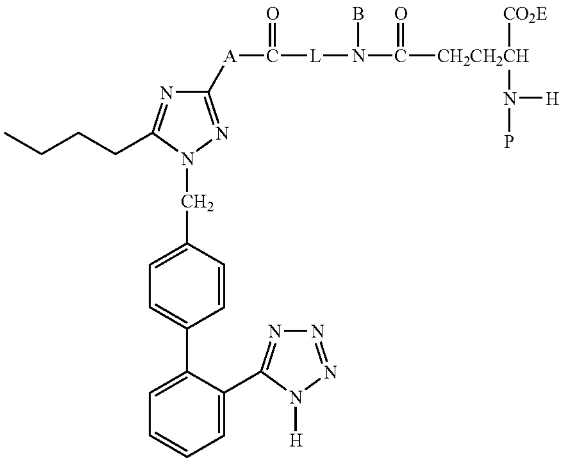
| Ex. # | A | L | B | E | P |
|---|---|---|---|---|---|
| 688 | 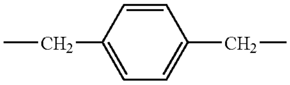 | 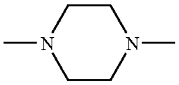 | * | H | H |
| 689 | 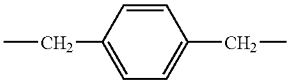 | 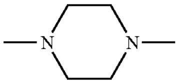 | H | $CH_3$ | H |
| 690 | 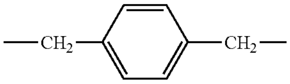 | 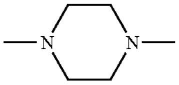 | H | $C_2H_5$ | H |
| 691 | 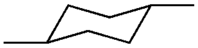 | —NH— | H | H | $COCH_3$ |
| 692 | 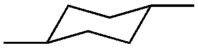 | —NH— | H | H | $COCH_2Cl$ |
| 693 | 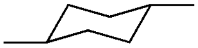 | —NH— | H | H | $COC_4H_9$ |
| 694 | 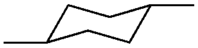 | —NH— | H | $CH_3$ | $COCH_3$ |
| 695 | 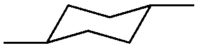 | —NH— | H | $C_2H_5$ | $COCH_3$ |
| 696 | 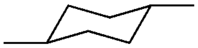 | —NH— | H | H | H |
| 697 | 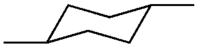 | —NH— | H | $CH_3$ | H |
| 698 | 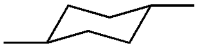 | —NH— | H | $C_2H_5$ | H |
| 699 | 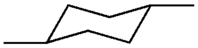 | $—NHCH_2CH_2—$ | H | H | $COCH_3$ |
| 700 | 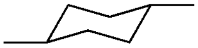 | $—NHCH_2CH_2—$ | H | H | $COCH_2Cl$ |
| 701 | 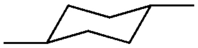 | $—NHCH_2CH_2—$ | H | H | $COC_4H_9$ |
| 702 | 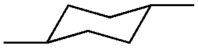 | $—NHCH_2CH_2—$ | H | $CH_3$ | $COCH_3$ |

TABLE VI-continued
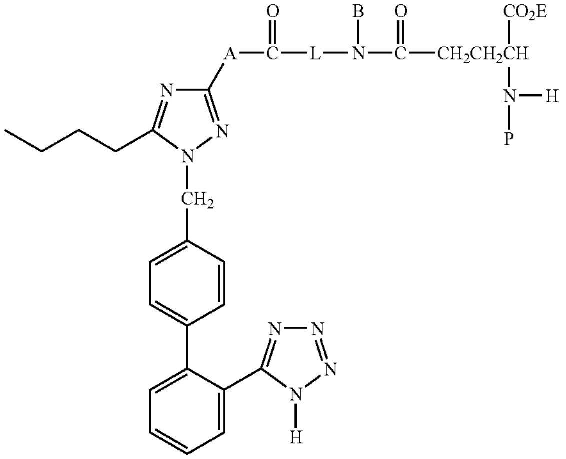
| Ex. # | A | L | B | E | P |
|---|---|---|---|---|---|
| 703 | 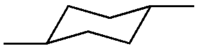 | —$NHCH_2CH_2$— | H | $C_2H_5$ | $COCH_3$ |
| 704 | 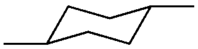 | —$NHCH_2CH_2$— | H | H | H |
| 705 | 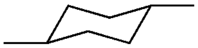 | —$NHCH_2CH_2$— | H | $CH_3$ | H |
| 706 | 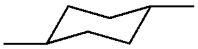 | —$NHCH_2CH_2$— | H | $C_2H_5$ | H |
| 707 | 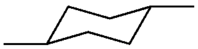 | 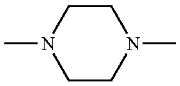 | * | H | $COCH_3$ |
| 708 | 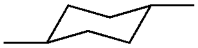 | 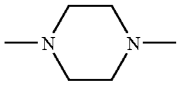 | H | H | $COCH_2Cl$ |
| 709 | 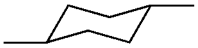 | 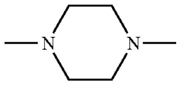 | H | H | $COC_4H_9$ |
| 710 | 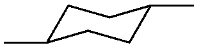 | 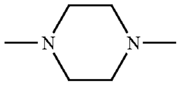 | H | $CH_3$ | $COCH_3$ |
| 711 | 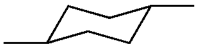 | 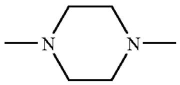 | H | $C_2H_5$ | $COCH_3$ |
| 712 | 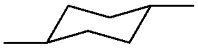 | 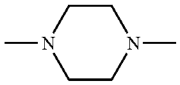 | * | H | H |
| 713 | 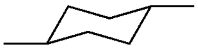 | 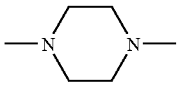 | H | $CH_3$ | H |
| 714 | 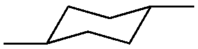 | 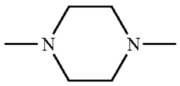 | H | $C_2H_5$ | H |

TABLE VI-continued
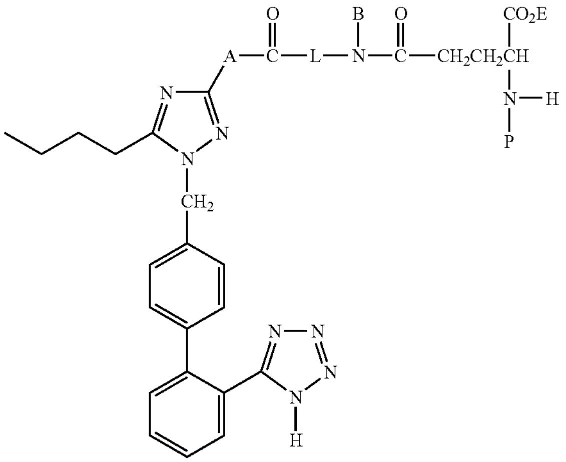
| Ex. # | A | L | B | E | P |
|---|---|---|---|---|---|
| 715 | 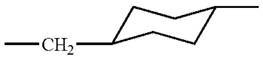 | —NH— | H | H | $COCH_3$ |
| 716 | 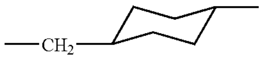 | —NH— | H | H | $COCH_2Cl$ |
| 717 | 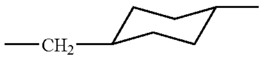 | —NH— | H | H | $COC_4H_9$ |
| 718 | 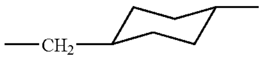 | —NH— | H | $CH_3$ | $COCH_3$ |
| 719 | 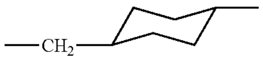 | —NH— | H | $C_2H_5$ | $COCH_3$ |
| 720 | 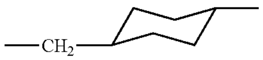 | —NH— | H | H | H |
| 721 | 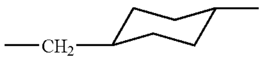 | —NH— | H | $CH_3$ | H |
| 722 | 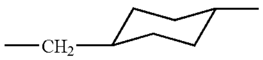 | —NH— | H | $C_2H_5$ | H |
| 723 | 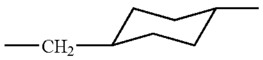 | $—NHCH_2CH_2—$ | H | H | $COCH_3$ |
| 724 | 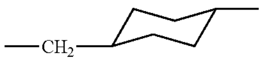 | $—NHCH_2CH_2—$ | H | H | $COCH_2Cl$ |
| 725 | 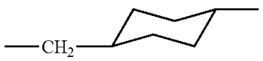 | $—NHCH_2CH_2—$ | H | H | $COC_4H_9$ |
| 726 | 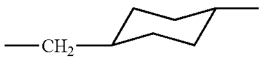 | $—NHCH_2CH_2—$ | H | $CH_3$ | $COCH_3$ |
| 727 | 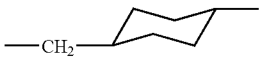 | $—NHCH_2CH_2—$ | H | $C_2H_5$ | $COCH_3$ |
| 728 | 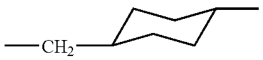 | $—NHCH_2CH_2—$ | H | H | H |

TABLE VI-continued
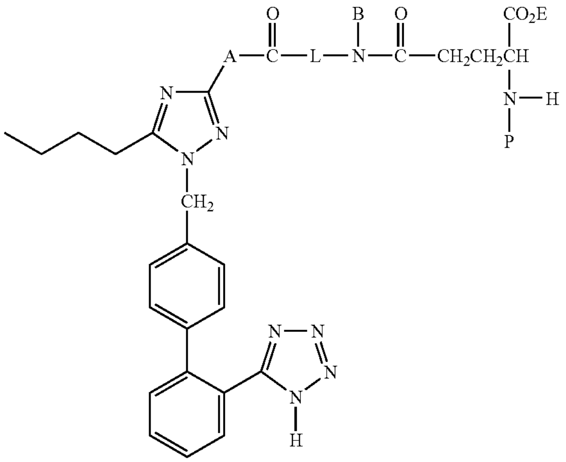
| Ex. # | A | L | B | E | P |
|---|---|---|---|---|---|
| 729 | 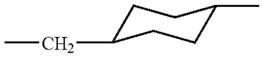 | —$NHCH_2CH_2$— | H | $CH_3$ | H |
| 730 | 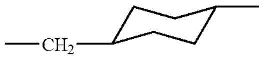 | —$NHCH_2CH_2$— | H | $C_2H_5$ | H |
| 731 | 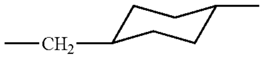 | 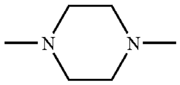 | * | H | $COCH_3$ |
| 732 | 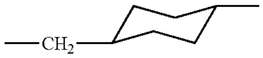 | 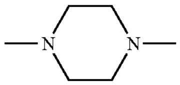 | H | H | $COCH_2Cl$ |
| 733 | 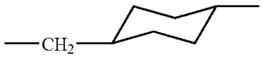 | 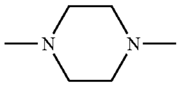 | H | H | $COC_4H_9$ |
| 734 | 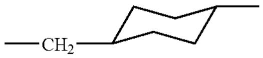 | 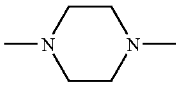 | H | $CH_3$ | $COCH_3$ |
| 735 | 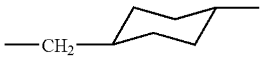 | 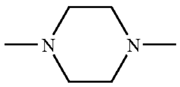 | H | $C_2H_5$ | $COCH_3$ |
| 736 | 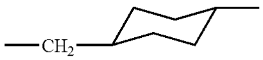 | 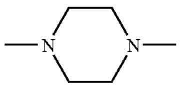 | * | H | H |
| 737 | 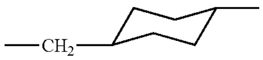 | 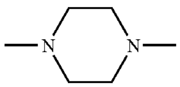 | H | $CH_3$ | H |
| 738 | 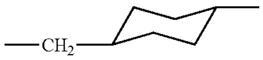 | 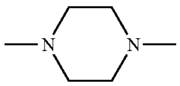 | H | $C_2H_5$ | H |
| 739 | 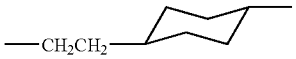 | —NH— | H | H | $COCH_3$ |
| 740 | 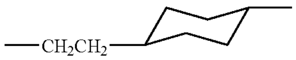 | —NH— | H | H | $COCH_2Cl$ |

TABLE VI-continued
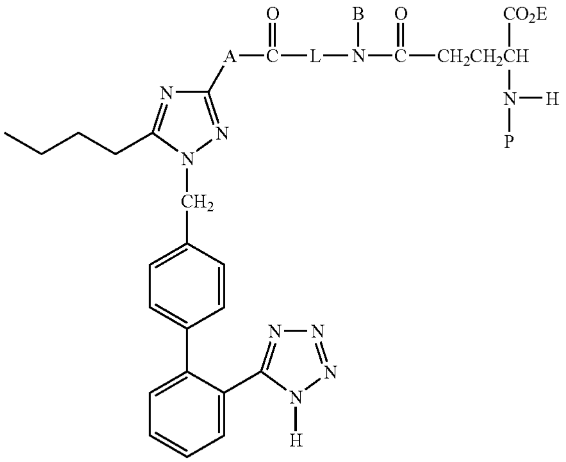
| Ex. # | A | L | B | E | P |
|---|---|---|---|---|---|
| 741 | —$CH_2CH_2$— 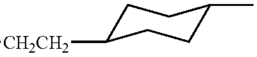 | —NH— | H | H | $COC_4H_9$ |
| 742 | —$CH_2CH_2$— 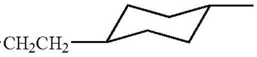 | —NH— | H | $CH_3$ | $COCH_3$ |
| 743 | —$CH_2CH_2$— 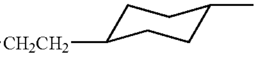 | —NH— | H | $C_2H_5$ | $COCH_3$ |
| 744 | —$CH_2CH_2$— 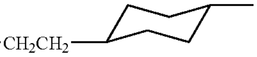 | —NH— | H | H | H |
| 745 | —$CH_2CH_2$— 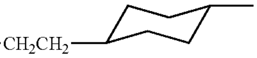 | —NH— | H | $CH_3$ | H |
| 746 | —$CH_2CH_2$— 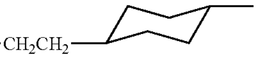 | —NH— | H | $C_2H_5$ | H |
| 747 | —$CH_2CH_2$— 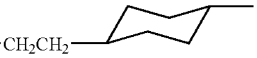 | —$NHCH_2CH_2$— | H | H | $COCH_3$ |
| 748 | —$CH_2CH_2$— 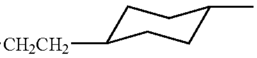 | —$NHCH_2CH_2$— | H | H | $COCH_2Cl$ |
| 749 | —$CH_2CH_2$— 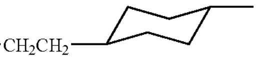 | —$NHCH_2CH_2$— | H | H | $COC_4H_9$ |
| 750 | —$CH_2CH_2$— 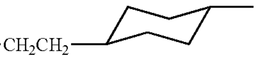 | —$NHCH_2CH_2$— | H | $CH_3$ | $COCH_3$ |
| 751 | —$CH_2CH_2$— 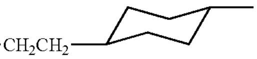 | —$NHCH_2CH_2$— | H | $C_2H_5$ | $COCH_3$ |
| 752 | —$CH_2CH_2$— 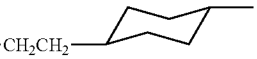 | —$NHCH_2CH_2$— | H | H | H |
| 753 | —$CH_2CH_2$— 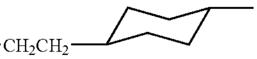 | —$NHCH_2CH_2$— | H | $CH_3$ | H |
| 754 | —$CH_2CH_2$— 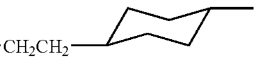 | —$NHCH_2CH_2$— | H | $C_2H_5$ | H |

TABLE VI-continued
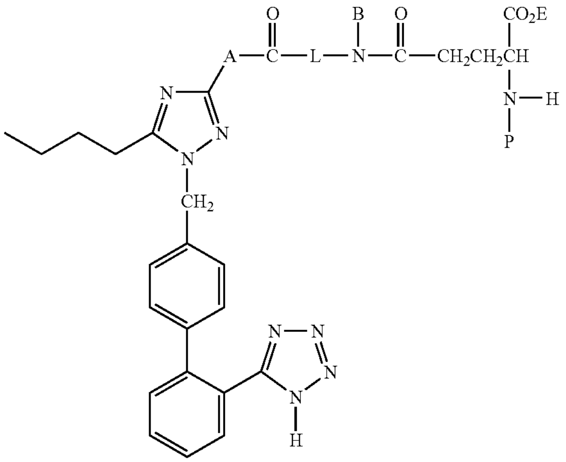
| Ex. # | A | L | B | E | P |
|---|---|---|---|---|---|
| 755 | 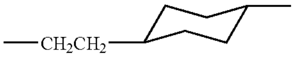 | 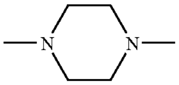 | * | H | $COCH_3$ |
| 756 | 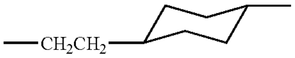 | 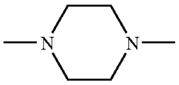 | H | H | $COCH_2Cl$ |
| 757 | 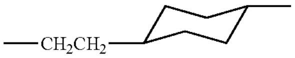 | 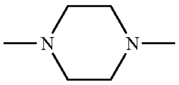 | H | H | $COC_4H_9$ |
| 758 | 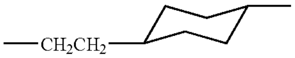 | 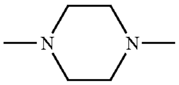 | H | $CH_3$ | $COCH_3$ |
| 759 | 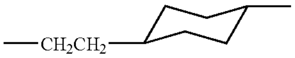 | 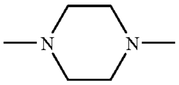 | H | $C_2H_5$ | $COCH_3$ |
| 760 | 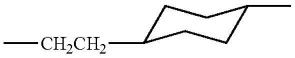 | 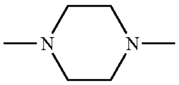 | * | H | H |
| 761 | 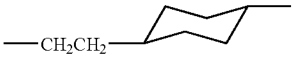 | 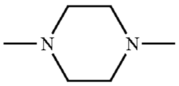 | H | $CH_3$ | H |
| 762 | 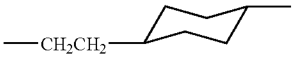 | 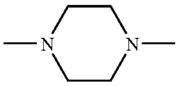 | H | $C_2H_5$ | H |
| 763 | 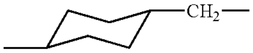 | —NH— | H | H | $COCH_3$ |
| 764 | 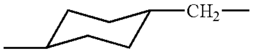 | —NH— | H | H | $COCH_2Cl$ |
| 765 | 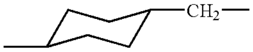 | —NH— | H | H | $COC_4H_9$ |
| 766 | 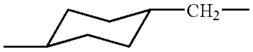 | —NH— | H | $CH_3$ | $COCH_3$ |

TABLE VI-continued
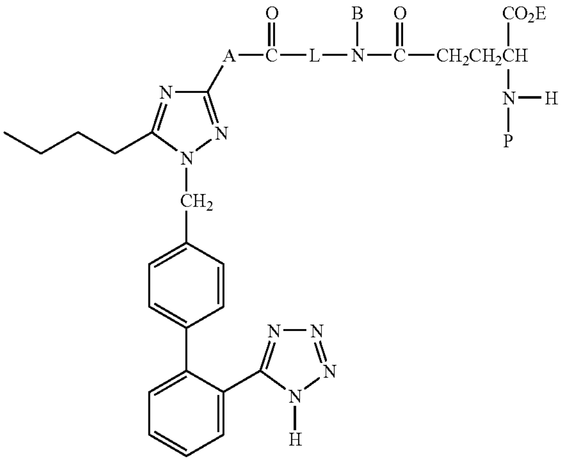
| Ex. # | A | L | B | E | P |
|---|---|---|---|---|---|
| 767 | 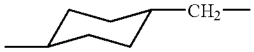 | —NH— | H | $C_2H_5$ | $COCH_3$ |
| 768 | 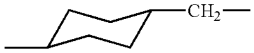 | —NH— | H | H | H |
| 769 | 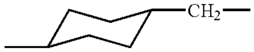 | —NH— | H | $CH_3$ | H |
| 770 | 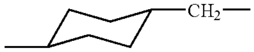 | —NH— | H | $C_2H_5$ | H |
| 771 | 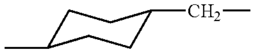 | $—NHCH_2CH_2—$ | H | H | $COCH_3$ |
| 772 | 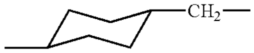 | —NH— | H | H | $COCH_2Cl$ |
| 773 | 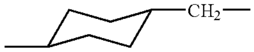 | —NH— | H | H | $COC_4H_9$ |
| 774 | 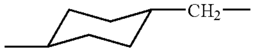 | —NH— | H | $CH_3$ | $COCH_3$ |
| 775 | 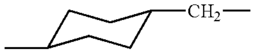 | —NH— | H | $C_2H_5$ | $COCH_3$ |
| 776 | 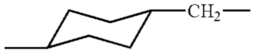 | $—NHCH_2CH_2—$ | H | H | H |
| 777 | 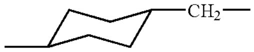 | $—NHCH_2CH_2—$ | H | $CH_3$ | H |
| 778 | 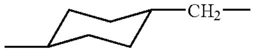 | $—NHCH_2CH_2—$ | H | $C_2H_5$ | H |
| 779 | 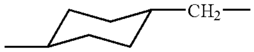 | 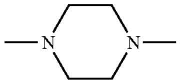 | * | H | $COCH_3$ |
| 780 | 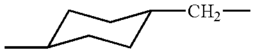 | 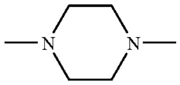 | H | H | $COCH_2Cl$ |

TABLE VI-continued
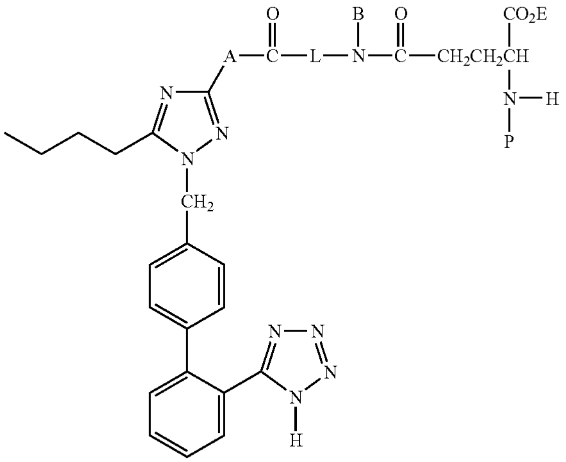
| Ex. # | A | L | B | E | P |
|---|---|---|---|---|---|
| 781 | 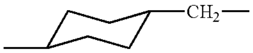 | 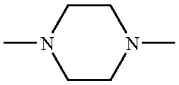 | H | H | $COC_4H_9$ |
| 782 | 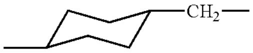 | 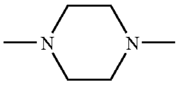 | H | $CH_3$ | $COCH_3$ |
| 783 | 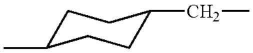 | 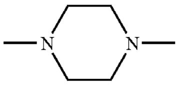 | $C_2H_5$ | | $COCH_3$ |
| 784 | 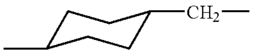 | 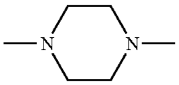 | * | H | H |
| 785 | 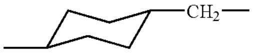 | 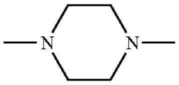 | H | $CH_3$ | H |
| 786 | 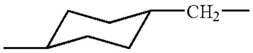 | 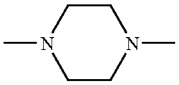 | H | $C_2H_5$ | H |
| 787 | 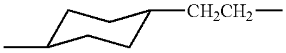 | —NH— | H | H | $COCH_3$ |
| 788 | 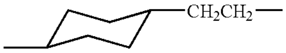 | —NH— | H | H | $COCH_2Cl$ |
| 789 | 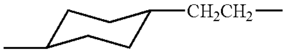 | —NH— | H | H | $COC_4H_9$ |
| 790 | 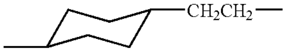 | —NH— | H | $CH_3$ | $COCH_3$ |
| 791 | 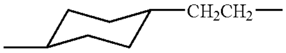 | —NH— | H | $C_2H_5$ | $COCH_3$ |
| 792 | 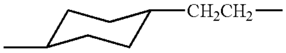 | —NH— | H | H | H |
| 793 | 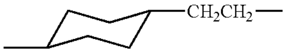 | —NH— | H | $CH_3$ | H |

TABLE VI-continued
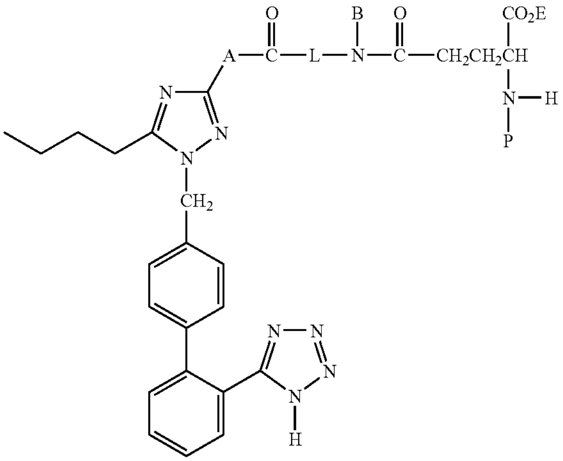
| Ex. # | A | L | B | E | P |
|---|---|---|---|---|---|
| 794 | 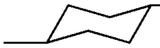CH₂CH₂— | —NH— | H | $C_2H_5$ | H |
| 795 | 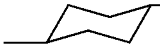$CH_2CH_2$— | —$NHCH_2CH_2$— | H | H | $COCH_3$ |
| 796 | 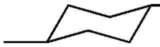$CH_2CH_2$— | —$NHCH_2CH_2$— | H | H | $COCH_2Cl$ |
| 797 | 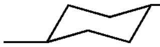$CH_2CH_2$— | —$NHCH_2CH_2$— | H | H | $COC_4H_9$ |
| 798 | 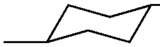$CH_2CH_2$— | —$NHCH_2CH_2$— | H | $CH_3$ | $COCH_3$ |
| 799 | 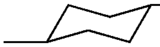$CH_2CH_2$— | —$NHCH_2CH_2$— | H | $C_2H_5$ | $COCH_3$ |
| 800 | 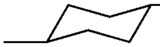$CH_2CH_2$— | —$NHCH_2CH_2$— | H | H | H |
| 801 | 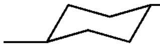$CH_2CH_2$— | —$NHCH_2CH_2$— | H | $CH_3$ | H |
| 802 | 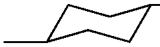$CH_2CH_2$— | —$NHCH_2CH_2$— | H | $C_2H_5$ | H |
| 803 | 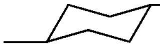$CH_2CH_2$— | 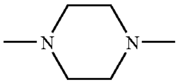 | * | H | $COCH_3$ |
| 804 | 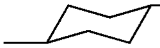$CH_2CH_2$— | 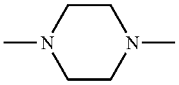 | H | H | $COCH_2Cl$ |
| 805 | 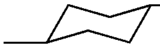$CH_2CH_2$— | 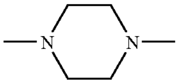 | H | H | $COC_4H_9$ |
| 806 | 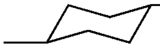$CH_2CH_2$— | 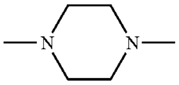 | H | $CH_3$ | $COCH_3$ |

TABLE VI-continued
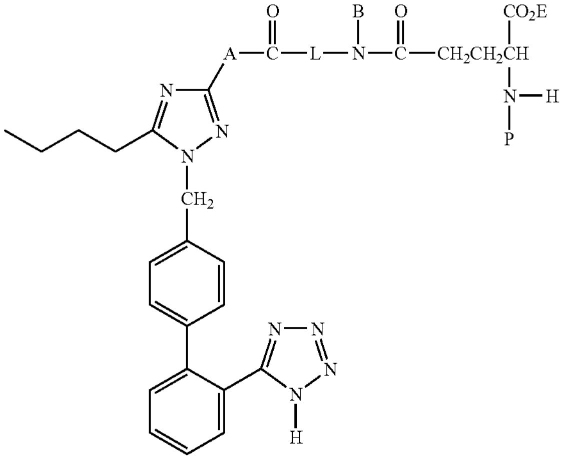
| Ex. # | A | L | B | E | P |
|---|---|---|---|---|---|
| 807 | 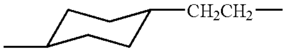 | 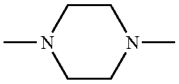 | H | $C_2H_5$ | $COCH_3$ |
| 808 | 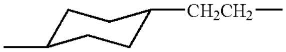 | 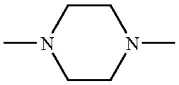 | * | H | H |
| 809 | 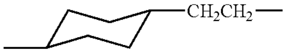 | 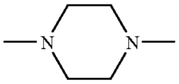 | H | $CH_3$ | H |
| 810 | 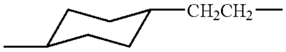 | 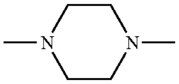 | H | $C_2H_5$ | H |
| 811 | 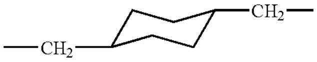 | —NH— | H | H | $COCH_3$ |
| 812 | 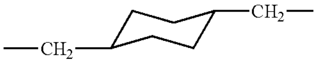 | —NH— | H | H | $COCH_2Cl$ |
| 813 | 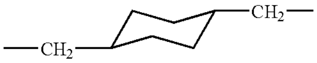 | —NH— | H | H | $COC_4H_9$ |
| 814 | 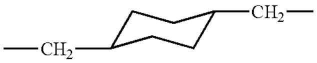 | —NH— | H | $CH_3$ | $COCH_3$ |
| 815 | 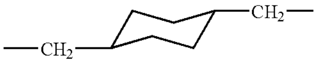 | —NH— | H | $C_2H_5$ | $COCH_3$ |
| 816 | 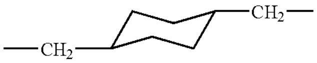 | —NH— | H | H | H |
| 817 | 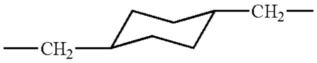 | —NH— | H | $CH_3$ | H |
| 818 | 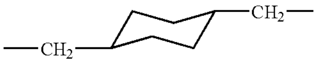 | —NH— | H | $C_2H_5$ | H |

TABLE VI-continued
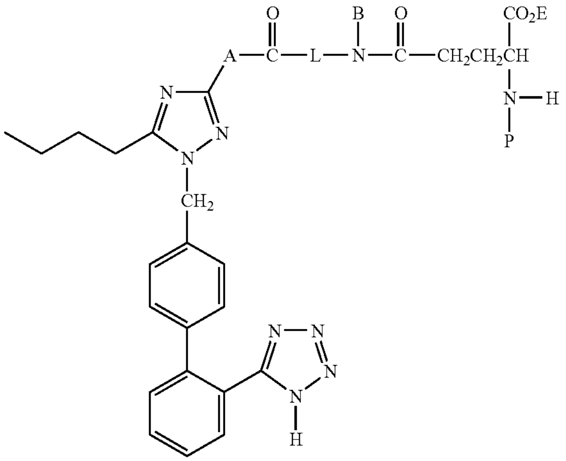
| Ex. # | A | L | B | E | P |
|---|---|---|---|---|---|
| 819 | 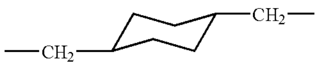 | —$NHCH_2CH_2$— | H | H | $COCH_3$ |
| 820 | 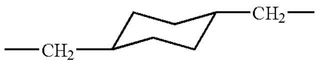 | —$NHCH_2CH_2$— | H | H | $COCH_2Cl$ |
| 821 | 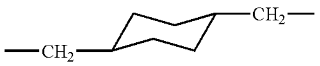 | —$NHCH_2CH_2$— | H | H | $COC_4H_9$ |
| 822 | 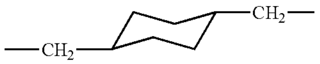 | —$NHCH_2CH_2$— | H | $CH_3$ | $COCH_3$ |
| 823 | 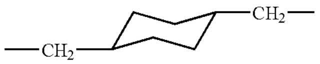 | —$NHCH_2CH_2$— | H | $C_2H_5$ | $COCH_3$ |
| 824 | 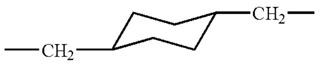 | —$NHCH_2CH_2$— | H | H | H |
| 825 | 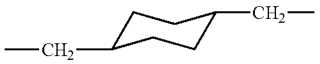 | —$NHCH_2CH_2$— | H | $CH_3$ | H |
| 826 | 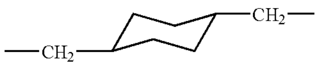 | —$NHCH_2CH_2$— | H | $C_2H_5$ | H |
| 827 | 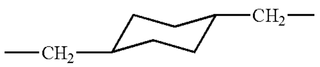 | 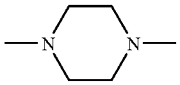 | * | H | $COCH_3$ |
| 828 | 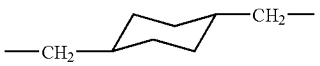 | 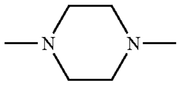 | H | H | $COCH_2Cl$ |
| 829 | 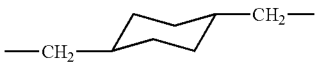 | 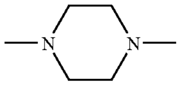 | H | H | $COC_4H_9$ |
| 830 | 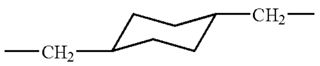 | 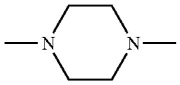 | H | $CH_3$ | $COCH_3$ |

TABLE VI-continued

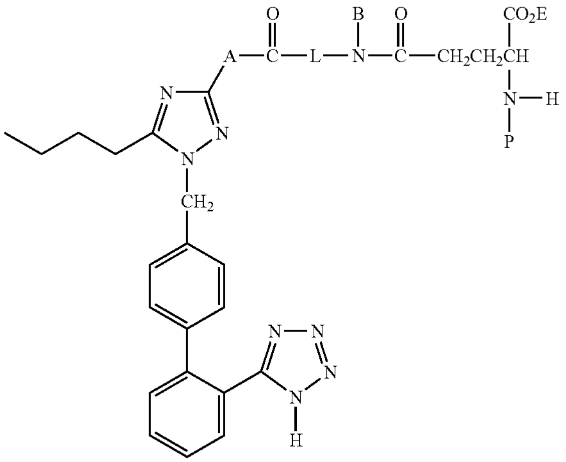

| Ex. # | A | L | B | E | P |
| --- | --- | --- | --- | --- | --- |
| 831 | 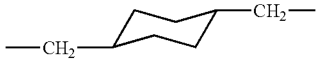 | 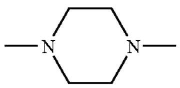 | H | $C_2H_5$ | $COCH_3$ |
| 832 | 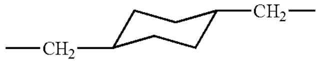 | 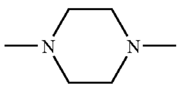 | * | H | H |
| 833 | 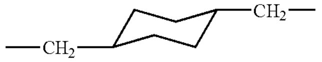 | 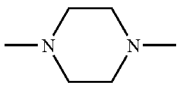 | H | $CH_3$ | H |
| 834 | 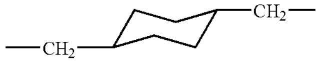 | 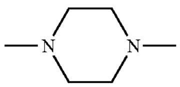 | H | $C_2H_5$ | H |

Biological Evaluation

In order to identify suitable angiotension II antagonists for use as the first component of the conjugate of the invention, certain compounds of Examples 1–17 were evaluated variously in three biological assays (Assays "A", "B" and "C"). In a fourth assay, blood-pressure lowering effects of conjugate of the invention of Example 18 were evaluated (Assay "D").

Assay A: Angiotensin II Binding Activity

Compounds of Formula I were tested for ability to bind to the smooth muscle angiotensin II receptor using a rat uterine membrane preparation. Angiotensin II (AII) was purchased from Peninsula Labs. $^{125}$]-angiotensin II (specific activity of 2200 Ci/mmol) was purchased from Du Pont-New England Nuclear. Other chemicals were obtained from Sigma Chemical Co. This assay was carried out according to the method of Douglas et al [*Endocrinology,* 106, 120–124 (1980)]. Rat uterine membranes were prepared from fresh tissue. All procedures were carried out at 4° C. Uteri were stripped of fat and homogenized in phosphate-buffered saline at pH 7.4 containing 5 mM EDTA. The homogenate was centrifuged at 1500×g for 20 min., and the supernatant was recentrifuged at 100,000×g for 60 min. The pellet was resuspended in buffer consisting of 2 mM EDTA and 50 mM Tris-HCl (pH 7.5) to a final protein concentration of 4 mg/ml. Assay tubes were charged with 0.25 ml of a solution containing 5 mM $MgCl_2$, 2 mM EDTA, 0.5% bovine serum albumin, 50 mM Tris-HCl, pH 7.5 and $^{125}$I-AII (approximately $10^5$ cpm) in the absence or in the presence of unlabelled ligand. The reaction was initiated by the addition of membrane protein and the mixture was incubated at 25° C. for 60 min. The incubation was terminated with ice-cold 50 mM Tris-HCl (pH 7.5) and the mixture was filtered to separate membrane-bound labelled peptide from the free ligand. The incubation tube and filter were washed with ice-cold buffer. Filters were assayed for radioactivity in a Micromedic gamma counter. Nonspecific binding was defined as binding in the presence of 10 μM of unlabelled AII. Specific binding was calculated as total binding minus nonspecific binding. The receptor binding affinity of an AII antagonist compound was indicated by the concentration ($IC_{50}$) of the tested AII antagonist which gives 50% displacement of the total specifically bound $^{125}$I-AII from the high affinity AII receptor. Binding data were analyzed by a nonlinear least-squares curve fitting program. Results are reported in Table VI.

Assay B: In Vitro Vascular Smooth Muscle-Response for ATT

Compounds of Formula I were tested for antagonist activity in rabbit aortic rings. Male New Zealand white rabbits (2–2.5 kg) were sacrificed using an overdose of pentobarbital and exsanguinated via the carotid arteries. The thoracic aorta was removed, cleaned of adherent fat and connective tissue and then cut into 3-mm ring segments. The endothelium was removed from the rings by gently sliding a rolled-up piece of filter paper into the vessel lumen. The rings were then mounted in a water-jacketed tissue bath, maintained at 37° C., between moveable and fixed ends of a stainless steel wire with the moveable end attached to an FT03 Grass transducer coupled to a Model 7D Grass Polygraph for recording isometric force responses. The bath was filled with 20 ml of oxygenated (95% oxygen/5% carbon dioxide) Krebs solution of the following composition (nM): 130 NaCl, 15 $NaHCO_3$, 15 KCl, 1.2 $NaH_2PO_4$, 1.2 $MgSO_4$, 2.5 $CaCl_2$, and 11.4 glucose. The preparations were equilibrated for one hour before approximately one gram of passive tension was placed on the rings. Angiotensin II concentration-response curves were then recorded ($3\times10^{-10}$ to 1x10–5 M). Each concentration of AII was allowed to elicit its maximal contraction, and then AII was washed out repeatedly for 30 minutes before rechallenging with a higher concentration of AII. Aorta rings were exposed to the test antagonist at $10^{-5}$ M for 5 minutes before challenging with AII. Adjacent segments of the same aorta ring were used for all concentration-response curves in the presence or absence of the test antagonist. The effectiveness of the test compound was expressed in terms of $pA_2$ values and were calculated according to H. O. Schild [*Br. J. Pharmacol. Chemother.*, 2, 189–206 (1947)]. The $pA_2$ value is the concentration of the antagonist which increases the $EC_{50}$ value for AII by a factor of 2. Each test antagonist was evaluated in aorta rings from two rabbits. Results are reported in Table VI.

Assay C: In Vivo Intraduodenal Pressor Assay Response for AII Antagonists

Male Sprague-Dawley rats weighing 225–300-grams were anesthetized with Inactin (100 mg/kg, i.p.) and catheters were implanted into the trachea, femoral artery, femoral vein and duodenum. Arterial pressure was recorded from the femoral artery catheter on a Gould chart recorder (Gould, Cleveland, Ohio). The femoral vein catheter was used for injections of angiotensin II, mecamylamine and atropine. The tracheal catheter allow for airway patency, and the duodenal catheter was used for intraduodenal (i.d.) administration of test compounds. After surgery, the rats were allowed to equilibrate for 30 minutes. Mecamylamine (3 mg/kg, 0.3 ml/kg) and atropine (400 ug/kg, 0.3 ml/kg) were then given i.v. to produce ganglion blockade. These compounds were administered every 90 minutes throughout the test procedure. Angiotensin II was given in bolus does i.v. (30 ng/kg in saline with 0.5% bovine serum albumin, 0.1 ml/kg) every 10 minutes three times or until the increase in arterial pressure produced was within 3 mmHg for two consecutive AII injections. The last two AII injections were averaged and were taken as the control AII pressor response. Ten minutes after the final control AII injection, the test compound of Formula I (dissolved in sodium bicarbonate) was administered i.d. at a dose of 30 or 100 mg/kg in a volume of 0.2 ml. Angiotensin II injections were then given 5, 10, 20, 30, 45, 60, 75, 90, and 120 minutes after administration of the test compound and response of arterial pressure was monitored. The response to AII was calculated as percent of the control response and then the percent inhibition is calculated as 100 minus the percent control response. Duration of action of a test compound was defined as the time from peak percent inhibition to 50% of peak. One compound at one dose was tested in each rat. Each test compound was tested in two rats and the values for the two rats were averaged. Results are reported in Table IV.

TABLE IV

In Vivo and In Vitro Angiotensin II Activity of Compounds of the Invention

| Test Compound Example # | [1]Assay A $IC_{50}$ (nM) | [2]Assay B $pA_2$ | Dose (mg/kg) | [3]Assay C Inhibition (%) | Duration (min.) |
|---|---|---|---|---|---|
| 1 | NT | NT | NT | NT | NT |
| 2 | 95 | 7.37/7.59 | 10 | 95 | 60 |
| | | | 30 | 98 | 90–120 |
| 3 | 5.4 | 8.70 ± 0.2 | 10 | 50 | >180 |
| | | | 30 | 100 | 200+ |
| 4 | NT | NT | NT | NT | NT |
| 5 | 200 | 7.48/6.91 | 30 | 38 | 20–30 |
| 6 | 1300 | 6.55/6.82 | 100 | 90 | 120 |
| 7 | 84 | 8.01/8.05 | 30 | 90 | 130 |
| 8 | 17,000 | NT | NT | NT | NT |
| 9 | 700 | 6.67/6.12 | 30 | 80 | 75 |
| | | | 100 | 100 | 130 |
| 10 | 4.9 | 8.19/7.59 | 3 | 86 | 100 |
| | | | 30 | 100 | 240 |
| 11 | 160 | 6.45/6.77 | NT | NT | NT |
| 12 | 6.0 | 8.66/8.59 | NT | NT | NT |
| 13 | 17 | 8.70/8.85 | NT | NT | NT |
| 14 | 7.2 | 8.84/8.71 | NT | NT | NT |
| 15 | 16 | 8.31/8.30 | NT | NT | NT |
| 16 | 6.4 | 8.95/9.24 | NT | NT | NT |
| 17 | 4.0 | 8.64/8.40 | NT | NT | NT |
| 18 | 970 | 6.14/6.09 | NT | NT | NT |
| 19 | 12,000 | 5.18/5.35 | NT | NT | NT |
| 20 | 78,000 | 5.89/5.99 | 100 | 10 | 45 |
| 21 | 87 | 7.71.7.21 | NT | NT | NT |
| 22 | 460 | 6.60/6.46 | NT | NT | NT |
| 23 | 430 | 6.48/7.15 | NT | NT | NT |
| 24 | 10 | 7.56/7.73 | NT | NT | NT |
| 25 | 480 | 6.80/6.73 | NT | NT | NT |
| 26 | 3.2 | 9.83/9.66 | 10 | 50 | >180 |
| 27 | 180 | NT | NT | NT | NT |
| 28 | 570 | 5.57/6.00 | NT | NT | NT |
| 29 | 160 | NT | NT | NT | NT |
| 30 | 22 | 7.73/7.88 | 30 | 50 | >180 |
| 31 | 14 | NT | NT | NT | NT |
| 32 | 16 | 7.68/7.29 | NT | NT | NT |
| 33 | 630 | 6.73/6.36 | NT | NT | NT |
| 34 | 640 | 5.34/5.69 | NT | NT | NT |
| 35 | 41 | 7.25/7.47 | NT | NT | NT |
| 36 | 1400 | 5.92/5.68 | NT | NT | NT |
| 37 | 340 | 6.90/6.85 | NT | NT | NT |
| 38 | 10 | 7.82/8.36 | NT | NT | NT |
| 39 | 10 | 7.88/7.84 | NT | NT | NT |
| 40 | 83 | 7.94/7.61 | NT | NT | NT |
| 41 | 3700 | 5.68/5.96 | NT | NT | NT |
| 42 | 370 | 6.56/6.26 | NT | NT | NT |
| 43 | 19 | 8.97/8.61 | NT | NT | NT |
| 44 | 16 | 8.23/7.70 | NT | NT | NT |
| 45 | 4.4 | 8.41/8.24 | NT | NT | NT |
| 46 | 110 | 6.80/6.64 | NT | NT | NT |
| 47 | 21 | 7.85/7.58 | NT | NT | NT |
| 48 | 680 | 6.27/6.75 | NT | NT | NT |
| 49 | 120 | 7.06/7.07 | NT | NT | NT |
| 50 | 54 | 7.71/7.89 | NT | NT | NT |
| 51 | 8.7 | 8.39/8.51 | NT | NT | NT |
| 52 | 100 | 8.14/8.12 | NT | NT | NT |
| 53 | 65 | 7.56/7.83 | NT | NT | NT |
| 54 | 3100 | 6.02 | NT | NT | NT |
| 55 | 80 | 6.56/7.13 | NT | NT | NT |
| 56 | 5.0 | 9.04/8.35 | NT | NT | NT |
| 57 | 2300 | 6.00 | NT | NT | NT |
| 58 | 140 | 6.45/6.57 | NT | NT | NT |
| 59 | 120 | 7.23/7.59 | NT | NT | NT |

TABLE IV-continued

In Vivo and In Vitro Angiotensin II Activity of Compounds of the Invention

| Test Compound Example # | [1]Assay A $IC_{50}$ (nM) | [2]Assay B $pA_2$ | Dose (mg/kg) | [3]Assay C Inhibition (%) | Duration (min.) |
|---|---|---|---|---|---|
| 60 | 2200 | 6.40/6.03 | NT | NT | NT |
| 61 | 110 | 7.29/7.70 | NT | NT | NT |
| 62 | 26 | 8.69/8.61 | NT | NT | NT |
| 63 | 61 | 7.77/7.67 | NT | NT | NT |
| 64 | 54 | 7.00/6.77 | NT | NT | NT |
| 65 | 23 | 7.85/7.75 | NT | NT | NT |
| 66 | 12 | 9.34/8.58 | NT | NT | NT |
| 67 | 3100 | 5.88/5.78 | NT | NT | NT |
| 68 | 8.6 | 8.19/8.65 | NT | NT | NT |
| 69 | 15 | 7.80/8.28 | NT | NT | NT |
| 70 | 44 | 7.71/8.05 | NT | NT | NT |
| 71 | 12,000 | * | NT | NT | NT |
| 72 | 83 | 6.11/6.10 | NT | NT | NT |
| 73 | 790 | 7.65/7.46 | NT | NT | NT |
| 74 | 6.5 | 8.56/8.39 | NT | NT | NT |
| 75 | 570 | 6.00/5.45 | NT | NT | NT |
| 76 | 5400 | 5.52/5.78 | NT | NT | NT |
| 77 | 15,000 | 5.77 | NT | NT | NT |
| 78 | 480 | 6.41/6.35 | NT | NT | NT |

NT = NOT TESTED
* Antagonist activity not observed up to 10 μM of test compound.
[1]Assay A: Angiotensin II Binding Activity
[2]Assay B: In Vitro Vascular Smooth Muscle Response
[3]Assays C/D: In Vivo Pressor Response (test compounds administered intraduodenally, except for compounds of Examples #3, #26 and #30 which were given intragastrically).

Assay D: In Vivo Effects of Chronic Infusion of Conjugate of the Invention

Figure 2:
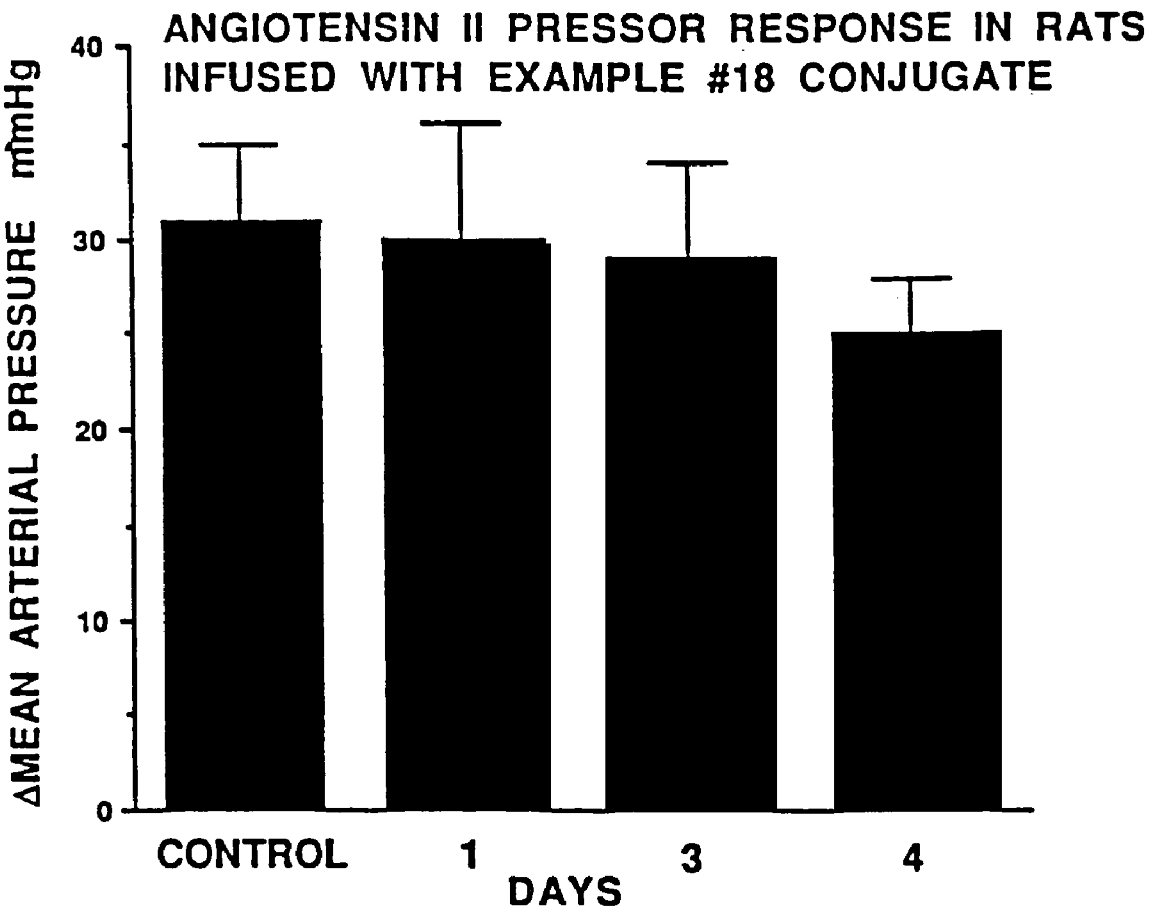
FIG. 2 is a graph showing angiotensin II pressor response by intravenous administration of a conjugate of the invention to rats over a period of four days.
Figure 3:
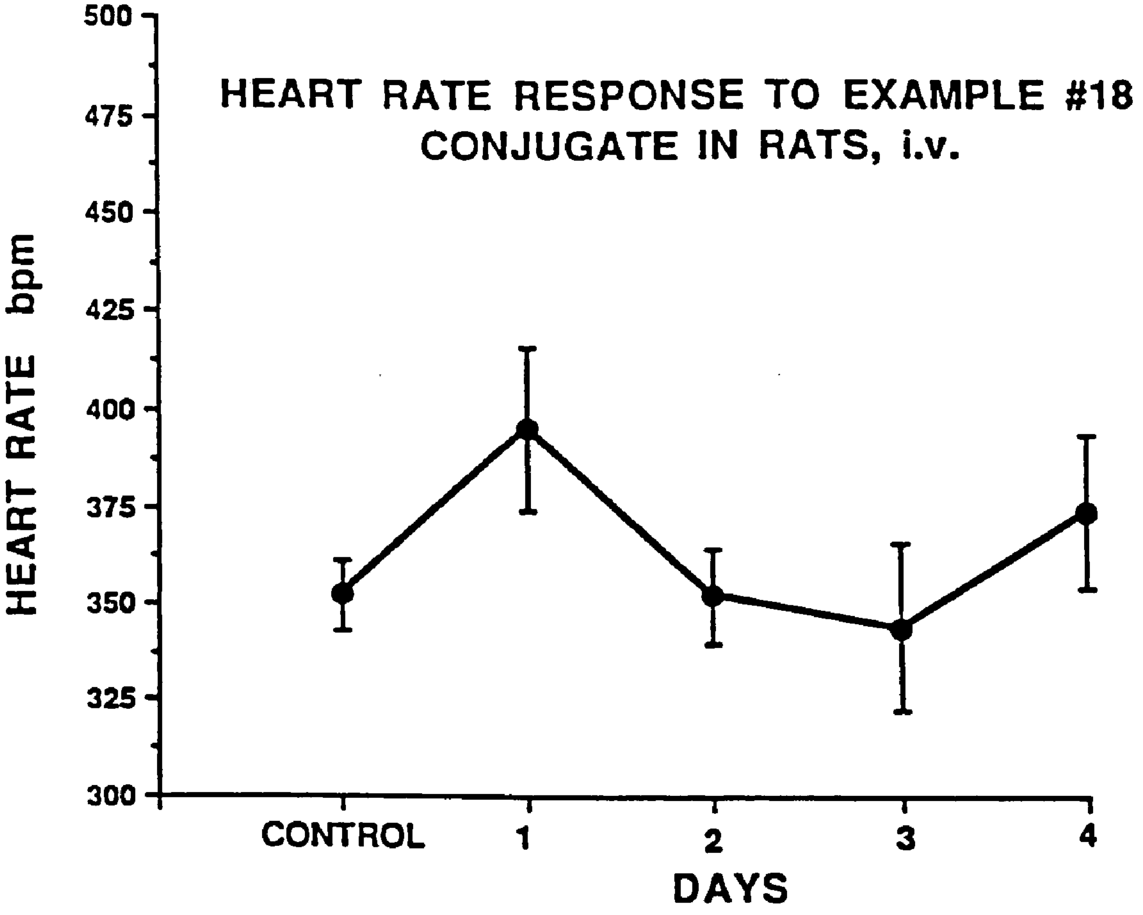
FIG. 3 is a graph showing change in heart rate upon intravenous administration of a conjugate of the invention to rats over a period of four days.

A conjugate of the invention as synthesized in Example 79 was evaluated biologically by in vivo assays to determine the ability of the conjugate to selectively inhibit renal action and thereby control blood pressure. This in vivo experiment was conducted to characterize the effects of the Example 79 conjugate on spontaneously hypertensive rats (SHR) by acute administration i.v. and by chronic administration i.v. The Example 18 compound or saline vehicle was infused continuously for four days in SHR. Mean arterial pressure was measured (Gould Chart Recorder, model 3800; Statham P23 Db pressure transducer) via an indwelling femoral artery catheter between 10:00 a.m. and 2:00 P.M. each day. The Example 79 conjugate (10 mg/hr) or saline was infused via a jugular vein catheter with a Harvard infusion pump. After administration of the Example 79 conjugate, there was observed a lowered mean arterial pressure as compared to the saline vehicle control as reported in Table V and also in FIG. 1. A test was conducted to determine whether the Example 79 conjugate would antagonize non-renal, vascular angiotensin II receptors. In this test AII was administered by bolus injection (100 ng/kg) to the SHR rats (described above) on the control day and on days 1, 3 and 4 during conjugate infusion. No evidence for systemic angiotensin II receptor antagonism was observed, given the similar pressor responses to injections of angiotensin II on the control day and days 1, 3 and 4 of infusion of the Example 79 conjugate (see FIG. 2). Tachycardia was observed on day 1 of the conjugate infusion, but heart rate was returned to control level during the next three days (see FIG. 3).

TABLE V

Effect of Ex. #79 Conjugate on Mean Arterial Pressure: Chronic Administration

| | Time (days): | | | | |
|---|---|---|---|---|---|
| | Control | 1 | 2 | 3 | 4 |
| | | Ex. #18 Conjugate (10 mg/hr) | | | |
| MAP (mm Hg): (SD) | 183 ± 5 | 159 ± 7 | 155 ± 4 | 154 ± 6 | 166 ± 9 |

TABLE VI

Effect of Ex. #18 Conjugate on AII Pressor Response

| | Time (days): | | | |
|---|---|---|---|---|
| | Control | 1 | 3 | 4 |
| | | Ex. #18 Conjugate (10 mg/hr) | | |
| (SD) | 31 ± 4 | 30 ± 6 | 29 ± 5 | 25 ± 3 |

TABLE VII

Effect of Ex. #79 Conjugate on Heart Rate

| | Time (days): | | | | |
|---|---|---|---|---|---|
| | Control | 1 | 2 | 3 | 4 |
| | | Ex. #18 Conjugate (10 mg/hr) | | | |
| Beats/min.: (SD) | 352 ± 9 | 395 ± 21 | 352 ± 12 | 344 ± 22 | 374 ± 20 |

Also embraced within this invention is a class of pharmaceutical compositions comprising one or more conjugates which comprises a first component selected from angiotensin II antagonist compounds of Formula I linked to a second component provided by an enzyme-cleavable moiety. Such pharmaceutical compositions further comprise one or more non-toxic, pharmaceutically acceptable carriers and/or diluents and/or adjuvants (collectively referred to herein as "carrier" materials) and, if desired, other active ingredients. The conjugates of the present invention may be administered by any suitable route, preferably in the form of a pharmaceutical composition adapted to such a route, and in a dose effective for the treatment intended. Therapeutically effective doses of a conjugate of the present invention required to prevent or arrest the progress of the medical condition are readily ascertained by one of ordinary skill in the art. The conjugates and composition may, for example, be administered intravascularly, intraperitoneally, subcutaneously, intramuscularly or topically.

For oral administration, the pharmaceutical composition may be in the form of, for example, a tablet, capsule, suspension or liquid. The pharmaceutical composition is preferably made in the form of a dosage unit containing a particular amount of the conjugate. Examples of such dosage units are tablets or capsules. These may with advantage contain an amount of conjugate from about 1 to 250 mg, preferably from about 25 to 150 mg. A suitable daily dose for a mammal may vary widely depending on the condition of the patient and other factors. However, a dose of from about 0.1 to 3000 mg/kg body weight, particularly from about 1 to 100 mg/kg body weight, may be appropriate.

The conjugate may also be administered by injection as a composition wherein, for example, saline, dextrose or water may be used as a suitable carrier. A suitable daily dose is from about 0.1 to 100 mg/kg body weight injected per day in multiple doses depending on the disease being treated. A preferred daily dose would be from about 1 to 30 mg/kg body weight. Conjugates indicated for prophylactic therapy will preferably be administered in a daily dose generally in a range from about 0.1 mg to about 100 mg per kilogram of body weight per day. A more preferred dosage will be a range from about 1 mg to about 100 mg per kilogram of body weight. Most preferred is a dosage in a range from about 1 to about 50 mg per kilogram of body weight per day. A suitable dose can be administered, in multiple sub-doses per day. These sub-doses may be administered in unit dosage forms. Typically, a dose or sub-dose may contain from about 1 mg to about 100 mg of active compound per unit dosage form. A more preferred dosage will contain from about 2 mg to about 50 mg of active compound per unit dosage form. Most preferred is a dosage form containing from about 3 mg to about 25 mg of active compound per unit dose.

The dosage regimen for treating a disease condition with the conjugates and/or compositions of this invention is selected in accordance with a variety of factors, including the type, age, weight, sex and medical condition of the patient, the severity of the disease, the route of administration, and the particular conjugate employed, and thus may vary widely.

For therapeutic purposes, the conjugates of this invention are ordinarily combined with one or more adjuvants appropriate to the indicated route of administration. If administered per os, the conjugate may be admixed with lactose, sucrose, starch powder, cellulose esters of alkanoic acids, cellulose alkyl esters, talc, stearic acid, magnesium stearate, magnesium oxide, sodium and calcium salts of phosphoric and sulfuric acids, gelatin, acacia gum, sodium alginate, polyvinylpyrrolidone, and/or polyvinyl alcohol, and then tableted or encapsulated for convenient administration. Such capsules or tablets may contain a controlled-release formulation as may be provided in a dispersion of conjugate in hydroxypropylmethyl cellulose. Formulations for parenteral administration may be in the form of aqueous or non-aqueous isotonic sterile injection solutions or suspensions. These solutions and suspensions may be prepared from sterile powders or granules having one or more of the carriers or diluents mentioned for use in the formulations for oral administration. The conjugates may be dissolved in water, polyethylene glycol, propylene glycol, ethanol, corn oil, cottonseed oil, peanut oil, sesame oil, benzyl alcohol, sodium chloride, and/or various buffers. Other adjuvants and modes of administration are well and widely known in the pharmaceutical art.

Although this invention has been described with respect to specific embodiments, the details of these embodiments are not to be construed as limitations. Various equivalents, changes and modifications may be made without departing from the spirit and scope of this invention, and it is understood that such equivalent embodiments are part of this invention.

What is claimed is:

1. A conjugate consisting of a first radical and second radical connected together by a kidney-enzyme-cleavable amide bond, wherein said first radical is an angiotensin II antagonist compound selected from a class of compounds defined by Formula I:

(I)

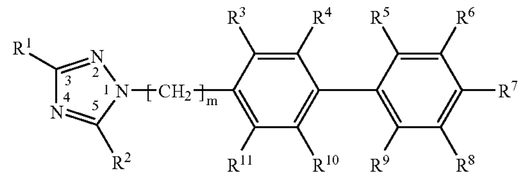

wherein m is a number selected from one to four, inclusive;

wherein each of $R^1$ through $R^{11}$ is independently selected from hydrido, alkyl, hydroxyalkyl, halo, haloalkyl, cycloalkyl, cycloalkylalkyl, formyl, alkoxy, aralkyl, aryl, aroyl, aryloxy, aryloxyalkyl, aralkoxy, alkoxyalkyl, alkylcarbonyl, alkylcarbonylalkyl, alkoxycarbonyl, alkenyl, cycloalkenyl, alkynyl, cyano, nitro, carboxyl, alkylthio, cycloalkylthio, alkylthiocarbonyl, alkylcarbonylthio, alkylthiocarbonyloxy, alkylthiocarbonylthio, alkylthiothiocarbonyl, alkylthiothiocarbonylthio, arylthio, arylthiocarbonyl, arylcarbonylthio, arylthiocarbonyloxy, arylthiocarbonylthio, arylthiothiocarbonyl, arylthiothiocarbonylthio, aralkylthio, aralkylthiocarbonyl, aralkylcarbonylthio, aralkylthiocarbonyloxy, aralkylthiocarbonylthio, alkylthiocarbonyl, aralkylthiocarbonylthio, mercapto, alkylsulfinyl, alkylsulfonyl, aralkylsulfinyl, aralkylsulfonyl, arylsulfinyl, arylsulfonyl, or tetrazol, and wherein each of $R^1$ through $R^{11}$ may be further independently selected front amino and amido radicals of the formula

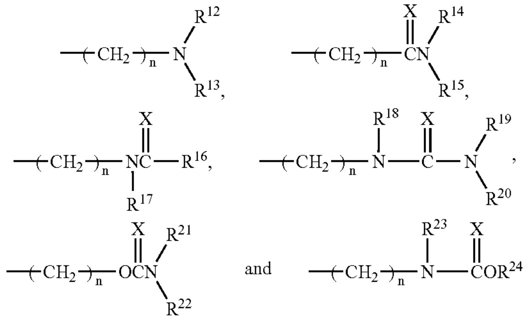

and wherein X is oxygen atom or sulfur atom;

wherein each n is a number independently selected from zero to six, inclusive;

wherein each of $R^{12}$ through $R^{24}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;

and wherein each of $R^3$ through $R^{11}$ may be further independently selected from hydroxy and from acidic moieties of the formula $$—Y_nA$$

wherein n is a number selected from zero through three, inclusive, and wherein A is an acidic group selected to contain at least one acidic hydrogen atom, and the amide, ester and salt derivatives of said acidic moieties;

wherein Y is a spacer group independently selected from one or more of alkyl, cycloalkyl, cycloalkylalkyl, alkenyl, alkynyl, aryl, aralkyl;

and wherein any of the foregoing $R^1$ through $R^{24}$, Y and A groups having a substitutable position may be substituted with one or more groups selected from hydroxy, alkyl, alkenyl, alkynyl, aralkyl, hydroxyalkyl, trifluoromethyl, difluoroalkyl, oxo, alkoxy, aryloxy, aralkoxy, aralkylthio, alkoxyalkyl, cycloalkyl, cycloalkylalkyl, aryl, aroyl, cycloalkenyl, cyano, cyanoamino, nitro, alkylcarbonyloxy, alkoxycarbonyloxy, alkylcarbonyl, alkoxycarbonyl, carboxyl, mercapto, mercaptocarbonyl, alkylthio, arylthio, alkylthiocarbonyl, alkylsulfinyl, alkylsulfonyl, aralkylsulfinyl, aralkylsulfonyl, arylsulfinyl, arylsulfonyl, tetrazole, and amino and amido radicals of the formula

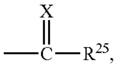

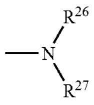

and

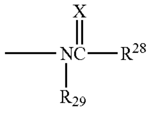

wherein X is selected from oxygen atom and sulfur atom; wherein each of $R^{25}$, $R^{26}$, $R^{27}$, $R^{28}$ and $R^{29}$ is selected from hydrido, alkyl, cycloalkyl, cycloalkylalkyl, aralkyl, aryl, $DR^{30}$ and

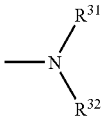

wherein D is selected from oxygen atom and sulfur atom and $R^{30}$ is selected from hydrido, alkyl, cycloalkyl, cycloalkylalkyl, aralkyl and aryl; wherein each of $R^{25}$, $R^{26}$, $R^{27}$, $R^{28}$, $R^{29}$, $R^{31}$ and $R^{32}$ is independently selected from hydrido, alkyl, cycloalkyl, cyano, hydroxyalkyl, haloalkyl, cycloalkylalkyl, alkoxyalkyl, alkylcarbonyl, alkoxycarbonyl, carboxyl, alkylsulfinyl, alkylsulfonyl, arylsulfinyl, arylsulfonyl, haloalkylsulfinyl, haloalkylsulfonyl, aralkyl and aryl, and wherein each of $R^{25}$, $R^{26}$, $R^{27}$, $R^{28}$, $R^{29}$, $R^{31}$ and $R^{32}$ is further independently selected from amino and amido radicals of the formula

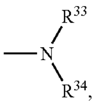

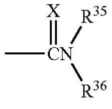

and

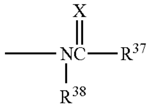

wherein X is oxygen atom or sulfur atom;

wherein each of $R^{33}$, $R^{34}$, $R^{35}$, $R^{36}$, $R^{37}$ and $R^{38}$ is independently selected from hydrido, alkyl, cycloalkyl, cyano, amino, monoalkylamino, dialkylamino, hydroxyalkyl, cycloalkylalkyl, alkoxyalkyl, haloalkylsulfinyl, haloalkylsulfonyl, aralkyl and aryl;

with the proviso that at least one of said $R^1$ through $R^{24}$, Y and A substituents contains a terminal primary or secondary amino moiety or a moiety convertible to a primary or secondary amino moiety;

wherein said second residue is selected from a class of compounds of Formula II:

(II)

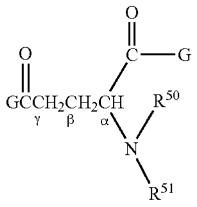

wherein each of $R^{50}$ and $R^{51}$ may be independently selected from hydrido, alkylcarbonyl, alkoxycarbonyl, alkoxyalkyl, hydroxyalkyl and haloalkyl; and wherein G is selected from hydroxyl, halo, mercapto, —$OR^{52}$, —$SR^{53}$ and

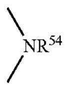

with each of $R^{52}$, $R^{53}$ and $R^{54}$ independently selected from alkyl; and wherein $R^{54}$ may be further selected from hydrido; with the proviso that said Formula II compound is selected such that formation of the cleavable amide bond occurs at carbonyl moiety attached at the gamma-position carbon of said Formula II compound; and wherein the kidney-enzyme-cleavable amide bond is a divalent radical of Formula III:

(III)

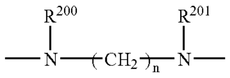

wherein each of $R^{200}$ and $R^{201}$ may be independently selected from hydrido, alkyl, cycloalkyl, cycloalkylalkyl, alkoxyalkyl, hydroxyalkyl, aralkyl, aryl, haloalkyl, amino, monoalkylamino, dialkylamino, cyanoamino, carboxyalkyl, alkylsulfinyl, alkylsulfonyl, arylsulfinyl and arylsulfonyl; and wherein n is zero or a number selected from three through seven, inclusive;

or a tautomer thereof or a pharmaceutically-acceptable salt thereof.

2. Conjugate of claim 1 wherein m is one; wherein each of $R^1$ through $R^{11}$ is independently selected from alkyl, hydroxyalkyl, halo, haloalkyl, cycloalkyl, cycloalkylalkyl, alkoxy, aralkyl, aryl, aroyl, aryloxy, aryloxyalkyl, aralkoxy, alkoxyalkyl, alkylcarbonyl, alkoxycarbonyl, alkenyl, cycloalkenyl, alkynyl, cycloalkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptothiocarbonyl, mercaptoalkyl, alkoxycarbonyloxy, alkylthio, cycloalkylthio, alkylthiocarbonyl, alkylcarbonylthio, alkylthiocarbonyloxy, alkylthiocarbonylthio, alkylthiothiocarbonyl, alkylthiothiocarbonylthio, arylthio, arylthiocarbonyl, arylcarbonylthio, arylthiocarbonyloxy, arylthiocarbonylthio, arylthiothiocarbonyl, arylthiothiocarbonylthio, aralkylthio, aralkylthiocarbonyl, aralkylcarbonylthio, aralkylthiocarbonyloxy, aralkylthiocarbonylthio, aralkylthiocarbonyl, aralkylthiocarbonylthio, mercapto, alkylsulfinyl, alkylsulfonyl, aralkylsulfinyl, aralkylsulfonyl, arylsulfinyl, arylsulfonyl, tetrazole, and wherein each of $R^1$ through $R^{11}$ may be further independently selected from amino and amido radicals of the formula

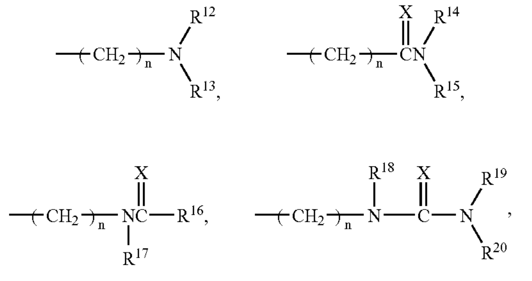

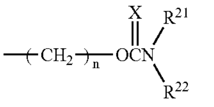

and

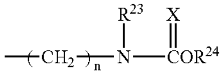

wherein X is selected from oxygen atom or sulfur atom;

wherein each n is a number independently selected from zero to six, inclusive;

wherein each of $R^{12}$ through $R^{24}$ is independently selected from hydride, alkyl, cycloalkyl, cyano, amino, monoalkylamino, dialkylamino, hydroxyalkyl, cycloalkylalkyl, alkoxyalkyl, aralkyl and aryl;

and wherein each of $R^3$ through $R^{11}$ may be further independently selected from hydroxy and from acidic moieties of the formula $$-Y_nA$$

wherein n is a number selected from zero through three, inclusive; wherein A is an acidic group selected from acids containing one or more atoms selected from oxygen, sulfur, phosphorus and nitrogen atoms, and wherein said acidic group is selected to contain at least one acidic hydrogen atom, and the amide, ester and salt derivatives of said acidic moieties; wherein Y is a spacer group independently selected from one or more of alkyl, cycloalkyl, cycloalkylalkyl, alkenyl, alkynyl, aryl, and aralkyl;

and wherein any of the foregoing $R^1$ through $R^{24}$, Y and A groups having a substitutable position may be substituted with one or more groups selected from alkyl, alkenyl, aralkyl, hydroxyalkyl, trifluoromethyl, difluoroalkyl, alkoxy, aryloxy, aralkoxy, alkoxyalkyl, alkylcarbonyl, alkoxycarbonyl, carboxyl, mercaptocarbonyl, alkylthio, alkylthiocarbonyl, and amino and amido radicals of the formula

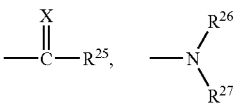

and

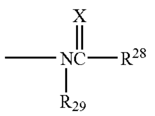

wherein X is selected from oxygen atom and sulfur atom; wherein each of $R^{25}$, $R^{26}$, $R^{27}$, $R^{28}$ and $R^{29}$ is selected from hydrido, alkyl, cycloalkyl, cycloalkylalkyl, aralkyl, aryl, and and $DR^{30}$ and

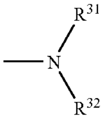

wherein D is selected from oxygen atom and sulfur atom, and $R^{30}$ is selected from hydrido, alkyl, cycloalkyl, cycloalkylalkyl, aralkyl and aryl; wherein each of $R^{25}$, $R^{26}$, $R^{27}$, $R^{28}$, $R^{29}$, $R^{31}$ and $R^{32}$ is independently selected from hydrido, alkyl, cycloalkyl, cyano, hydroxyalkyl, haloalkyl, cycloalkylalkyl, alkoxyalkyl, alkanoyl, alkoxycarbonyl, carboxyl, haloalkylsulfinyl, haloalkylsulfonyl, aralkyl and aryl, and wherein each of $R^{25}$, $R^{26}$, $R^{27}$, $R^{28}$, $R^{29}$, $R^{31}$ and $R^{32}$ is further independently selected from amino and amido radicals of the formula

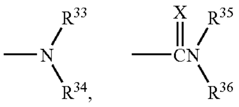

and

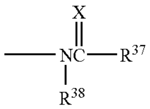

wherein X is selected from oxygen atom or sulfur atom;

wherein each of $R^{33}$ through $R^{38}$ is independently selected from hydrido, alkyl, cycloalkyl, cyano, ammo, monoalkylamino, dialkylamino, hydroxyalkyl, cycloalkylalkyl, alkoxyalkyl, haloalkylsulfinyl, haloalkylsulfonyl, aralkyl and aryl;

with the proviso that at least one of said $R^1$ through $R^{24}$, Y and A substituents contains a terminal primary or secondary amino moiety or a moiety convertible to a primary or secondary amino moiety;

or a tautomer thereof or a pharmaceutically-acceptable salt thereof.

3. Conjugate of claim 2 wherein m is one; wherein each of $R^1$ through $R^{11}$ is independently selected from alkyl, hydroxyalkyl, halo, haloalkyl, cycloalkyl, cycloalkylalkyl, alkoxy, aralkyl, aryl, aroyl, aryloxy, aryloxyalkyl, aralkoxy, alkoxyalkyl, alkylcarbonyl, alkoxycarbonyl, alkenyl, cycloalkenyl, alkynyl, cycloalkynyl, cyano, nitro, carboxyl, carboxyalkyl, alkylcarbonyloxy, mercaptocarbonyl, alkoxycarbonyloxy, alkylcarbonyloxyalkyl, alkoxycarbonylalkyl, aralkoxycarbonylalkyl, aralkylcarbonyloxyalkyl, alkylthio, cycloalkylthio, arylthio, aralkylthio, aralkylthiocarbonylthio, mercapto, alkylsulfinyl, alkylsulfonyl, aralkylsulfinyl, aralkylsulfonyl, arylsulfinyl, arylsulfonyl, tetrazole, and wherein each of $R^1$ through $R^{11}$ may be further independently selected from amino and amido radicals of the formula

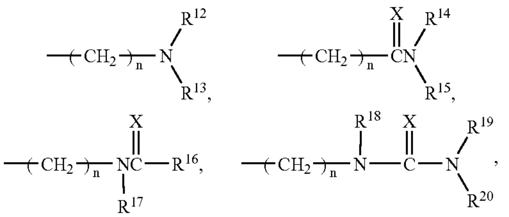

-continued

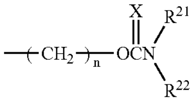

and

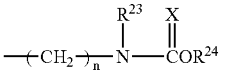

wherein X is selected from oxygen atom or sulfur atom;

wherein each n is a number independently selected from zero to six, inclusive;

wherein each of $R^{12}$ through $R^{24}$ is independently selected from hydrido, alkyl, cycloalkyl, cyano, amino, monoalkylamino, dialkylamino, hydroxyalkyl, cycloalkylalkyl, alkoxyalkyl, aralkyl and aryl;

and wherein each of $R^3$ through $R^{11}$ may be further independently selected from hydroxy and from acidic moieties of the formula $$—Y_nA$$

wherein n is a number selected from zero through three, inclusive;

wherein A is selected from carboxylic acid and bioisosteres of carboxylic acid selected from

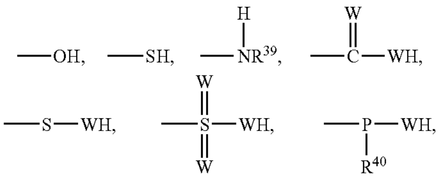

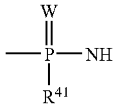

and

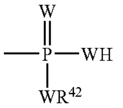

wherein each W is independently selected from oxygen atom, sulfur atom and $NR^{43}$; wherein each of $R^{39}$, $R^{40}$, $R^{41}$, $R^{42}$ and $R^{43}$ is independently selected from hydrido, alkyl, haloalkyl, haloalkylsulfonyl, haloalkylcarbonyl, cycloalkyl, cycloalkylalkyl, aryl and aralkyl; wherein each of $R^{39}$, $R^{40}$, $R^{41}$ and $R^{42}$ may he further independently selected from amino radical of the formula

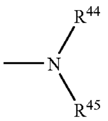

wherein each of $R^{44}$ and $R^{45}$ is independently selected from hydrido, alkyl, cycloalkyl, hydroxyalkyl, haloalkyl, cycloalkylalkyl, alkoxyalkyl, aralkyl and aryl; wherein each of $R^{44}$ and $R^{45}$ may be further independently selected from hydroxy, alkoxy, alkylthio, aryloxy, arylthio, aralkylthio and aralkoxy; and the amide, ester and salt derivatives of said acidic groups;

wherein said bioisostere of carboxylic acid may be tetrazole;

wherein Y is a spacer group independently selected from one or more of alkyl, cycloalkyl, cycloalkylalkyl, alkenyl, aryl and aralkyl;

and wherein any of the foregoing $R^1$ through $R^{24}$, Y and A groups having a substitutable position may be substituted by one or mare groups selected from alkyl, difluoroalkyl, alkenyl, aralkyl, hydroxyalkyl, trifluoromethyl, alkoxy, aryloxy, aralkoxy, alkoxyalkyl, alkylcarbonyl, alkoxycarbonyl, carboxyl, mercaptocarbonyl, alkylthio, alkylthiocarbonyl, and amino and amido radicals of the formula

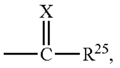

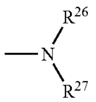

and

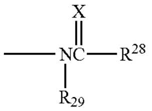

wherein X is selected from oxygen atom and sulfur atom; wherein each of $R^{25}$, $R^{26}$, $R^{27}$, $R^{28}$ and $R^{29}$ is selected from hydrido, alkyl, cycloalkyl, cycloalkylalkyl, aralkyl, aryl and $DR^{30}$ and

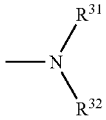

wherein D is selected from oxygen atom and sulfur atom, wherein $R^{30}$ is selected from hydrido, alkyl, cycloalkyl, cycloalkylalkyl, aralkyl and aryl;

wherein each of $R^{25}$, $R^{26}$, $R^{27}$, $R^{28}$, $R^{29}$, $R^{31}$ and $R^{32}$ is independently selected from hydrido, alkyl, cycloalkyl, cyano, hydroxyalkyl, haloalkyl, cycloalkylalkyl, alkoxyalkyl, alkanoyl, alkoxycarbonyl, carboxyl, haloalkylsulfinyl, haloalkylsulfonyl, aralkyl and aryl;

with the proviso that at least one of said $R^1$ through $R^{24}$, Y and A substituents contains a terminal primary or secondary amino moiety or a moiety convertible to a primary or secondary amino moiety;

or a tautomer thereof or a pharmaceutically-acceptable salt thereof.

4. Conjugate of claim 3 wherein m is one; wherein each of $R^1$ and $R^2$ is independently selected from alkyl, hydroxyalkyl, halo, haloalkyl, cycloalkyl, cycloalkylalkyl, alkoxy, aralkyl, aryl, aroyl, aryloxy, aryloxyalkyl, aralkoxy, alkoxyalkyl, alkylcarbonyl, alkoxycarbonyl, alkenyl, cycloalkenyl, alkynyl, cycloalkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptoalkyl, alkoxycarbonyloxy, alkylthio, cycloalkylthio, arylthio, aralkylthio, mercapto, alkylsulfinyl, alkylsulfonyl, aralkylsulfinyl, aralkylsulfonyl, arylsulfinyl, arylsulfonyl, tetrazole, and wherein each of $R^1$ through $R^{11}$ may be further independently selected from amino and amido radicals of the formula

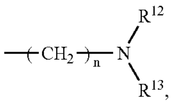

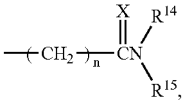

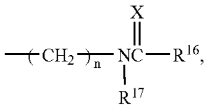

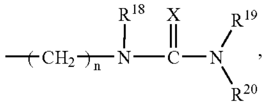

-continued

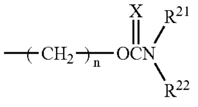

and

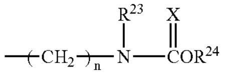

wherein X is selected from oxygen atom and sulfur atom;

wherein each n is a number independently selected from zero to six, inclusive;

wherein each of $R^{12}$ through $R^{24}$ is independently selected from hydride, alkyl, cycloalkyl, cyano, amino, monoalkylamino, dialkylamino, hydroxyalkyl, cycloalkylalkyl, alkoxyalkyl, aralkyl and aryl;

wherein each of $R^3$ through $R^{11}$ is independently selected from hydrido, hydroxy, alkyl, hydroxyalkyl, halo, haloalkyl, cycloalkyl, cycloalkylalkyl, alkoxy, aralkyl, aryl, aroyl, aryloxy, aralkoxy, alkoxyalkyl, alkylcarbonyl, alkoxycarbonyl, alkenyl, cycloalkenyl, alkynyl, cycloalkynyl, cyano, nitro, carboxyl, alkylthio, aralkylthio, mercapto, alkylsulfinyl, alkylsulfonyl, aralkylsulfinyl, aralkylsulfonyl, arylsulfinyl, arylsulfonyl and tetrazole;

and wherein each of $R^3$ through $R^{11}$ may be an acidic moiety further independently selected from acidic moieties of the formula $-Y_nA$ wherein n is a number selected from zero through three, inclusive; wherein A is selected from carboxylic acid and bioisosteres of carboxylic acid selected from

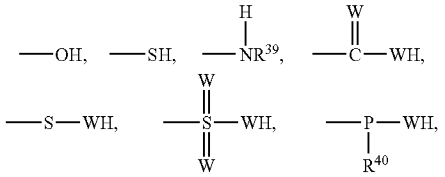

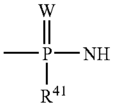

and

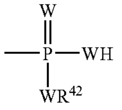

wherein each W is independently selected from oxygen atom, sulfur atom and $NR^{43}$; wherein each of $R^{39}$, $R^{42}$ and $R^{43}$ is independently selected from hydrido, alkyl, haloalkyl, haloalkylsulfonyl, haloalkylcarbonyl, cycloalkyl, cycloalkylalkyl, aryl and aralkyl; wherein each of $R^{39}$ and $R^{42}$ may be further independently selected from amino radical of the formula

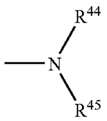

wherein each of $R^{44}$ and $R^{45}$ is independently selected from hydride, alkyl, cycloalkyl, hydroxyalkyl, haloalkyl, cycloalkylalkyl, alkoxyalkyl, aralkyl and aryl;

wherein Y is a spacer group independently selected from one or more of alkyl, cycloalkyl, cycloalkylalkyl, alkenyl, aryl and aralkyl;

wherein each of $R^1$ through $R^{11}$, Y and A independently may be substituted at any substitutable position with one or more groups selected from alkyl, cycloalkyl, cycloalkylalkyl, hydroxy, oxo, trifluoromethyl, difluoroalkyl, alkoxycarbonyl, cyano, nitro, alkylsulfonyl, haloalkylsulfonyl, aryl, aralkyl, alkoxy, aryloxy and aralkoxy;

with the proviso that at least one of said $R^1$ through $R^{24}$, Y and A substituents contains a terminal primary or secondary amino moiety or a moiety convertible to a primary or secondary amino moiety;

or a tautomer thereof or a pharmaceutically-acceptable salt thereof.

5. Conjugate of claim 4 wherein m is one; wherein each of $R^1$ and $R^2$ is independently selected from alkyl, hydroxyalkyl, halo, haloalkyl, cycloalkyl, cycloalkylalkyl, alkoxy, aralkyl, aryl, benzoyl, phenoxy, phenoxyalkyl, phenalkyloxy, phenylthio, phenalkylthio, aralkoxy, alkoxyalkyl, alkylcarbonyl, alkoxycarbonyl, alkenyl, cycloalkenyl, alkynyl, cyano, nitro, carboxyl, carboxyalkyl, alkylcarbonyloxy, alkylcarbonyloxyalkyl, alkoxycarbonylalkyl, aralkoxycarbonylalkyl, aralkylcarbonyloxyalkyl, mercaptocarbonyl, mercaptoalkyl, alkoxycarbonyloxy, alkylthio, cycloalkylthio, tetrazole, and wherein each of $R^1$ through $R^{11}$ may be further independently selected from amino and amido radicals of the formula

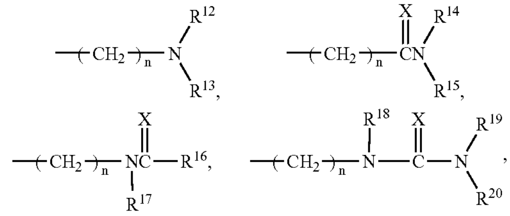

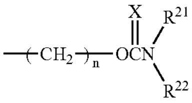

and

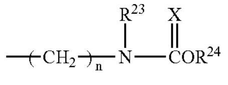

wherein X is selected from oxygen atom and sulfur atom;

wherein each n is a number independently selected from zero to six, inclusive;

wherein each of $R^{12}$ through $R^{24}$ is independently selected from hydrido, alkyl, cycloalkyl, cyano, amino, hydroxyalkyl, alkoxyalkyl, phenalkyl and phenyl;

wherein each of $R^3$ through $R^{11}$ is independently selected from hydrido, hydroxy, alkyl, hydroxyalkyl, halo, halo alkyl, cycloalkyl, cycloalkylalkyl, alkoxy, phenalkyl, phenyl, benzoyl, phenoxy, phenalkyloxy, alkoxyalkyl, alkylcarbonyl, alkoxycarbonyl, alkenyl, cyano, nitro, carboxyl, alkylthio, and mercapto;

and wherein each of $R^3$ through $R^{11}$ may be an acidic moiety further independently selected from acidic moieties of the formula $-Y_nA$ wherein n is a number selected from zero through two, inclusive; wherein A is selected from carboxylic acid and bioisosteres of carboxylic acid selected from

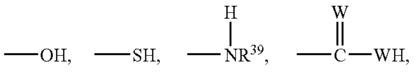

-continued

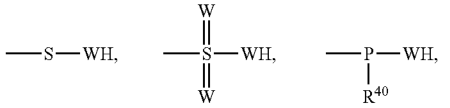

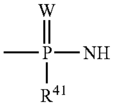

and

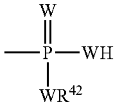

wherein each W is independently selected from oxygen atom, sulfur atom and $NR^{43}$; wherein each of $R^{39}$, $R^{42}$ and $R^{43}$ is independently selected from hydrido, alkyl, haloalkyl, haloalkylsulfonyl, haloalkylcarbonyl, cycloalkyl, phenyl and benzyl; wherein each of $R^{39}$ and $R^{42}$ may be further independently selected from amino radical of the formula

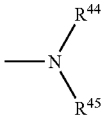

wherein each of $R^{44}$ and $R^{45}$ is independently selected from hydrido, alkyl, cycloalkyl, hydroxyalkyl, haloalkyl, alkoxyalkyl, benzyl and phenyl; and the amide, ester and salt derivatives of said acidic groups;

wherein Y is a spacer group independently selected from one or more of alkyl, cycloalkyl, cycloalkylalkyl, alkenyl, phenyl, phenalkyl and aralkyl;

wherein each of $R^1$ through $R^{11}$, Y and A and independently may be substituted at any substitutable position with one or more groups selected from alkyl, cycloalkyl, cycloalkylalkyl, hydroxy, oxo, trifluoromethyl, difluoroalkyl, alkoxycarbonyl, cyano, nitro, alkylsulfonyl, haloalkylsulfonyl, aryl, aralkyl, alkoxy, aryloxy and aralkoxy;

with the proviso that at least one of said $R^1$ through $R^{24}$, Y and A substituents contains a terminal primary or secondary amino moiety or a moiety convertible to a primary or secondary amino moiety;

or a tautomer thereof or a pharmaceutically-acceptable salt thereof.

6. Conjugate of claim 5 wherein m is one; wherein each of $R^1$ and $R^2$ is independently selected from alkyl, aminoalkyl, hydroxyalkyl, halo, haloalkyl, cycloalkyl, cycloalkylalkyl, alkoxy, aralkyl, aryl, benzoyl, phenoxy, phenoxyalkyl, phenalkyloxy, phenylthio, phenalkylthio, aralkoxy, alkoxyalkyl, acetyl, alkoxycarbonyl, alkenyl, cycloalkenyl, alkynyl, cyano, nitro, carboxyl, carboxyalkyl, alkylcarbonyloxy, mercaptoalkyl, mercaptocarbonyl, alkoxycarbonyloxy, alkylcarbonyloxyalkyl, alkoxycarbonylalkyl, aralkoxycarbonylalkyl, aralkylcarbonyloxyalkyl, tetrazole, tetrazolealkyl, alkylthio, cycloalkylthio, and amino and amido radicals of the formula

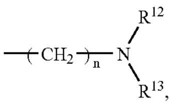

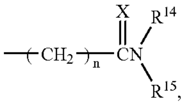

-continued

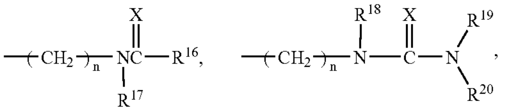

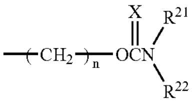

and

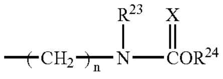

wherein X is selected front oxygen atom and sulfur atom;

wherein each n is a number independently selected from zero to six, inclusive;

wherein each of $R^{12}$ through $R^{24}$ is independently selected from hydrido, alkyl, cycloalkyl, cyano, amino, hydroxyalkyl, alkoxyalkyl, phenalkyl and phenyl;

wherein each of $R^3$ through $R^{11}$ is independently selected from hydrido, hydroxy, alkyl, hydroxyalkyl, halo, haloalkyl, cycloalkyl, cycloalkylalkyl, alkoxy, phenalkyl, phenyl, benzoyl, phenoxy, phenalkyloxy, alkoxyalkyl, acetyl, alkoxycarbonyl, alkenyl, cyano, nitro, carboxyl, alkylthio and mercapto;

and wherein each of $R^3$ through $R^{11}$ may be an acidic moiety further independently selected from acidic moieties consisting of $CO_2H$, $CO_2CH_3$, SH, $CH_2SH$, $C_2H_4SH$, $PO_3H_2$, $NHSO_2CF_3$, $NHSO_2C_6F_5$, $SO_3H$, $CONHNH_2$, $CONHNHSO_2CF_3$, $CONHOCH_3$, $CONHOC_2H_5$, $CONHCF_3$, OH, $CH_2OH$, $C_2H_4OH$, $OPO_3H_2$, $OSO_3H$, and

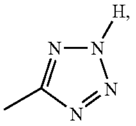

and the esters, amities and salts of said acidic moieties;

with the proviso that at least one of said $R^1$ through $R^{24}$ substituents contains a terminal primary or secondary amino moiety or a moiety convertible to a primary or secondary amino moiety;

or a tautomer thereof or a pharmaceutically-acceptable salt thereof.

7. Conjugate of claim 6 wherein m is one; wherein each of $R^1$ and $R^2$ is independently selected from amino, aminomethyl, aminoethyl, aminopropyl, $CH_2OH$, $CH_2OCOCH_3$, $CH_2Cl$, Cl, $CH_2OCH_3$, $CH_2OCH(CH_3)_2$, I, CHO, $CH_2CO_2H$, $CH(CH_3)CO_2H$, $NO_2$, Cl,

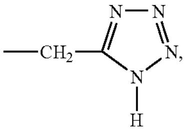

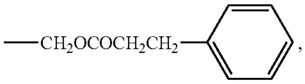

$CO_2CH_3$, $—CONH_2$, $—CONHCH_3$, $CON(CH_3)_2$, $—CH_2—NHCO_2C_2H_5$,

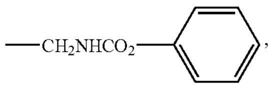

$—CH_2NHCO_2CH_3$, $—CH_2NHCO_2C_3H_7$, $—CH_2NHCO_2CH_2(CH_3)_2$, $—CH_2NHCO_2C_4H_9$, $CH_2NHCO_2$-adamantyl, $—CH_2NHCO_2$-(1-napthyl), $—CH_2NHCONHCH_3$, $—CH_2NHCONHC_2H_5$, $—CH_2NHCONHC_3H_7$, $—CH_2NHCONHC_4H_9$, $—CH_2NHCONHCH(CH_3)_2$, $—CH_2NHCONH$(1-napthyl), $—CH_2NHCONH$(1-adamantyl), $CO_2H$, $—CH_2CH_2CH_2CO_2H$, $—CH_2CH_2F$, $—CH_2OCONHCH_3$, $—CH_2OCSNHCH_3$, $—CH_2NHCSOC_3H_7$, $—CH_2CH_2CH_2F$, $—CH_2ONO_2$, $—CH_2SH$,

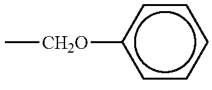

H, Cl, $NO_2$, $CF_3$, $CH_2OH$, Br, F, I, methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, 1-oxoethyl, 1-oxopropyl, 1-oxobutyl, 1 -oxopentyl, 1,1-dimethoxypropyl, 1,1-dimethoxybutyl, 1,1-dimethoxypentyl, hydroxyalkyl, halo, difluoromethyl, 1,1-difluoroethyl, 1,1-difluoropropyl, 1,1-difluorobutyl and 1,1-difluoropentyl; wherein each of $R^3$ through $R^{11}$ is hydrido, with the proviso that at least one of $R^5$, $R^6$, $R^8$ and $R^9$ is an acidic group selected from $CO_2H$, SH, $PO_3H_2$, $SO_3H$, $CONHNH_2$, $CONHNHSO_2CF_3$, OH, and

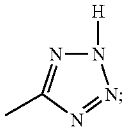

with the proviso that at least one of said $R^1$ through $R^{11}$ substituents contains a terminal primary or secondary amino moiety or a moiety convertible to a primary or secondary amino moiety;

or a tautomer thereof or a pharmaceutically-acceptable salt thereof.

8. Conjugate of claim 7 wherein m is one; wherein $R^1$ is selected from amino, aminomethyl, aminoethyl, aminopropyl, methyl, ethyl, n-propyl, isopropyl, n-butyl, sec-butyl, isobutyl, tert-butyl, n-pentyl, isopentyl, neopentyl, phenyl, benzyl, phenethyl, cyclohexyl, cyclohexylmethyl, 1-oxoethyl, 1-oxopropyl, 1-oxobutyl, 1-oxopentyl, 1,1-dimethoxypropyl, 1,1-dimethoxybutyl, 1,1-dimethoxypentyl, hydroxyalkyl, halo, difluoromethyl, 1,1-difluoroethyl, 1,1-difluoropropyl, 1,1-difluorobutyl and 1,1-difluoropentyl; wherein $R^2$ is selected from ethyl, n-propyl, isopropyl, n-butyl, sec-butyl, isobutyl, 4-methylbutyl, tert-butyl, n-pentyl and neopentyl; wherein each of $R^3$, $R^4$, $R^6$, $R^7$, $R^8$, $R^{10}$, and $R^{11}$ is hydrido; wherein one of $R^5$ and $R^9$ is hydrido and the other of $R^5$ and $R^9$ is an acidic group selected from $CO_2H$, SH, $PO_3H_2$, $SO_3H$, $CONHNH_2$, $CONHNHSO_2CF_3$, OH, and

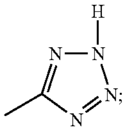

with the proviso that at least one of said $R^1$ through $R^{11}$ substituents contains a terminal primary or secondary amino moiety or a moiety convertible to a primary or secondary amino moiety;

or a tautomer thereof or a pharmaceutically-acceptable salt thereof.

9. Conjugate of claim 1 wherein said second residue forms a kidney-enzyme-cleavable amide bond with the residue of said angiotensin II antagonist compound.

10. Conjugate of claim 1 wherein the second residue is selected from a class of compounds of Formula II and each G substituent is hydroxy.

11. Conjugate of claim 10 wherein each G substituent is hydroxy; wherein $R^{50}$ is hydrido; and wherein $R^{51}$ is selected from

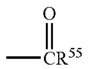

wherein $R^{55}$ is selected from methyl, ethyl, n-propyl, isopropyl, n-butyl, sec-butyl, iso-butyl, tert-butyl, n-pentyl, neopentyl, n-hexyl and chloromethyl.

12. Conjugate of claim 1 wherein said second residue is

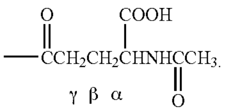

13. Conjugate of claim 1 wherein each of $R^{200}$ and $R^{201}$ is hydrido.

14. Conjugate of claim 1 wherein said angiotensin II antagonist compound is selected from the group consisting of methyl 4'-[(3,5-dibutyl-1H-1,2,4-triazol-1-yl)methyl][1,1'-biphenyl]-2-carboxylate;

4'-[(3,5-dibutyl-1H-1,2,4-triazol-1-yl)methyl][1,1'-biphenyl]-2-carboxylic acid;

4'-[(3,5-dibutyl-1H-1,2,4-triazol-1-yl)methyl][1,1'-biphenyl]-2-carboxylic acid, hydrazide;

4'-[(5-butyl-3-chloro-1H-1,2,4-triazol-1-yl)methyl][1,1'-biphenyl]-2-carboxylic acid;

4'-[(3-butyl-5-chloro-1H-1,2,4-triazol-1-yl)methyl][1,1'-biphenyl]-2-carboxylic acid;

4'-[(5-butyl-3-propyl-1H-1,2,4-triazol-1-yl)methyl][1,1'-biphenyl]-2-carboxylic acid;

4'-[(5-butyl-3-isopropyl-1H-1,2,4-triazol-1-yl)methyl][1,1'-biphenyl]-2-carboxylic acid;

4'-[(5-butyl-3-secbutyl-1H-1,2,4-triazol-1-yl)methyl][1,1'-biphenyl]-2-carboxylic acid;

4'-[(5-butyl-3-isobutyl-1H-1,2,4-triazol-1-yl)methyl][1,1'-biphenyl]-2-carboxylic acid;

4'-[(5-butyl-3-tertbutyl-1H-1,2,4-triazol-1-yl)methyl][1,1'-biphenyl]-2-carboxylic acid;

4'-[(5-butyl-3-pentyl-1H-1,2,4-triazol-1-yl)methyl][1,1'-biphenyl]-2-carboxylic acid;

4'-[(5-butyl-3-isopentyl-1H-1,2,4-triazol-1-yl)methyl][1,1'-biphenyl]-2-carboxylic acid;

4'-[(5-butyl-3-cyclohexyl-1H-1,2,4-triazol-1-yl)methyl][1,1'-biphenyl]-2-carboxylic acid;
4'-[(5-butyl-3-cyclohexylmethyl-1H-1,2,4-triazol-1-yl)methyl][1,1'-biphenyl]-2-carboxylic acid;
4'-[[5-butyl-3-(2-cyclohexylethyl))-1H-1,2,4-triazol-1-yl]methyl][1,1'-biphenyl]-2-carboxylic acid;
4'-[(5-butyl-3-cyclohexanoyl-1,2,4,-triazol-1-yl)methyl][1,1'-biphenyl]-2-carboxylic acid;
4'-[[5-butyl-3-(1-oxo-2-cyclohexylethyl)-1H-1,2,4-triazol-1-yl]methyl][1,1'-biphenyl]-2-carboxylic acid;
4'-[(5-butyl-3-phenyl-1,2,4,-triazol-1-yl)methyl][1,1'-biphenyl]-2-carboxylic acid;
4'-[(5-butyl-3-phenylmethyl-1,2,4,-triazol-1-yl)methyl][1,1'-biphenyl]-2-carboxylic acid;
4'-[[5-butyl-3-(2-phenylethyl)-1H-1,2,4-triazol-1-yl]methyl][1,1'-biphenyl]-2-carboxylic acid;
4'-[(5-butyl-3-benzoyl-1,2,4,-triazol-1-yl)methyl][1,1'-biphenyl]-2-carboxylic acid;
4'-[[5-butyl-3-(1-oxo-2-phenylethyl)-1H-1,2,4-triazol-1-yl]methyl][1,1'-biphenyl]-2-carboxylic acid;
4'-[[5-butyl-3-(1,1-dimethoxypropyl)-1H-1,2,4-triazol-1-yl]methyl][1,1'-biphenyl]-2-carboxylic acid;
4'-[[5-butyl-3-(1,1-dimethoxybutyl)-1H-1,2,4-triazol-1-yl]methyl][1,1'-biphenyl]-2-carboxylic acid;
4'-[[5-butyl-3-(1-oxopropyl)-1H-1,2,4-triazol-1-yl]methyl][1,1'-biphenyl]-2-carboxylic acid;
4'-[[5-butyl-3-(1-oxobutyl)-1H-1,2,4-triazol-1-yl]methyl][1,1'-biphenyl]-2-carboxylic acid;
4'-[[5-butyl-3-(1-oxopentyl)-1H-1,2,4-triazol-1-yl]methyl][1,1'-biphenyl]-2-carboxylic acid;
4'-[[5-butyl-3-(1,1-difluoroethyl)-1H-1,2,4-triazol-1-yl]methyl][1,1'-biphenyl]-2-carboxylic acid;
4'-[[5-butyl-3-(1,1-difluoropropyl)-1H-1,2,4-triazol-1-yl]methyl][1,1'-biphenyl]-2-carboxylic acid;
4'-[[5-butyl-3-(1,1-difluorobutyl)-1H-1,2,4-triazol-1-yl]methyl][1,1'-biphenyl]-2-carboxylic acid;
4'-[[3-butyl-5-(1,1-difluorobutyl)-1H-1,2,4-triazol-1-yl]methyl][1,1'-biphenyl]-2-carboxylic acid;
4'-[[5-butyl-3-(1,1-difluoropentyl)-1H-1,2,4-triazol-1-yl]methyl][1,1'-biphenyl]-2-carboxylic acid;
4'-[(3,5-dipropyl-1H-1,2,4-triazol-1-yl)methyl][1,1'-biphenyl]-2-carboxylic acid;
4'-[(3,5-isopropyl-1H-1,2,4-triazol-1-yl)methyl][1,1-biphenyl]-2-carboxylic acid;
4'-[(3,5-disecbutyl-1H-1,2,4-triazol-1-yl)methyl][1,1'-biphenyl]-2-carboxylic acid;
4'-[(3,5-diisobutyl-1H-1,2,4-triazol-1-yl)methyl][1,1'-biphenyl]-2-carboxylic acid;
4'-[(3,5-ditertbutyl-1H-1,2,4-triazol-1-yl)methyl][1,1'-biphenyl]-2-carboxylic acid;
4'-[(3,5-dipentyl-1H-1,2,4-triazol-1-yl)methyl][1,1-biphenyl]-2-carboxylic acid;
4'-[(3,5-diisopentyl-1H-1,2,4-triazol-1-yl)methyl][1,1'-biphenyl]-2-carboxylic acid;
5-[4'-[(5-butyl-3-amino-1H-1,2,4-triazol-1-yl)methyl][1,1'-biphenyl]-2-yl]-1H-tetrazole;
5-[4'-[(5-butyl-3-aminomethyl-1H-1,2,4-triazol-1-yl)methyl][1,1'-biphenyl]-2-yl]-1H-tetrazole;
5-[4'-[(5-butyl-3-aminoethyl-1H-1,2,4-triazol-1-yl)methyl][1,1'-biphenyl]-2-yl]-1H-tetrazole;
5-[4'-[(5-butyl-3-aminopropyl-1H-1,2,4-triazol-1-yl)methyl][1,1'-biphenyl]-2-yl]-1H-tetrazole;
5-[4'-[(5-butyl-3-aminobutyl-1H-1,2,4-triazol-1-yl)methyl][1,1'-biphenyl]-2-yl]-1H-tetrazole;
5-[4'-[[3-butyl-5-(4-aminophenyl)-1H-1,2,4-triazol-1-yl]methyl][1,1'-biphenyl]-2-yl]-1H-tetrazole;
5-[4'-[[3-butyl-5-(4-aminophenylmethyl)-1H-1,2,4-triazol-1-yl]methyl][1,1'-biphenyl]-2-yl]-1H-tetrazole;
5-[4'-[[3-butyl-5-(4-aminophenylethyl)-1H-1,2,4-triazol-1-yl]methyl][1,1'-biphenyl]-2-yl]-1H-tetrazole;
5-[4'-[[3-butyl-5-(4-aminomethylphenylmethyl)-1H-1,2,4-triazol-1-yl]methyl][1,1'-biphenyl]-2-yl]-1H-tetrazole;
5-[4'-[[3-butyl-5-(4-aminomethylphenyl)-1H-1,2,4-triazol-1-yl]methyl][1,1'-biphenyl]-2-yl]-1H-tetrazole;
5-[4'-[[3-butyl-5-(4-aminoethylphenyl)-1H-1,2,4-triazol-1-yl]methyl][1,1'-biphenyl]-2-yl]-1H-tetrazole;
5-[4'-[[3-butyl-5-(4-aminocyclohexyl)-1H-1,2,4-triazol-1-yl]methyl][1,1'-biphenyl]-2-yl]-1H-tetrazole;
5-[4'-[[3-butyl-5-(4-aminocyclohexylmethyl)-1H-1,2,4-triazol-1-yl]methyl][1,1'-biphenyl]-2-yl]-1H-tetrazole;
5-[4'-[[3-butyl-5-(4-aminocyclohexylethyl)-1H-1,2,4-triazol-1-yl]methyl][1,1'-biphenyl]-2-yl]-1H-tetrazole;
5-[4'-[[3-butyl-5-(4-aminomethylcyclohexylmethyl)-1H-1,2,4-triazol-1-yl]methyl][1,1'-biphenyl]-2-yl]-1H-tetrazole;
5-[4'-[[3-butyl-5-(4-aminomethylcyclohexyl)-1H-1,2,4-triazol-1-yl]methyl][1,1'-biphenyl]-2-yl]-1H-tetrazole;
5-[4'-[[3-butyl-5-(4-aminoethylcyclohexyl)-1H-1,2,4-triazol-1-yl]methyl][1,1'-biphenyl]-2-yl]-1H-tetrazole;
5-[4'-[(5-butyl-3-carboxy-1H-1,2,4-triazol-1-yl)methyl][1,1'-biphenyl]-2-yl]-1H-tetrazole;
5-[4'-[(5-butyl-3-carboxymethyl-1H-1,2,4-triazol-1-yl)methyl][1,1'-biphenyl]-2-yl]-1H-tetrazole;
5-[4'-[(5-butyl-3-carboxyethyl-1H-1,2,4-triazol-1-yl)methyl][1,1'-biphenyl]-2-yl]-1H-tetrazole;
5-[4'-[(5-butyl-3-carboxypropyl-1H-1,2,4-triazol-1-yl)methyl][1,1'-biphenyl]-2-yl]-1H-tetrazole;
5-[4'-[(5-butyl-3-carboxybutyl-1H-1,2,4-triazol-1-yl)methyl][1,1'-biphenyl]-2-yl]-1H-tetrazole;
5-[4'-[[3-butyl-5-(4-carboxyphenyl)-1H-1,2,4-triazol-1-yl]methyl][1,1'-biphenyl]-2-yl]-1H-tetrazole;
5-[4'-[[3-butyl-5-(4-carboxyphenylmethyl)-1H-1,2,4-triazol-1-yl]methyl][1,1'-biphenyl]-2-yl]-1H-tetrazole;
5-[4'-[[3-butyl-5-(4-carboxyphenylethyl)-1H-1,2,4-triazol-1-yl]methyl][1,1'-biphenyl]-2-yl]-1H-tetrazole;
5-[4'-[[3-butyl-5-(4-carboxymethylphenylmethyl)-1H-1,2,4-triazol-1-yl]methyl][1,1'-biphenyl]-2-yl]-1H-tetrazole;
5-[4'-[[3-butyl-5-(4-carboxymethylphenyl)-1H-1,2,4-triazol-1-yl]methyl][1,1'-biphenyl]-2-yl]-1H-tetrazole;
5-[4'-[[3-butyl-5-(4-carboxyethylphenyl)-1H-1,2,4-triazol-1-yl]methyl][1,1'-biphenyl]-2-yl]-1H-tetrazole;
5-[4'-[[3-butyl-5-(4-carboxycyclohexyl)-1H-1,2,4-triazol-1-yl]methyl][1,1'-biphenyl]-2-yl]-1H-tetrazole;
5-[4'-[[3-butyl-5-(4-carboxycyclohexylmethyl)-1H-1,2,4-triazol-1-yl]methyl][1,1'-biphenyl]-2-yl]-1H-tetrazole;
5-[4'-[[3-butyl-5-(4-carboxycyclohexylethyl)-1H-1,2,4-triazol-1-yl]methyl][1,1'-biphenyl]-2-yl]-1H-tetrazole;
5-[4'-[[3-butyl-5-(4-carboxymethylcyclohexylmethyl)-1H-1,2,4-triazol-1-yl]methyl][1,1'-biphenyl]-2-yl]-1H-tetrazole;
5-[4'-[[3-butyl-5-(4-carboxymethylcyclohexyl)-1H-1,2,4-triazol-1-yl]methyl][1,1'-biphenyl]-2-yl]-1H-tetrazole; and
5-[4'-[[3-butyl-5-(4-carboxyethylcyclohexyl)-1H-1,2,4-triazol-1-yl]methyl][1,1'-biphenyl]-2-yl]-1H-tetrazole.

15. Conjugate of claim 1 which is N-acetylglutamic acid, 5-[[4'[(3,5-dibutyl-1H-1,2,4-triazol-1-yl)methyl][1,1'-biphenyl]-2-yl]]carbonylhydrazide.

16. Conjugate of claim 1 which is $N^2$-acetyl-N-[[5-butyl-1-[[2'-(1H-tetrazol-5-yl)[(1,1'-biphenyl]-4-yl]methyl]-1H-1,2,4-triazol-3-yl]methyl]-L-glutamine.

17. Conjugate of claim 1 which is N-acetyl-L-glutamic acid, 5-[5-butyl-1-[[2'-(1H-tetrazol-5-yl)[1,1'-biphenyl]-4-yl]methyl-1H-1,2,4-triazol-3-yl]acetylhydrazide.

18. A pharmaceutical composition comprising one or more pharmaceutically-acceptable carriers or diluents and a therapeutically-effective amount of a conjugate of claim 1.

* * * * *